US009109025B2

(12) United States Patent
Gurney et al.

(10) Patent No.: US 9,109,025 B2
(45) Date of Patent: Aug. 18, 2015

(54) ANTI-RSPO2 ANTIBODIES

(71) Applicant: OncoMed Pharmaceuticals, Inc., Redwood City, CA (US)

(72) Inventors: Austin L. Gurney, San Francisco, CA (US); Fumiko Takada Axelrod, Palo Alto, CA (US); Timothy Charles Hoey, Hillsborough, CA (US); Cecile Chartier-Courtaud, Palo Alto, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 0 days.

(21) Appl. No.: 14/318,253

(22) Filed: Jun. 27, 2014

(65) Prior Publication Data

US 2015/0010571 A1 Jan. 8, 2015

Related U.S. Application Data

(62) Division of application No. 13/549,050, filed on Jul. 13, 2012, now Pat. No. 8,802,097.

(60) Provisional application No. 61/508,403, filed on Jul. 15, 2011, provisional application No. 61/521,547, filed on Aug. 9, 2011, provisional application No. 61/570,629, filed on Dec. 14, 2011.

(51) Int. Cl.

| | |
|---|---|
| ***A61K 39/00*** | (2006.01) |
| ***A61K 39/395*** | (2006.01) |
| ***C07K 16/00*** | (2006.01) |
| ***C07K 16/18*** | (2006.01) |
| ***C07K 16/30*** | (2006.01) |
| ***G01N 33/574*** | (2006.01) |
| ***A61K 45/06*** | (2006.01) |
| ***C07K 16/28*** | (2006.01) |

(52) U.S. Cl.

CPC ............ *C07K 16/18* (2013.01); *A61K 39/3955* (2013.01); *A61K 39/39533* (2013.01); *A61K 39/39558* (2013.01); *A61K 45/06* (2013.01); *C07K 16/2863* (2013.01); *C07K 16/303* (2013.01); *C07K 16/3015* (2013.01); *C07K 16/3023* (2013.01); *C07K 16/3046* (2013.01); *C07K 16/3069* (2013.01); *G01N 33/57415* (2013.01); *G01N 33/57423* (2013.01); *G01N 33/57449* (2013.01); *A61K 2039/505* (2013.01); *A61K 2039/507* (2013.01); *C07K 2317/14* (2013.01); *C07K 2317/24* (2013.01); *C07K 2317/30* (2013.01); *C07K 2317/31* (2013.01); *C07K 2317/33* (2013.01); *C07K 2317/565* (2013.01); *C07K 2317/76* (2013.01); *C07K 2317/92* (2013.01); *C07K 2319/30* (2013.01); *G01N 2800/52* (2013.01)

(58) Field of Classification Search

None

See application file for complete search history.

(56) References Cited

U.S. PATENT DOCUMENTS

| | | | |
|---|---|---|---|
| 6,004,528 | A | 12/1999 | Bergstein |
| 7,193,069 | B2 | 3/2007 | Isogai et al. |
| 7,319,141 | B2 | 1/2008 | Tang et al. |
| 7,320,880 | B2 | 1/2008 | Nishikawa et al. |
| 7,411,052 | B2 | 8/2008 | Tang |
| 7,439,332 | B2 | 10/2008 | Nishikawa |
| 7,498,416 | B2 | 3/2009 | Yayon et al. |
| 7,541,431 | B2 | 6/2009 | Yoon |
| 7,723,112 | B2 | 5/2010 | Clarke et al. |
| 7,951,381 | B2 | 5/2011 | Funk et al. |
| 8,088,374 | B2 | 1/2012 | Niehrs et al. |
| 8,158,757 | B2 | 4/2012 | Gurney et al. |
| 8,158,758 | B2 | 4/2012 | Gurney et al. |
| 8,540,989 | B2 | 9/2013 | Gurney et al. |
| 8,628,774 | B2 | 1/2014 | Gurney et al. |
| 8,802,097 | B2 | 8/2014 | Gurney et al. |
| 8,883,736 | B2 | 11/2014 | Gurney |
| 2002/0065394 | A1 | 5/2002 | Jacobs et al. |
| 2003/0022217 | A1 | 1/2003 | Ceccardi et al. |
| 2003/0100741 | A1 | 5/2003 | Muller et al. |
| 2004/0197778 | A1 | 10/2004 | Morris et al. |
| 2005/0054829 | A1 | 3/2005 | Wiley et al. |
| 2005/0130145 | A1 | 6/2005 | Yue et al. |

(Continued)

FOREIGN PATENT DOCUMENTS

| | | |
|---|---|---|
| AU | 2008270972 A1 | 1/2009 |
| CA | 2 691 378 | 1/2009 |

(Continued)

OTHER PUBLICATIONS

Al-Hajj, M., et al., "Prospective identification of tumorigenic breast cancer cells," *Proc. Natl. Acad. Sci. USA* 100(7):3983-8, National Academy of Sciences, United States (2003).

Aubele, M. and Werner, M., "Heterogeneity in breast cancer and the problem of relevance of findings," *Anal. Cell Pathol.* 19(2):53-8, IOS Press, Netherlands (1999).

Beachy, P.A., et al., "Tissue repair and stem cell renewal in carcinogenesis," *Nature* 432(7015):324-31, Nature Publishing Group, England (2004).

Beerman, H., et al., "Flow cytometric analysis of DNA stemline heterogeneity in primary and metastatic breast cancer," *Cytometry* 12(2):147-54, Wiley-Liss, United States (1991).

(Continued)

*Primary Examiner* — Christine J Saoud
*Assistant Examiner* — Jon M Lockard
(74) *Attorney, Agent, or Firm* — Sterne, Kessler, Goldstein & Fox, P.L.L.C.

(57) ABSTRACT

The present invention relates to RSPO-binding agents and methods of using the agents for treating diseases such as cancer. The present invention provides antibodies that specifically bind human RSPO proteins and modulate β-catenin activity. The present invention further provides methods of using agents that modulate the activity of RSPO proteins, such as antibodies that specifically bind RSPO1, RSPO2, and/or RSPO3 and inhibit tumor growth. Also described are methods of treating cancer comprising administering a therapeutically effect amount of an agent or antibody of the present invention to a patient having a tumor or cancer.

19 Claims, 22 Drawing Sheets

(56) References Cited

U.S. PATENT DOCUMENTS

2005/0142600 A1 6/2005 Warren et al.
2005/0232927 A1 10/2005 Clarke et al.
2005/0256036 A1 11/2005 Boyle et al.
2005/0256044 A1 11/2005 Boyle et al.
2006/0019256 A1 1/2006 Clarke et al.
2006/0263803 A1 11/2006 Tang
2007/0117751 A1 5/2007 Gurney et al.
2007/0124581 A1 5/2007 Khare et al.
2007/0237770 A1 10/2007 Lai et al.
2007/0244061 A1 10/2007 Niehrs et al.
2008/0064049 A1 3/2008 Clarke et al.
2008/0131434 A1 6/2008 Lewicki et al.
2008/0306004 A1 12/2008 Tang
2009/0036369 A1 2/2009 Kakitani et al.
2009/0074782 A1* 3/2009 Gurney ..................... 424/139.1
2009/0118176 A1 5/2009 Emtage et al.
2009/0191205 A1 7/2009 Gurney
2009/0208484 A1 8/2009 Christiano
2010/0047257 A1 2/2010 Blanc et al.
2010/0071078 A1 3/2010 Niehrs
2010/0278800 A1 11/2010 Boyle et al.
2011/0123532 A1 5/2011 Gurney et al.
2011/0287444 A1 11/2011 Kanamori et al.
2012/0039912 A1 2/2012 Rawadi et al.
2012/0082659 A1 4/2012 Land et al.
2012/0088727 A1 4/2012 Niehrs et al.
2012/0171226 A1 7/2012 Horwitz
2012/0184616 A9 7/2012 Rabbani et al.
2012/0263730 A1 10/2012 Niehrs et al.
2013/0095116 A1 4/2013 Gurney et al.
2013/0115206 A1 5/2013 Gurney et al.
2013/0121993 A1 5/2013 Gurney
2014/0017253 A1 1/2014 Gurney et al.
2014/0127223 A1 5/2014 Yamazaki et al.
2014/0134177 A1 5/2014 Gurney et al.
2015/0010565 A1 1/2015 Gurney et al.
2015/0010571 A1 1/2015 Gurney et al.

FOREIGN PATENT DOCUMENTS

DE 10339820 A1 3/2005
EP 2 081 586 7/2009
EP 2 157 192 A1 2/2010
EP 1 673 475 4/2010
EP 2 173 379 4/2010
EP 2 419 133 2/2012
EP 1 427 747 B1 4/2012
EP 2 515 933 10/2012
JP 2010-532169 A 10/2010
WO WO 98/049302 11/1998
WO WO 99/15660 4/1999
WO WO 01/77169 A2 10/2001
WO WO 01/87338 A1 11/2001
WO WO 02/12447 A2 2/2002
WO WO 02/102972 A2 12/2002
WO WO 03/029405 A2 4/2003
WO WO 03/050502 A2 6/2003
WO WO 03/054152 A2 7/2003
WO WO 2004/074436 A2 9/2004
WO WO 2005/040418 A2 5/2005
WO WO 2006/110581 A2 10/2006
WO WO 2007/096149 A1 8/2007
WO WO 2008/020942 A2 2/2008
WO WO 2008/046649 A1 4/2008
WO WO-2008042236 A2 4/2008
WO WO 2008/075796 A1 6/2008
WO WO 2008/088524 A2 7/2008
WO WO 2009/005809 A2 1/2009
WO WO 2009/045443 A2 4/2009
WO WO 2010/121923 A1 10/2010
WO WO 2011/076932 A1 6/2011
WO WO 2012092336 A2 7/2012
WO WO 2012/140274 A2 10/2012
WO WO 2013/012747 A1 1/2013
WO WO 2014/012007 A2 1/2014

OTHER PUBLICATIONS

Bonsing, B.A., et al., "High level of DNA index heterogeneity in advanced breats carcinomas. Evidence for DNA ploidy differences between lymphatic and hematogenous metastases," *Cancer* 71(2):382-391, Wiley, United States (1993).

Bonsing, B.A., et al., "Allelotype analysis of flow-sorted breast cancer cells demonstrates genetically related diploid and aneuploid subpopulations in primary tumors and lymph node metastases," *Genes Chromosomes Cancer* 28(2):173-183, Wiley-Liss, United States (2000).

Brennan, K.R. and Brown, A.M., "Wnt proteins in mammary development and cancer," *J. Mammary Gland Biol. Neoplasia* 9(2):119-131, Kluwer Academic/Plenum Publishers, United States (2004).

Cabrera, C.V., et al., "Phenocopies induced with antisense RNA identify the wingless gene," *Cell* 50(4):659-663, Cell Press, United States (1987).

Campbell, A.M., *Monoclonal Antibody Technology Eds*., pp. 1-29, Elsevier Science Publishers B.V., Netherlands (1984).

Casset, F., et al., "A peptide mimetic of an anti-CD4 monoclonal antibody by rational design," *Biochem. Biophys. Res. Commun.* 307(1):198-205, Academic Press, United States (2003).

Chien, A.J., et al., "Activated Wnt/beta-catenin signaling in melanoma is associated with decreased proliferation in patient tumors and a murine melanoma model," *Proc. Natl. Acad. Sci. USA* 106(4):1193-1198, National Academy of Sciences, United States (2009).

Dermer, G.B., "Another Anniversary for the War on Cancer," *Bio/Technology* 12:320, Nature Publishing Co., United States (1994).

Freshney, R.I., *Culture of Animal Cells, A Manual of Basic Technique*, pp. 4, Alan R. Liss, Inc., United States (1983).

Gazit, A., et al., "Human frizzled I interacts with transforming Wnts to transduce a TCF dependent transcriptional response," *Oncogene* 18(44):5959-5966, Nature Publishing Group, England (1999).

Gradl, D., et al., "The Wnt/Wg signal transducer beta-catenin controls fibronectin expression," *Mol. Cell Biol.* 19(8):5576-5587, American Society for Microbiology, United States (1999).

Gura, T., "Systems for identifying new drugs are often faulty," *Science* 278(5340):1041-1042, American Association for the Advancement of Science, United States (1997).

Harada, N., et al., "Intestinal polyposis in mice with a dominant stable mutation of the beta-catenin gene," *EMBO J.* 18(21):5931-5942, IRL Press, England (1999).

Hatsell, S., et al., "Beta-catenin and Tcfs in mammary development and cancer," *J. Mammary Gland Biol. Neoplasia* 8(2):145-158, Kluwer Academic/Plenum Publishers, United States (2003).

He, T.C., et al., "Identification of c-MYC as a target of the APC pathway," *Science* 281(5382):1509-1512, American Association for the Advancement of Science, United States (1998).

Hsu, S.Y., et al, "Activation of Orphan Receptors by the Hormone Relaxin," *Science*, 295:671-674, American Association for the Advancement of Science, United States (2002).

Imbert, A., et al., "Delta N89 beta-catenin induces precocious development, differentiation, and neoplasia in mammary gland," *J. Cell. Biol.* 153(3):555-568, Rockefeller University Press, United States (2001).

Jain, R.K., "Barriers to drug delivery in solid tumors," *Sci. Am.* 271(1):58-65, Scientific American, United States (1994).

Jemal, A., et al.,"Cancer Statistics, 2003," CA Cancer J. Clin. 53(1):5-26, American Cancer Society, United States (2003).

Kamata, T., et al., "R-spondin, a novel gene with thrombospondin type 1 domain, was expressed in the dorsal neural tube and affected in Wnts mutants," *Biochim. Biophys. Acta* 1676(1):51-62, Elsevier Pub. Co., Netherlands (2004).

Kazanskaya, O., et al., "R-Spondin2 is a secreted activator of Wnt/beta-catenin signaling and is required for *Xenopus* myogenesis," *Dev. Cell* 7(4):525-534, Cell Press, United States (2004).

Kim, K.A., et al., "Mitogenic influence of human R-spondin1 on the intestinal epithelium," *Science* 309(5738):1256-1259, American Association for the Advancement of Science, United States (2005).

Kim, K.A., et al., "R-Spondin proteins: a novel link to beta-catenin activation," *Cell Cycle* 5(1):23-26, Landes Bioscience, United States (2006).

(56) References Cited

OTHER PUBLICATIONS

Kuukasjrvi, P., et al., "Overview of systematic reviews on invasive treatment of stable coronary artery disease," Int. J. Technol. Assess Health Care 22(2):219-34, Cambridge University Press, England (2006).
Larue, L. and Delmas, V., "The WNT/Beta-catenin pathway in melanoma," *Front Biosci.* 11:733-742, Frontiers in Bioscience Publications, United States (2006).
Mazerbourg, S., et al., "Leucine-Rich Repeat-Containing, G Protein-Coupled Receptor 4 Null Mice Exhibit Intrauterine Growth Retardation Associated with Embryonic and Perinatal Lethality," *Molecular Endocrinology*, 18(9):2241-2254, The Endocrine Society, United States (2004).
McClanahan, T., et al, "Identification of Overexpression of Orphan G Protein-Coupled Receptor GPR49 in Human Colon and Ovarian Primary Tumors," *Cancer Biology and Therapy*, 5(4):419-426, Landes Bioscience, United States (2006).
Milovanovic, T., et al., "Expression of Wnt genes and frizzled 1 and 2 receptors in normal breats epithelium and infiltrating breast carcinoma," *Int. J. Oncol.* 25:1337-1342, D.A. Spandidos, Greece (2004).
Michaelson, J.S. and Leder, P., "beta-catenin is a downstream effector of Wnt-mediated tumorigenesis in the mammary gland," *Oncogene* 20(37):5093-5099, Nature Publishing Group, England (2001).
Miller, J.R., et al., "Mechanism and function of signal transduction by the Wnt/betac-atenin and Wnt/Ca2+ pathways," *Oncogene* 18(55):7860-7872, Nature Publishing Group, England (1999).
Morita, H., et al, "Neonatal Lethality of LGR5 Null Mice is Associated with Ankyloglossia and Gastrointestinal Distension," *Mol. Cell. Biol.*, 24(22):9736-9743, American Society for Microbiology, United States (2004).
Morrison, S.J., et al., "The biology of hematopoietic stem cells," Annu. Rev. Cell Dev. Biol. 11:35-71, Annual Reviews, United States (1995).
Morrison, S.J., et al., "Regulatory mechanisms in stem cell biology," Cell 88(3):287-98, Cell Press, United States (1997).
Morrison, S.J., et al., "Hematopoietic stem cells: challenges to expectations," Curr. Opin. Immunol. 9(2):216-221, Elsevier, England (1997).
Nam, J.S., et al., "Mouse cristin/R-spondin family proteins are novel ligands for the Fizzled 8 and LRP6 receptors and activate beta-catenin-dependent gene expression," J. Biol. Chem. 281(19):13247-13257, American Society for Biochemistry and Molecular Biology, United States (2006).
Nusse, R. and Varmus, H.E., "Many tumors induced by the mouse mammary tumor virus contain a provirus integrated in the same region of the host genome," *Cell* 31(1):99-109, Cell Press, United States (1982).
Oshima, H., et al., "Morphological and molecular processes of polyp formation in Apc(delta716) knockout mice," *Cancer Res.* 57(9):1644-1649, American Association for Cancer Research, United States (1997).
Pandis, N., et al., "Cytogenic Comparison of Primary Tumors and Lymph Node Metastases in Breast Cancer Patients," *Genes, Chromosomes & Cancer* 22:122-129, Wiley-Liss, Inc., United States (1998).
De Pascalis, R., et al., "Grafting of "abbreviated" complimentarity-determining regions containing specificit-determining residues essential for ligand contact to engineer a less immunogenic humanized monoclonal antibody," *J. Immunol.* 169(6):3076-3084, American Association of Immunologists, United States (2002).
Paul, W.D., *Fundamental Immunology*, 3rd Edition, pp. 292-295, Raven Press, Ltd., United States (1993).
Reya, T. and Clevers, H., "Wnt signlaing in stem cells and cancer," *Nature* 434(7035):843-50, Nature Publishing Group, England (2005).
Rijsewijk, F., et al.,"The Drosophila homolog of the mouse mammary oncogene int-1 is identical to the segment polarity gene wingless," *Cell* 50(4):649-657, Cell Press, United States (1987).
Rudikoff, S., et al., "Single amino acid substitution altering antigen-binding specificity," *Proc. Natl. Acad. Sci. USA* 79(6):1979-1983, National Academy of Sciences, United States (1982).
Shen, C.Y., et al., "Genome-wide search for loss of heterozygosity using laser capture microdissected tissue of breast carcinoma: an implication for mutator phenotype and breats cancer pathogenesis," Cancer Res. 60(14):3884-92, American Association for Cancer Research, United States (2000).
Tepera, S.B., et al., "A beta-catenin survival signal is required for normal lobular development in the mammary gland," *J. Cell. Sci.* 116(Pt 6):1137-1149, Company of Biologists, England (2003).
Tetsu, O. and McCormick, F., "Beta-catenin regulates expression of cyclin D1 in colon carcinoma cells," *Nature* 398(6726):422-426, Nature Publishing Group, England (1999).
Van Ooyen, A. and Nusse, R., "Structure and nucelotide sequence of the putative mammary oncogene int-1; proviral insertions leave the protein-encoding domain intact," *Cell* 39(1):233-240, Cell Press, United States (1984).
Wu, C.H. and Nusse, R., "Ligand receptor interactions in the Wnt signlaing pathway in *Drosophila,*" *J. Biol. Chem.* 277(44):41762-41769, American Society for Biochemistry and Molecular Biology, United States (2002).
Zhao, J., et al., "R-spondin1, A Novel Intestinotrophic Mitogen, Ameliorates Experimental Colitis in Mice," *Gastroenterology*, 132(4):1331-1334, Elsevier, United States (2007).
International Search Report for International Application No. PCT/US2008/008210, European Patent Office, Netherlands, mailed on Mar. 2, 2009.
The Written Opinion of the International Searching Authority for International Application No. PCT/US2008/008210, European Patent Office, Netherlands, mailed on Jan. 5, 2010.
International Preliminary Report on Patentability for International Application No. PCT/US2008/008210, dated Jan. 5, 2010 from the International Bureau of WIPO, Geneva, Switzerland.
International Search Report for International Application No. PCT/US2012/046746, dated Oct. 23,2012, from the International Searching Authority, Alexandria.
The Written Opinion of the International Searching Authority for International Application No. PCT/US2012/046746, dated Oct. 4, 2012.
Notice of Allowance dated Feb. 23, 2012 in U.S. Appl. No. 12/167,176, filed Jul. 2, 2008.
Notice of Allowance dated Jan. 18, 2012 in U.S. Appl. No. 12/167,176, filed Jul. 2, 2008.
Smalley, M.J. and Dale, T.C., "Wnt signaling in mammalian development and cancer," *Cancer and Metastasis Reviews* 18:215-230, Khuwer Academic Publishers, Netherlands (1999) (D15 as submitted in OPPO_EP2157192).
Bienz, M. and Clevers, H., "Linking Colorectal cancer to Wnt Signaling," *Cell* 103:311-320, Cell Press, United States (2000) (D16 as submitted in OPPO_EP2157192).
Korinek, V., et al., "Constitutive Transcriptional Activation by a β-Catenin-Tcf Complex in APC−/− Colon Carcinoma," *Science* 275:1784-1787, American Association for the Advancement of Science, United States (1997) (D17 as submitted in OPPO_EP2157192).
Notice of Allowance dated Jan. 23, 2012 in U.S. Appl. No. 12/167,172, filed Jul. 2, 2008.
Fischer, L., et al., "Wnt-3A Enhances Bone Morphogenetic Protein-2-mediated Chondrogenesis of Mruine C3H10T1/2 Mesenchymal Cells," *The Journal of Biological Chemistry* 277(34):30870-30878, JBC Papers in Press, American Society for Biochemistry and Molecular Biology, United States (2002) (D18 as submitted in OPPO_EP2157192).
Boyden, L.M., et al., "High Bone Density Due to a Mutation in LDL-Receptor-Related Protein 5," *The New England Journal of Medicine* 346(20):1513-1521, Massachusetts Medical Society, United States (2002) (D19 as submitted in OPPO_EP2157192).
Gong, Y., et al., "LDL Receptor-Related Protein 5 (LRP5) Affects Bone Accrual and Eye Development," *Cell* 107:513-523, Cell Press, United States (2001) (D20 as submitted in OPPO_EP2157192).
English language abstract of DE 10339820 A1, espacenet database, Worldwide, published Mar. 17, 2005.

(56) References Cited

OTHER PUBLICATIONS

English language abstract of JP 2010-532169 A, espacenet database, Worldwide, published Jan. 8, 2009.
Luu, H.H., et al., "Wnt/β-Catenin Signaling Pathway as Novel Cancer Drug Targets," *Current Cancer Drug Targets* 4:653-671, Bentham Science Publishers Ltd., Netherlands (2004).
Carmon, K.S., et al., "R-spondins function as ligands of the orphan receptors LGR4 and LGR5 to regulate Wnt/β-catenin signaling," *Proc. Natl. Acad. Sci. USA* 108(28):11452-11457, National Academy of Sciences, United States (2011).
Takahashi-Yanaga, F. and Sasaguri, T., "The Wnt/β-Catenin Signaling Pathway as a Target in Drug Discovery," *J. Pharmacol. Sci.* 104:293-302, The Japanese Pharmacological Society, Japan (2007).
Co-pending U.S. Appl. No. 13/408,704, filed Feb. 29, 2012, inventor Gurney, A. (published and cited herewith as US42 on PTO/SB/08a).
Co-pending U.S. Appl. No. 13/408,731, filed Feb. 29, 2012, inventor Gurney, A. (published and cited herewith as US41 on PTO/SB/08a).
Chen, J-Z., et al., "Cloning and identification of a cDNA that encodes a novel human protein with thrombospondin type I repeat domain, *hPWTSR,*" *Mol. Biol. Rep.* 29:287-292, Kluwer Academic Publishers, Netherlands (2002).
U.S. Appl. No. 13/323,534, filed Dec. 12, 2011, inventors Boyle et al. (Unpublished).
Kim, K-A., et al., "R-Spondin Family Members Regulate the Wnt Pathway by a Common Mechanism," Mol. Biol. of the Cell 19:2588-2596, The American Society for Cell Biology, United States (2008).
Chen, Y., et al., "Selection and Analysis of an Optimized Anti-VEGF Antibody: Crystal Structure of an Affinity-matured Fab in Complex with Antigen," *J Mol Bio* 293:865-881, Academic Press, United States (1999).
MacCallum, R.M., et al. "Antibody-antigen Interactions: Contact Analysis and Binding Site Topography," *J Mol Bio* 262:732-745, Academic Press, United States (1996).
Wu, H., et al., "Humanization of a Murine Monoclonal Antibody by Simultaneous Optimization of Framework and CDR Residues," *J Mol Bio* 294:151-162, Academic Press, United States (1999).
Office Action dated Dec. 3, 2013 in U.S. Appl. No. 13/549,050, filed Jul. 13, 2012.
Surendran, K., et al, "A role for Wnt-4 in renal fibrosis," *Am J Physiol Renal Physiol* 282:F431-F441, American Physiological Society, United Sates (2002) (D21 as submitted in OPPO_EP2157192).
Saadi-Kheddouci, S., et al., "Early development of polycystic kidney disease in transgenic mice expressing an activated mutant of the β-catenin gene," *Oncogene* 20:5972-5981, Nature Publishing Group, England (2001) (D22 as submitted in OPPO_EP2157192).
UniProt "Thrombospondin-1", identifying No. P07996-TSPI_HUMAN, accessed at http://www.uniprot.org/uniprot/P07996, accessed on Sep. 25, 2014, 14 pages (D24 as submitted in OPPO_EP2157192).
Fujino, T., et al., "Low-density lipoprotein receptor-related protein 5 (LRP5) is essential for normal cholesterol metabolism and glucose-induced insulin secretion," *PNAS* 100(I):229-234, National Academy of Sciences, United States (2003) (D23 as submitted in OPPO_EP2157192).
Reply to European Opposition Brief for European Patent No. 2157192 filed Jan. 8, 2015, 40 pages.
European Opposition Brief for European Patent No. 2157192 filed May 28, 2014, 46 pages.
Easwaran, V., et al., "β-Catenin Regulates Vascular Endothelial Growth Factor Expression in Colon Cancer," *Cancer Research* 63:3145-3153, American Association for Cancer Research, United States (2003) (D5 as submitted in OPPO_EP2157192).
Goldblum, S.E., et al., "Thrombospondin-1 Induces Tyrosine Phosphorylation of Adherens Junction Proteins and Regulates an Endothelial Paracellular Pathway," *Molecular Biology of the Cell* 10:1537-1551, The American Society for Cell Biology, United States (1999) (D3 as submitted in OPPO_EP2157192).
Hartmann, C., "Wnt-signaling and skeletogenesis," *J Musculoskelet Neuronal Interact* 2(3):274-276, International Society of Musculoskeletal and Neuronal Interactions, Greece (2002) (Abstract) (D9 as submitted in OPPO_EP2157192).
Horesh, Y., et al., "A rapid method for detection of putative RNAi target genes in genomic data," *Bioinformatics* 19(*Suppl* 2):ii73-ii80, Oxford University Press, England (2003) (D14 as submitted in OPPO_EP2157192).
Jackson, A.L. and Linsley, P.S., "Noise amidst the silence: off-target effects of siRNAs?" *Trends in Genetics* 20(11):521-524, Science Publishers B.V., Netherlands (2004) (D2 as submitted in OPPO_EP2157192).
Lonberg, N., "Human antibodies from transgenic animals," *Nature Biotechnology* 23(9):1117-1125, Nature Publishing Group, United Kingdom (2005) (D4 as submitted in OPPO_EP2157192).
Meniel, V. and Clarke, A.R., "Wnt-cadherin connections in normal and neoplastic mammary epithelium," *J Mammary Gland Biol Neoplasia* 8(4):435-447, Plenum Publishers, United States (2003) (Abstract) (D8 as submitted in OPPO_EP2157192).
Perantoni, A.O., "Renal development: perspectives on a Wnt-dependent process," *Semin Cell Dev Biol* 14(4):201-208, Academic Press, United Kingdom (2003) (Abstract) (D10 as submitted in OPPO_EP2157192).
Polakis, P., "Wnt signaling and cancer," *Genes Dev* 14:1837-1851, Cold Springs Harbor Laboratory Press, United States (2000) (D13 as submitted in OPPO_EP2157192).
Polesskaya, A., et al., "Wnt signaling induces the myogenic specification of resident CD45+ adult stem cells during muscle regeneration," *Cell* 113(7):841-852, MIT Press, United States (2003) (Abstract) (D7 as submitted in OPPO_EP2157192).
Stump, R.J., et al., "A role for Wnt/beta catenin signaling in lens epithelial differentiation," *Dev Biol*259(1):48-61, Elsevier Inc., United States (2003) (Abstract) (D11 as submitted in OPPO_EP2157192).
Wu, W., et al., "Mutual antagonism between *dickkopf1* and *dickkopf2* regulates Wnt/β-catenin signalling," *Current Biology* 10:1611-1614, Elsevier Science Ltd., England (2000) (D6 as submitted in OPPO_EP2157192).
Li, S.J. et al., "Loss-of-function point mutations and two-furin domain derivatives provide insights about R-spondin2 structure and function," *Cellular Signalling* 21(6):916-925 , Elsevier Inc., United States (2009).
Annonymous "Human R-Spondin 2 Antibody, Antigen Affinity-purified Polyclonal Goat IgG, Catalog No. AF3266; R&D Systems, Tools for Cell Biology and Research" Retrieved from http://www.rndsystems.com/pdf/AF3266.pdf on Jan. 1, 2015.
Almagro, J.C. and Fransson, J., "Humanization of Antibodies," Frontiers in Bioscience 13:1619-1633, Frontiers in Bioscience Publications, United States (2008).
Campbell, A.M., "General Properties and Applications of Monoclonal Antibodies," Monoclonal Antibody Technology, 1-32, Elsevier Science Publishers B.V., Amsterdam (1984).
Carter, P.J., "Potent Antibody Therapeutics by Design," Nature Reviews, Immunology 6(5):343-357, Nature Pub. Group, England (2006).
Tan, B.T., et al., "The Cancer Stem Cell Hypothesis: A Work in Progress," Laboratory Investigation 86(12):1203-1207, USCAP, United States (2006).
Transmittal of third party observations sent on Dec. 17, 2014 in European Application No. 08779932,2, 6 pages.
De Genst, E., et al., "Antibody Repertoire Development in Camelids," Developmental and Comparative Immunology 30(1-2):187-198, Elsevier Science, United States (2006).
Examination Report mailed Jan. 22, 2015, from the Intellectual Property Office of Australia for the Australian Patent Application No. AU2012284254.
Extended European Search Report for EP Application No. 12814264, European Patent Office, Germany, mailed on Jan. 28, 2015.
International Search Report for International Application No. PCT/US2013/050300, from the International Bureau of WO, Geneva Switzerland, mailed Feb. 7, 2014.
Written Opinion of the International Searching Authority for International Application No. PCT/US2013/050300, mailed Feb. 7, 2014.

* cited by examiner

Figure 1

A. RSPO1

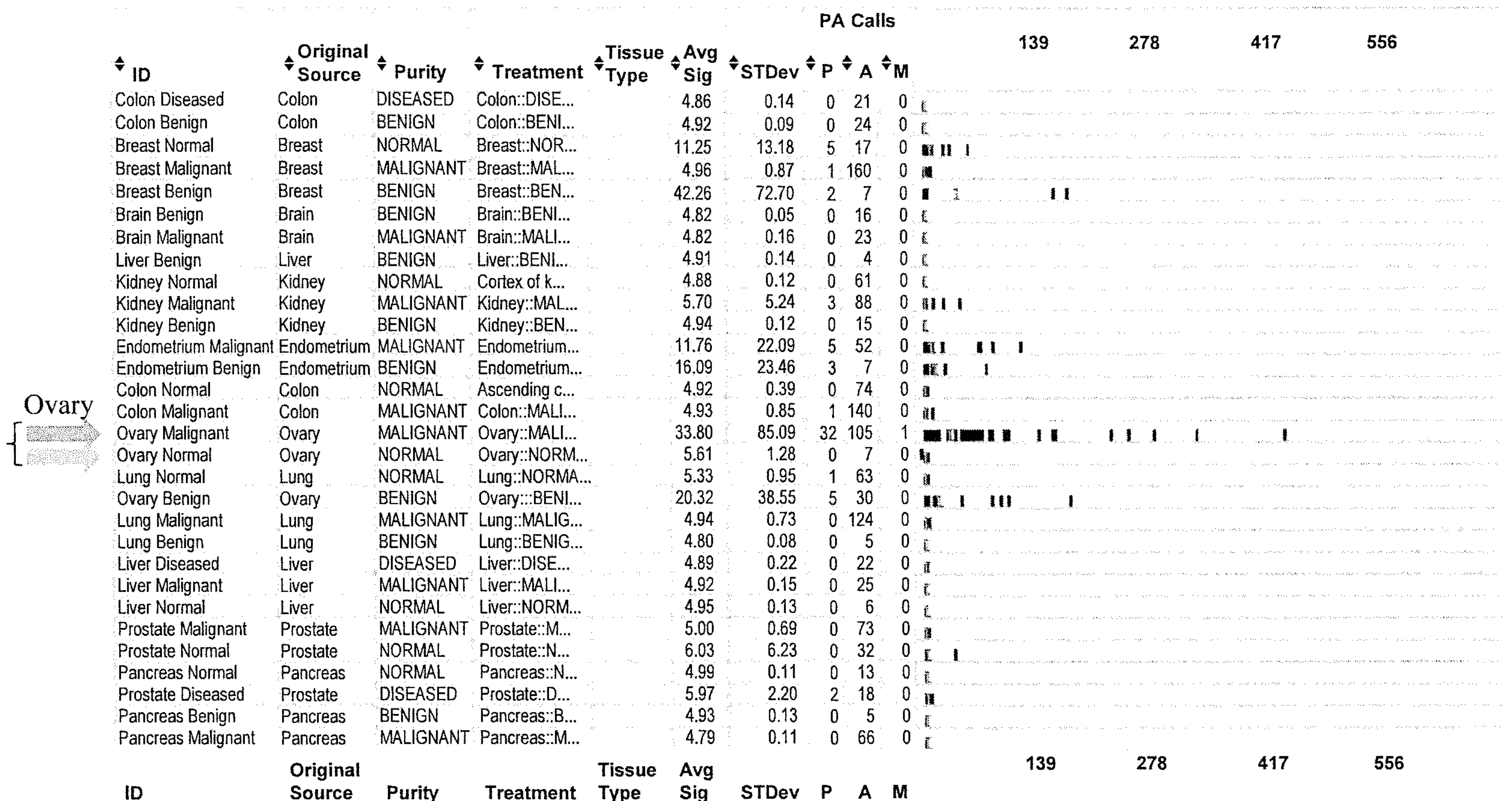

| ID | Original Source | Purity | Treatment | Tissue Type | Avg Sig | STDev | P | A | M |
|---|---|---|---|---|---|---|---|---|---|
| Colon Diseased | Colon | DISEASED | Colon::DISE... | | 4.86 | 0.14 | 0 | 21 | 0 |
| Colon Benign | Colon | BENIGN | Colon::BENI... | | 4.92 | 0.09 | 0 | 24 | 0 |
| Breast Normal | Breast | NORMAL | Breast::NOR... | | 11.25 | 13.18 | 5 | 17 | 0 |
| Breast Malignant | Breast | MALIGNANT | Breast::MAL... | | 4.96 | 0.87 | 1 | 160 | 0 |
| Breast Benign | Breast | BENIGN | Breast::BEN... | | 42.26 | 72.70 | 2 | 7 | 0 |
| Brain Benign | Brain | BENIGN | Brain::BENI... | | 4.82 | 0.05 | 0 | 16 | 0 |
| Brain Malignant | Brain | MALIGNANT | Brain::MALI... | | 4.82 | 0.16 | 0 | 23 | 0 |
| Liver Benign | Liver | BENIGN | Liver::BENI... | | 4.91 | 0.14 | 0 | 4 | 0 |
| Kidney Normal | Kidney | NORMAL | Cortex of k... | | 4.88 | 0.12 | 0 | 61 | 0 |
| Kidney Malignant | Kidney | MALIGNANT | Kidney::MAL... | | 5.70 | 5.24 | 3 | 88 | 0 |
| Kidney Benign | Kidney | BENIGN | Kidney::BEN... | | 4.94 | 0.12 | 0 | 15 | 0 |
| Endometrium Malignant | Endometrium | MALIGNANT | Endometrium... | | 11.76 | 22.09 | 5 | 52 | 0 |
| Endometrium Benign | Endometrium | BENIGN | Endometrium... | | 16.09 | 23.46 | 3 | 7 | 0 |
| Colon Normal | Colon | NORMAL | Ascending c... | | 4.92 | 0.39 | 0 | 74 | 0 |
| Colon Malignant | Colon | MALIGNANT | Colon::MALI... | | 4.93 | 0.85 | 1 | 140 | 0 |
| Ovary Malignant | Ovary | MALIGNANT | Ovary::MALI... | | 33.80 | 85.09 | 32 | 105 | 1 |
| Ovary Normal | Ovary | NORMAL | Ovary::NORM... | | 5.61 | 1.28 | 0 | 7 | 0 |
| Lung Normal | Lung | NORMAL | Lung::NORMA... | | 5.33 | 0.95 | 1 | 63 | 0 |
| Ovary Benign | Ovary | BENIGN | Ovary:::BENI... | | 20.32 | 38.55 | 5 | 30 | 0 |
| Lung Malignant | Lung | MALIGNANT | Lung::MALIG... | | 4.94 | 0.73 | 0 | 124 | 0 |
| Lung Benign | Lung | BENIGN | Lung::BENIG... | | 4.80 | 0.08 | 0 | 5 | 0 |
| Liver Diseased | Liver | DISEASED | Liver::DISE... | | 4.89 | 0.22 | 0 | 22 | 0 |
| Liver Malignant | Liver | MALIGNANT | Liver::MALI... | | 4.92 | 0.15 | 0 | 25 | 0 |
| Liver Normal | Liver | NORMAL | Liver::NORM... | | 4.95 | 0.13 | 0 | 6 | 0 |
| Prostate Malignant | Prostate | MALIGNANT | Prostate::M... | | 5.00 | 0.69 | 0 | 73 | 0 |
| Prostate Normal | Prostate | NORMAL | Prostate::N... | | 6.03 | 6.23 | 0 | 32 | 0 |
| Pancreas Normal | Pancreas | NORMAL | Pancreas::N... | | 4.99 | 0.11 | 0 | 13 | 0 |
| Prostate Diseased | Prostate | DISEASED | Prostate::D... | | 5.97 | 2.20 | 2 | 18 | 0 |
| Pancreas Benign | Pancreas | BENIGN | Pancreas::B... | | 4.93 | 0.13 | 0 | 5 | 0 |
| Pancreas Malignant | Pancreas | MALIGNANT | Pancreas::M... | | 4.79 | 0.11 | 0 | 66 | 0 |

Figure 1

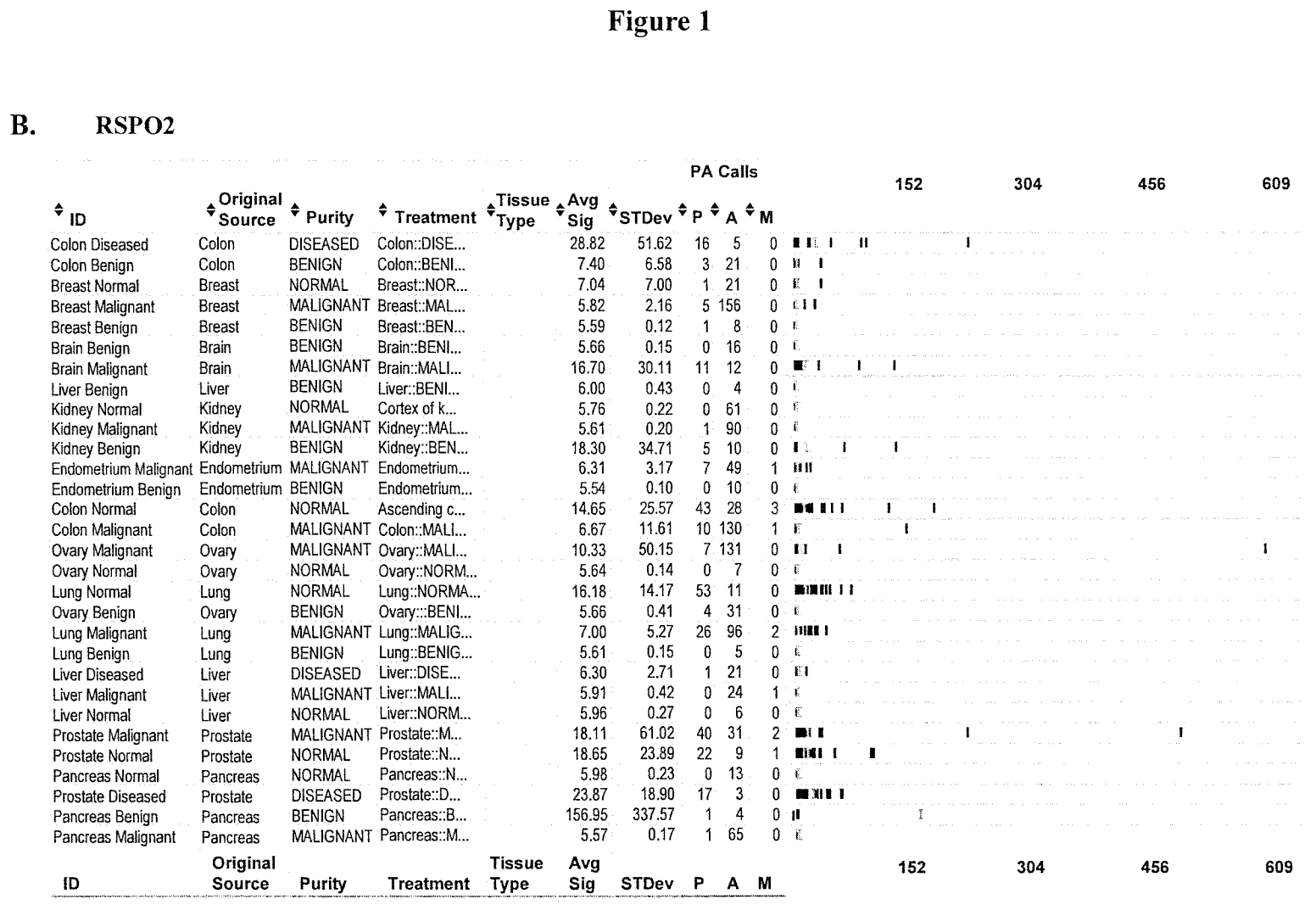

B. RSPO2

| ID | Original Source | Purity | Treatment | Tissue Type | Avg Sig | STDev | P | A | M |
|---|---|---|---|---|---|---|---|---|---|
| Colon Diseased | Colon | DISEASED | Colon::DISE... | | 28.82 | 51.62 | 16 | 5 | 0 |
| Colon Benign | Colon | BENIGN | Colon::BENI... | | 7.40 | 6.58 | 3 | 21 | 0 |
| Breast Normal | Breast | NORMAL | Breast::NOR... | | 7.04 | 7.00 | 1 | 21 | 0 |
| Breast Malignant | Breast | MALIGNANT | Breast::MAL... | | 5.82 | 2.16 | 5 | 156 | 0 |
| Breast Benign | Breast | BENIGN | Breast::BEN... | | 5.59 | 0.12 | 1 | 8 | 0 |
| Brain Benign | Brain | BENIGN | Brain::BENI... | | 5.66 | 0.15 | 0 | 16 | 0 |
| Brain Malignant | Brain | MALIGNANT | Brain::MALI... | | 16.70 | 30.11 | 11 | 12 | 0 |
| Liver Benign | Liver | BENIGN | Liver::BENI... | | 6.00 | 0.43 | 0 | 4 | 0 |
| Kidney Normal | Kidney | NORMAL | Cortex of k... | | 5.76 | 0.22 | 0 | 61 | 0 |
| Kidney Malignant | Kidney | MALIGNANT | Kidney::MAL... | | 5.61 | 0.20 | 1 | 90 | 0 |
| Kidney Benign | Kidney | BENIGN | Kidney::BEN... | | 18.30 | 34.71 | 5 | 10 | 0 |
| Endometrium Malignant | Endometrium | MALIGNANT | Endometrium... | | 6.31 | 3.17 | 7 | 49 | 1 |
| Endometrium Benign | Endometrium | BENIGN | Endometrium... | | 5.54 | 0.10 | 0 | 10 | 0 |
| Colon Normal | Colon | NORMAL | Ascending c... | | 14.65 | 25.57 | 43 | 28 | 3 |
| Colon Malignant | Colon | MALIGNANT | Colon::MALI... | | 6.67 | 11.61 | 10 | 130 | 1 |
| Ovary Malignant | Ovary | MALIGNANT | Ovary::MALI... | | 10.33 | 50.15 | 7 | 131 | 0 |
| Ovary Normal | Ovary | NORMAL | Ovary::NORM... | | 5.64 | 0.14 | 0 | 7 | 0 |
| Lung Normal | Lung | NORMAL | Lung::NORMA... | | 16.18 | 14.17 | 53 | 11 | 0 |
| Ovary Benign | Ovary | BENIGN | Ovary:::BENI... | | 5.66 | 0.41 | 4 | 31 | 0 |
| Lung Malignant | Lung | MALIGNANT | Lung::MALIG... | | 7.00 | 5.27 | 26 | 96 | 2 |
| Lung Benign | Lung | BENIGN | Lung::BENIG... | | 5.61 | 0.15 | 0 | 5 | 0 |
| Liver Diseased | Liver | DISEASED | Liver::DISE... | | 6.30 | 2.71 | 1 | 21 | 0 |
| Liver Malignant | Liver | MALIGNANT | Liver::MALI... | | 5.91 | 0.42 | 0 | 24 | 1 |
| Liver Normal | Liver | NORMAL | Liver::NORM... | | 5.96 | 0.27 | 0 | 6 | 0 |
| Prostate Malignant | Prostate | MALIGNANT | Prostate::M... | | 18.11 | 61.02 | 40 | 31 | 2 |
| Prostate Normal | Prostate | NORMAL | Prostate::N... | | 18.65 | 23.89 | 22 | 9 | 1 |
| Pancreas Normal | Pancreas | NORMAL | Pancreas::N... | | 5.98 | 0.23 | 0 | 13 | 0 |
| Prostate Diseased | Prostate | DISEASED | Prostate::D... | | 23.87 | 18.90 | 17 | 3 | 0 |
| Pancreas Benign | Pancreas | BENIGN | Pancreas::B... | | 156.95 | 337.57 | 1 | 4 | 0 |
| Pancreas Malignant | Pancreas | MALIGNANT | Pancreas::M... | | 5.57 | 0.17 | 1 | 65 | 0 |
| ID | Original Source | Purity | Treatment | Tissue Type | Avg Sig | STDev | P | A | M |

Figure 1

C. RSPO3

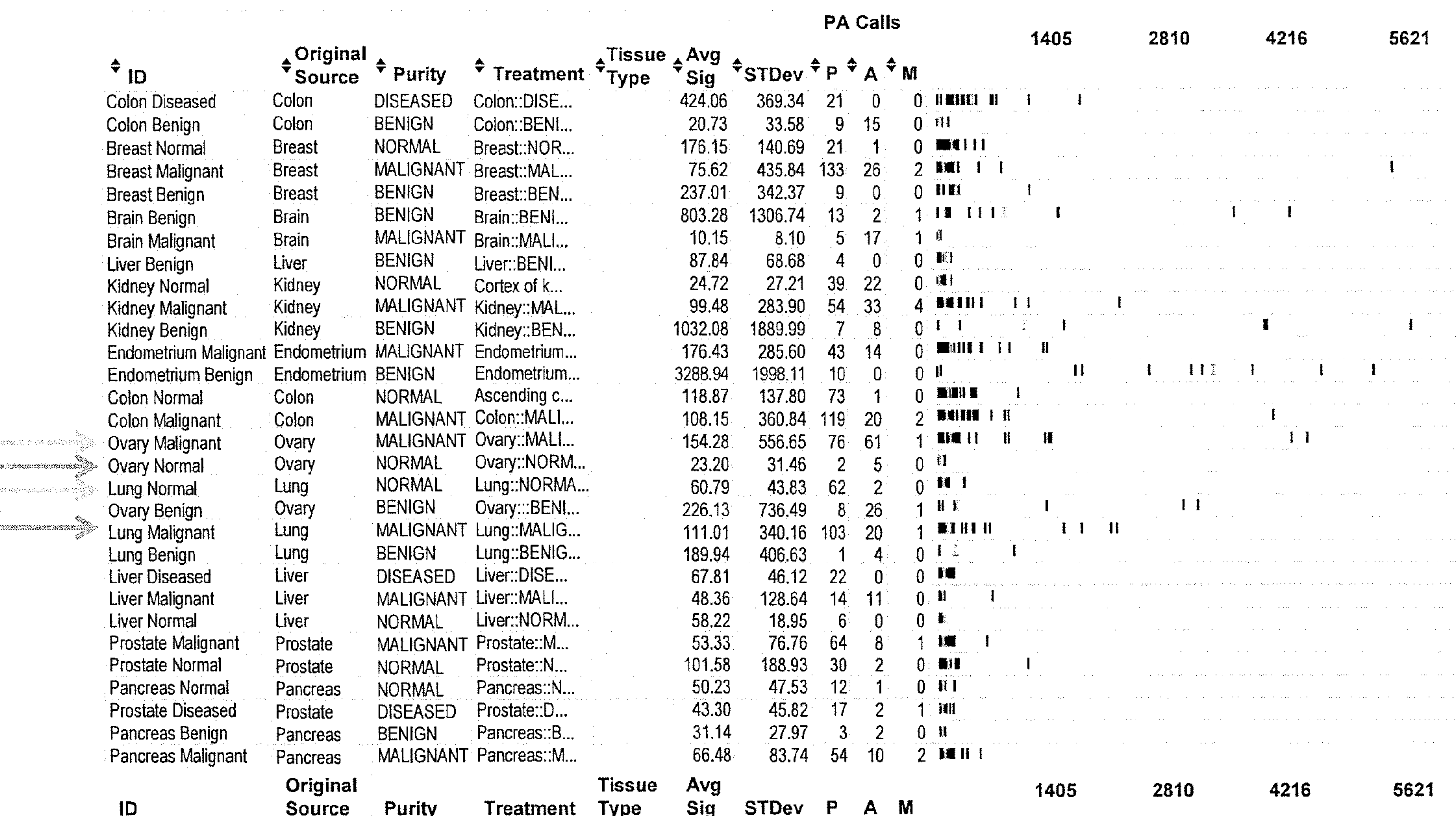

| ID | Original Source | Purity | Treatment | Tissue Type | Avg Sig | STDev | P | A | M |
|---|---|---|---|---|---|---|---|---|---|
| Colon Diseased | Colon | DISEASED | Colon::DISE... | | 424.06 | 369.34 | 21 | 0 | 0 |
| Colon Benign | Colon | BENIGN | Colon::BENI... | | 20.73 | 33.58 | 9 | 15 | 0 |
| Breast Normal | Breast | NORMAL | Breast::NOR... | | 176.15 | 140.69 | 21 | 1 | 0 |
| Breast Malignant | Breast | MALIGNANT | Breast::MAL... | | 75.62 | 435.84 | 133 | 26 | 2 |
| Breast Benign | Breast | BENIGN | Breast::BEN... | | 237.01 | 342.37 | 9 | 0 | 0 |
| Brain Benign | Brain | BENIGN | Brain::BENI... | | 803.28 | 1306.74 | 13 | 2 | 1 |
| Brain Malignant | Brain | MALIGNANT | Brain::MALI... | | 10.15 | 8.10 | 5 | 17 | 1 |
| Liver Benign | Liver | BENIGN | Liver::BENI... | | 87.84 | 68.68 | 4 | 0 | 0 |
| Kidney Normal | Kidney | NORMAL | Cortex of k... | | 24.72 | 27.21 | 39 | 22 | 0 |
| Kidney Malignant | Kidney | MALIGNANT | Kidney::MAL... | | 99.48 | 283.90 | 54 | 33 | 4 |
| Kidney Benign | Kidney | BENIGN | Kidney::BEN... | | 1032.08 | 1889.99 | 7 | 8 | 0 |
| Endometrium Malignant | Endometrium | MALIGNANT | Endometrium... | | 176.43 | 285.60 | 43 | 14 | 0 |
| Endometrium Benign | Endometrium | BENIGN | Endometrium... | | 3288.94 | 1998.11 | 10 | 0 | 0 |
| Colon Normal | Colon | NORMAL | Ascending c... | | 118.87 | 137.80 | 73 | 1 | 0 |
| Colon Malignant | Colon | MALIGNANT | Colon::MALI... | | 108.15 | 360.84 | 119 | 20 | 2 |
| Ovary Malignant | Ovary | MALIGNANT | Ovary::MALI... | | 154.28 | 556.65 | 76 | 61 | 1 |
| Ovary Normal | Ovary | NORMAL | Ovary::NORM... | | 23.20 | 31.46 | 2 | 5 | 0 |
| Lung Normal | Lung | NORMAL | Lung::NORMA... | | 60.79 | 43.83 | 62 | 2 | 0 |
| Ovary Benign | Ovary | BENIGN | Ovary:::BENI... | | 226.13 | 736.49 | 8 | 26 | 1 |
| Lung Malignant | Lung | MALIGNANT | Lung::MALIG... | | 111.01 | 340.16 | 103 | 20 | 1 |
| Lung Benign | Lung | BENIGN | Lung::BENIG... | | 189.94 | 406.63 | 1 | 4 | 0 |
| Liver Diseased | Liver | DISEASED | Liver::DISE... | | 67.81 | 46.12 | 22 | 0 | 0 |
| Liver Malignant | Liver | MALIGNANT | Liver::MALI... | | 48.36 | 128.64 | 14 | 11 | 0 |
| Liver Normal | Liver | NORMAL | Liver::NORM... | | 58.22 | 18.95 | 6 | 0 | 0 |
| Prostate Malignant | Prostate | MALIGNANT | Prostate::M... | | 53.33 | 76.76 | 64 | 8 | 1 |
| Prostate Normal | Prostate | NORMAL | Prostate::N... | | 101.58 | 188.93 | 30 | 2 | 0 |
| Pancreas Normal | Pancreas | NORMAL | Pancreas::N... | | 50.23 | 47.53 | 12 | 1 | 0 |
| Prostate Diseased | Prostate | DISEASED | Prostate::D... | | 43.30 | 45.82 | 17 | 2 | 1 |
| Pancreas Benign | Pancreas | BENIGN | Pancreas::B... | | 31.14 | 27.97 | 3 | 2 | 0 |
| Pancreas Malignant | Pancreas | MALIGNANT | Pancreas::M... | | 66.48 | 83.74 | 54 | 10 | 2 |

C.
Tumor Volume mm3
400
300
200
100
0
Control
18R5
130M23
18R5 + 130M23
Gemcitabine
18R5 + Gemcitabine
FZD8-Fc + Gemcitabine
130M23 + Gemcitabine
18R5 + 130M23 + Gemcitabine
FZD8-Fc + 130M23 + Gemcitabine

ANTI-RSPO2 ANTIBODIES

CROSS-REFERENCE TO RELATED APPLICATIONS

This application is a divisional of U.S. Non-Provisional application Ser. No. 13/549,050, filed Jul. 13, 2012, which claims the priority benefit of U.S. Provisional Application No. 61/508,403, filed Jul. 15, 2011, U.S. Provisional Application No. 61/521,547, filed Aug. 9, 2011, and U.S. Provisional Application No. 61/570,629, filed Dec. 14, 2011, each of which is hereby incorporated by reference herein in its entirety.

FIELD OF THE INVENTION

The field of this invention generally relates to antibodies and other agents that bind R-Spondin proteins (RSPO), particularly human R-Spondin proteins including RSPO1, RSPO2 and RSPO3, as well as to methods of using the antibodies or other agents for the treatment of diseases such as cancer.

BACKGROUND OF THE INVENTION

The R-Spondin (RSPO) family of proteins is conserved among vertebrates and comprises four members, RSPO1, RSPO2, RSPO3 and RSPO4. These proteins have been referred to by a variety of names, including roof plate-specific spondins, hPWTSR (hRSPO3), THS2D (RSPO3), Cristin 1-4, and Futrin 1-4. The RSPOs are small secreted proteins that overall share approximately 40-60% sequence homology and domain organization. All RSPO proteins contain two furin-like cysteine-rich domains at the N-terminus followed by a thrombospondin domain and a basic charged C-terminal tail (Kim et al., 2006, *Cell Cycle,* 5:23-26).

Studies have shown that RSPO proteins have a role during vertebrate development (Kamata et al., 2004, *Biochim. Biophys Acta,* 1676:51-62) and in *Xenopus* myogenesis (Kazanskaya et al., 2004, *Dev. Cell,* 7:525-534). RSPO1 has also been shown to function as a potent mitogen for gastrointestinal epithelial cells (Kim et al., 2005, *Science,* 309:1256-1259). RSPO proteins are known to activate 3-catenin signaling similar to Wnt signaling, however the relationship between RSPO proteins and Wnt signaling is still being investigated. It has been reported that RSPO proteins possess a positive modulatory activity on Wnt ligands (Nam et al., 2006, *JBC* 281:13247-57). This study also reported that RSPO proteins could function as Frizzled8 and LRP6 receptor ligands and induce β-catenin signaling (Nam et al., 2006, *JBC* 281:13247-57). Recent studies have identified an interaction between RSPO proteins and LGR (leucine-rich repeat containing, G protein-coupler receptor) proteins, such as LGR5 (U.S. Patent Publication Nos. 2009/0074782 and 2009/0191205), and these data present an alternative pathway for the activation of β-catenin signaling.

The Wnt signaling pathway has been identified as a potential target for cancer therapy. The Wnt signaling pathway is one of several critical regulators of embryonic pattern formation, post-embryonic tissue maintenance, and stem cell biology. More specifically, Wnt signaling plays an important role in the generation of cell polarity and cell fate specification including self-renewal by stem cell populations. Unregulated activation of the Wnt pathway is associated with numerous human cancers where it is believed the activation can alter the developmental fate of cells. The activation of the Wnt pathway may maintain tumor cells in an undifferentiated state and/or lead to uncontrolled proliferation. Thus carcinogenesis can proceed by overtaking homeostatic mechanisms which control normal development and tissue repair (reviewed in Reya & Clevers, 2005, *Nature,* 434:843-50; Beachy et al., 2004, *Nature,* 432:324-31).

The Wnt signaling pathway was first elucidated in the *Drosophila* developmental mutant wingless (wg) and from the murine proto-oncogene int-1, now Wnt1 (Nusse & Varmus, 1982, *Cell,* 31:99-109; Van Ooyen & Nusse, 1984, *Cell,* 39:233-40; Cabrera et al., 1987, *Cell,* 50:659-63; Rijsewijk et al., 1987, *Cell,* 50:649-57). Wrt genes encode secreted lipid-modified glycoproteins of which 19 have been identified in mammals. These secreted ligands activate a receptor complex consisting of a Frizzled (FZD) receptor family member and low-density lipoprotein (LDL) receptor-related protein 5 or 6 (LRP5/6). The FZD receptors are seven transmembrane domain proteins of the G-protein coupled receptor (GPCR) superfamily and contain a large extracellular N-terminal ligand binding domain with 10 conserved cysteines, known as a cysteine-rich domain (CRD) or Fri domain. There are ten human FZD receptors, FZD1, FZD2, FZD3, FZD4, FZD5, FZD6, FZD7, FZD8, FZD9, and FZD10. Different FZD CRDs have different binding affinities for specific Wnt proteins (Wu & Nusse, 2002, *J. Biol. Chem.,* 277:41762-9), and FZD receptors have been grouped into those that activate the canonical β-catenin pathway and those that activate non-canonical pathways (Miller et al., 1999, *Oncogene,* 18:7860-72).

A role for Wnt signaling in cancer was first uncovered with the identification of Wnt1 (originally int1) as an oncogene in mammary tumors transformed by the nearby insertion of a murine virus (Nusse & Varmus, 1982, *Cell,* 31:99-109). Additional evidence for the role of Wnt signaling in breast cancer has since accumulated. For instance, transgenic over-expression of 1-catenin in the mammary glands results in hyperplasias and adenocarcinomas (Imbert et al., 2001, *J. Cell Biol.,* 153:555-68; Michaelson & Leder, 2001, *Oncogene,* 20:5093-9) whereas loss of Wnt signaling disrupts normal mammary gland development (Tepera et al., 2003, *J. Cell Sci.,* 116: 1137-49; Hatsell et al., 2003, *J. Mammary Gland Biol. Neoplasia,* 8:145-58). In human breast cancer, β-catenin accumulation implicates activated Wnt signaling in over 50% of carcinomas, and though specific mutations have not been identified, up-regulation of Frizzled receptor expression has been observed (Brennan & Brown, 2004, *J. Mammary Gland Biol. Neoplasia,* 9:119-31; Malovanovic et al., 2004, *Int. J. Oncol.,* 25:1337-42).

Activation of the Wnt pathway is also associated with colorectal cancer. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Mutations have also been identified in other Wnt pathway components including Axin and β-catenin. Individual adenomas are clonal outgrowths of epithelial cells containing a second inactivated allele, and the large number of FAP adenomas inevitably results in the development of adenocarcinomas through additional mutations in oncogenes and/or tumor suppressor genes. Furthermore, activation of the Wnt signaling pathway, including loss-of-function mutations in APC and stabilizing mutations in β-catenin, can induce hyperplastic development and tumor growth in mouse models (Oshima et al., 1997, *Cancer Res.,* 57:1644-9; Harada et al., 1999, *EMBO J.,* 18:5931-42).

Similar to breast cancer and colon cancer, melanoma often has constitutive activation of the Wnt pathway, as indicated by the nuclear accumulation of β-catenin. Activation of the Wnt/β-catenin pathway in some melanoma tumors and cell lines is due to modifications in pathway components, such as APC, ICAT, LEF1 and β-catenin (see e.g., Larue et al. 2006, *Frontiers Biosci.,* 11:733-742). However, there are conflicting reports in the literature as to the exact role of Wnt/β-catenin signaling in melanoma. For example, one study found that elevated levels of nuclear β-catenin correlated with improved survival from melanoma, and that activated Wnt/β-catenin signaling was associated with decreased cell proliferation (Chien et al., 2009, *PNAS,* 106:1193-1198).

The focus of cancer drug research is shifting toward targeted therapies aimed at genes, proteins, and pathways involved in human cancer. There is a need for new agents targeting signaling pathways and new combinations of agents that target multiple pathways that could provide therapeutic benefit for cancer patients. Thus, biomolecules (e.g., anti-RSPO antibodies) that disrupt β-catenin signaling are a potential source of new therapeutic agents for cancer, as well as other β-catenin-associated diseases.

BRIEF SUMMARY OF THE INVENTION

The present invention provides binding agents, such as antibodies, that bind RSPO proteins, as well as compositions, such as pharmaceutical compositions, comprising the binding agents. In certain embodiments, the RSPO-binding agents are novel polypeptides, such as antibodies, antibody fragments, and other polypeptides related to such antibodies. In certain embodiments, the binding agents are antibodies that specifically bind human RSPO1, RSPO2, and/or RSPO3. The invention further provides methods of inhibiting the growth of a tumor by administering the RSPO-binding agents to a subject with a tumor. The invention further provides methods of treating cancer by administering the RSPO-binding agents to a subject in need thereof. In some embodiments, the methods of treating cancer or inhibiting tumor growth comprise targeting cancer stem cells with the RSPO-binding agents. In certain embodiments, the methods comprise reducing the frequency of cancer stem cells in a tumor, reducing the number of cancer stem cells in a tumor, reducing the tumorigenicity of a tumor, and/or reducing the tumorigenicity of a tumor by reducing the number or frequency of cancer stem cells in the tumor.

In one aspect, the invention provides a binding agent, such as an antibody, that specifically binds human RSPO1. In certain embodiments, the RSPO1-binding agent binds within amino acids 21-263 of human RSPO1. In certain embodiments, the RSPO1-binding agent binds within amino acids 34-135 of human RSPO1. In certain embodiments, the RSPO1-binding agent binds within amino acids 91-135 of human RSPO1. In some embodiments, the RSPO1-binding agent (e.g., an antibody) specifically binds at least one other human RSPO selected from the group consisting of RSPO2, RSPO3, and RSPO4. In some embodiments, the RSPO1-binding agent or antibody modulates β-catenin activity, is an antagonist of β-catenin signaling, inhibits β-catenin signaling, and/or inhibits activation of β-catenin. In some embodiments, the RSPO1-binding agent inhibits RSPO1 signaling. In some embodiments, the RSPO1-binding agent inhibits or interferes with binding of RSPO1 to one or more LGR protein (e.g., LGR4, LGR5, and/or LGR6). In some embodiments, the RSPO1-binding agent inhibits binding of RSPO1 to LGR5.

In another aspect, the invention provides a binding agent, such as an antibody, that specifically binds human RSPO2. In certain embodiments, the RSPO2-binding agent binds within amino acids 22-243 of human RSPO2. In certain embodiments, the RSPO2-binding agent binds within amino acids 22-205 of human RSPO2. In certain embodiments, the RSPO2-binding agent binds within amino acids 34-134 of human RSPO2. In certain embodiments, the RSPO2-binding agent binds within amino acids 90-134 of human RSPO2. In some embodiments, the RSPO2-binding agent (e.g., an antibody) specifically binds at least one other human RSPO selected from the group consisting of RSPO1, RSPO3, and RSPO4. In some embodiments, the RSPO2-binding agent or antibody modulates β-catenin activity, is an antagonist of β-catenin signaling, inhibits β-catenin signaling, and/or inhibits activation of β-catenin. In some embodiments, the RSPO2-binding agent inhibits RSPO2 signaling. In some embodiments, the RSPO2-binding agent inhibits or interferes with binding of RSPO2 to one or more LGR protein (e.g., LGR4, LGR5, and/or LGR6). In some embodiments, the RSPO2-binding agent inhibits binding of RSPO2 to LGR5.

In certain embodiments of each of the aforementioned aspects and embodiments, as well as other aspects and embodiments described herein, the RSPO-binding agent is an antibody. In certain embodiments, the antibody is a monoclonal antibody. In certain embodiments, the antibody is a humanized antibody. In certain embodiments, the antibody binds human RSPO1. In certain embodiments, the antibody binds human RSPO1 and mouse RSPO1. In certain embodiments, the antibody binds human RSPO1 with a $K_D$ of less than 1 nM and mouse RSPO1 with a $K_D$ of less than nM.

In certain embodiments, the RSPO1-binding agent is an antibody which comprises a heavy chain CDR1 comprising TGYTMH (SEQ ID NO: 12), a heavy chain CDR2 comprising GINPNNGGTTYNQNFKG (SEQ ID NO: 13), and a heavy chain CDR3 comprising KEFSDGYYFFAY (SEQ ID NO: 14). In some embodiments, the antibody further comprises a light chain CDR1 comprising KASQDVIFAVA (SEQ ID NO: 15), a light chain CDR2 comprising WASTRHT (SEQ ID NO: 16), and a light chain CDR3 comprising QQHYSTPW (SEQ ID NO:17). In certain embodiments, the RSPO1-binding agent is an antibody which comprises a light chain CDR1 comprising KASQDVIFAVA (SEQ ID NO: 15), a light chain CDR2 comprising WASTRHT (SEQ ID NO: 16), and a light chain CDR3 comprising QQHYSTPW (SEQ ID NO:17). In certain embodiments, the RSPO1-binding agent is an antibody which comprises: (a) a heavy chain CDR1 comprising TGYTMH (SEQ ID NO: 12), or a variant thereof comprising 1, 2, 3, or 4 amino acid substitutions; (b) a heavy chain CDR2 comprising GINPNNGGTTYNQNFKG (SEQ ID NO: 13), or a variant thereof comprising 1, 2, 3, or 4 amino acid substitutions; (c) a heavy chain CDR3 comprising KEFSDGYYFFAY (SEQ ID NO: 14), or a variant thereof comprising 1, 2, 3, or 4 amino acid substitutions; (d) a light chain CDR1 comprising KASQDVIFAVA (SEQ ID NO: 15), or a variant thereof comprising 1, 2, 3, or 4 amino acid substitutions; (e) a light chain CDR2 comprising WASTRHT (SEQ ID NO:16), or a variant thereof comprising 1, 2, 3, or 4 amino acid substitutions; and (f) a light chain CDR3 comprising QQHYSTPW (SEQ ID NO: 17), or a variant thereof comprising 1, 2, 3, or 4 amino acid substitutions. In some embodiments, the amino acid substitutions are conservative amino acid substitutions.

In certain embodiments, the RSPO1-binding agent is an antibody which comprises: (a) a heavy chain variable region having at least 80% sequence identity to SEQ ID NO: 10; and/or (b) a light chain variable region having at least 80% sequence identity to SEQ ID NO: 11. In certain embodiments, the RSPO1-binding agent is an antibody that comprises: (a) a heavy chain variable region having at least 90% sequence identity to SEQ ID NO:10; and/or (b) a light chain variable region having at least 90% sequence identity to SEQ ID NO: 11.

In certain embodiments, the RSPO1-binding agent is an antibody which comprises: (a) a heavy chain variable region having at least 80% sequence identity to SEQ ID NO:55; and/or (b) a light chain variable region having at least 80% sequence identity to SEQ ID NO:59. In certain embodiments, the RSPO1-binding agent is an antibody that comprises: (a) a heavy chain variable region having at least 90% sequence identity to SEQ ID NO:55; and/or (b) a light chain variable region having at least 90% sequence identity to SEQ ID NO:59.

In some embodiments, the RSPO1-binding agent is monoclonal antibody 89M5 and is produced by the hybridoma cell line 89M5 deposited on Jun. 30, 2011 with ATCC having deposit no. PTA-11970. In some embodiments, the RSPO1-binding agent is a humanized form of antibody 89M5. In some embodiments, the RSPO1-binding agent is humanized monoclonal antibody h89M5-H2L2.

In certain embodiments, the RSPO2-binding agent is an antibody which binds human RSPO2. In some embodiments, the antibody binds human RSPO2 and mouse RSPO2. In certain embodiments, the antibody comprises a heavy chain CDR1 comprising SSYAMS (SEQ ID NO:29), a heavy chain CDR2 comprising SISSGGSTYYPDSVKG (SEQ ID NO:30), and a heavy chain CDR3 comprising RGGDPGVYNGDYEDAMDY (SEQ ID NO:31). In some embodiments, the antibody further comprises a light chain CDR1 comprising KASQDVSSAVA (SEQ ID NO:32), a light chain CDR2 comprising WASTRHT (SEQ ID NO:33), and a light chain CDR3 comprising QQHYSTP (SEQ ID NO:34). In certain embodiments, the RSPO2-binding agent is an antibody which comprises a light chain CDR1 comprising KASQDVSSAVA (SEQ ID NO:32), a light chain CDR2 comprising WASTRHT (SEQ ID NO:33), and a light chain CDR3 comprising QQHYSTP (SEQ ID NO:34). In certain embodiments, the RSPO2-binding agent is an antibody which comprises: (a) a heavy chain CDR1 comprising SSYAMS (SEQ ID NO:29), or a variant thereof comprising 1, 2, 3, or 4 amino acid substitutions; (b) a heavy chain CDR2 comprising SISSGGSTYYPDSVKG (SEQ ID NO:30), or a variant thereof comprising 1, 2, 3, or 4 amino acid substitutions; (c) a heavy chain CDR3 comprising RGGDPGVYNGDYEDAMDY (SEQ ID NO:31), or a variant thereof comprising 1, 2, 3, or 4 amino acid substitutions; (d) a light chain CDR1 comprising KASQDVSSAVA (SEQ ID NO:32), or a variant thereof comprising 1, 2, 3, or 4 amino acid substitutions; (e) a light chain CDR2 comprising WASTRHT (SEQ ID NO:33), or a variant thereof comprising 1, 2, 3, or 4 amino acid substitutions; and (f) a light chain CDR3 comprising QQHYSTP (SEQ ID NO:34), or a variant thereof comprising 1, 2, 3, or 4 amino acid substitutions. In some embodiments, the amino acid substitutions are conservative amino acid substitutions.

In certain embodiments, the RSPO2-binding agent is an antibody which comprises: (a) a heavy chain variable region having at least 80% sequence identity to SEQ ID NO:27; and/or (b) a light chain variable region having at least 80% sequence identity to SEQ ID NO:28. In certain embodiments, the RSPO2-binding agent is an antibody that comprises: (a) a heavy chain variable region having at least 90% sequence identity to SEQ ID NO:27; and/or (b) a light chain variable region having at least 90% sequence identity to SEQ ID NO:28.

In certain embodiments, the RSPO2-binding agent is an antibody which comprises: (a) a heavy chain variable region having at least 80% sequence identity to SEQ ID NO:63; and/or (b) a light chain variable region having at least 80% sequence identity to SEQ ID NO:67. In certain embodiments, the RSPO2-binding agent is an antibody that comprises: (a) a heavy chain variable region having at least 90% sequence identity to SEQ ID NO:63; and/or (b) a light chain variable region having at least 90% sequence identity to SEQ ID NO:67.

In certain embodiments, the RSPO2-binding agent is an antibody which comprises: (a) a heavy chain variable region having at least 80% sequence identity to SEQ ID NO:63; and/or (b) a light chain variable region having at least 80% sequence identity to SEQ ID NO:76. In certain embodiments, the RSPO2-binding agent is an antibody that comprises: (a) a heavy chain variable region having at least 90% sequence identity to SEQ ID NO:63; and/or (b) a light chain variable region having at least 90% sequence identity to SEQ ID NO:76.

In some embodiments, the RSPO2-binding agent is monoclonal antibody 130M23 and is produced by the hybridoma cell line 130M23 deposited on Aug. 10, 2011 with ATCC having deposit no. PTA-12021. In some embodiments, the RSPO2-binding agent is a humanized form of antibody 130M23. In some embodiments, the RSPO2-binding agent is humanized monoclonal antibody h130M23-H1L2. In some embodiments, the RSPO2-binding agent is humanized monoclonal antibody h130M23-H1L6.

In another aspect, the invention provides a binding agent (e.g., an antibody) that competes for specific binding to a human RSPO protein with an antibody of the invention. In some embodiments, the binding agent (e.g., an antibody) competes for specific binding to human RSPO1 with an antibody that comprises a heavy chain variable region comprising SEQ ID NO: 10, and a light chain variable region comprising SEQ ID NO:11. In some embodiments, the binding agent (e.g., an antibody) competes for specific binding to human RSPO1 with an antibody that comprises a heavy chain variable region comprising SEQ ID NO:55, and a light chain variable region comprising SEQ ID NO:59. In some embodiments, the antibody with which the RSPO1-binding agent competes is 89M5 or h89M5-H2L2. In some embodiments, the binding agent competes for specific binding to RSPO1 with an antibody of the invention in an in vitro competitive binding assay.

In certain embodiments, the antibody binds the same epitope, or essentially the same epitope, on RSPO1 as an antibody of the invention (e.g., 89M5).

In still another aspect, the binding agent is an antibody that binds an epitope on RSPO1 that overlaps with the epitope on RSPO1 bound by an antibody of the invention (e.g., 89M5).

In another aspect, the invention provides a binding agent (e.g., an antibody) that competes for specific binding to human RSPO2 with an antibody of the invention. In some embodiments, the binding agent (e.g., an antibody) competes for specific binding to human RSPO2 with an antibody that comprises a heavy chain variable region comprising SEQ ID NO:27, and a light chain variable region comprising SEQ ID NO:28. In some embodiments, the binding agent (e.g., an antibody) competes for specific binding to human RSPO2 with an antibody that comprises a heavy chain variable region comprising SEQ ID NO:63, and a light chain variable region comprising SEQ ID NO:67. In some embodiments, the binding agent (e.g., an antibody) competes for specific binding to human RSPO2 with an antibody that comprises a heavy chain variable region comprising SEQ ID NO:63, and a light chain variable region comprising SEQ ID NO:76. In some embodiments, the antibody with which the RSPO2-binding agent competes is 130M23, h130M23-H1L2, or h130M23-H1L6. In some embodiments, the binding agent competes for specific binding to RSPO2 with an antibody of the invention in an in vitro competitive binding assay.

In certain embodiments, the antibody binds the same epitope, or essentially the same epitope, on RSPO2 as an antibody of the invention (e.g., 130M23).

In still another aspect, the binding agent is an antibody that binds an epitope on RSPO2 that overlaps with the epitope on RSPO2 bound by an antibody of the invention (e.g., 130M23).

In certain embodiments of each of the aforementioned aspects, as well as other aspects and/or embodiments described elsewhere herein, the RSPO-binding agent or antibody is isolated.

In another aspect, the invention provides a polypeptide comprising SEQ ID NO: 10 and/or SEQ ID NO: 1. In another aspect, the invention provides a polypeptide comprising SEQ ID NO: 55 and/or SEQ ID NO:59. In another aspect, the invention provides a polypeptide comprising SEQ ID NO:27 and/or SEQ ID NO:28. In another aspect, the invention provides a polypeptide comprising SEQ ID NO:63 and/or SEQ ID NO:67. In another aspect, the invention provides a polypeptide comprising SEQ ID NO:63 and/or SEQ ID NO:76. In some embodiments, a polypeptide that binds RSPO1 comprises a polypeptide comprising SEQ ID NO:25 and/or SEQ ID NO:26. In some embodiments, a polypeptide that binds RSPO1 comprises a polypeptide comprising SEQ ID NO:68 and/or SEQ ID NO:69. In some embodiments, a polypeptide that binds RSPO2 comprises a polypeptide comprising SEQ ID NO:41 and/or SEQ ID NO:42. In some embodiments, a polypeptide that binds RSPO2 comprises a polypeptide comprising SEQ ID NO:70 and/or SEQ ID NO:71. In some embodiments, a polypeptide that binds RSPO2 comprises a polypeptide comprising SEQ ID NO:70 and/or SEQ ID NO:74. In some embodiments, the polypeptide is isolated. In certain embodiments, the polypeptide is substantially pure. In certain embodiments, the polypeptide is an antibody.

In another aspect, the invention provides isolated polynucleotide molecules comprising a polynucleotide that encodes the antibodies and/or polypeptides of each of the aforementioned aspects, as well as other aspects and/or embodiments described herein. In some embodiments, the polynucleotide comprises a sequence selected from the group consisting of SEQ ID NO: 19, SEQ ID NO:20, SEQ ID NO:23, SEQ ID NO:24, SEQ ID NO:52, SEQ ID NO:54, SEQ ID NO:56, and SEQ ID NO:58. In some embodiments, the polynucleotide comprises a sequence selected from the group consisting of SEQ ID NO:35, SEQ ID NO:36, SEQ ID NO:39, SEQ ID NO:40, SEQ ID NO:60, SEQ ID NO:62, SEQ ID NO:64, SEQ ID NO:66, SEQ ID NO:72, and SEQ ID NO:75. The invention further provides expression vectors that comprise the polynucleotides, as well as cells that comprise the expression vectors and/or the polynucleotides. In some embodiments, the cell is a hybridoma cell line. In certain embodiments, the cell is a hybridoma cell line having the ATCC deposit number PTA-11970. In certain embodiments, the cell is a hybridoma cell line having the ATCC deposit number PTA-12021.

In other aspects, the invention provides methods of inhibiting growth of a tumor, comprising contacting the tumor with an effective amount of a RSPO-binding agent or antibody, including each of those described herein.

In another aspect, the invention provides a method of inhibiting the growth of a tumor in a subject, comprising administering to the subject a therapeutically effective amount of a RSPO-binding agent or antibody, including each of those described herein.

In another aspect, the invention provides a method of inhibiting β-catenin signaling in a cell, comprising contacting the cell with an effective amount of a RSPO-binding agent or antibody, including each of those described herein. In some embodiments, the cell is a tumor cell. In some embodiments, the tumor is a colorectal tumor. In some embodiments, the tumor is an ovarian tumor. In some embodiments, the tumor is a pancreatic tumor. In some embodiments, the tumor is a lung tumor. In some embodiments, the tumor expresses elevated levels of at least one RSPO protein. In some embodiments, the tumor expresses elevated levels of RSPO1. In some embodiments, the tumor expresses elevated levels of RSPO2. In some embodiments, the tumor expresses elevated levels of RSPO3. In certain embodiments, the RSPO-binding agent inhibits growth of the tumor, for example, by reducing the number and/or frequency of cancer stem cells in the tumor.

In another aspect, the invention provides methods of treating cancer in a subject. In some embodiments, the method comprises administering to a subject a therapeutically effective amount of any of the RSPO-binding agents or antibodies described above, as well as those described elsewhere herein. In some embodiments, the cancer is pancreatic cancer. In some embodiments, the cancer is colorectal cancer. In some embodiments, the colorectal cancer comprises an inactivating mutation in the adenomatous polyposis coli (APC) gene. In some embodiments, the colorectal cancer does not comprise an inactivating mutation in the APC gene. In some embodiments, the colorectal cancer comprises a wild-type APC gene. In some embodiments, the cancer is ovarian cancer. In some embodiments, the cancer is breast cancer. In some embodiments, the cancer is lung cancer. In some embodiments, the cancer expresses elevated levels of at least one RSPO protein. In some embodiments, the cancer is an ovarian cancer that expresses elevated levels of RSPO1. In some embodiments, the cancer is colon cancer that expresses elevated levels of RSPO2. In some embodiments, the cancer is a pancreatic cancer that expresses elevated levels of RSPO2. In some embodiments, the cancer is a breast cancer that expresses elevated levels of RSPO2. In some embodiments, the cancer is a lung cancer that expresses elevated levels of RSPO2.

In another aspect, the invention provides methods of treating a disease in a subject wherein the disease is associated with activation of β-catenin, and/or aberrant β-catenin signaling comprising administering a therapeutically effective amount of a RSPO-binding agent or antibody, including each of those described herein.

In certain embodiments of each of the aforementioned aspects, as well as other aspects and/or embodiments described elsewhere herein, the treatment methods comprise administering a RSPO-binding agent in combination with at least one additional therapeutic agent. In some embodiments, the treatment methods comprise administering a RSPO1-binding agent in combination with a second RSPO-binding agent such as a RSPO2-binding agent, a RSPO3-binding agent, and/or a RSPO4-binding agent. In some embodiments, the treatment methods comprise administering a RSPO2-binding agent in combination with a second RSPO-binding agent such as a RSPO1-binding agent, a RSPO3-binding agent, and/or a RSPO4-binding agent. In some embodiments, the treatment methods comprise administering a RSPO1-binding agent in combination with a RSPO2-binding agent. In some embodiments, the treatment methods comprise administering a combination of a RSPO1-binding agent, a RSPO2-binding agent, and a chemotherapeutic agent.

In certain embodiments of each of the aforementioned aspects, as well as other aspects and/or embodiments described elsewhere herein, the treatment methods further comprise a step of determining the level of at least one RSPO protein expression in the tumor or cancer.

In another aspect, the invention provides a method of identifying a human subject or selecting a human subject for treatment with a RSPO-binding agent or antibody, including but not limited to, each of those described herein. In some embodiments, the method comprises determining if the subject has a tumor that has an elevated expression level of a specific RSPO (e.g., RSPO1 or RSPO2) as compared to the expression of the same RSPO protein in normal tissue. In some embodiments, the method comprises identifying a subject for treatment or selecting a subject for treatment if the tumor has an elevated level of RSPO expression. In some embodiments, the method comprises determining if the subject has a tumor that comprises an inactivating mutation in the APC gene. In some embodiments, the method comprises identifying a subject for treatment or selecting a subject for treatment if the tumor comprises an inactivating mutation in the APC gene.

Pharmaceutical compositions comprising a RSPO-binding agent or antibody described herein and a pharmaceutically acceptable carrier are further provided, as are cell lines that produce the RSPO-binding agents. Methods of treating cancer and/or inhibiting tumor growth in a subject (e.g., a human) comprising administering to the subject an effective amount of a composition comprising the RSPO-binding agents are also provided.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF THE FIGURES

FIG. 1. RSPO expression in tumors and normal tissues. Shown is a summary of microarray data from normal, benign, and malignant tissue human samples. Individual tick marks indicate the expression level of RSPO mRNA. A) RSPO1 B) RSPO2 C) RSPO3

DETAILED DESCRIPTION OF THE INVENTION

The present invention provides novel agents, including, but not limited to polypeptides such as antibodies, that bind RSPO proteins (e.g., human RSPO1, RSPO2, and/or RSPO3). The RSPO-binding agents include antagonists of β-catenin signaling. Related polypeptides and polynucleotides, compositions comprising the RSPO-binding agents, and methods of making the RSPO-binding agents are also provided. Methods of using the novel RSPO-binding agents, such as methods of inhibiting tumor growth, methods of treating cancer, methods of reducing the frequency of cancer stem cells in a tumor, methods of inhibiting β-catenin signaling, and/or methods of identifying and/or selecting subjects for treatment, are further provided.

Figure 5:
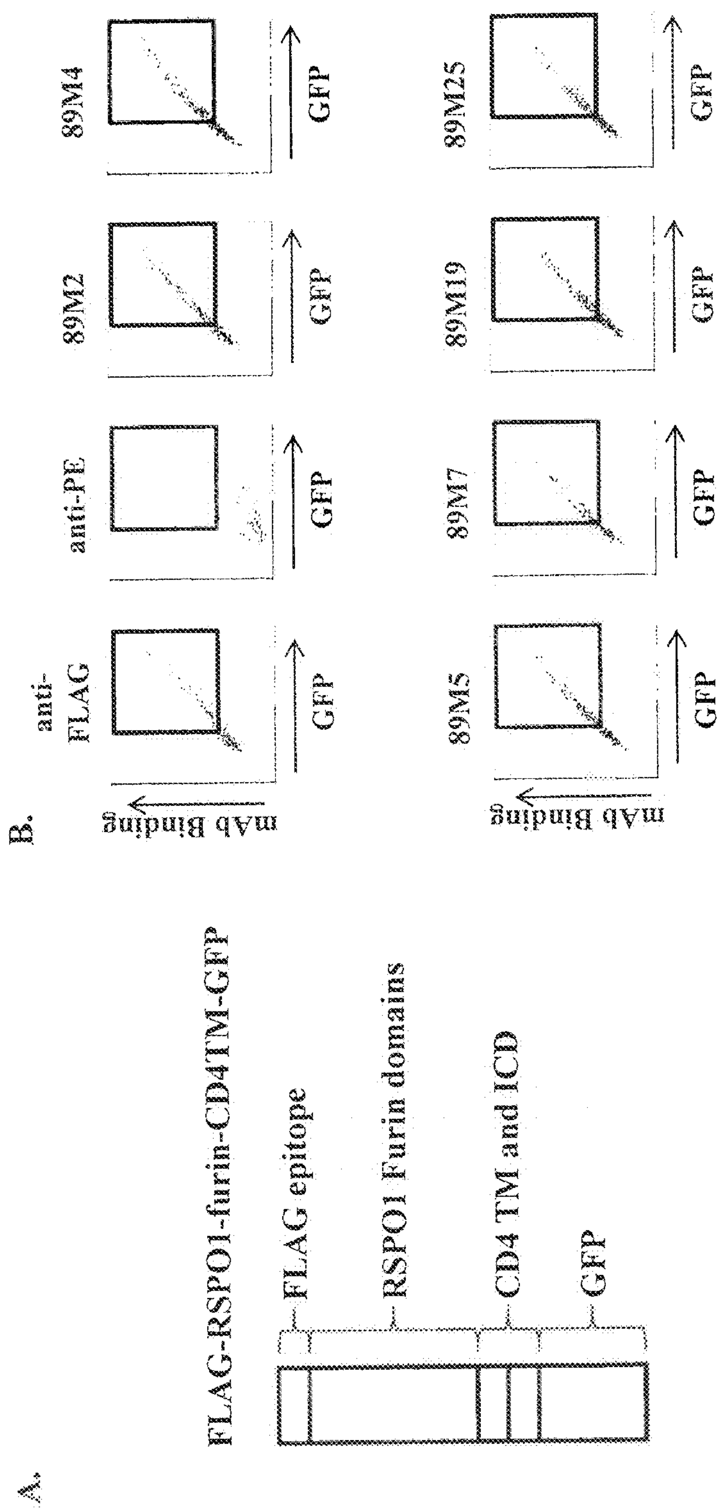
FIG. 5. Identification of antibodies that bind RSPO1. A) A diagram of the fusion protein FLAG-RSPO1furin-CD4TM-GFP. B) FACS analyses of antibodies generated to human RSPO1. Relative antibody binding is shown on the y-axis and expression of the FLAG-RSPO1 furin-CD4TM-GFP fusion protein is indicated on the x-axis. Positive binding is indicated by the presence of signal within the dark lined box overlay on each FACS plot. An anti-FLAG antibody was used as a positive control. An anti-PE antibody was used as a negative control.

Monoclonal antibodies that specifically bind human RSPO1 have been identified—monoclonal antibodies 89M2, 89M4, 89M5, 89M7, 89M19 and 89M25 (Example 5, FIG. 5). Anti-RSPO1 antibodies 89M2, 89M4, 89M5, and 89M25 inhibit β-catenin signaling (Example 6, FIG. 6). Anti-RSPO1 antibodies 89M2, 89M4, 89M5, and 89M25 block soluble RSPO1 binding to LGR5 (Example 7, FIG. 7). Sequence data subsequently demonstrated that antibodies 89M2, 89M4, 89M5, and 89M25 contain the same heavy chain and light chain variable regions, and it was concluded that these antibodies would comprise the same antigen-binding site. Anti-RSPO1 antibodies 89M4, 89M5, 89M7 and 89M25 have binding affinities for both human and mouse RSPO 1 of less than 0.1 nM (Example 8). A humanized version of 89M5 was produced, h89M5-H2L2 (Example 19) and has a binding affinity for human RSPO1 of less than 0.1 nM (Example 20). Anti-RSPO antibodies 89M5 and 89M25 have been found to inhibit tumor cell growth in vivo in an ovarian tumor xenograft model as single agents and in combination with a chemotherapeutic agent (Example 9, FIG. 8). Anti-RSPO1 antibody 89M5 has been shown to inhibit tumor cell growth in vivo in a pancreatic tumor xenograft model in combination with a chemotherapeutic agent (Example 17, FIG. 15). Preliminary epitope mapping studies suggest that amino acids within the furin2 domain of RSPO1 are involved in the binding site for anti-RSPO1 antibody 89M5 (Example 10, FIG. 9).

Figure 10:
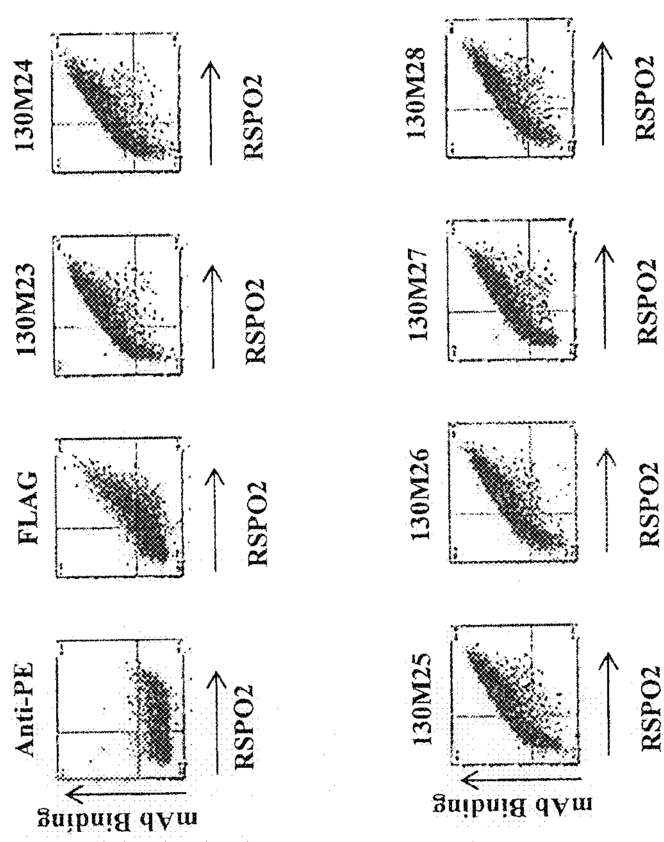
FIG. 10. Identification of antibodies that bind RSPO2. FACS analyses of antibodies generated to human RSPO2. Relative antibody binding is shown on the y-axis and expression of the FLAG-RSPO2furin-CD4TM-GFP fusion protein is indicated on the x-axis. An anti-FLAG antibody was used as a positive control. An anti-PE antibody was used as a negative control.

In addition, monoclonal antibodies that specifically bind human RSPO2 have been identified—monoclonal antibodies 130M23, 130M24, 130M25, 130M26, 130M27, and 130M28 (Example 11, FIG. 10). Anti-RSPO2 antibodies 130M23, 130M24, 130M25, 130M26, 130M27, and 130M28 were shown to reduce or completely block β-catenin signaling (Example 12, FIG. 11). Anti-RSPO2 antibodies 130M23 and 130M24 block soluble RSPO2 binding to LGR5 (Example 13, FIG. 12). Anti-RSPO2 antibody 130M23 has a binding affinity for human RSPO2 of 0.14 nM and mouse RSPO2 of 0.35 nM (Example 15). Humanized versions of 130M23 were produced, h130M23-H1L2 and h130M23-H1L6 (Example 19). Anti-RSPO2 antibody h130M23-H1L2 has a binding affinity for human RSPO2 of 0.13 nM and h130M23-H1L6 has a binding affinity for human RSPO2 of 0.15 nM (Example 20). Anti-RSPO2 antibody 130M23 has been shown to inhibit tumor cell growth in vivo in a pancreatic tumor xenograft model as a single agent and in combination with additional therapeutic agents (Examples 17 and 18, FIGS. 15 and 16).

I. Definitions

To facilitate an understanding of the present invention, a number of terms and phrases are defined below.

The terms "antagonist" and "antagonistic" as used herein refer to any molecule that partially or fully blocks, inhibits, reduces or neutralizes a biological activity of a target and/or signaling pathway (e.g., the β-catenin signaling). The term "antagonist" is used herein to include any molecule that partially or fully blocks, inhibits, reduces or neutralizes the activity of a protein (e.g., a RSPO protein). Suitable antagonist molecules specifically include, but are not limited to, antagonist antibodies or antibody fragments.

The terms "modulation" and "modulate" as used herein refer to a change or an alteration in a biological activity. Modulation includes, but is not limited to, stimulating or inhibiting an activity. Modulation may be an increase or a decrease in activity (e.g., a decrease in RSPO signaling; a decrease in β-catenin signaling), a change in binding characteristics, or any other change in the biological, functional, or immunological properties associated with the activity of a protein, pathway, or other biological point of interest.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) antibodies, multispecific antibodies such as bispecific antibodies generated from at least two intact antibodies, monospecific antibodies, monovalent antibodies, chimeric antibodies, humanized antibodies, human antibodies, fusion proteins comprising an antigen determination portion of an antibody, and any other modified immunoglobulin molecule comprising an antigen recognition site as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope binding site.

The term "variable region" of an antibody refers to the variable region of the antibody light chain, or the variable region of the antibody heavy chain, either alone or in combination. The variable regions of the heavy and light chain each consist of four framework regions (FR) connected by three complementarity determining regions (CDRs), also known as "hypervariable regions". The CDRs in each chain are held together in close proximity by the framework regions and, with the CDRs from the other chain, contribute to the formation of the antigen-binding sites of the antibody. There are at least two techniques for determining CDRs: (1) an approach based on cross-species sequence variability (i.e., Kabat et al., 1991, *Sequences of Proteins of Immunological Interest, 5th Edition*, National Institutes of Health, Bethesda Md.), and (2) an approach based on crystallographic studies of antigen-antibody complexes (Al-Lazikani et al., 1997, *J. Mol. Biol.,* 273:927-948). In addition, combinations of these two approaches are sometimes used in the art to determine CDRs.

The term "monoclonal antibody" as used herein refers to a homogenous antibody population involved in the highly specific recognition and binding of a single antigenic determinant or epitope. This is in contrast to polyclonal antibodies that typically include a mixture of different antibodies directed against different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody portion, and any other modified immunoglobulin molecule comprising an antigen recognition site (antigen-binding site). Furthermore, "monoclonal antibody" refers to such antibodies made by any number of techniques, including but not limited to, hybridoma production, phage selection, recombinant expression, and transgenic animals.

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability (Jones et al., 1986, *Nature,* 321: 522-525; Riechmann et al., 1988, *Nature,* 332:323-327; Verhoeyen et al., 1988, *Science,* 239:1534-1536). In some instances, the Fv framework region residues of a human immunoglobulin are replaced with the corresponding residues in an antibody from a non-human species that has the desired specificity, affinity, and/or binding capability. The humanized antibody can be further modified by the substitution of additional residues either in the Fv framework region and/or within the replaced non-human residues to refine and optimize antibody specificity, affinity, and/or binding capability. In general, the humanized antibody will comprise substantially all of at least one, and typically two or three, variable domains containing all or substantially all of the CDRs that correspond to the non-human immunoglobulin whereas all or substantially all of the framework regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in, for example, U.S. Pat. No. 5,225,539.

The term "human antibody" as used herein refers to an antibody produced by a human or an antibody having an amino acid sequence corresponding to an antibody produced by a human made using any of the techniques known in the art. This definition of a human antibody specifically excludes a humanized antibody comprising non-human antigen-binding residues.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or binding capability, while the constant regions are homologous to the sequences in antibodies derived from another species (usually human) to avoid eliciting an immune response in that species.

The phrase "affinity matured antibody" as used herein refers to an antibody with one or more alterations in one or more CDRs thereof that result in an improvement in the affinity of the antibody for antigen, compared to a parent antibody that does not possess those alterations(s). Preferred affinity matured antibodies will have nanomolar or even picomolar affinities for the target antigen. Affinity matured antibodies are produced by procedures known in the art. For example, Marks et al., 1992, *Bio/Technology* 10:779-783, describes affinity maturation by VH and VL domain shuffling. Random mutagenesis of CDR and/or framework residues is described by Barbas et al., 1994, *PNAS,* 91:3809-3813; Schier et al., 1995, *Gene,* 169:147-155; Yelton et al., 1995, *J. Immunol.* 155:1994-2004; Jackson et al., 1995, *J. Immunol.,* 154:3310-9; and Hawkins et al., 1992, *J. Mol. Biol.,* 226:889-896.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

The terms "selectively binds" or "specifically binds" mean that a binding agent or an antibody reacts or associates more frequently, more rapidly, with greater duration, with greater affinity, or with some combination of the above to the epitope, protein or target molecule than with alternative substances, including unrelated proteins. In certain embodiments "specifically binds" means, for instance, that an antibody binds a protein with a $K_D$ of about 0.1 mM or less, but more usually less than about 1 μM. In certain embodiments, "specifically binds" means that an antibody binds a target at times with a $K_D$ of at least about 0.1 μM or less, at other times at least about 0.01 μM or less, and at other times at least about 1 nM or less. Because of the sequence identity between homologous proteins in different species, specific binding can include an antibody that recognizes a protein in more than one species (e.g., human RSPO1 and mouse RSPO1). Likewise, because of homology within certain regions of polypeptide sequences of different proteins, specific binding can include an antibody (or other polypeptide or binding agent) that recognizes more than one protein (e.g., human RSPO1 and human RSPO2). It is understood that, in certain embodiments, an antibody or binding moiety that specifically binds a first target may or may not specifically bind a second target. As such, "specific binding" does not necessarily require (although it can include) exclusive binding, i.e. binding to a single target. Thus, an antibody may, in certain embodiments, specifically bind more than one target. In certain embodiments, multiple targets may be bound by the same antigen-binding site on the antibody. For example, an antibody may, in certain instances, comprise two identical antigen-binding sites, each of which specifically binds the same epitope on two or more proteins (e.g., RSPO1 and RSPO2). In certain alternative embodiments, an antibody may be bispecific or multispecific and comprise at least two antigen-binding sites with differing specificities. By way of non-limiting example, a bispecific antibody may comprise one antigen-binding site that recognizes an epitope on one protein (e.g., human RSPO1) and further comprise a second, different antigen-binding site that recognizes a different epitope on a second protein. Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies, in certain embodiments, the polypeptides can occur as single chains or associated chains.

The terms "polynucleotide" and "nucleic acid" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

"Conditions of high stringency" may be identified by those that: (I) employ low ionic strength and high temperature for washing, for example 15 mM sodium chloride/1.5 mM sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75M NaCl, 75 mM sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC and 50% formamide at 55° C., followed by a high-stringency wash consisting of 0.1×SSC containing EDTA at 55° C.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value therebetween. In some embodiments, identity exists over a longer region than 60-80 residues, such as at least about 80-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s), i.e., the one or more RSPO protein(s) to which the polypeptide or antibody binds. Methods of identifying nucleotide and amino acid conservative substitutions which do not eliminate antigen binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some embodiments, a polypeptide, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The terms "cancer" and "cancerous" as used herein refer to or describe the physiological condition in mammals in which a population of cells are characterized by unregulated cell growth.

Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (noncancerous) or malignant (cancerous) including pre-cancerous lesions.

The term "metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell" and "CSC" and "tumor stem cell" and "tumor initiating cell" are used interchangeably herein and refer to cells from a cancer or tumor that: (1) have extensive proliferative capacity; 2) are capable of asymmetric cell division to generate one or more types of differentiated cell progeny wherein the differentiated cells have reduced proliferative or developmental potential; and (3) are capable of symmetric cell divisions for self-renewal or self-maintenance. These properties confer on the cancer stem cells the ability to form or establish a tumor or cancer upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein refers to the ability of a random sample of cells from the tumor to form palpable tumors upon serial transplantation into immunocompromised hosts (e.g., mice).

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to approved or approvable by a regulatory agency of the Federal or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one binding agent (e.g., an antibody) of the present disclosure, and which does not destroy the pharmacological activity thereof and is nontoxic when administered in doses sufficient to deliver a therapeutic effect.

The terms "effective amount" or "therapeutically effective amount" or "therapeutic effect" refer to an amount of a binding agent, an antibody, polypeptide, polynucleotide, small organic molecule, or other drug effective to "treat" a disease or disorder in a subject or mammal. In the case of cancer, the therapeutically effective amount of a drug (e.g., an antibody) has a therapeutic effect and as such can reduce the number of cancer cells; decrease tumorigenicity, tumorigenic frequency or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects. To the extent the agent, for example an antibody, prevents growth and/or kills existing cancer cells, it can be referred to as cytostatic and/or cytotoxic.

The terms "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder, and those in whom the disorder is to be prevented. In some embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of"consisting of" and/or "consisting essentially of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. RSPO-binding Agents

The present invention provides agents that bind human RSPO proteins. These agents are referred to herein as "RSPO-binding agents". In some embodiments, the RSPO-binding agents are antibodies. In some embodiments, the RSPO-binding agents are polypeptides. In certain embodiments, the RSPO-binding agents bind RSPO. In certain embodiments, the RSPO-binding agents bind RSPO2. In certain embodiments, the RSPO-binding agents bind RSPO3. In certain embodiments, the RSPO-agents specifically bind at least one other human RSPO. In some embodiments, the at least one other human RSPO bound by a RSPO1-binding agent is selected from the group consisting of RSPO2, RSPO3, and RSPO4. In some embodiments, the at least one other human RSPO bound by a RSPO2-binding agent is selected from the group consisting of RSPO1, RSPO3, and RSPO4. In some embodiments, the at least one other human RSPO bound by a RSPO3-binding agent is selected from the group consisting of RSPO1, RSPO2, and RSPO4. The full-length amino acid (aa) sequences for human RSPO1, RSPO2, RSPO3, and RSPO4 are known in the art and are provided herein as SEQ ID NO:1 (RSPO1), SEQ ID NO:2 (RSPO2), SEQ ID NO:3 (RSPO3), and SEQ ID NO:4 (RSPO4).

In certain embodiments, the antigen-binding site of a RSPO-binding agent (e.g., antibody) described herein is capable of binding (or binds) one, two, three, or four RSPOs. In certain embodiments, the antigen-binding site of a RSPO 1-binding agent (e.g., antibody) described herein is capable of binding (or binds) RSPO1 as well as one, two, or three other RSPOs. For example, in certain embodiments, the antigen-binding site of a RSPO1-binding agent is capable of specifically binding RSPO1 as well as at least one other RSPO selected from the group consisting of RSPO2, RSPO3, and RSPO4. In certain embodiments, the RSPO1-binding agent specifically binds RSPO1 and RSPO2. In certain embodiments, the RSPO1-binding agent specifically binds RSPO1 and RSPO3. In certain embodiments, the RSPO1-binding agent specifically binds RSPO1 and RSPO4. In certain embodiments, the RSPO1-binding agent specifically binds RSPO1, RSPO2, and RSPO3. In certain embodiments, the RSPO1-binding agent specifically binds RSPO1, RSPO2, and RSPO4. In certain embodiments, the RSPO1-binding agent specifically binds RSPO1, RSPO3, and RSPO4. In some embodiments, the RSPO1-binding agent specifically binds human RSPO1. In some embodiments, the RSPO1-binding agent (e.g., antibody) specifically binds both human RSPO1 and mouse RSPO1.

In certain embodiments, the agent-binding agent is an antibody that specifically binds within amino acids 21-263 of human RSPO1. In certain embodiments, the agent-binding agent is an antibody that specifically binds within amino acids 31-263 of human RSPO 1. In certain embodiments, the antigen-binding agent is an antibody that specifically binds within amino acids 34-135 of human RSPO1. In certain embodiments, the antigen-binding agent is an antibody that specifically binds within amino acids 91-135 of human RSPO1. In certain embodiments, the RSPO1-binding agent binds within SEQ ID NO:5. In some embodiments, the RSPO1-binding agent binds within SEQ ID NO:9. In certain embodiments, the RSPO1-binding agent or antibody binds a furin-like cysteine-rich domain of RSPO1. In some embodiments, the agent or antibody binds at least one amino acid within a furin-like cysteine-rich domain of RSPO1. In certain embodiments, the RSPO1-binding agent or antibody binds within sequence SEQ ID NO:6 or SEQ ID NO:7. In certain embodiments, the RSPO1-binding agent or antibody binds within sequence SEQ ID NO:6 and SEQ ID NO:7. In some embodiments, the RSPO1-binding agent binds the thrombospondin domain of RSPO1. In some embodiments, the RSPO1-binding agent or antibody binds at least one amino acid within the thrombospondin domain of RSPO1. In some embodiments, the RSPO1-binding agent or antibody binds within SEQ ID NO:8.

In certain embodiments, the antigen-binding site of a RSPO2-binding agent (e.g., antibody) described herein is capable of binding (or binds) RSPO2 as well as one, two, or three other RSPOs. For example, in certain embodiments, the antigen-binding site of a RSPO2-binding agent is capable of specifically binding RSPO2 as well as at least one other RSPO selected from the group consisting of RSPO1, RSPO3, and RSPO4. In certain embodiments, the RSPO2-binding agent specifically binds RSPO2 and RSPO1. In certain embodiments, the RSPO2-binding agent specifically binds RSPO2 and RSPO3. In certain embodiments, the RSPO2-binding agent specifically binds RSPO2 and RSPO4. In certain embodiments, the RSPO2-binding agent specifically binds RSPO2, RSPO3, and RSPO4. In certain embodiments, the RSPO2-binding agent specifically binds RSPO2, RSPO1, and RSPO3. In certain embodiments, the RSPO2-binding agent specifically binds RSPO2, RSPO1, and RSPO4. In some embodiments, the RSPO2-binding agent specifically binds human RSPO2. In some embodiments, the RSPO2-binding agent (e.g., antibody) specifically binds both human RSPO2 and mouse RSPO2.

In certain embodiments, the agent-binding agent is an antibody that specifically binds within amino acids 22-243 of human RSPO2. In certain embodiments, the agent-binding agent is an antibody that specifically binds within amino acids 22-205 of human RSPO2. In certain embodiments, the antigen-binding agent is an antibody that specifically binds within amino acids 31-146 of human RSPO2. In certain embodiments, the antigen-binding agent is an antibody that specifically binds within amino acids 31-89 of human RSPO2. In certain embodiments, the antigen-binding agent is an antibody that specifically binds within amino acids 90-134 of human RSPO2. In certain embodiments, the antigen-binding agent is an antibody that specifically binds within amino acids 90-146 of human RSPO2. In certain embodiments, the RSPO2-binding agent binds within SEQ ID NO:43. In some embodiments, the RSPO2-binding agent binds within SEQ ID NO:44. In certain embodiments, the RSPO2-binding agent or antibody binds a furin-like cysteine-rich domain of RSPO2. In some embodiments, the agent or antibody binds at least one amino acid within a furin-like cysteine-rich domain of RSPO2. In certain embodiments, the RSPO2-binding agent or antibody binds within sequence SEQ ID NO:45 or SEQ ID NO:46. In certain embodiments, the RSPO2-binding agent or antibody binds within sequence SEQ ID NO:45 and SEQ ID NO:46. In some embodiments, the RSPO2-binding agent binds the thrombospondin domain of RSPO2. In some embodiments, the RSPO2-binding agent or antibody binds at least one amino acid within the thrombospondin domain of RSPO2. In some embodiments, the RSPO2-binding agent or antibody binds within SEQ ID NO:47.

In certain embodiments, the antigen-binding site of a RSPO3-binding agent (e.g., antibody) described herein is capable of binding (or binds) RSPO3 as well as one, two, or three other RSPOs. For example, in certain embodiments, the antigen-binding site of a RSPO3-binding agent is capable of specifically binding RSPO3 as well as at least one other RSPO selected from the group consisting of RSPO1, RSPO2, and RSPO4. In certain embodiments, the RSPO3-binding agent specifically binds RSPO3 and RSPO1. In certain embodiments, the RSPO3-binding agent specifically binds RSPO3 and RSPO2. In certain embodiments, the RSPO3-binding agent specifically binds RSPO3 and RSPO4. In certain embodiments, the RSPO3-binding agent specifically binds RSPO3, RSPO1, and RSPO2. In certain embodiments, the RSPO3-binding agent specifically binds RSPO3, RSPO1, and RSPO4. In certain embodiments, the RSPO3-binding agent specifically binds RSPO3, RSPO2, and RSPO4. In some embodiments, the RSPO3-binding agent specifically binds human RSPO3. In some embodiments, the RSPO3-binding agent (e.g., antibody) specifically binds both human RSPO3 and mouse RSPO3.

In certain embodiments, the agent-binding agent is an antibody that specifically binds within amino acids 22-272 of human RSPO3. In certain embodiments, the agent-binding agent is an antibody that specifically binds within amino acids 22-207 of human RSPO3. In certain embodiments, the antigen-binding agent is an antibody that specifically binds within amino acids 35-135 of human RSPO3. In certain embodiments, the antigen-binding agent is an antibody that specifically binds within amino acids 35-86 of human RSPO3. In certain embodiments, the antigen-binding agent is an antibody that specifically binds within amino acids 92-135 of human RSPO3. In certain embodiments, the RSPO3-binding agent binds within SEQ ID NO:48. In certain embodiments, the RSPO3-binding agent or antibody binds a furin-like cysteine-rich domain of RSPO3. In some embodiments, the agent or antibody binds at least one amino acid within a furin-like cysteine-rich domain of RSPO3. In certain embodiments, the RSPO3-binding agent or antibody binds within sequence SEQ ID NO:49 or SEQ ID NO:50. In certain embodiments, the RSPO3-binding agent or antibody binds within sequence SEQ ID NO:49 and SEQ ID NO:50. In some embodiments, the RSPO3-binding agent binds the thrombospondin domain of RSPO3. In some embodiments, the RSPO3-binding agent or antibody binds at least one amino acid within the thrombospondin domain of RSPO3. In some embodiments, the RSPO3-binding agent or antibody binds within SEQ ID NO:51.

In certain embodiments, the RSPO-binding agent or antibody binds at least one RSPO protein with a dissociation constant ($K_D$) of about 1 μM or less, about 100 nM or less, about 40 nM or less, about 20 nM or less, about 10 nM or less, about 1 nM or less, or about 0.1 nM or less. In certain embodiments, a RSPO1-binding agent or antibody binds RSPO1 with a dissociation constant ($K_D$) of about 1 μM or less, about 100 nM or less, about 40 nM or less, about 20 nM or less, about 10 nM or less, about 1 nM or less, or about 0.1 nM or less. In some embodiments, a RSPO1-binding agent or antibody binds RSPO1 with a $K_D$ of about 1 nM or less. In some embodiments, a RSPO1-binding agent or antibody binds RSPO1 with a $K_D$ of about 0.1 nM or less. In certain embodiments, a RSPO1-binding agent or antibody described herein binds at least one other RSPO. In certain embodiments, a RSPO1-binding agent or antibody described herein that binds at least one other RSPO, binds at least one other RSPO with a $K_D$ of about 100 nM or less, about 20 nM or less, about 10 nM or less, about 1 nM or less or about 0.1 nM or less. For example, in some embodiments, a RSPO1-binding agent or antibody also binds RSPO2, RSPO3, and/or RSPO4 with a $K_D$ of about 10 nM or less. In some embodiments, a RSPO1-binding agent (e.g., antibody) binds human RSPO1 with a $K_D$ of about 0.1 nM or less. In some embodiments, the RSPO-binding agent binds both human RSPO and mouse RSPO with a $K_D$ of about 10nM or less. In some embodiments, a RSPO1-binding agent binds both human RSPO1 and mouse RSPO1 with a $K_D$ of about 1 nM or less. In some embodiments, a RSPO1-binding agent binds both human RSPO1 and mouse RSPO1 with a $K_D$ of about 0.1 nM or less. In certain embodiments, a RSPO2-binding agent or antibody binds RSPO2 with a dissociation constant ($K_D$) of about 1 μM or less, about 100 nM or less, about 40 nM or less, about 20 nM or less, about 10 nM or less, about 1 nM or less, or about 0.1 nM or less. In some embodiments, a RSPO2-binding agent or antibody binds RSPO2 with a $K_D$ of about 10 nM or less. In some embodiments, a RSPO2-binding agent or antibody binds RSPO2 with a $K_D$ of about 1 nM or less. In certain embodiments, a RSPO2-binding agent or antibody described herein binds at least one other RSPO. In certain embodiments, a RSPO2-binding agent or antibody described herein that binds at least one other RSPO, binds at least one other RSPO with a $K_D$ of about 100 nM or less, about 20 nM or less, about 10 nM or less, about 1 nM or less or about 0.1 nM or less. For example, in some embodiments, a RSPO2-binding agent or antibody also binds RSPO1, RSPO3, and/or RSPO4 with a $K_D$ of about 10 nM or less. In some embodiments, a RSPO2-binding agent (e.g., antibody) binds human RSPO2 with a $K_D$ of about 1 nM or less. In some embodiments, the RSPO-binding agent binds both human RSPO and mouse RSPO with a $K_D$ of about 10nM or less. In some embodiments, a RSPO2-binding agent binds both human RSPO2 and mouse RSPO2 with a $K_D$ of about 1 nM or less. In some embodiments, a RSPO2-binding agent binds both human RSPO2 and mouse RSPO2 with a $K_D$ of about 0.1 nM or less. In some embodiments, the dissociation constant of the binding agent (e.g., an antibody) to a RSPO protein is the dissociation constant determined using a RSPO fusion protein comprising at least a portion of the RSPO protein immobilized on a Biacore chip.

In certain embodiments, the RSPO-binding agent (e.g., an antibody) binds to at least one human RSPO protein with a half maximal effective concentration ($EC_{50}$) of about 1 μM or less, about 100 nM or less, about 40 nM or less, about 20 nM or less, about 10 nM or less, about 1 nM or less, or about 0.1 nM or less. In certain embodiments, a RSPO1-binding agent (e.g., an antibody) binds to human RSPO1 with a half maximal effective concentration ($EC_{50}$) of about 1 μM or less, about 100 nM or less, about 40 nM or less, about 20 nM or less, about 10 nM or less, about 1 nM or less, or about 0.1 nM or less. In certain embodiments, a RSPO1-binding agent (e.g., an antibody) also binds to human RSPO2, RSPO3, and/or RSPO4 with an $EC_{50}$ of about 40 nM or less, about 20 nM or less, about 10 nM or less, about 1 nM or less or about 0.1 nM or less. In certain embodiments, a RSPO2-binding agent (e.g., an antibody) binds to human RSPO2 with a half maximal effective concentration ($EC_{50}$) of about 1 μM or less, about 100 nM or less, about 40 nM or less, about 20 nM or less, about 10 nM or less, about 1 nM or less, or about 0.1 nM or less. In certain embodiments, a RSPO2-binding agent (e.g., an antibody) also binds to human RSPO1, RSPO3, and/or RSPO4 with an $EC_{50}$ of about 40 nM or less, about 20 nM or less, about 10 nM or less, about 1 nM or less or about 0.1 nM or less.

In certain embodiments, the RSPO-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In certain embodiments, the antibody is an IgG1 antibody. In certain embodiments, the antibody is an IgG2 antibody. In certain embodiments, the antibody is an antibody fragment comprising an antigen-binding site. In some embodiments, the antibody is monovalent, monospecific, bivalent, bispecific, or multispecific. In some embodiments, the antibody is conjugated to a cytotoxic moiety. In some embodiments, the antibody is isolated. In some embodiments, the antibody is substantially pure.

The RSPO-binding agents (e.g., antibodies) of the present invention can be assayed for specific binding by any method known in the art. The immunoassays that can be used include, but are not limited to, competitive and non-competitive assay systems using techniques such as Biacore analysis, FACS analysis, immunofluorescence, immunocytochemistry, Western blots, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are routine and well-known in the art (see, e.g., Ausubel et al., Editors, 1994-present, *Current Protocols in Molecular Biology*, John Wiley & Sons, Inc., New York, N.Y.).

For example, the specific binding of an antibody to human RSPO1 may be determined using ELISA. An ELISA assay comprises preparing antigen, coating wells of a 96 well microtiter plate with antigen, adding the RSPO1-binding antibody or other RSPO1-binding agent conjugated to a detectable compound such as an enzymatic substrate (e.g. horseradish peroxidase or alkaline phosphatase) to the well, incubating for a period of time and detecting the presence of the antibody bound to the antigen. In some embodiments, the RSPO1-binding antibody or agent is not conjugated to a detectable compound, but instead a second conjugated antibody that recognizes the RSPO1-binding antibody or agent is added to the well. In some embodiments, instead of coating the well with the antigen, the RSPO-binding antibody or agent can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art.

In another example, the specific binding of an antibody to human RSPO1 may be determined using FACS. A FACS screening assay may comprise generating a cDNA construct that expresses an antigen as a fusion protein (e.g., RSPO1-Fc or RSPO1-CD4TM), transfecting the construct into cells, expressing the antigen on the surface of the cells, mixing the RSPO1-binding antibody or other RSPO1-binding agent with the transfected cells, and incubating for a period of time. The cells bound by the RSPO1-binding antibody or other RSPO-binding agent may be identified by using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of an antibody or other binding-agent to an antigen (e.g., a RSPO protein) and the off-rate of an antibody-antigen interaction can be determined by competitive binding assays. One example of a competitive binding assay is a radioimmunoassay comprising the incubation of labeled antigen (e.g., $^{3}H$ or $^{125}I$), or fragment or variant thereof, with the antibody of interest in the presence of increasing amounts of unlabeled antigen followed by the detection of the antibody bound to the labeled antigen. The affinity of the antibody for an antigen (e.g., a RSPO protein) and the binding off-rates can be determined from the data by Scatchard plot analysis. In some embodiments, Biacore kinetic analysis is used to determine the binding on and off rates of antibodies or agents that bind an antigen (e.g., a RSPO protein). Biacore kinetic analysis comprises analyzing the binding and dissociation of antibodies from chips with immobilized antigen (e.g., a RSPO protein) on their surface.

In certain embodiments, the invention provides a RSPO1-binding agent (e.g., an antibody) that specifically binds human RSPO1, wherein the RSPO1-binding agent (e.g., an antibody) comprises one, two, three, four, five, and/or six of the CDRs of antibody 89M5 (see Table 1). In some embodiments, the RSPO1-binding agent comprises one or more of the CDRs of 89M5, two or more of the CDRs of 89M5, three or more of the CDRs of 89M5, four or more of the CDRs of 89M5, five or more of the CDRs of 89M5, or all six of the CDRs of 89M5.

TABLE 1

| | 89M5 | 130M23 |
|---|---|---|
| HC CDR1 | TGYTMH (SEQ ID NO: 12) | SSYAMS (SEQ ID NO: 29) |
| HC CDR2 | GINPNNGGTTYNQNFKG (SEQ ID NO: 13) | SISSGGSTYYPDSVKG (SEQ ID NO: 30) |
| HC CDR3 | KEFSDGYYFFAY (SEQ ID NO: 14) | RGGDPGVYNGDYDAMDY (SEQ ID NO: 31) |
| LC CDR1 | KASQDVIFAVA (SEQ ID NO: 15) | KASQDVSSAVA (SEQ ID NO: 32) |
| LC CDR2 | WASTRHT (SEQ ID NO: 16) | WASTRHT (SEQ ID NO: 33) |
| LC CDR3 | QQHYSTPW (SEQ ID NO: 17) | QQHYSTP (SEQ ID NO: 34) |

In certain embodiments, the invention provides a RSPO1-binding agent (e.g., an antibody) that specifically binds human RSPO1, wherein the RSPO1-binding agent comprises a heavy chain CDR1 comprising TGYTMH (SEQ ID NO: 12), a heavy chain CDR2 comprising GINPNNGGTTYNQNFKG (SEQ ID NO: 13), and a heavy chain CDR3 comprising KEFSDGYYFFAY (SEQ ID NO: 14). In some embodiments, the RSPO1-binding agent further comprises a light chain CDR1 comprising KASQDVIFAVA (SEQ ID NO: 15), a light chain CDR2 comprising WASTRHT (SEQ ID NO: 16), and a light chain CDR3 comprising QQHYSTPW (SEQ ID NO:17). In some embodiments, the RSPO1-binding agent comprises a light chain CDR1 comprising KASQDVIFAVA (SEQ ID NO: 15), a light chain CDR2 comprising WASTRHT (SEQ ID NO: 16), and a light chain CDR3 comprising QQHYSTPW (SEQ ID NO:17). In certain embodiments, the RSPO1-binding agent comprises: (a) a heavy chain CDR1 comprising TGYTMH (SEQ ID NO: 12), a heavy chain CDR2 comprising GINPNNGGTTYNQNFKG (SEQ ID NO:13), and a heavy chain CDR3 comprising KEFSDGYYFFAY (SEQ ID NO:14), and (b) a light chain CDR1 comprising KASQDVIFAVA (SEQ ID NO: 15), a light chain CDR2 comprising WASTRHT (SEQ ID NO: 16), and a light chain CDR3 comprising QQHYSTPW (SEQ ID NO: 17).

In certain embodiments, the invention provides a RSPO1-binding agent (e.g., an antibody) that specifically binds human RSPO1, wherein the RSPO1-binding agent comprises: (a) a heavy chain CDR1 comprising TGYTMH (SEQ ID NO: 12), or a variant thereof comprising 1, 2, 3, or 4 amino acid substitutions; (b) a heavy chain CDR2 comprising GINPNNGGTTYNQNFKG (SEQ ID NO: 13), or a variant thereof comprising 1, 2, 3, or 4 amino acid substitutions; (c) a heavy chain CDR3 comprising KEFSDGYYFFAY (SEQ ID NO: 14), or a variant thereof comprising 1, 2, 3, or 4 amino acid substitutions; (d) a light chain CDR1 comprising KASQDVIFAVA (SEQ ID NO: 15), or a variant thereof comprising 1, 2, 3, or 4 amino acid substitutions; (e) a light chain CDR2 comprising WASTRHT (SEQ ID NO: 16), or a variant thereof comprising 1, 2, 3, or 4 amino acid substitutions; and (f) a light chain CDR3 comprising QQHYSTPW (SEQ ID NO:17), or a variant thereof comprising 1, 2, 3, or 4 amino acid substitutions. In certain embodiments, the amino acid substitutions are conservative substitutions.

In certain embodiments, the invention provides a RSPO1-binding agent (e.g., an antibody) that specifically binds RSPO1, wherein the RSPO1-binding agent comprises a heavy chain variable region having at least about 80% sequence identity to SEQ ID NO: 10, and/or a light chain variable region having at least 80% sequence identity to SEQ ID NO: 11. In certain embodiments, the RSPO1-binding agent comprises a heavy chain variable region having at least about 85%, at least about 90%, at least about 95%, at least about 97%, or at least about 99% sequence identity to SEQ ID NO: 10. In certain embodiments, the RSPO1-binding agent comprises a light chain variable region having at least about 85%, at least about 90%, at least about 95%, at least about 97%, or at least about 99% sequence identity to SEQ ID NO: 11. In certain embodiments, the RSPO1-binding agent comprises a heavy chain variable region having at least about 95% sequence identity to SEQ ID NO:10, and/or a light chain variable region having at least about 95% sequence identity to SEQ ID NO:11. In certain embodiments, the RSPO1-binding agent comprises a heavy chain variable region comprising SEQ ID NO:10, and/or a light chain variable region comprising SEQ ID NO: 11. In certain embodiments, the RSPO1-binding agent comprises a heavy chain variable region consisting essentially of SEQ ID NO: 10, and a light chain variable region consisting essentially of SEQ ID NO: 11.

In certain embodiments, the invention provides a RSPO1-binding agent (e.g., an antibody) that specifically binds RSPO1, wherein the RSPO1-binding agent comprises a heavy chain variable region having at least about 80% sequence identity to SEQ ID NO:55, and/or a light chain variable region having at least 80% sequence identity to SEQ ID NO:59. In certain embodiments, the RSPO1-binding agent comprises a heavy chain variable region having at least about 85%, at least about 90%, at least about 95%, at least about 97%, or at least about 99% sequence identity to SEQ ID NO:55. In certain embodiments, the RSPO1-binding agent comprises a light chain variable region having at least about 85%, at least about 90%, at least about 95%, at least about 97%, or at least about 99% sequence identity to SEQ ID NO:59. In certain embodiments, the RSPO1-binding agent comprises a heavy chain variable region having at least about 95% sequence identity to SEQ ID NO:55, and/or a light chain variable region having at least about 95% sequence identity to SEQ ID NO:59. In certain embodiments, the RSPO1-binding agent comprises a heavy chain variable region comprising SEQ ID NO:55, and/or a light chain variable region comprising SEQ ID NO:59. In certain embodiments, the RSPO1-binding agent comprises a heavy chain variable region consisting essentially of SEQ ID NO:55, and a light chain variable region consisting essentially of SEQ ID NO:59.

In certain embodiments, the invention provides a RSPO1-binding agent (e.g., an antibody) that specifically binds RSPO1, wherein the RSPO1-binding agent comprises: (a) a heavy chain having at least 90% sequence identity to SEQ ID NO:25; and/or (b) a light chain having at least 90% sequence identity to SEQ ID NO:26. In some embodiments, the RSPO1-binding agent comprises: (a) a heavy chain having at least 95% sequence identity to SEQ ID NO:25; and/or (b) a light chain having at least 95% sequence identity to SEQ ID NO:26. In some embodiments, the RSPO1-binding agent comprises a heavy chain comprising SEQ ID NO:25, and/or a light chain comprising SEQ ID NO:26. In some embodiments, the RSPO1-binding agent comprises a heavy chain consisting essentially of SEQ ID NO:25, and a light chain consisting essentially of SEQ ID NO:26.

In certain embodiments, the invention provides a RSPO1-binding agent (e.g., an antibody) that specifically binds RSPO1, wherein the RSPO1-binding agent comprises: (a) a heavy chain having at least 90% sequence identity to SEQ ID NO:68; and/or (b) a light chain having at least 90% sequence identity to SEQ ID NO:69. In some embodiments, the RSPO1-binding agent comprises: (a) a heavy chain having at least 95% sequence identity to SEQ ID NO:68; and/or (b) a light chain having at least 95% sequence identity to SEQ ID NO:69. In some embodiments, the RSPO1-binding agent comprises a heavy chain comprising SEQ ID NO:68, and/or a light chain comprising SEQ ID NO:69. In some embodiments, the RSPO1-binding agent comprises a heavy chain consisting essentially of SEQ ID NO:68, and a light chain consisting essentially of SEQ ID NO:69.

In certain embodiments, the invention provides a RSPO2-binding agent (e.g., an antibody) that specifically binds human RSPO2, wherein the RSPO2-binding agent (e.g., an antibody) comprises one, two, three, four, five, and/or six of the CDRs of antibody 130M23 (see Table 1). In some embodiments, the RSPO2-binding agent comprises one or more of the CDRs of 130M23, two or more of the CDRs of 130M23, three or more of the CDRs of 130M23, four or more of the CDRs of 130M23, five or more of the CDRs of 130M23, or all six of the CDRs of 130M23.

In certain embodiments, the invention provides a RSPO2-binding agent (e.g., an antibody) that specifically binds human RSPO2, wherein the RSPO2-binding agent comprises a heavy chain CDR1 comprising SSYAMS (SEQ ID NO:29), a heavy chain CDR2 comprising SISSGGSTYYPDSVKG (SEQ ID NO:30), and a heavy chain CDR3 comprising RGGDPGVYNGDYEDAMDY (SEQ ID NO:31). In some embodiments, the RSPO2-binding agent further comprises a light chain CDR1 comprising KASQDVSSAVA (SEQ ID NO:32), a light chain CDR2 comprising WASTRHT (SEQ ID NO:33), and a light chain CDR3 comprising QQHYSTP (SEQ ID NO:34). In some embodiments, the RSPO2-binding agent comprises a light chain CDR1 comprising KASQDVSSAVA (SEQ ID NO:32), a light chain CDR2 comprising WASTRHT (SEQ ID NO:33), and a light chain CDR3 comprising QQHYSTP (SEQ ID NO:34). In certain embodiments, the RSPO2-binding agent comprises: (a) a heavy chain CDR1 comprising SSYAMS (SEQ ID NO:29), a heavy chain CDR2 comprising SISSGGSTYYPDSVKG (SEQ ID NO:30), and a heavy chain CDR3 comprising RGGDPGVYNGDYEDAMDY (SEQ ID NO:31), and (b) a light chain CDR1 comprising KASQDVSSAVA (SEQ ID NO:32), a light chain CDR2 comprising WASTRHT (SEQ ID NO:33), and a light chain CDR3 comprising QQHYSTP (SEQ ID NO:34).

In certain embodiments, the invention provides a RSPO2-binding agent (e.g, an antibody) that specifically binds human RSPO2, wherein the RSPO2-binding agent comprises: (a) a heavy chain CDR1 comprising SSYAMS (SEQ ID NO:29), or a variant thereof comprising 1, 2, 3, or 4 amino acid substitutions; (b) a heavy chain CDR2 comprising SISSGGSTYYPDSVKG (SEQ ID NO:30), or a variant thereof comprising 1, 2, 3, or 4 amino acid substitutions; (c) a heavy chain CDR3 comprising RGGDPGVYNGDYEDAMDY (SEQ ID NO:31), or a variant thereof comprising 1, 2, 3, or 4 amino acid substitutions; (d) a light chain CDR1 comprising KASQDVSSAVA (SEQ ID NO:32), or a variant thereof comprising 1, 2, 3, or 4 amino acid substitutions; (e) a light chain CDR2 comprising WASTRHT (SEQ ID NO:33), or a variant thereof comprising 1, 2, 3, or 4 amino acid substitutions; and (f) a light chain CDR3 comprising QQHYSTP (SEQ ID NO:34), or a variant thereof comprising 1, 2, 3, or 4 amino acid substitutions. In certain embodiments, the amino acid substitutions are conservative substitutions.

In certain embodiments, the invention provides a RSPO2-binding agent (e.g., an antibody) that specifically binds RSPO2, wherein the RSPO2-binding agent comprises a heavy chain variable region having at least about 80% sequence identity to SEQ ID NO:27, and/or a light chain variable region having at least 80% sequence identity to SEQ ID NO:28. In certain embodiments, the RSPO2-binding agent comprises a heavy chain variable region having at least about 85%, at least about 90%, at least about 95%, at least about 97%, or at least about 99% sequence identity to SEQ ID NO:27. In certain embodiments, the RSPO2-binding agent comprises a light chain variable region having at least about 85%, at least about 90%, at least about 95%, at least about 97%, or at least about 99% sequence identity to SEQ ID NO:28. In certain embodiments, the RSPO2-binding agent comprises a heavy chain variable region having at least about 95% sequence identity to SEQ ID NO:27, and/or a light chain variable region having at least about 95% sequence identity to SEQ ID NO:28. In certain embodiments, the RSPO2-binding agent comprises a heavy chain variable region comprising SEQ ID NO:27, and/or a light chain variable region comprising SEQ ID NO:28. In certain embodiments, the RSPO2-binding agent comprises a heavy chain variable region consisting essentially of SEQ ID NO:27, and a light chain variable region consisting essentially of SEQ ID NO:28.

In certain embodiments, the invention provides a RSPO2-binding agent (e.g., an antibody) that specifically binds RSPO2, wherein the RSPO2-binding agent comprises a heavy chain variable region having at least about 80% sequence identity to SEQ ID NO:63, and/or a light chain variable region having at least 80% sequence identity to SEQ ID NO:67 or SEQ ID NO:76. In certain embodiments, the RSPO2-binding agent comprises a heavy chain variable region having at least about 85%, at least about 90%, at least about 95%, at least about 97%, or at least about 99% sequence identity to SEQ ID NO:63. In certain embodiments, the RSPO2-binding agent comprises a light chain variable region having at least about 85%, at least about 90%, at least about 95%, at least about 97%, or at least about 99% sequence identity to SEQ ID NO:67 or SEQ ID NO:76. In certain embodiments, the RSPO2-binding agent comprises a heavy chain variable region having at least about 95% sequence identity to SEQ ID NO:63, and/or a light chain variable region having at least about 95% sequence identity to SEQ ID NO:67 or SEQ ID NO:76. In certain embodiments, the RSPO2-binding agent comprises a heavy chain variable region comprising SEQ ID NO:63, and/or a light chain variable region comprising SEQ ID NO:67. In certain embodiments, the RSPO2-binding agent comprises a heavy chain variable region comprising SEQ ID NO:63, and/or a light chain variable region comprising SEQ ID NO:76. In certain embodiments, the RSPO2-binding agent comprises a heavy chain variable region consisting essentially of SEQ ID NO:63, and a light chain variable region consisting essentially of SEQ ID NO:67. In certain embodiments, the RSPO2-binding agent comprises a heavy chain variable region consisting essentially of SEQ ID NO:63, and a light chain variable region consisting essentially of SEQ ID NO:76.

In certain embodiments, the invention provides a RSPO2-binding agent (e.g., an antibody) that specifically binds RSPO2, wherein the RSPO2-binding agent comprises: (a) a heavy chain having at least 90% sequence identity to SEQ ID NO:41; and/or (b) a light chain having at least 90% sequence identity to SEQ ID NO:42. In some embodiments, the RSPO2-binding agent comprises: (a) a heavy chain having at least 95% sequence identity to SEQ ID NO:41; and/or (b) a light chain having at least 95% sequence identity to SEQ ID NO:42. In some embodiments, the RSPO1-binding agent comprises a heavy chain comprising SEQ ID NO:41, and/or a light chain comprising SEQ ID NO:42. In some embodiments, the RSPO1-binding agent comprises a heavy chain consisting essentially of SEQ ID NO:41, and a light chain consisting essentially of SEQ ID NO:42.

In certain embodiments, the invention provides a RSPO2-binding agent (e.g., an antibody) that specifically binds RSPO2, wherein the RSPO2-binding agent comprises: (a) a heavy chain having at least 90% sequence identity to SEQ ID NO:70; and/or (b) a light chain having at least 90% sequence identity to SEQ ID NO:71 or SEQ ID NO:74. In some embodiments, the RSPO2-binding agent comprises: (a) a heavy chain having at least 95% sequence identity to SEQ ID NO:70; and/or (b) a light chain having at least 95% sequence identity to SEQ ID NO:71 or SEQ ID NO:74. In some embodiments, the RSPO2-binding agent comprises a heavy chain comprising SEQ ID NO:70, and/or a light chain comprising SEQ ID NO:71. In some embodiments, the RSPO2-binding agent comprises a heavy chain comprising SEQ ID NO:70, and/or a light chain comprising SEQ ID NO:74. In some embodiments, the RSPO2-binding agent comprises a heavy chain consisting essentially of SEQ ID NO:70, and a light chain consisting essentially of SEQ ID NO:71. In some embodiments, the RSPO2-binding agent comprises a heavy chain consisting essentially of SEQ ID NO:70, and a light chain consisting essentially of SEQ ID NO:74.

The invention provides polypeptides, including, but not limited to, antibodies that specifically bind human RSPO proteins. In some embodiments, the polypeptides bind human RSPO1. In some embodiments, the polypeptides bind human RSPO2. In some embodiments, the polypeptides bind human RSPO3.

In certain embodiments, the polypeptide comprises one, two, three, four, five, and/or six of the CDRs of antibody 89M5 (see Table 1 herein). In certain embodiments, the polypeptide comprises one, two, three, four, five, and/or six of the CDRs of antibody 130M23 (see Table 1 herein). In some embodiments, the polypeptide comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

In some embodiments, the invention provides a polypeptide that specifically binds human RSPO1, wherein the polypeptide comprises an amino acid sequence having at least about 80% sequence identity to SEQ ID NO: 10 or SEQ ID NO:55, and/or an amino acid sequence having at least about 80% sequence identity to SEQ ID NO:11 or SEQ ID NO:59. In certain embodiments, the polypeptide comprises an amino acid sequence having at least about 85%, at least about 90%, at least about 95%, at least about 97%, or at least about 99% sequence identity to SEQ ID NO: 10 or SEQ ID NO:55. In certain embodiments, the polypeptide comprises an amino acid sequence having at least about 85%, at least about 90%, at least about 95%, at least about 97%, or at least about 99% sequence identity to SEQ ID NO: 1 or SEQ ID NO:59. In certain embodiments, the polypeptide comprises an amino acid sequence having at least about 95% sequence identity to SEQ ID NO:10 or SEQ ID NO:55, and/or an amino acid sequence having at least about 95% sequence identity to SEQ ID NO: 11 or SEQ ID NO:59. In certain embodiments, the polypeptide comprises an amino acid sequence comprising SEQ ID NO: 10, and/or an amino acid sequence comprising SEQ ID NO:11. In certain embodiments, the polypeptide comprises an amino acid sequence comprising SEQ ID NO:55, and/or an amino acid sequence comprising SEQ ID NO:59.

In some embodiments, the invention provides a polypeptide that specifically binds human RSPO2, wherein the polypeptide comprises an amino acid sequence having at least about 80% sequence identity to SEQ ID NO:27 or SEQ ID NO:63, and/or an amino acid sequence having at least about 80% sequence identity to SEQ ID NO:28, SEQ ID NO:67, or SEQ ID NO:76. In certain embodiments, the polypeptide comprises an amino acid sequence having at least about 85%, at least about 90%, at least about 95%, at least about 97%, or at least about 99% sequence identity to SEQ ID NO:27 or SEQ ID NO:63. In certain embodiments, the polypeptide comprises an amino acid sequence having at least about 85%, at least about 90%, at least about 95%, at least about 97%, or at least about 99% sequence identity to SEQ ID NO:28, SEQ ID NO:67, or SEQ ID NO:76. In certain embodiments, the polypeptide comprises an amino acid sequence having at least about 95% sequence identity to SEQ ID NO:27 or SEQ ID NO:63, and/or an amino acid sequence having at least about 95% sequence identity to SEQ ID NO:28, SEQ ID NO:67, or SEQ ID NO:76. In certain embodiments, the polypeptide comprises an amino acid sequence comprising SEQ ID NO:27, and/or an amino acid sequence comprising SEQ ID NO:28. In certain embodiments, the polypeptide comprises an amino acid sequence comprising SEQ ID NO:63, and/or an amino acid sequence comprising SEQ ID NO:67. In certain embodiments, the polypeptide comprises an amino acid sequence comprising SEQ ID NO:63, and/or an amino acid sequence comprising SEQ ID NO:76.

In some embodiments, the invention provides a polypeptide that specifically binds human RSPO1, wherein the polypeptide comprises an amino acid sequence having at least about 80% sequence identity to SEQ ID NO:25, and/or an amino acid sequence having at least about 80% sequence identity to SEQ ID NO:26. In certain embodiments, the polypeptide comprises an amino acid sequence having at least about 85%, at least about 90%, at least about 95%, at least about 97%, or at least about 99% sequence identity to SEQ ID NO:25. In certain embodiments, the polypeptide comprises an amino acid sequence having at least about 85%, at least about 90%, at least about 95%, at least about 97%, or at least about 99% sequence identity to SEQ ID NO:26. In certain embodiments, the polypeptide comprises an amino acid sequence having at least about 95% sequence identity to SEQ ID NO:25, and/or an amino acid sequence having at least about 95% sequence identity to SEQ ID NO:26. In certain embodiments, the polypeptide comprises an amino acid sequence comprising SEQ ID NO:25, and/or an amino acid sequence comprising SEQ ID NO:26. In certain embodiments, the polypeptide consists essentially of SEQ ID NO:25, and/or SEQ ID NO:26.

In some embodiments, the invention provides a polypeptide that specifically binds human RSPO1, wherein the polypeptide comprises an amino acid sequence having at least about 80% sequence identity to SEQ ID NO:68, and/or an amino acid sequence having at least about 80% sequence identity to SEQ ID NO:69. In certain embodiments, the polypeptide comprises an amino acid sequence having at least about 85%, at least about 90%, at least about 95%, at least about 97%, or at least about 99% sequence identity to SEQ ID NO:68. In certain embodiments, the polypeptide comprises an amino acid sequence having at least about 85%, at least about 90%, at least about 95%, at least about 97%, or at least about 99% sequence identity to SEQ ID NO:69. In certain embodiments, the polypeptide comprises an amino acid sequence having at least about 95% sequence identity to SEQ ID NO:68, and/or an amino acid sequence having at least about 95% sequence identity to SEQ ID NO:69. In certain embodiments, the polypeptide comprises an amino acid sequence comprising SEQ ID NO:68, and/or an amino acid sequence comprising SEQ ID NO:69. In certain embodiments, the polypeptide consists essentially of SEQ ID NO:68, and/or SEQ ID NO:69.

In some embodiments, the invention provides a polypeptide that specifically binds human RSPO2, wherein the polypeptide comprises an amino acid sequence having at least about 80% sequence identity to SEQ ID NO:41, and/or an amino acid sequence having at least about 80% sequence identity to SEQ ID NO:42. In certain embodiments, the polypeptide comprises an amino acid sequence having at least about 85%, at least about 90%, at least about 95%, at least about 97%, or at least about 99% sequence identity to SEQ ID NO:41. In certain embodiments, the polypeptide comprises an amino acid sequence having at least about 85%, at least about 90%, at least about 95%, at least about 97%, or at least about 99% sequence identity to SEQ ID NO:42. In certain embodiments, the polypeptide comprises an amino acid sequence having at least about 95% sequence identity to SEQ ID NO:41, and/or an amino acid sequence having at least about 95% sequence identity to SEQ ID NO:42. In certain embodiments, the polypeptide comprises an amino acid sequence comprising SEQ ID NO:41, and/or an amino acid sequence comprising SEQ ID NO:42. In certain embodiments, the polypeptide consists essentially of SEQ ID NO:41, and/or SEQ ID NO:42.

In some embodiments, the invention provides a polypeptide that specifically binds human RSPO2, wherein the polypeptide comprises an amino acid sequence having at least about 80% sequence identity to SEQ ID NO:70, and/or an amino acid sequence having at least about 80% sequence identity to SEQ ID NO:71 or SEQ ID NO:74. In certain embodiments, the polypeptide comprises an amino acid sequence having at least about 85%, at least about 90%, at least about 95%, at least about 97%, or at least about 99% sequence identity to SEQ ID NO:70. In certain embodiments, the polypeptide comprises an amino acid sequence having at least about 85%, at least about 90%, at least about 95%, at least about 97%, or at least about 99% sequence identity to SEQ ID NO:71 or SEQ ID NO:74. In certain embodiments, the polypeptide comprises an amino acid sequence having at least about 95% sequence identity to SEQ ID NO:70, and/or an amino acid sequence having at least about 95% sequence identity to SEQ ID NO:71 or SEQ ID NO:74. In certain embodiments, the polypeptide comprises an amino acid sequence comprising SEQ ID NO:70, and/or an amino acid sequence comprising SEQ ID NO:71. In certain embodiments, the polypeptide comprises an amino acid sequence comprising SEQ ID NO:70, and/or an amino acid sequence comprising SEQ ID NO:74. In certain embodiments, the polypeptide consists essentially of SEQ ID NO:70, and/or SEQ ID NO:71. In certain embodiments, the polypeptide consists essentially of SEQ ID NO:70, and/or SEQ ID NO:74.

In some embodiments, a RSPO1-binding agent comprises a polypeptide comprising a sequence selected from the group consisting of: SEQ ID NO: 10, SEQ ID NO: 11, SEQ ID NO:21, SEQ ID NO:22, SEQ ID NO:25, SEQ ID NO:26, SEQ ID NO:53, SEQ ID NO:55, SEQ ID NO:57, SEQ ID NO:59, SEQ ID NO:68, and SEQ ID NO:69. In some embodiments, a RSPO2-binding agent comprises a polypeptide comprising a sequence selected from the group consisting of: SEQ ID NO:27, SEQ ID NO:28, SEQ ID NO:37, SEQ ID NO:38, SEQ ID NO:41, SEQ ID NO:42, SEQ ID NO:61, SEQ ID NO:63, SEQ ID NO:65, SEQ ID NO:67, SEQ ID NO:70, SEQ ID NO:71, SEQ ID NO:73, SEQ ID NO:74, and SEQ ID NO:76.

In certain embodiments, a RSPO1-binding agent comprises the heavy chain variable region and light chain variable region of the 89M5 antibody. In certain embodiments, a RSPO1-binding agent comprises the heavy chain and light chain of the 89M5 antibody (with or without the leader sequence). In certain embodiments, a RSPO1-binding agent is the 89M5 antibody. In certain embodiments, a RSPO1-binding agent comprises the heavy chain variable region and/or light chain variable region of the 89M5 antibody in a humanized form of the antibody. In certain embodiments, the RSPO1-binding agent comprises the heavy chain variable region and/or light chain variable region of the h89M5-H2L2 antibody. In certain embodiments, a RSPO1-binding agent comprises the heavy chain and light chain of the 89M5 antibody (with or without the leader sequence) in a humanized form of the antibody. In certain embodiments, a RSPO1-binding agent comprises the heavy chain and light chain of the h89M5-H2L2 antibody (with or without the leader sequence). In some embodiments, the humanized version of 89M5 is an IgG1 antibody. In some embodiments, the humanized version of 89M5 is an IgG2 antibody. The hybridoma cell line producing the 89M5 antibody was deposited with the American Type Culture Collection (ATCC), 10801 University Boulevard, Manassas, Va., USA, under the conditions of the Budapest Treaty on Jun. 30, 2011 and assigned ATCC deposit designation number PTA-11970.

In certain embodiments, a RSPO1-binding agent comprises, consists essentially of, or consists of, the antibody 89M5. In certain embodiments, a RSPO1-binding agent comprises, consists essentially of, or consists of, the antibody h89M5-H2L2.

In certain embodiments, a RSPO2-binding agent comprises the heavy chain variable region and light chain variable region of the 130M23 antibody. In certain embodiments, a RSPO2-binding agent comprises the heavy chain and light chain of the 130M23 antibody (with or without the leader sequence). In certain embodiments, a RSPO2-binding agent is the 130M23 antibody. In certain embodiments, a RSPO2- binding agent comprises the heavy chain variable region and/or light chain variable region of the 130M23 antibody in a humanized form of the antibody. In certain embodiments, the RSPO2-binding agent comprises the heavy chain variable region and/or light chain variable region of the h130M23-H1L2 antibody. In certain embodiments, the RSPO2-binding agent comprises the heavy chain variable region and/or light chain variable region of the h130M23-H1L6 antibody. In certain embodiments, a RSPO2-binding agent comprises the heavy chain and light chain of the 130M23 antibody (with or without the leader sequence) in a humanized form of the antibody. In certain embodiments, a RSPO2-binding agent comprises the heavy chain and light chain of the h130M23-H1L2 antibody (with or without the leader sequence). In certain embodiments, a RSPO2-binding agent comprises the heavy chain and light chain of the h130M23-H1L6 antibody (with or without the leader sequence). In some embodiments, the humanized version of 130M23 is an IgG1 antibody. In some embodiments, the humanized version of 130M23 is an IgG2 antibody. The hybridoma cell line producing the 130M23 antibody was deposited with the American Type Culture Collection (ATCC), 10801 University Boulevard, Manassas, Va., USA, under the conditions of the Budapest Treaty on Aug. 10, 2011 and assigned ATCC deposit designation number PTA-12021.

In certain embodiments, a RSPO2-binding agent comprises, consists essentially of, or consists of, the antibody 130M23. In certain embodiments, a RSPO2-binding agent comprises, consists essentially of, or consists of, the antibody h130M23-H1L2. In certain embodiments, a RSPO2-binding agent comprises, consists essentially of, or consists of, the antibody h130M23-H1L6.

Many proteins, including antibodies, contain a signal sequence that directs the transport of the proteins to various locations. Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell's outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or may be used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides as described herein may comprise a mixture of polypeptides with different N-termini. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions as compared to a "native" or "parental" signal sequence. In some embodiments, the signal sequence of the polypeptide comprises amino acid substitutions and/or deletions that allow one cleavage site to be dominant, thereby resulting in a substantially homogeneous polypeptide with one N-terminus. In some embodiments, the signal sequence of the polypeptide is replaced with a different signal sequence. In some embodiments, a signal sequence of the polypeptide affects the expression level of the polypeptide. In some embodiments, a signal sequence of the polypeptide increases the expression level of the polypeptide. In some embodiments, a signal sequence of the polypeptide decreases the expression level of the polypeptide.

In certain embodiments, a RSPO1-binding agent (e.g., antibody) competes for specific binding to RSPO1 with an antibody that comprises a heavy chain variable region comprising SEQ ID NO: 10 and a light chain variable region comprising SEQ ID NO:11. In certain embodiments, a RSPO1-binding agent (e.g., antibody) competes for specific binding to RSPO1 with an antibody that comprises a heavy chain variable region comprising SEQ ID NO:55 and a light chain variable region comprising SEQ ID NO:59. In certain embodiments, a RSPO1-binding agent (e.g., antibody) competes for specific binding to RSPO1 with an antibody that comprises a heavy chain comprising SEQ ID NO:25 and a light chain comprising SEQ ID NO:26. In certain embodiments, a RSPO1-binding agent (e.g., antibody) competes for specific binding to RSPO1 with an antibody that comprises a heavy chain comprising SEQ ID NO:68 and a light chain comprising SEQ ID NO:69. In certain embodiments, a RSPO1-binding agent competes with antibody 89M5 or h89M5-H2L2 for specific binding to human RSPO1. In some embodiments, a RSPO1-binding agent or antibody competes for specific binding to RSPO1 in an in vitro competitive binding assay. In some embodiments, the RSPO1 is human RSPO1. In some embodiments, the RSPO1 is mouse RSPO1.

In certain embodiments, a RSPO1-binding agent (e.g., an antibody) binds the same epitope, or essentially the same epitope, on RSPO1 as an antibody of the invention. In another embodiment, a RSPO1-binding agent is an antibody that binds an epitope on RSPO1 that overlaps with the epitope on RSPO1 bound by an antibody of the invention. In certain embodiments, a RSPO 1-binding agent (e.g., an antibody) binds the same epitope, or essentially the same epitope, on RSPO1 as antibody 89M5 or h89M5-H2L2. In another embodiment, the RSPO1-binding agent is an antibody that binds an epitope on RSPO1 that overlaps with the epitope on RSPO1 bound by antibody 89M5 or h89M5-H2L2.

In certain embodiments, the RSPO1-binding agent is an agent that competes for specific binding to RSPO1 with an antibody produced by the hybridoma having ATCC deposit designation number PTA-11970 (e.g., in a competitive binding assay).

In certain embodiments, a RSPO2-binding agent (e.g., antibody) competes for specific binding to RSPO2 with an antibody that comprises a heavy chain variable region comprising SEQ ID NO:27 and a light chain variable region comprising SEQ ID NO:28. In certain embodiments, a RSPO2-binding agent (e.g., antibody) competes for specific binding to RSPO2 with an antibody that comprises a heavy chain variable region comprising SEQ ID NO:63 and a light chain variable region comprising SEQ ID NO:67 or SEQ ID NO:76. In certain embodiments, a RSPO2-binding agent (e.g., antibody) competes for specific binding to RSPO2 with an antibody that comprises a heavy chain comprising SEQ ID NO:41 and a light chain comprising SEQ ID NO:42. In certain embodiments, a RSPO2-binding agent (e.g., antibody) competes for specific binding to RSPO2 with an antibody that comprises a heavy chain comprising SEQ ID NO:70 and a light chain comprising SEQ ID NO:71 or SEQ ID NO:74. In certain embodiments, a RSPO2-binding agent competes with antibody 130M23, h130M23-H1L2, or h130M23-H1L6 for specific binding to human RSPO2. In some embodiments, a RSPO2-binding agent or antibody competes for specific binding to RSPO2 in an in vitro competitive binding assay. In some embodiments, the RSPO2 is human RSPO2. In some embodiments, the RSPO2 is mouse RSPO2.

In certain embodiments, a RSPO2-binding agent (e.g., an antibody) binds the same epitope, or essentially the same epitope, on RSPO2 as an antibody of the invention. In another embodiment, a RSPO2-binding agent is an antibody that binds an epitope on RSPO2 that overlaps with the epitope on RSPO2 bound by an antibody of the invention. In certain embodiments, a RSPO2-binding agent (e.g., an antibody) binds the same epitope, or essentially the same epitope, on RSPO2 as antibody 130M23, h130M23-H1L2, or h130M23-H1L6. In another embodiment, the RSPO2-binding agent is an antibody that binds an epitope on RSPO2 that overlaps with the epitope on RSPO2 bound by antibody 130M23, h130M23-H1L2, or h130M23-H1L6.

In certain embodiments, the RSPO2-binding agent is an agent that competes for specific binding to RSPO2 with an antibody produced by the hybridoma having ATCC deposit designation number PTA-12021 (e.g., in a competitive binding assay).

In certain embodiments, the RSPO-binding agent (e.g., an antibody) described herein binds at least one human RSPO protein and modulates RSPO activity. In some embodiments, the RSPO-binding agent is a RSPO antagonist and decreases RSPO activity. In some embodiments, the RSPO-binding agent is a RSPO antagonist and decreases β-catenin activity.

In certain embodiments, a RSPO1-binding agent (e.g., an antibody) described herein binds human RSPO1 and modulates RSPO1 activity. In some embodiments, a RSPO1-binding agent is a RSPO1 antagonist and decreases RSPO1 activity. In some embodiments, a RSPO1-binding agent is a RSPO1 antagonist and decreases β-catenin activity.

In certain embodiments, a RSPO2-binding agent (e.g., an antibody) described herein binds human RSPO2 and modulates RSPO2 activity. In some embodiments, a RSPO2-binding agent is a RSPO2 antagonist and decreases RSPO2 activity. In some embodiments, a RSPO2-binding agent is a RSPO2 antagonist and decreases β-catenin activity.

In certain embodiments, a RSPO3-binding agent (e.g., an antibody) described herein binds human RSPO3 and modulates RSPO3 activity. In some embodiments, a RSPO3-binding agent is a RSPO3 antagonist and decreases RSPO3 activity. In some embodiments, a RSPO3-binding agent is a RSPO3 antagonist and decreases β-catenin activity.

In certain embodiments, the RSPO-binding agent (e.g., an antibody) is an antagonist of at least one human RSPO protein. In some embodiments, the RSPO-binding agent is an antagonist of at least one RSPO and inhibits RSPO activity. In certain embodiments, the RSPO-binding agent inhibits RSPO activity by at least about 10%, at least about 20%, at least about 30%, at least about 50%, at least about 75%, at least about 90%, or about 100%. In some embodiments, the RSPO-binding agent inhibits activity of one, two, three, or four RSPO proteins. In some embodiments, the RSPO-binding agent inhibits activity of human RSPO1, RSPO2, RSPO3, and/or RSPO4. In certain embodiments, a RSPO1-binding agent that inhibits human RSPO1 activity is antibody 89M5 or h89M5-H2L2. In certain embodiments, a RSPO2-binding agent that inhibits human RSPO2 activity is antibody 130M23, h130M23-H1L2, or h130M23-H1L6.

In certain embodiments, the RSPO-binding agent (e.g., antibody) is an antagonist of at least one human RSPO protein. In certain embodiments, the RSPO-binding agent inhibits RSPO signaling by at least about 10%, at least about 20%, at least about 30%, at least about 50%, at least about 75%, at least about 90%, or about 100%. In some embodiments, the RSPO-binding agent inhibits signaling by one, two, three, or four RSPO proteins. In some embodiments, the RSPO-binding agent inhibits signaling of human RSPO1, RSPO2, RSPO3, and/or RSPO4. In certain embodiments, a RSPO1-binding agent that inhibits RSPO1 signaling is antibody 89M5 or h89M5-H2L2. In certain embodiments, a RSPO2-binding agent that inhibits RSPO2 signaling is antibody 130M23, h130M23-H1L2, or h130M23-H1L6.

In certain embodiments, the RSPO-binding agent (e.g., antibody) is an antagonist of β-catenin signaling. In certain embodiments, the RSPO-binding agent inhibits β-catenin signaling by at least about 10%, at least about 20%, at least about 30%, at least about 50%, at least about 75%, at least about 90%, or about 100%. In certain embodiments, a RSPO1-binding agent that inhibits β-catenin signaling is antibody 89M5 or h89M5-H2L2. In certain embodiments, a RSPO2-binding agent that inhibits β-catenin signaling is antibody 130M23, h130M23-H1L2, or h130M23-H1L6.

In certain embodiments, the RSPO-binding agent (e.g., antibody) inhibits binding of at least one RSPO protein to a receptor. In certain embodiments, the RSPO-binding agent inhibits binding of a human RSPO protein to one or more of its receptors. In some embodiments, the RSPO-binding agent inhibits binding of a RSPO protein to at least one LGR protein. In some embodiments, the RSPO-binding agent inhibits binding of a RSPO protein to LGR4, LGR5, and/or LGR6. In some embodiments, a RSPO1-binding agent inhibits binding of RSPO1 to LGR4. In some embodiments, a RSPO1-binding agent inhibits binding of RSPO1 to LGR5. In some embodiments, a RSPO1-binding agent inhibits binding of RSPO1 to LGR6. In some embodiments, a RSPO2-binding agent inhibits binding of RSPO2 to LGR4. In some embodiments, a RSPO2-binding agent inhibits binding of RSPO2 to LGR5. In some embodiments, a RSPO2-binding agent inhibits binding of RSPO2 to LGR6. In certain embodiments, the inhibition of binding of a RSPO-binding agent to at least one LGR protein is at least about 10%, at least about 25%, at least about 50%, at least about 75%, at least about 90%, or at least about 95%. In certain embodiments, a RSPO-binding agent that inhibits binding of at least one RSPO to at least one LGR protein further inhibits β-catenin signaling. In certain embodiments, a RSPO1-binding agent that inhibits binding of human RSPO1 to at least one LGR protein is antibody 89M5 or h89M5-H2L2. In certain embodiments, a RSPO2-binding agent that inhibits binding of human RSPO2 to at least one LGR protein is antibody 130M23, h130M23-H1L2, or h130M23-H1L6.

In certain embodiments, the RSPO-binding agent (e.g., antibody) blocks binding of at least one RSPO to a receptor. In certain embodiments, the RSPO-binding agent blocks binding of a human RSPO protein to one or more of its receptors. In some embodiments, the RSPO-binding agent blocks binding of a RSPO to at least one LGR protein. In some embodiments, the RSPO-binding agent blocks binding of at least one RSPO protein to LGR4, LGR5, and/or LGR6. In some embodiments, a RSPO1-binding agent blocks binding of RSPO1 to LGR4. In some embodiments, a RSPO1-binding agent blocks binding of RSPO1 to LGR5. In some embodiments, a RSPO1-binding agent blocks binding of RSPO1 to LGR6. In some embodiments, a RSPO2-binding agent blocks binding of RSPO2 to LGR4. In some embodiments, a RSPO2-binding agent blocks binding of RSPO2 to LGR5. In some embodiments, a RSPO2-binding agent blocks binding of RSPO2 to LGR6. In certain embodiments, the blocking of binding of a RSPO-binding agent to at least one LGR protein is at least about 10%, at least about 25%, at least about 50%, at least about 75%, at least about 90%, or at least about 95%. In certain embodiments, a RSPO-binding agent that blocks binding of at least one RSPO protein to at least one LGR protein further inhibits β-catenin signaling. In certain embodiments, a RSPO1-binding agent that blocks binding of human RSPO1 to at least one LGR protein is antibody 89M5 or h89M5-H2L2. In certain embodiments, a RSPO2-binding agent that blocks binding of human RSPO2 to at least one LGR protein is antibody 130M23, h130M23-H1L2, or h130M23-H1L6.

In certain embodiments, the RSPO-binding agent (e.g., an antibody) inhibits β-catenin signaling. It is understood that a RSPO-binding agent that inhibits β-catenin signaling may, in certain embodiments, inhibit signaling by one or more receptors in the β-catenin signaling pathway but not necessarily inhibit signaling by all receptors. In certain alternative embodiments, β-catenin signaling by all human receptors may be inhibited. In certain embodiments, β-catenin signaling by one or more receptors selected from the group consisting of LGR4, LGR5, and LGR6 is inhibited. In certain embodiments, the inhibition of β-catenin signaling by a RSPO-binding agent is a reduction in the level of β-catenin signaling of at least about 10%, at least about 25%, at least about 50%, at least about 75%, at least about 90%, or at least about 95%. In some embodiments, a RSPO1-binding agent that inhibits β-catenin signaling is antibody 89M5 or h89M5-H2L2. In some embodiments, a RSPO2-binding agent that inhibits β-catenin signaling is antibody 130M23, h130M23-H1L2, or h130M23-H1L6.

In certain embodiments, the RSPO-binding agent (e.g., an antibody) inhibits activation of 3-catenin. It is understood that a RSPO-binding agent that inhibits activation of β-catenin may, in certain embodiments, inhibit activation of β-catenin by one or more receptors, but not necessarily inhibit activation of β-catenin by all receptors. In certain alternative embodiments, activation of β-catenin by all human receptors may be inhibited. In certain embodiments, activation of β-catenin by one or more receptors selected from the group consisting of LGR4, LGR5, and LGR6 is inhibited. In certain embodiments, the inhibition of activation of t-catenin by a RSPO-binding agent is a reduction in the level of activation of β-catenin of at least about 10%, at least about 25%, at least about 50%, at least about 75%, at least about 90%, or at least about 95%. In some embodiments, a RSPO1-binding agent that inhibits activation of β-catenin is antibody 89M5 or h89M5-H2L2. In some embodiments, a RSPO2-binding agent that inhibits activation of β-catenin is antibody 130M23, h130M23-H1L2, or h130M23-H1L6.

In vivo and in vitro assays for determining whether a RSPO-binding agent (or candidate RSPO-binding agent) inhibits β-catenin signaling are known in the art. For example, cell-based, luciferase reporter assays utilizing a TCF/Luc reporter vector containing multiple copies of the TCF-binding domain upstream of a firefly luciferase reporter gene may be used to measure β-catenin signaling levels in vitro (Gazit et al., 1999, *Oncogene,* 18; 5959-66; TOPflash, Millipore, Billerica Mass.). The level of β-catenin signaling in the presence of one or more Wnts (e.g., Wnt(s) expressed by transfected cells or provided by Wnt-conditioned media) with or without a RSPO protein or RSPO-conditioned media in the presence of a RSPO-binding agent is compared to the level of signaling without the RSPO-binding agent present. In addition to the TCF/Luc reporter assay, the effect of a RSPO-binding agent (or candidate agent) on β-catenin signaling may be measured in vitro or in vivo by measuring the effect of the agent on the level of expression of β-catenin-regulated genes, such as c-myc (He et al., 1998, *Science,* 281:1509-12), cyclin DI (Tetsu et al., 1999, *Nature,* 398:422-6) and/or fibronectin (Gradl et al. 1999, *Mol. Cell Biol.,* 19:5576-87). In certain embodiments, the effect of a RSPO-binding agent on β-catenin signaling may also be assessed by measuring the effect of the agent on the phosphorylation state of Dishevelled-1, Dishevelled-2, Dishevelled-3, LRP5, LRP6, and/or β-catenin.

In certain embodiments, the RSPO-binding agents have one or more of the following effects: inhibit proliferation of tumor cells, inhibit tumor growth, reduce the tumorigenicity of a tumor, reduce the tumorigenicity of a tumor by reducing the frequency of cancer stem cells in the tumor, inhibit tumor growth, trigger cell death of tumor cells, induce cells in a tumor to differentiate, differentiate tumorigenic cells to a non-tumorigenic state, induce expression of differentiation markers in the tumor cells, prevent metastasis of tumor cells, or decrease survival of tumor cells.

In certain embodiments, the RSPO-binding agents are capable of inhibiting tumor growth. In certain embodiments, the RSPO-binding agents are capable of inhibiting tumor growth in vivo (e.g., in a xenograft mouse model, and/or in a human having cancer).

In certain embodiments, the RSPO-binding agents are capable of reducing the tumorigenicity of a tumor. In certain embodiments, the RSPO-binding agent or antibody is capable of reducing the tumorigenicity of a tumor comprising cancer stem cells in an animal model, such as a mouse xenograft model. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication Number WO 2008/042236, U.S. Patent Publication No. 2008/0064049, and U.S. Patent Publication No. 2008/0178305.

In certain embodiments, the RSPO-binding agents described herein have a circulating half-life in mice, cynomolgus monkeys, or humans of at least about 5 hours, at least about 10 hours, at least about 24 hours, at least about 3 days, at least about 1 week, or at least about 2 weeks. In certain embodiments, the RSPO-binding agent is an IgG (e.g., IgG1 or IgG2) antibody that has a circulating half-life in mice, cynomolgus monkeys, or humans of at least about 5 hours, at least about 10 hours, at least about 24 hours, at least about 3 days, at least about 1 week, or at least about 2 weeks. Methods of increasing (or decreasing) the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0 (see, e.g., U.S. Patent Publication Nos. 2005/0276799, 2007/0148164, and 2007/0122403). Known methods of increasing the circulating half-life of antibody fragments lacking the Fc region include such techniques as PEGylation.

In some embodiments, the RSPO-binding agents are polyclonal antibodies. Polyclonal antibodies can be prepared by any known method. In some embodiments, polyclonal antibodies are raised by immunizing an animal (e.g., a rabbit, rat, mouse, goat, donkey) by multiple subcutaneous or intraperitoneal injections of the relevant antigen (e.g., a purified peptide fragment, full-length recombinant protein, or fusion protein). The antigen can be optionally conjugated to a carrier such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from blood, ascites, and the like, of the immunized animal. The polyclonal antibodies can be purified from serum or ascites according to standard methods in the art including, but not limited to, affinity chromatography, ion-exchange chromatography, gel electrophoresis, and dialysis.

In some embodiments, the RSPO-binding agents are monoclonal antibodies. Monoclonal antibodies can be prepared using hybridoma methods known to one of skill in the art (see e.g., Kohler and Milstein, 1975, *Nature,* 256:495-497). In some embodiments, using the hybridoma method, a mouse, hamster, or other appropriate host animal, is immunized as described above to elicit from lymphocytes the production of antibodies that will specifically bind the immunizing antigen. In some embodiments, lymphocytes can be immunized in vitro. In some embodiments, the immunizing antigen can be a human protein or a portion thereof. In some embodiments, the immunizing antigen can be a mouse protein or a portion thereof.

Following immunization, lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen may be identified by a variety of methods including, but not limited to, immunoprecipitation, immunoblotting, and in vitro binding assay (e.g., flow cytometry, FACS, ELISA, and radioimmunoassay). The hybridomas can be propagated either in in vitro culture using standard methods (J. W. Goding, 1996, *Monoclonal Antibodies: Principles and Practice, 3rd Edition*, Academic Press, San Diego, Calif.) or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art (see e.g., U.S. Pat. No. 4,816,567). The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional techniques. The isolated polynucleotides encoding the heavy and light chains are then cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin proteins. In other embodiments, recombinant monoclonal antibodies, or fragments thereof, can be isolated from phage display libraries expressing CDRs of the desired species (see e.g., McCafferty et al., 1990, *Nature,* 348:552-554; Clackson et al., 1991, *Nature,* 352:624-628; and Marks et al., 1991, *J. Mol. Biol.,* 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted for those regions of, for example, a human antibody to generate a chimeric antibody, or for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against a human RSPO protein is a humanized antibody. Typically, humanized antibodies are human immunoglobulins in which residues from the CDRs are replaced by residues from a CDR of a non-human species (e.g., mouse, rat, rabbit, hamster, etc.) that have the desired specificity, affinity, and/or binding capability using methods known to one skilled in the art. In some embodiments, the Fv framework region residues of a human immunoglobulin are replaced with the corresponding residues in an antibody from a non-human species that has the desired specificity, affinity, and/or binding capability. In some embodiments, the humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domain regions containing all, or substantially all, of the CDRs that correspond to the non-human immunoglobulin whereas all, or substantially all, of the framework regions are those of a human immunoglobulin consensus sequence. In some embodiments, the humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject. One skilled in the art would be able to obtain a functional humanized antibody with reduced immunogenicity following known techniques (see e.g., U.S. Pat. Nos. 5,225,539; 5,585,089; 5,693,761; and 5,693,762).

In certain embodiments, the RSPO-binding agent is a human antibody. Human antibodies can be directly prepared using various techniques known in the art. In some embodiments, immortalized human B lymphocytes immunized in vitro or isolated from an immunized individual that produces an antibody directed against a target antigen can be generated (see, e.g., Cole et al., 1985, *Monoclonal Antibodies and Cancer Therapy*, Alan R. Liss, p. 77; Boemer et al., 1991, *J. Immunol.,* 147:86-95; and U.S. Pat. Nos. 5,750,373; 5,567,610 and 5,229,275). In some embodiments, the human antibody can be selected from a phage library, where that phage library expresses human antibodies (Vaughan et al., 1996, *Nature Biotechnology,* 14:309-314; Sheets et al., 1998, *PNAS,* 95:6157-6162; Hoogenboom and Winter, 1991, *J. Mol. Biol.,* 227:381; Marks et al., 1991, *J. Mol. Biol.,* 222:581). Alternatively, phage display technology can be used to produce human antibodies and antibody fragments in vitro, from immunoglobulin variable domain gene repertoires from unimmunized donors. Techniques for the generation and use of antibody phage libraries are also described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., 2008, *J. Mol. Bio.,* 376:1182-1200. Affinity maturation strategies including, but not limited to, chain shuffling (Marks et al., 1992, *Bio/Technology,* 10:779-783) and site-directed mutagenesis, are known in the art and may be employed to generate high affinity human antibodies.

In some embodiments, human antibodies can be made in transgenic mice that contain human immunoglobulin loci. These mice are capable, upon immunization, of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize at least one human RSPO protein. Bispecific antibodies are capable of specifically recognizing and binding at least two different epitopes. The different epitopes can either be within the same molecule (e.g., two epitopes on human RSPO1) or on different molecules (e.g., one epitope on RSPO1 and one epitope on RSPO2). In some embodiments, the bispecific antibodies are monoclonal human or humanized antibodies. In some embodiments, the antibodies can specifically recognize and bind a first antigen target, (e.g., RSPO1) as well as a second antigen target, such as an effector molecule on a leukocyte (e.g., CD2, CD3, CD28, or B7) or a Fc receptor (e.g., CD64, CD32, or CD16) so as to focus cellular defense mechanisms to the cell expressing the first antigen target. In some embodiments, the antibodies can be used to direct cytotoxic agents to cells which express a particular target antigen. These antibodies possess an antigen-binding arm and an arm which binds a cytotoxic agent or a radionuclide chelator, such as EOTUBE, DPTA, DOTA, or TETA. In certain embodiments, the bispecific antibody specifically binds RSPO1, as well as either an additional RSPO protein selected from the group consisting of RSPO2, RSPO3, and RSPO4. In certain embodiments, the bispecific antibody specifically binds RSPO2, as well as either an additional RSPO protein selected from the group consisting of RSPO1, RSPO3, and RSPO4.

Techniques for making bispecific antibodies are known by those skilled in the art, see for example, Millstein et al., 1983, *Nature,* 305:537-539; Brennan et al., 1985, *Science,* 229:81; Suresh et al., 1986, *Methods in Enzymol.,* 121:120; Traunecker et al., 1991, *EMBO J.,* 10:3655-3659; Shalaby et al., 1992, *J. Exp. Med.,* 175:217-225; Kostelny et al., 1992, *J. Immunol.,* 148:1547-1553; Gruber et al., 1994, *J. Immunol.,* 152:5368; U.S. Pat. No. 5,731,168; and U.S. Patent Publication No. 2011/0123532). Bispecific antibodies can be intact antibodies or antibody fragments. Antibodies with more than two valencies are also contemplated. For example, trispecific antibodies can be prepared (Tutt et al., 1991, *J. Immunol.,* 147:60). Thus, in certain embodiments the antibodies to RSPO1 are multispecific.

In certain embodiments, the antibodies (or other polypeptides) described herein may be monospecific. For example, in certain embodiments, each of the one or more antigen-binding sites that an antibody contains is capable of binding (or binds) a homologous epitope on RSPO proteins. In certain embodiments, an antigen-binding site of a monospecific antibody described herein is capable of binding (or binds), for example, RSPO1 and RSPO2 (i.e., the same epitope is found on both RSPO1 and RSPO2 proteins).

In certain embodiments, the RSPO-binding agent is an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in and secreted from *E. coli* or other host cells, allowing for the production of large amounts of these fragments. In some embodiments, antibody fragments are isolated from antibody phage libraries as discussed herein. For example, methods can be used for the construction of Fab expression libraries (Huse et al., 1989, *Science,* 246:1275-1281) to allow rapid and effective identification of monoclonal Fab fragments with the desired specificity for a RSPO protein or derivatives, fragments, analogs or homologs thereof. In some embodiments, antibody fragments are linear antibody fragments. In certain embodiments, antibody fragments are monospecific or bispecific. In certain embodiments, the RSPO-binding agent is a scFv. Various techniques can be used for the production of single-chain antibodies specific to one or more human RSPOs (see, e.g., U.S. Pat. No. 4,946,778).

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is also contemplated that the heteroconjugate antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the target (i.e., a human RSPO1 or human RSPO2). In this regard, the variable region may comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or rabbit origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification and/or alteration. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with all of the CDRs from the donor variable region to transfer the antigen binding capacity of one variable domain to another. Rather, it may only be necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or increased serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the modified antibodies will comprise domain deleted constructs or variants wherein the entire CH2 domain has been removed (ΔCH2 constructs). In some embodiments, the omitted constant region domain is replaced by a short amino acid spacer (e.g., 10 amino acid residues) that provides some of the molecular flexibility typically imparted by the absent constant region.

In some embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fe binding and thereby increase cancer cell localization and/or tumor penetration. Similarly, it may be desirable to simply delete the part of one or more constant region domains that control a specific effector function (e.g. complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In certain embodiments, the RSPO-binding antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody (e.g., anti-RSPO1 antibody) thereby increasing cancer cell localization and/or tumor penetration. In other embodiments, the constant region modifications increase or reduce the serum half-life of the antibody. In some embodiments, the constant region is modified to eliminate disulfide linkages or oligosaccharide moieties. Modifications to the constant region in accordance with this invention may easily be made using well known biochemical or molecular engineering techniques well within the purview of the skilled artisan.

In certain embodiments, a RSPO-binding agent that is an antibody does not have one or more effector functions. For instance, in some embodiments, the antibody has no ADCC activity, and/or no complement-dependent cytotoxicity (CDC) activity. In certain embodiments, the antibody does not bind an Fc receptor, and/or complement factors. In certain embodiments, the antibody has no effector function.

The present invention further embraces variants and equivalents which are substantially homologous to the chimeric, humanized, and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art and described herein.

Thus, the present invention provides methods for producing an antibody that binds at least one RSPO protein. In some embodiments, the method for producing an antibody that binds at least one RSPO protein comprises using hybridoma techniques. In some embodiments, a method for producing an antibody that binds human RSPO1 is provided. In some embodiments, the method comprises using amino acids 31-263 of human RSPO1. In some embodiments, the method comprises using amino acids 31-263 of SEQ ID NO: 1. In some embodiments, a method for producing an antibody that binds human RSPO2 is provided. In some embodiments, the method comprises using amino acids 22-205 of human RSPO2. In some embodiments, the method comprises using amino acids 22-205 of SEQ ID NO:2. In some embodiments, a method for producing an antibody that binds human RSPO3 is provided. In some embodiments, the method comprises using amino acids 22-272 of human RSPO3. In some embodiments, the method comprises using amino acids 22-272 of SEQ ID NO:3. In some embodiments, the method of generating an antibody that binds at least one human RSPO protein comprises screening a human phage library. The present invention further provides methods of identifying an antibody that binds at least one RSPO protein. In some embodiments, the antibody is identified by screening by FACS for binding to a RSPO protein or a portion thereof. In some embodiments, the antibody is identified by screening using ELISA for binding to a RSPO protein. In some embodiments, the antibody is identified by screening by FACS for blocking of binding of a RSPO protein to a human LGR protein. In some embodiments, the antibody is identified by screening for inhibition or blocking of β-catenin signaling.

In some embodiments, a method of generating an antibody to human RSPO1 protein comprises immunizing a mammal with a polypeptide comprising amino acids 31-263 of human RSPO1. In some embodiments, a method of generating an antibody to human RSPO1 protein comprises immunizing a mammal with a polypeptide comprising at least a portion of amino acids 21-263 of human RSPO1. In some embodiments, the method further comprises isolating antibodies or antibody-producing cells from the mammal. In some embodiments, a method of generating a monoclonal antibody which binds RSPO1 protein comprises: (a) immunizing a mammal with a polypeptide comprising at least a portion of amino acids 21-263 of human RSPO1; (b) isolating antibody producing cells from the immunized mammal; (c) fusing the antibody-producing cells with cells of a myeloma cell line to form hybridoma cells. In some embodiments, the method further comprises (d) selecting a hybridoma cell expressing an antibody that binds RSPO1 protein. In some embodiments, the at least a portion of amino acids 21-263 of human RSPO1 is selected from the group consisting of SEQ ID NOs:5-9. In some embodiments, the at least a portion of amino acids 21-263 of human RSPO1 is SEQ ID NO:9. In some embodiments, the at least a portion of amino acids 21-263 of human RSPO1 is SEQ ID NO:6 or SEQ ID NO:7. In some embodiments, the at least a portion of amino acids 21-263 of human RSPO1 is SEQ ID NO:6 and SEQ ID NO:7. In certain embodiments, the mammal is a mouse. In some embodiments, the antibody is selected using a polypeptide comprising at least a portion of amino acid 21-263 of human RSPO1. In certain embodiments, the polypeptide used for selection comprising at least a portion of amino acids 21-263 of human RSPO1 is selected from the group consisting of SEQ ID NOs:5-9. In some embodiments, the antibody binds RSPO1 and at least one other RSPO protein. In certain embodiments, the at least one other RSPO protein is selected from the group consisting of RSPO2, RSPO3 and RSPO4. In certain embodiments, the antibody binds RSPO1 and RSPO2. In certain embodiments, the antibody binds RSPO1 and RSPO3. In certain embodiments, the antibody binds RSPO1 and RSPO4. In certain embodiments, the antibody binds RSPO1, RSPO2, and RSPO3. In certain embodiments, the antibody binds RSPO1, RSPO2, and RSPO4. In certain embodiments, the antibody binds RSPO1, RSPO3, and RSPO4. In some embodiments, the antibody binds both human RSPO1 and mouse RSPO1.

In some embodiments, a method of generating an antibody to human RSPO2 protein comprises immunizing a mammal with a polypeptide comprising amino acids 22-205 of human RSPO2. In some embodiments, a method of generating an antibody to human RSPO2 protein comprises immunizing a mammal with a polypeptide comprising at least a portion of amino acids 22-243 of human RSPO2. In some embodiments, the method further comprises isolating antibodies or antibody-producing cells from the mammal. In some embodiments, a method of generating a monoclonal antibody which binds RSPO2 protein comprises: (a) immunizing a mammal with a polypeptide comprising at least a portion of amino acids 22-243 of human RSPO2; (b) isolating antibody producing cells from the immunized mammal; (c) fusing the antibody-producing cells with cells of a myeloma cell line to form hybridoma cells. In some embodiments, the method further comprises (d) selecting a hybridoma cell expressing an antibody that binds RSPO2 protein. In some embodiments, the at least a portion of amino acids 22-243 of human RSPO2 is selected from the group consisting of SEQ ID NOs:44-47. In some embodiments, the at least a portion of amino acids 22-243 of human RSPO2 is SEQ ID NO:44. In some embodiments, the at least a portion of amino acids 22-243 of human RSPO2 is SEQ ID NO:45 or SEQ ID NO:46. In some embodiments, the at least a portion of amino acids 22-243 of human RSPO2 is SEQ ID NO:45 and SEQ ID NO:46. In certain embodiments, the mammal is a mouse. In some embodiments, the antibody is selected using a polypeptide comprising at least a portion of amino acid 22-243 of human RSPO2. In certain embodiments, the polypeptide used for selection comprising at least a portion of amino acids 22-243 of human RSPO2 is selected from the group consisting of SEQ ID NOs:44-47. In some embodiments, the antibody binds RSPO2 and at least one other RSPO protein. In certain embodiments, the at least one other RSPO protein is selected from the group consisting of RSPO1, RSPO3 and RSPO4. In certain embodiments, the antibody binds RSPO2 and RSPO1. In certain embodiments, the antibody binds RSPO2 and RSPO3. In certain embodiments, the antibody binds RSPO2 and RSPO4. In certain embodiments, the antibody binds RSPO2, RSPO1, and RSPO3. In certain embodiments, the antibody binds RSPO2, RSPO3, and RSPO4. In certain embodiments, the antibody binds RSPO2, RSPO1, and RSPO4. In some embodiments, the antibody binds both human RSPO2 and mouse RSPO2.

In some embodiments, a method of generating an antibody to human RSPO3 protein comprises immunizing a mammal with a polypeptide comprising amino acids 22-272 of human RSPO3. In some embodiments, a method of generating an antibody to human RSPO3 protein comprises immunizing a mammal with a polypeptide comprising at least a portion of amino acids 22-272 of human RSPO3. In some embodiments, the method further comprises isolating antibodies or antibody-producing cells from the mammal. In some embodiments, a method of generating a monoclonal antibody which binds RSPO3 protein comprises: (a) immunizing a mammal with a polypeptide comprising at least a portion of amino acids 22-272 of human RSPO3; (b) isolating antibody producing cells from the immunized mammal; (c) fusing the antibody-producing cells with cells of a myeloma cell line to form hybridoma cells. In some embodiments, the method further comprises (d) selecting a hybridoma cell expressing an antibody that binds RSPO3 protein. In some embodiments, the at least a portion of amino acids 22-272 of human RSPO3 is selected from the group consisting of SEQ ID NOs:48-51. In some embodiments, the at least a portion of amino acids 22-272 of human RSPO3 is SEQ ID NO:48. In some embodiments, the at least a portion of amino acids 22-272 of human RSPO3 is SEQ ID NO:49 or SEQ ID NO:50. In some embodiments, the at least a portion of amino acids 22-272 of human RSPO3 is SEQ ID NO:49 and SEQ ID NO:50. In certain embodiments, the mammal is a mouse. In some embodiments, the antibody is selected using a polypeptide comprising at least a portion of amino acid 22-272 of human RSPO3. In certain embodiments, the polypeptide used for selection comprising at least a portion of amino acids 22-272 of human RSPO3 is selected from the group consisting of SEQ ID NOs:48-51. In some embodiments, the antibody binds RSPO3 and at least one other RSPO protein. In certain embodiments, the at least one other RSPO protein is selected from the group consisting of RSPO2, RSPO4 and RSPO1. In certain embodiments, the antibody binds RSPO3 and RSPO1. In certain embodiments, the antibody binds RSPO3 and RSPO2. In certain embodiments, the antibody binds RSPO3 and RSPO4. In certain embodiments, the antibody binds RSPO3, RSPO1, and RSPO2. In certain embodiments, the antibody binds RSPO3, RSPO1, and RSPO4. In certain embodiments, the antibody binds RSPO3, RSPO2, and RSPO4. In some embodiments, the antibody binds both human RSPO3 and mouse RSPO3.

In some embodiments, the antibody generated by the methods described herein is a RSPO antagonist. In some embodiments, the antibody generated by the methods described herein inhibits β-catenin signaling.

In some embodiments, a method of producing an antibody to at least one human RSPO protein comprises identifying an antibody using a membrane-bound heterodimeric molecule comprising a single antigen-binding site. In some non-limiting embodiments, the antibody is identified using methods and polypeptides described in International Publication WO 2011/100566, which is incorporated by reference herein in its entirety.

In some embodiments, a method of producing an antibody to at least one human RSPO protein comprises screening an antibody-expressing library for antibodies that bind a human RSPO protein. In some embodiments, the antibody-expressing library is a phage library. In some embodiments, the screening comprises panning. In some embodiments, the antibody-expressing library (e.g., phage library) is screened using at least a portion of amino acids 21-263 of human RSPO1. In some embodiments, antibodies identified in the first screening, are screened again using a different RSPO protein thereby identifying an antibody that binds RSPO1 and a second RSPO protein. In certain embodiments, the polypeptide used for screening comprises at least a portion of amino acids 21-263 of human RSPO1 selected from the group consisting of SEQ ID NOs:5-9. In some embodiments, the antibody identified in the screening binds RSPO1 and at least one other RSPO protein. In certain embodiments, the at least one other RSPO protein is selected from the group consisting of RSPO2, RSPO3 and RSPO4. In certain embodiments, the antibody identified in the screening binds RSPO1 and RSPO2. In certain embodiments, the antibody identified in the screening binds RSPO1 and RSPO3. In certain embodiments, the antibody identified in the screening binds RSPO1 and RSPO4. In some embodiments, the antibody identified in the screening binds both human RSPO1 and mouse RSPO1. In some embodiments, the antibody identified in the screening is a RSPO1 antagonist. In some embodiments, the antibody identified in the screening inhibits β-catenin signaling induced by RSPO1. In some embodiments, the antibody-expressing library (e.g., phage library) is screened using at least a portion of amino acids 22-205 of human RSPO2. In some embodiments, antibodies identified in the first screening, are screened again using a different RSPO protein thereby identifying an antibody that binds RSPO2 and a second RSPO protein. In certain embodiments, the polypeptide used for screening comprises at least a portion of amino acids 22-205 of human RSPO2 selected from the group consisting of SEQ ID NOs:44-47. In some embodiments, the antibody identified in the screening binds RSPO2 and at least one other RSPO protein. In certain embodiments, the at least one other RSPO protein is selected from the group consisting of RSPO 1, RSPO3 and RSPO4. In certain embodiments, the antibody identified in the screening binds RSPO2 and RSPO3. In certain embodiments, the antibody identified in the screening binds RSPO2 and RSPO4. In certain embodiments, the antibody identified in the screening binds RSPO2 and RSPO1. In some embodiments, the antibody identified in the screening binds both human RSPO2 and mouse RSPO2. In some embodiments, the antibody identified in the screening is a RSPO2 antagonist. In some embodiments, the antibody identified in the screening inhibits β-catenin signaling induced by RSPO2.

In certain embodiments, the antibodies described herein are isolated. In certain embodiments, the antibodies described herein are substantially pure.

In some embodiments of the present invention, the RSPO-binding agents are polypeptides. The polypeptides can be recombinant polypeptides, natural polypeptides, or synthetic polypeptides comprising an antibody, or fragment thereof, that bind at least one human RSPO protein. It will be recognized in the art that some amino acid sequences of the invention can be varied without significant effect of the structure or function of the protein. Thus, the invention further includes variations of the polypeptides which show substantial activity or which include regions of an antibody, or fragment thereof, against a human RSPO protein. In some embodiments, amino acid sequence variations of RSPO-binding polypeptides include deletions, insertions, inversions, repeats, and/or other types of substitutions.

The polypeptides, analogs and variants thereof, can be further modified to contain additional chemical moieties not normally part of the polypeptide. The derivatized moieties can improve the solubility, the biological half-life, and/or absorption of the polypeptide. The moieties can also reduce or eliminate any undesirable side effects of the polypeptides and variants. An overview for chemical moieties can be found in *Remington: The Science and Practice of Pharmacy,* $21^{st}$ *Edition,* 2005, University of the Sciences, Philadelphia, Pa.

The isolated polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., 1984, *PNAS,* 81:5662-5066 and U.S. Pat. No. 4,588,585.

In some embodiments, a DNA sequence encoding a polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against a human RSPO protein. For example, recombinant expression vectors can be replicable DNA constructs which have synthetic or cDNA-derived DNA fragments encoding a polypeptide chain of a RSPO-binding agent, an anti-RSPO antibody, or fragment thereof, operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Suitable host cells for expression of a RSPO-binding polypeptide or antibody (or a RSPO protein to use as an antigen) include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described below. Cell-free translation systems may also be employed. Appropriate cloning and expression vectors for use with bacterial, fungal, yeast, and mammalian cellular hosts are described by Pouwels et al. (1985, *Cloning Vectors: A Laboratory Manual*, Elsevier, New York, N.Y.). Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823.

Various mammalian or insect cell culture systems are used to express recombinant polypeptides. Expression of recombinant proteins in mammalian cells can be preferred because such proteins are generally correctly folded, appropriately modified, and completely functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), and HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are well-known to those of skill in the art (see, e.g., Luckow and Summers, 1988, *Bio/Technology,* 6:47).

Thus, the present invention provides cells comprising the RSPO-binding agents described herein. In some embodiments, the cells produce the RSPO-binding agents described herein. In certain embodiments, the cells produce an antibody. In certain embodiments, the cells produce antibody 89M5. In certain embodiments, the cells produce antibody h89M5-H2L2. In certain embodiments, the cells produce antibody 130M23. In certain embodiments, the cells produce antibody h130M23-H1L2. In certain embodiments, the cells produce antibody h130M23-H1L6. In some embodiments, the cell is a hybridoma cell line having ATCC deposit number PTA-11970. In some embodiments, the cell is a hybridoma cell line having ATCC deposit number PTA-12021.

The proteins produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Isolated proteins can also be physically characterized using such techniques as proteolysis, mass spectrometry (MS), nuclear magnetic resonance (NMR), high performance liquid chromatography (HPLC), and x-ray crystallography.

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite media can be employed, including but not limited to, ceramic hydroxyapatite (CHT). In certain embodiments, one or more reverse-phase HPLC steps employing hydrophobic RP-HPLC media, e.g., silica gel having pendant methyl or other aliphatic groups, can be employed to further purify a RSPO-binding agent. Some or all of the foregoing purification steps, in various combinations, can also be employed to provide a homogeneous recombinant protein.

In some embodiments, recombinant protein produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005.

In certain embodiments, the RSPO-binding agent is a polypeptide that is not an antibody. A variety of methods for identifying and producing non-antibody polypeptides that bind with high affinity to a protein target are known in the art. See, e.g., Skerra, 2007, *Curr. Opin. Biotechnol.,* 18:295-304; Hosse et al., 2006, *Protein Science,* 15:14-27; Gill et al., 2006, *Curr. Opin. Biotechnol.,* 17:653-658; Nygren, 2008, *FEBS J.,* 275:2668-76; and Skerra, 2008, *FEBS J.,* 275:2677-83. In certain embodiments, phage display technology may be used to produce and/or identify a RSPO-binding polypeptide. In certain embodiments, the polypeptide comprises a protein scaffold of a type selected from the group consisting of protein A, protein G, a lipocalin, a fibronectin domain, an ankyrin consensus repeat domain, and thioredoxin.

In certain embodiments, the RSPO-binding agents or antibodies can be used in any one of a number of conjugated (i.e. an immunoconjugate or radioconjugate) or non-conjugated forms. In certain embodiments, the antibodies can be used in a non-conjugated form to harness the subject's natural defense mechanisms including complement-dependent cytotoxicity and antibody dependent cellular toxicity to eliminate the malignant or cancer cells.

In some embodiments, the RSPO-binding agent (e.g., an antibody or polypeptide) is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated antibody. A variety of radionuclides are available for the production of radioconjugated antibodies including, but not limited to, $^{90}$Y, $^{125}$I, $^{131}$I, $^{123}$I, $^{111}$In, $^{131}$In, $^{155}$Rh, $^{153}$Sm, $^{67}$Cu, $^{67}$Ga, $^{166}$Ho, $^{177}$Lu, $^{186}$Re, $^{188}$Re and $^{212}$Bi. Conjugates of an antibody and one or more small molecule toxins, such as a calicheamicin, maytansinoids, a trichothene, and CC1065, and the derivatives of these toxins that have toxin activity, can also be used. Conjugates of an antibody and cytotoxic agent are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

III. Polynucleotides

In certain embodiments, the invention encompasses polynucleotides comprising polynucleotides that encode a polypeptide that specifically binds at least one human RSPO or a fragment of such a polypeptide. The term "polynucleotides that encode a polypeptide" encompasses a polynucleotide which includes only coding sequences for the polypeptide as well as a polynucleotide which includes additional coding and/or non-coding sequences. For example, the invention provides a polynucleotide comprising a polynucleotide sequence that encodes an antibody to a human RSPO protein or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotide comprises a polynucleotide encoding a polypeptide comprising a sequence selected from the group consisting of SEQ ID NO: 10, SEQ ID NO: 11, SEQ ID NO:21, SEQ ID NO:22, SEQ ID NO:25, SEQ ID NO:26, SEQ ID NO:53, SEQ ID NO:55, SEQ ID NO:57, SEQ ID NO:59, SEQ ID NO:68, and SEQ ID NO:69. In certain embodiments, the polynucleotide comprises a polynucleotide encoding a polypeptide comprising a sequence selected from the group consisting of SEQ ID NO:27, SEQ ID NO:28, SEQ ID NO:37, SEQ ID NO:38, SEQ ID NO:41, SEQ ID NO:42, SEQ ID NO:61, SEQ ID NO:63, SEQ ID NO:65, SEQ ID NO:67, SEQ ID NO:70, SEQ ID NO:71, SEQ ID NO:73, SEQ ID NO:74, and SEQ ID NO:76. In some embodiments, the polynucleotide comprises a polynucleotide sequence selected from the group consisting of SEQ ID NO: 19, SEQ ID NO:20, SEQ ID NO:23, SEQ ID NO:24, SEQ ID NO:52, SEQ ID NO:54, SEQ ID NO:56 and SEQ ID NO:58. In some embodiments, the polynucleotide comprises a polynucleotide sequence selected from the group consisting of SEQ ID NO:35, SEQ ID NO:36, SEQ ID NO:39, SEQ ID NO:40, SEQ ID NO:60, SEQ ID NO:62, SEQ ID NO:64, SEQ ID NO:66, SEQ ID NO:72, and SEQ ID NO:75.

In some embodiments, a plasmid comprises a polynucleotide comprising SEQ ID NO:52. In some embodiments, a plasmid comprises a polynucleotide comprising polynucleotide sequence SEQ ID NO:56. In some embodiments, a plasmid comprises a polynucleotide comprising polynucleotide sequence SEQ ID NO:60. In some embodiments, a plasmid comprises a polynucleotide comprising polynucleotide sequence SEQ ID NO:64. In some embodiments, a plasmid comprises a polynucleotide comprising polynucleotide sequence SEQ ID NO:72. In some embodiments, a plasmid comprises a polynucleotide that encodes an amino acid sequence comprising SEQ ID NO:68 and/or SEQ ID NO:69. In some embodiments, a plasmid comprises a polynucleotide that encodes an amino acid sequence comprising SEQ ID NO:70 and/or SEQ ID NO:71. In some embodiments, a plasmid comprises a polynucleotide that encodes an amino acid sequence comprising SEQ ID NO:70 and/or SEQ ID NO:74.

In certain embodiments, the polynucleotide comprises a polynucleotide having a nucleotide sequence at least 80% identical, at least 85% identical, at least 90% identical, at least 95% identical, and in some embodiments, at least 96%, 97%, 98% or 99% identical to a polynucleotide comprising a sequence selected from the group consisting of SEQ ID NO:19, SEQ ID NO:20, SEQ ID NO:23, SEQ ID NO:24, SEQ ID NO:52, SEQ ID NO:54, SEQ ID NO:56, and SEQ ID NO:58. In certain embodiments, the polynucleotide comprises a polynucleotide having a nucleotide sequence at least 80% identical, at least 85% identical, at least 90% identical, at least 95% identical, and in some embodiments, at least 96%, 97%, 98% or 99% identical to a polynucleotide comprising a sequence selected from the group consisting of SEQ ID NO:35, SEQ ID NO:36, SEQ ID NO:39, SEQ ID NO:40, SEQ ID NO:60, SEQ ID NO:62, SEQ ID NO:64, SEQ ID NO:66, SEQ ID NO:72, and SEQ ID NO:75. Also provided is a polynucleotide that comprises a polynucleotide that hybridizes to SEQ ID NO: 19, SEQ ID NO:20, SEQ ID NO:23, SEQ ID NO:24, SEQ ID NO:52, SEQ ID NO:54, SEQ ID NO:56, and SEQ ID NO:58, SEQ ID NO:35, SEQ ID NO:36, SEQ ID NO:39, SEQ ID NO:40, SEQ ID NO:60, SEQ ID NO:62, SEQ ID NO:64, SEQ ID NO:66, SEQ ID NO:72, or SEQ ID NO:75. In certain embodiments, the hybridization is under conditions of high stringency.

In some embodiments, an antibody is encoded by a polynucleotide comprising SEQ ID NO:23 and SEQ ID NO:24. In some embodiments, an antibody is encoded by a polynucleotide comprising SEQ ID NO:52 and SEQ ID NO:56. In some embodiments, an antibody is encoded by a polynucleotide comprising SEQ ID NO:39 and SEQ ID NO:40. In some embodiments, an antibody is encoded by a polynucleotide comprising SEQ ID NO:60 and SEQ ID NO:64. In some embodiments, an antibody is encoded by a polynucleotide comprising SEQ ID NO:60 and SEQ ID NO:72.

In certain embodiments, the polynucleotides comprise the coding sequence for the mature polypeptide fused in the same reading frame to a polynucleotide which aids, for example, in expression and secretion of a polypeptide from a host cell (e.g., a leader sequence or signal sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments, the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDDK (SEQ ID NO: 18) which can be used in conjunction with other affinity tags.

The present invention further relates to variants of the hereinabove described polynucleotides encoding, for example, fragments, analogs, and/or derivatives.

In certain embodiments, the present invention provides polynucleotides comprising polynucleotides having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a RSPO-binding agent (e.g., an antibody), or fragment thereof, described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. In some embodiments, nucleotide variants comprise nucleotide sequences which result in expression differences (e.g., increased or decreased expression), even though the amino acid sequence is not changed. Polynucleotide variants can be produced for a variety of reasons, for example, to optimize codon expression for a particular host (i.e., change codons in the human mRNA to those preferred by a bacterial host such as *E. coli*).

In certain embodiments, the polynucleotides are isolated. In certain embodiments, the polynucleotides are substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule.

IV. Methods of Use and Pharmaceutical Compositions

The RSPO-binding agents (including polypeptides and antibodies) of the invention are useful in a variety of applications including, but not limited to, therapeutic treatment methods, such as the treatment of cancer. In certain embodiments, the agents are useful for inhibiting β-catenin signaling, inhibiting tumor growth, inducing differentiation, reducing tumor volume, reducing the frequency of cancer stem cells in a tumor, and/or reducing the tumorigenicity of a tumor. The methods of use may be in vitro, ex vivo, or in vivo methods. In certain embodiments, a RSPO-binding agent or polypeptide or antibody is an antagonist of human RSPO1. In certain embodiments, a RSPO-binding agent or polypeptide or antibody is an antagonist of human RSPO2. In certain embodiments, a RSPO-binding agent or polypeptide or antibody is an antagonist of human RSPO3.

In certain embodiments, the RSPO-binding agents are used in the treatment of a disease associated with activation of β-catenin, increased β-catenin signaling, and/or aberrant β-catenin signaling. In certain embodiments, the disease is a disease dependent upon β-catenin signaling. In certain embodiments, the disease is a disease dependent upon β-catenin activation. In certain embodiments, the RSPO-binding agents are used in the treatment of disorders characterized by increased levels of stem cells and/or progenitor cells. In some embodiments, the methods comprise administering a therapeutically effective amount of a RSPO1-binding agent (e.g., antibody) to a subject. In some embodiments, the methods comprise administering a therapeutically effective amount of a RSPO2-binding agent (e.g., antibody) to a subject. In some embodiments, the methods comprise administering a therapeutically effective amount of a RSPO3-binding agent (e.g., antibody) to a subject. In some embodiments, the subject is human.

The present invention provides methods for inhibiting growth of a tumor using the RSPO-binding agents or antibodies described herein. In certain embodiments, the method of inhibiting growth of a tumor comprises contacting a cell with a RSPO-binding agent (e.g., antibody) in vitro. For example, an immortalized cell line or a cancer cell line is cultured in medium to which is added an anti-RSPO antibody or other agent to inhibit tumor growth. In some embodiments, tumor cells are isolated from a patient sample such as, for example, a tissue biopsy, pleural effusion, or blood sample and cultured in medium to which is added a RSPO-binding agent to inhibit tumor growth.

In some embodiments, the method of inhibiting growth of a tumor comprises contacting the tumor or tumor cells with a RSPO-binding agent (e.g., antibody) in vivo. In certain embodiments, contacting a tumor or tumor cell with a RSPO-binding agent is undertaken in an animal model. For example, a RSPO-binding agent may be administered to immunocompromised mice (e.g. NOD/SCID mice) which have xenografts. In some embodiments, cancer cells or cancer stem cells are isolated from a patient sample such as, for example, a tissue biopsy, pleural effusion, or blood sample and injected into immunocompromised mice that are then administered a RSPO-binding agent to inhibit tumor cell growth. In some embodiments, a RSPO1-binding agent is administered to the animal. In some embodiments, a RSPO2-binding agent is administered to the animal. In some embodiments, a RSPO3-binding agent is administered to the animal. In some embodiments, the RSPO-binding agent is administered at the same time or shortly after introduction of tumorigenic cells into the animal to prevent tumor growth ("preventative model"). In some embodiments, the RSPO-binding agent is administered as a therapeutic after tumors have grown to a specified size ("therapeutic model"). In some embodiments, the RSPO-binding agent is an antibody. In some embodiments, the RSPO-binding agent is an anti-RSPO1 antibody.

In some embodiments, the anti-RSPO1 antibody is antibody 89M5. In some embodiments, the anti-RSPO1 antibody is antibody h89M5-H2L2. In some embodiments, the RSPO-binding agent is an anti-RSPO2 antibody. In some embodiments, the anti-RSPO2 antibody is antibody 130M23. In some embodiments, the anti-RSPO2 antibody is antibody h130M23-H1L2. In some embodiments, the anti-RSPO2 antibody is antibody h130M23-H1L6. In some embodiments, the RSPO-binding agent is an anti-RSPO3 antibody.

In certain embodiments, the method of inhibiting growth of a tumor comprises administering to a subject a therapeutically effective amount of a RSPO-binding agent which comprises a heavy chain CDR1 comprising TGYTMH (SEQ ID NO: 12), a heavy chain CDR2 comprising GINPNNGGTTYNQNFKG (SEQ ID NO: 13), and a heavy chain CDR3 comprising KEFSDGYYFFAY (SEQ ID NO: 14), and/or a light chain CDR1 comprising KASQDVIFAVA (SEQ ID NO: 15), a light chain CDR2 comprising WASTRHT (SEQ ID NO:16), and a light chain CDR3 comprising QQHYSTPW (SEQ ID NO:17). In certain embodiments, the method of inhibiting growth of a tumor comprises administering to a subject a therapeutically effective amount of a RSPO-binding agent which comprises a heavy chain CDR1 comprising SSYAMS (SEQ ID NO:29), a heavy chain CDR2 comprising SISSGGSTYYPDSVKG (SEQ ID NO:30), and a heavy chain CDR3 comprising RGGDPGVYNGDYEDAMDY (SEQ ID NO:31), and/or a light chain CDR1 comprising KASQDVSSAVA (SEQ ID NO:32), a light chain CDR2 comprising WASTRHT (SEQ ID NO:33), and a light chain CDR3 comprising QQHYSTP (SEQ ID NO:34).

In certain embodiments, the method of inhibiting growth of a tumor comprises administering to a subject a therapeutically effective amount of a RSPO-binding agent. In certain embodiments, the subject is a human. In certain embodiments, the subject has a tumor or has had a tumor which was removed. In some embodiments, the subject has a tumor with an elevated expression level of at least one RSPO protein (e.g., RSPO1, RSPO2, or RSPO3). In some embodiments, the RSPO-binding agent is a RSPO1-binding agent. In some embodiments, the RSPO1-binding agent is an antibody. In some embodiments, the RSPO1-binding agent is antibody 89M5. In some embodiments, the anti-RSPO1 antibody is antibody h89M5-H2L2. In some embodiments, the RSPO-binding agent is a RSPO2-binding agent. In some embodiments, the RSPO2-binding agent is an antibody. In some embodiments, the RSPO2-binding agent is antibody 130M23. In some embodiments, the anti-RSPO2 antibody is antibody h130M23-H1L2. In some embodiments, the RSPO-binding agent is a RSPO3-binding agent. In some embodiments, the RSPO3-binding agent is an antibody.

In certain embodiments, the tumor is a tumor in which β-catenin signaling is active. In some embodiments, the tumor is a tumor in which β-catenin signaling is aberrant. In certain embodiments, the tumor comprises an inactivating mutation (e.g., a truncating mutation) in the APC tumor suppressor gene. In certain embodiments, the tumor does not comprise an inactivating mutation in the APC tumor suppressor gene. In some embodiments, the tumor comprises a wild-type APC gene. In some embodiments, the tumor does not comprise an activating mutation in the β-catenin gene. In certain embodiments, a cancer for which a subject is being treated involves such a tumor.

In certain embodiments, the tumor expresses RSPO1 to which a RSPO1-binding agent or antibody binds. In certain embodiments, the tumor has elevated expression levels of RSPO1 or over-expresses RSPO1. In some embodiments, the tumor has a high expression level of RSPO1. In general, the phrase “a tumor has elevated expression levels of” a protein (or similar phrases) refers to expression levels of a protein in a tumor as compared to expression levels of the same protein in normal tissue of the same tissue type. However, in some embodiments, the expression levels of a protein in a tumor are “elevated” or “high” as compared to the average expression level of the protein within a group of tissue types. In some embodiments, the expression levels of a protein in a tumor are “elevated” or “high” as compared to the expression level of the protein in other tumors of the same tissue type or a different tissue type. In certain embodiments, the tumor expresses RSPO2 to which a RSPO2-binding agent or antibody binds. In certain embodiments, the tumor has elevated expression levels of RSPO2 or over-expresses RSPO2. In some embodiments, the tumor has a high expression level of RSPO2. In certain embodiments, the tumor expresses RSPO3 to which a RSPO3-binding agent or antibody binds. In certain embodiments, the tumor has elevated expression levels of RSPO3 or over-expresses RSPO3. In some embodiments, the tumor has a high expression level of RSPO3. In certain embodiments, the tumor expresses RSPO4 to which a RSPO4-binding agent or antibody binds. In certain embodiments, the tumor has elevated expression levels of RSPO4 or over-expresses RSPO4. In some embodiments, the tumor has a high expression level of RSPO4. In some embodiments, the tumor expresses elevated levels of RSPO1, RSPO2, RSPO3, and/or RSPO4 as compared to RSPO levels expressed in normal tissue. In some embodiments, the normal tissue is tissue of the same tissue type as the tumor.

In addition, the invention provides a method of inhibiting growth of a tumor in a subject, comprising administering a therapeutically effective amount of a RSPO-binding agent to the subject. In certain embodiments, the tumor comprises cancer stem cells. In certain embodiments, the frequency of cancer stem cells in the tumor is reduced by administration of the RSPO-binding agent. The invention also provides a method of reducing the frequency of cancer stem cells in a tumor, comprising contacting the tumor with an effective amount of a RSPO-binding agent (e.g., an anti-RSPO antibody). In some embodiments, a method of reducing the frequency of cancer stem cells in a tumor in a subject, comprising administering to the subject a therapeutically effective amount of a RSPO-binding agent (e.g., an anti-RSPO antibody) is provided. In some embodiments, the RSPO-binding agent is an antibody. In some embodiments, the RSPO-binding agent is an anti-RSPO1 antibody. In some embodiments, the anti-RSPO1 antibody is 89M5. In some embodiments, the anti-RSPO1 antibody is antibody h89M5-H2L2. In some embodiments, the RSPO-binding agent is an anti-RSPO2 antibody. In some embodiments, the anti-RSPO2 antibody is 130M23. In some embodiments, the anti-RSPO2 antibody is antibody h130M23-H1L2. In some embodiments, the anti-RSPO2 antibody is antibody h130M23-H1L6. In some embodiments, the RSPO-binding agent is an anti-RSPO3 antibody.

In some embodiments, the tumor is a solid tumor. In certain embodiments, the tumor is a tumor selected from the group consisting of colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is a colorectal tumor. In certain embodiments, the tumor is an ovarian tumor. In some embodiments, the tumor is a lung tumor. In certain embodiments, the tumor is a pancreatic tumor. In some embodiments, the tumor is a colorectal tumor that comprises an inactivating mutation in the APC gene. In some embodiments, the tumor is a colorectal tumor that does not comprise an inactivating mutation in the APC gene. In some embodiments, the tumor is an ovarian tumor with an elevated expression level of RSPO1. In some embodiments, the tumor is a pancreatic tumor with an elevated expression level of RSPO2. In some embodiments, the tumor is a colon tumor with an elevated expression level of RSPO2. In some embodiments, the tumor is a lung tumor with an elevated expression level of RSPO2. In some embodiments, the tumor is a melanoma tumor with an elevated expression level of RSPO2. In some embodiments, the tumor is a breast tumor with an elevated expression level of RSPO2. In some embodiments, the tumor is a lung tumor with an elevated expression level of RSPO3. In some embodiments, the tumor is an ovarian tumor with an elevated expression level of RSPO3. In some embodiments, the tumor is a breast tumor with an elevated expression level of RSPO3. In some embodiments, the tumor is a colon tumor with an elevated expression level of RSPO3. In some embodiments, the tumor is a breast tumor with an elevated expression level of RSPO4. In some embodiments, the tumor is a lung tumor with an elevated expression level of RSPO4. In some embodiments, the tumor is an ovarian tumor with an elevated expression level of RSPO4. In some embodiments, the tumor is an ovarian tumor with a high expression level of RSPO1. In some embodiments, the tumor is a pancreatic tumor with a high expression level of RSPO2. In some embodiments, the tumor is a colon tumor with a high expression level of RSPO2. In some embodiments, the tumor is a lung tumor with a high expression level of RSPO2. In some embodiments, the tumor is a melanoma tumor with a high expression level of RSPO2. In some embodiments, the tumor is a breast tumor with a high expression level of RSPO2. In some embodiments, the tumor is a lung tumor with a high expression level of RSPO3. In some embodiments, the tumor is an ovarian tumor with a high expression level of RSPO3. In some embodiments, the tumor is a breast tumor with a high expression level of RSPO3. In some embodiments, the tumor is a colon tumor with a high expression level of RSPO3. In some embodiments, the tumor is a breast tumor with a high expression level of RSPO4. In some embodiments, the tumor is a lung tumor with a high expression level of RSPO4. In some embodiments, the tumor is an ovarian tumor with a high expression level of RSPO4.

The present invention further provides methods for treating cancer comprising administering a therapeutically effective amount of a RSPO-binding agent to a subject. In certain embodiments, the cancer is characterized by cells expressing elevated levels of at least one RSPO protein as compared to expression levels of the same RSPO protein in normal tissue. In certain embodiments, the cancer is characterized by cells over-expressing RSPO1. In certain embodiments, the cancer is characterized by cells over-expressing RSPO2. In certain embodiments, the cancer is characterized by cells over-expressing RSPO3. In certain embodiments, the cancer over-expresses at least one RSPO protein selected from the group consisting of RSPO1, RSPO2, RSPO3, and/or RSPO4. In certain embodiments, the cancer is characterized by cells expressing β-catenin, wherein the RSPO-binding agent (e.g., an antibody) interferes with RSPO-induced β-catenin signaling and/or activation. In some embodiments, the RSPO-binding agent binds RSPO1, and inhibits or reduces growth of the cancer. In some embodiments, the RSPO-binding agent binds RSPO2, and inhibits or reduces growth of the cancer. In some embodiments, the RSPO-binding agent binds RSPO3, and inhibits or reduces growth of the cancer. In some embodiments, the RSPO-binding agent binds RSPO1, interferes with RSPO1/LGR interactions, and inhibits or reduces growth of the cancer. In some embodiments, the RSPO-binding agent binds RSPO2, interferes with RSPO2/LGR interactions, and inhibits or reduces growth of the cancer. In some embodiments, the RSPO-binding agent binds RSPO3, interferes with RSPO3/LGR interactions, and inhibits or reduces growth of the cancer. In some embodiments, the RSPO-binding agent binds RSPO1, inhibits β-catenin activation, and inhibits or reduces growth of the cancer. In some embodiments, the RSPO-binding agent binds RSPO2, inhibits β-catenin activation, and inhibits or reduces growth of the cancer. In some embodiments, the RSPO-binding agent binds RSPO3, inhibits β-catenin activation, and inhibits or reduces growth of the cancer. In some embodiments, the RSPO-binding agent binds RSPO1, and reduces the frequency of cancer stem cells in the cancer. In some embodiments, the RSPO-binding agent binds RSPO2, and reduces the frequency of cancer stem cells in the cancer. In some embodiments, the RSPO-binding agent binds RSPO3, and reduces the frequency of cancer stem cells in the cancer. In some embodiments, the RSPO-binding agent is an antibody. In some embodiments, the RSPO-binding agent is an anti-RSPO1 antibody. In some embodiments, the anti-RSPO1 antibody is antibody 89M5. In some embodiments, the anti-RSPO1 antibody is antibody h89M5-H2L2. In some embodiments, the RSPO-binding agent is an anti-RSPO2 antibody. In some embodiments, the anti-RSPO2 antibody is antibody 130M23. In some embodiments, the anti-RSPO2 antibody is antibody h130M23-H1L2. In some embodiments, the anti-RSPO2 antibody is antibody h130M23-H1L6. In some embodiments, the RSPO-binding agent is an anti-RSPO3 antibody.

The present invention provides for methods of treating cancer comprising administering a therapeutically effective amount of a RSPO-binding agent to a subject (e.g., a subject in need of treatment). In certain embodiments, the subject is a human. In certain embodiments, the subject has a cancerous tumor. In certain embodiments, the subject has had a tumor removed. In some embodiments, a method of treating cancer comprises administering a therapeutically effective amount of a RSPO-binding agent to a subject, wherein the subject has a tumor that has elevated expression of at least one RSPO protein. In some embodiments, the subject has an ovarian tumor that has elevated expression of RSPO1 and is administered a RSPO1-binding agent. In some embodiments, the subject has an ovarian tumor that has elevated expression of RSPO1 and is administered an anti-RSPO1 antibody. In some embodiments, the subject has an ovarian tumor that has elevated expression of RSPO1 and is administered antibody 89M5. In some embodiments, the subject has an ovarian tumor that has elevated expression of RSPO1 and is administered antibody h89M5-H2L2. In some embodiments, the subject has an ovarian tumor that has elevated expression of RSPO2 and is administered a RSPO2-binding agent. In some embodiments, the subject has an ovarian tumor that has elevated expression of RSPO2 and is administered an anti-RSPO2 antibody. In some embodiments, the subject has an ovarian tumor that has elevated expression of RSPO2 and is administered antibody 130M23. In some embodiments, the subject has an ovarian tumor that has elevated expression of RSPO2 and is administered antibody h130M23-H1L2. In some embodiments, the subject has a pancreatic tumor that has elevated expression of RSPO2 and is administered antibody 130M23. In some embodiments, the subject has a pancreatic tumor that has elevated expression of RSPO2 and is administered antibody h130M23-H1L2. In some embodiments, the subject has a pancreatic tumor that has elevated expression of RSPO2 and is administered antibody h130M23-H1L6. In some embodiments, the subject has a colon tumor that has elevated expression of RSPO2 and is administered antibody 130M23. In some embodiments, the subject has a colon tumor that has elevated expression of RSPO2 and is administered antibody h130M23-H1L2. In some embodiments, the subject has a colon tumor that has elevated expression of RSPO2 and is administered antibody h130M23-H1L6. In some embodiments, the subject has a lung tumor that has elevated expression of RSPO3 and is administered an anti-RSPO3 antibody.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, bladder cancer, glioblastoma, and head and neck cancer. In certain embodiments, the cancer is pancreatic cancer. In certain embodiments, the cancer is ovarian cancer. In certain embodiments, the cancer is colorectal cancer. In certain embodiments, the cancer is breast cancer. In certain embodiments, the cancer is prostate cancer. In certain embodiments, the cancer is lung cancer.

In addition, the invention provides a method of reducing the tumorigenicity of a tumor in a subject, comprising administering to a subject a therapeutically effective amount of a RSPO-binding agent. In certain embodiments, the tumor comprises cancer stem cells. In some embodiments, the tumorigenicity of a tumor is reduced by reducing the frequency of cancer stem cells in the tumor. In some embodiments, the methods comprise using the RSPO1-binding agents, RSPO2-binding agents, or RSPO3-binding agents described herein. In certain embodiments, the frequency of cancer stem cells in the tumor is reduced by administration of a RSPO-binding agent.

In certain embodiments, the methods further comprise a step of determining the level of at least one RSPO protein expression in the tumor or cancer. In some embodiments, the step of determining the level of RSPO expression in the tumor or cancer comprises determining the level of expression of RSPO1, RSPO2, RSPO3, and/or RSPO4. In some embodiments, the level of expression of RSPO1, RSPO2, RSPO3, and/or RSPO4 in a tumor or cancer is compared to the level of expression of RSPO1, RSPO2, RSPO3, and/or RSPO4 in normal tissue. In some embodiments, the level of expression of RSPO1, RSPO2, RSPO3, and/or RSPO4 in a tumor or cancer is compared to pre-determined level of expression of RSPO1, RSPO2, RSPO3, and/or RSPO4 in normal tissue. In certain embodiments, the methods further comprise a step of determining if the tumor or cancer has an inactivating mutation in the APC gene. In some embodiments, the methods further comprise a step of determining if the tumor or cancer has an activating mutation in the β-catenin gene. In some embodiments, determining the level of RSPO expression is done prior to treatment. In some embodiments, the subject is administered a RSPO-binding agent or antibody describe herein if the tumor or cancer has an elevated level of RSPO expression as compared to the expression of the same RSPO protein in normal tissue. For example, in some embodiments, the subject is administered a RSPO1-binding agent (e.g., anti-RSPO1 antibody) if the tumor or cancer has an elevated level of RSPO1 expression as compared to the level of RSPO1 expression in normal tissue. In some embodiments, the subject is administered a RSPO2-binding agent (e.g., anti-RSPO2 antibody) if the tumor or cancer has an elevated level of RSPO2 expression as compared to the level of RSPO2 expression in normal tissue. In some embodiments, the subject is administered a RSPO3-binding agent (e.g., anti-RSPO3 antibody) if the tumor or cancer has an elevated level of RSPO3 expression as compared to the level of RSPO3 expression in normal tissue. If a tumor has elevated expression levels of more than one RSPO protein, the subject is first administered a RSPO-binding agent or antibody to the RSPO protein that is the most over-expressed as compared to normal tissue. In some embodiments, the subject is administered a RSPO-binding agent or antibody describe herein if the tumor or cancer has a mutation in the APC gene.

In addition, the present invention provides methods of identifying a human subject for treatment with an RSPO-binding agent, comprising determining if the subject has a tumor that has an elevated level of RSPO expression as compared to expression of the same RSPO protein in normal tissue. In some embodiments, if the tumor has an elevated level of RSPO expression the subject is selected for treatment with an antibody that specifically binds a RSPO protein. In some embodiments, if selected for treatment, the subject is administered a RSPO-binding agent or antibody describe herein. In some embodiments, if the tumor has an elevated level of more than one RSPO protein, the subject is administered a RSPO-binding agent that binds the RSPO protein with the highest level of expression. In certain embodiments, the subject has had a tumor removed. For example, in some embodiments, the expression level of RSPO1, RSPO2, RSPO3, and/or RSPO4 in a tumor is determined, if the tumor has an elevated level of RSPO1 expression as compared to the level of RSPO1 in normal tissue, the subject is selected for treatment with an antibody that specifically binds RSPO1. If selected for treatment, the subject is administered an anti-RSPO1 antibody describe herein. In some embodiments, the RSPO1-binding agent is antibody 89M5. In some embodiments, the RSPO1-binding agent is antibody h89M5-H2L2. In certain embodiments, the subject has had a tumor removed. In some embodiments, the expression level of RSPO1, RSPO2, RSPO3, and/or RSPO4 in a tumor is determined, if the tumor has an elevated level of RSPO2 expression as compared to the level of RSPO2 in normal tissue, the subject is selected for treatment with an antibody that specifically binds RSPO2. If selected for treatment, the subject is administered an anti-RSPO2 antibody describe herein. In some embodiments, the anti-RSPO2 antibody is antibody 130M23. In some embodiments, the anti-RSPO2 antibody is antibody h130M23-H1L2. In some embodiments, the anti-RSPO2 antibody is antibody h130M23-H1L6. In certain embodiments, the subject has had a tumor removed.

The present invention provides methods of selecting a human subject for treatment with a RSPO-binding agent, comprising determining if the subject has a tumor that has an elevated expression level of at least one RSPO protein, wherein if the tumor has an elevated expression level of at least one RSPO protein, the subject is selected for treatment with an antibody that specifically binds the RSPO protein with the elevated expression level. The present invention provides methods of selecting a human subject for treatment with a RSPO-binding agent, comprising determining if the subject has a tumor that has a high expression level of at least one RSPO protein, wherein if the tumor has a high expression level of at least one RSPO protein, the subject is selected for treatment with an antibody that specifically binds the RSPO protein with the high expression level. In some embodiments, the "elevated" or "high" expression level is in comparison to the expression level of the same RSPO protein in normal tissue of the same tissue type. In some embodiments, the "elevated" or "high" expression level is in comparison to the expression level of the same RSPO protein in other tumors of the same tumor type. In some embodiments, if selected for treatment, the subject is administered a RSPO-binding agent or antibody describe herein. In certain embodiments, the subject has had a tumor removed. In some embodiments, the RSPO-binding agent is a RSPO1-binding agent. In some embodiments, the RSPO1-binding agent is antibody 89M5. In some embodiments, the anti-RSPO1 antibody is antibody h89M5-H2L2. In some embodiments, the RSPO-binding agent is a RSPO2-binding agent. In some embodiments, the RSPO2-binding agent is antibody 130M23. In some embodiments, the anti-RSPO2 antibody is antibody h130M23-H1L2. In some embodiments, the anti-RSPO2 antibody is antibody h130M23-H1L6. In some embodiments, the RSPO-binding agent is a RSPO3-binding agent.

The present invention also provides methods of treating cancer in a human subject, comprising: (a) selecting a subject for treatment based, at least in part, on the subject having a cancer that has an elevated or high expression level of RSPO1, and (b) administering to the subject a therapeutically effective amount of a RSPO1-binding agent described herein. In some embodiments, the RSPO1-binding agent is antibody 89M5. In some embodiments, the RSPO1-binding agent is antibody h89M5-H2L2.

The present invention also provides methods of treating cancer in a human subject, comprising: (a) selecting a subject for treatment based, at least in part, on the subject having a cancer that has an elevated or high expression level of RSPO2, and (b) administering to the subject a therapeutically effective amount of a RSPO2-binding agent described herein. In some embodiments, the RSPO2-binding agent is antibody 130M23. In some embodiments, the RSPO2-binding agent is antibody h130M23-H1L2. In some embodiments, the RSPO2-binding agent is antibody h130M23-H1L6.

The present invention also provides methods of treating cancer in a human subject, comprising: (a) selecting a subject for treatment based, at least in part, on the subject having a cancer that has an elevated or high expression level of RSPO3, and (b) administering to the subject a therapeutically effective amount of a RSPO3-binding agent described herein.

Methods for determining the level of RSPO expression in a cell, tumor or cancer are known by those of skill in the art. These methods include, but are not limited to, PCR-based assays, microarray analyses and nucleotide sequencing (e.g., NextGen sequencing) for nucleic acid expression. Other methods include, but are not limited, Western blot analysis, protein arrays, ELISAs, and FACS for protein expression.

Methods for determining whether a tumor or cancer has an elevated or high level of RSPO expression can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

Methods of treating a disease or disorder in a subject, wherein the disease or disorder is associated with aberrant (e.g., increased levels) β-catenin signaling are further provided. Methods of treating a disease or disorder in a subject, wherein the disease or disorder is characterized by an increased level of stem cells and/or progenitor cells are further provided. In some embodiments, the treatment methods comprise administering a therapeutically effective amount of a RSPO-binding agent, polypeptide, or antibody to the subject. In some embodiments, the RSPO-binding agent is a RSPO1-binding agent. In some embodiments, the RSPO1-binding agent is an antibody. In some embodiments, the RSPO1-binding agent is antibody 89M5. In some embodiments, the RSPO1-binding agent is antibody h89M5-H2L2. In some embodiments, the RSPO-binding agent is a RSPO2-binding agent. In some embodiments, the RSPO2-binding agent is an antibody. In some embodiments, the RSPO2-binding agent is antibody 130M23. In some embodiments, the RSPO2-binding agent is antibody h130M23-H1L2. In some embodiments, the RSPO2-binding agent is antibody h130M23-H1L6. In some embodiments, the RSPO-binding agent is a RSPO3-binding agent. In some embodiments, the RSPO3-binding agent is an antibody.

The invention also provides a method of inhibiting β-catenin signaling in a cell comprising contacting the cell with an effective amount of a RSPO-binding agent. In certain embodiments, the cell is a tumor cell. In certain embodiments, the method is an in vivo method wherein the step of contacting the cell with the RSPO-binding agent comprises administering a therapeutically effective amount of the RSPO-binding agent to the subject. In some embodiments, the method is an in vitro or ex vivo method. In certain embodiments, the RSPO-binding agent inhibits β-catenin signaling. In some embodiments, the RSPO-binding agent inhibits activation of β-catenin. In certain embodiments, the RSPO-binding agent interferes with a RSPO/LGR interaction. In certain embodiments, the LGR is LGR4, LGR5, and/or LGR6. In certain embodiments, the LGR is LGR4. In certain embodiments, the LGR is LGR5. In certain embodiments, the LGR is LGR6. In some embodiments, the RSPO-binding agent is a RSPO1-binding agent. In some embodiments, the RSPO1-binding agent is an antibody. In some embodiments, the RSPO1-binding agent is antibody 89M5. In some embodiments, the RSPO1-binding agent is antibody h89M5-H2L2. In some embodiments, the RSPO-binding agent is a RSPO2-binding agent. In some embodiments, the RSPO2-binding agent is an antibody. In some embodiments, the RSPO2-binding agent is antibody 130M23. In some embodiments, the RSPO2-binding agent is antibody h130M23-H1L2. In some embodiments, the RSPO2-binding agent is antibody h130M23-H1L6. In some embodiments, the RSPO-binding agent is a RSPO3-binding agent. In some embodiments, the RSPO3-binding agent is an antibody.

The use of the RSPO-binding agents, polypeptides, or antibodies described herein to induce the differentiation of cells, including, but not limited to tumor cells, is also provided. In some embodiments, methods of inducing cells to differentiate comprise contacting the cells with an effective amount of a RSPO-binding agent (e.g., an anti-RSPO antibody) described herein. In certain embodiments, methods of inducing cells in a tumor in a subject to differentiate comprise administering a therapeutically effective amount of a RSPO-binding agent, polypeptide, or antibody to the subject. In some embodiments, methods for inducing differentiation markers on tumor cells comprise administering a therapeutically effective amount of a RSPO-binding agent, polypeptide, or antibody. In some embodiments, the tumor is a solid tumor. In some embodiments, the tumor is selected from the group consisting of colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is an ovarian tumor. In certain other embodiments, the tumor is a colon tumor. In some embodiments, the tumor is a lung tumor. In certain embodiments, the method is an in vivo method. In certain embodiments, the method is an in vitro method. In some embodiments, the RSPO-binding agent is a RSPO1-binding agent. In some embodiments, the RSPO1-binding agent is an antibody. In some embodiments, the RSPO1-binding agent is antibody 89M5. In some embodiments, the RSPO-binding agent is a RSPO2-binding agent. In some embodiments, the RSPO2-binding agent is an antibody. In some embodiments, the RSPO2-binding agent is antibody 130M23. In some embodiments, the RSPO-binding agent is a RSPO3-binding agent. In some embodiments, the RSPO3-binding agent is an antibody.

The invention further provides methods of differentiating tumorigenic cells into non-tumorigenic cells comprising contacting the tumorigenic cells with a RSPO-binding agent. In some embodiments, the method comprises administering the RSPO-binding agent to a subject that has a tumor comprising tumorigenic cells or that has had such a tumor removed. In certain embodiments, the tumorigenic cells are ovarian tumor cells. In certain embodiments, the tumorigenic cells are colon tumor cells. In some embodiments, the tumorigenic cells are lung tumor cells. In some embodiments, the RSPO-binding agent is a RSPO1-binding agent. In some embodiments, the RSPO1-binding agent is an antibody. In some embodiments, the RSPO1-binding agent is antibody 89M5. In some embodiments, the RSPO-binding agent is a RSPO2-binding agent. In some embodiments, the RSPO2-binding agent is an antibody. In some embodiments, the RSPO2-binding agent is antibody 130M23. In some embodiments, the RSPO-binding agent is a RSPO3-binding agent. In some embodiments, the RSPO3-binding agent is an antibody.

In certain embodiments, the disease treated with the RSPO-binding agents described herein is not a cancer. For example, the disease may be a metabolic disorder such as obesity or diabetes (e.g., type II diabetes) (Jin T., 2008, *Diabetologia,* 51:1771-80). Alternatively, the disease may be a bone disorder such as osteoporosis, osteoarthritis, or rheumatoid arthritis (Corr M., 2008, *Nat. Clin. Pract. Rheumatol.,* 4:550-6; Day et al., 2008, *Bone Joint Surg. Am.,* 90 Suppi 1:19-24). The disease may also be a kidney disorder, such as a polycystic kidney disease (Harris et al., 2009, *Ann. Rev. Med.,* 60:321-337; Schmidt-Ott et al., 2008, *Kidney Int.,* 74:1004-8; Benzing et al., 2007, *J. Am. Soc. Nephrol.,* 18:1389-98). Alternatively, eye disorders including, but not limited to, macular degeneration and familial exudative vitreoretinopathy may be treated (Lad et al., 2009, *Stem Cells Dev.,* 18:7-16). Cardiovascular disorders, including myocardial infarction, atherosclerosis, and valve disorders, may also be treated (Al-Aly Z., 2008, *Transl. Res.,* 151:233-9; Kobayashi et al., 2009, *Nat. Cell Biol.,* 11:46-55; van Gijn et al., 2002, *Cardiovasc. Res.,* 55:16-24; Christman et al., 2008, *Am. J. Physiol. Heart Circ. Physiol.,* 294:H2864-70). In some embodiments, the disease is a pulmonary disorder such as idiopathic pulmonary arterial hypertension or pulmonary fibrosis (Laumanns et a., 2008, *Am. J. Respir. Cell Mol. Biol.,* 2009, 40:683-691; Königshoff et al., 2008, *PLoS ONE,* 3:e2142). In some embodiments, the disease treated with the RSPO-binding agent is a liver disease, such as cirrhosis or liver fibrosis (Cheng et al., 2008, *Am. J. Physiol. Gastrointest. Liver Physiol.,* 294:G39-49).

The present invention further provides pharmaceutical compositions comprising the RSPO-binding agents described herein. In certain embodiments, the pharmaceutical compositions further comprise a pharmaceutically acceptable vehicle. These pharmaceutical compositions find use in inhibiting tumor growth and treating cancer in a subject (e.g., a human patient).

In certain embodiments, formulations are prepared for storage and use by combining a purified antibody or agent of the present invention with a pharmaceutically acceptable vehicle (e.g., a carrier or excipient). Suitable pharmaceutically acceptable vehicles include, but are not limited to, non-toxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy, 21st Edition,* 2005, University of the Sciences in Philadelphia, Pa.).

The pharmaceutical compositions of the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The RSPO-binding agents or antibodies described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in *Remington: The Science and Practice of Pharmacy, 21st Edition,* 2005, University of the Sciences in Philadelphia, Pa.

In certain embodiments, pharmaceutical formulations include a RSPO-binding agent (e.g., an antibody) of the present invention complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations can be produced. Suitable examples of sustained-release preparations include semi-permeable matrices of solid hydrophobic polymers containing a RSPO-binding agent (e.g., an antibody), where the matrices are in the form of shaped articles (e.g., films or microcapsules). Examples of sustained-release matrices include polyesters, hydrogels such as poly (2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In certain embodiments, in addition to administering a RSPO-binding agent (e.g., an antibody), the method or treatment further comprises administering at least one additional therapeutic agent. An additional therapeutic agent can be administered prior to, concurrently with, and/or subsequently to, administration of the RSPO-binding agent. Pharmaceutical compositions comprising a RSPO-binding agent and the additional therapeutic agent(s) are also provided. In some embodiments, the at least one additional therapeutic agent comprises 1, 2, 3, or more additional therapeutic agents.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistant cancer cells will develop. In some embodiments, combination therapy comprises a therapeutic agent that affects (e.g., inhibits or kills) non-tumorigenic cells and a therapeutic agent that affects (e.g., inhibits or kills) tumorigenic CSCs.

In some embodiments, the combination of a RSPO-binding agent and at least one additional therapeutic agent results in additive or synergistic results. In some embodiments, the combination therapy results in an increase in the therapeutic index of the RSPO-binding agent. In some embodiments, the combination therapy results in an increase in the therapeutic index of the additional agent(s). In some embodiments, the combination therapy results in a decrease in the toxicity and/or side effects of the RSPO-binding agent. In some embodiments, the combination therapy results in a decrease in the toxicity and/or side effects of the additional agent(s).

Useful classes of therapeutic agents include, for example, antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an antimetabolite, an antimitotic, a topoisomerase inhibitor, or an angiogenesis inhibitor. In some embodiments, the second therapeutic agent is a platinum complex such as carboplatin or cisplatin. In some embodiments, the additional therapeutic agent is a platinum complex in combination with a taxane.

Therapeutic agents that may be administered in combination with the RSPO-binding agents include chemotherapeutic agents. Thus, in some embodiments, the method or treatment involves the administration of a RSPO1-binding agent or antibody of the present invention in combination with a chemotherapeutic agent or cocktail of multiple different chemotherapeutic agents. In some embodiments, the method or treatment involves the administration of a RSPO2-binding agent or antibody of the present invention in combination with a chemotherapeutic agent or cocktail of multiple different chemotherapeutic agents. In some embodiments, the method or treatment involves the administration of a RSPO3-binding agent or antibody of the present invention in combination with a chemotherapeutic agent or cocktail of multiple different chemotherapeutic agents. Treatment with a RSPO-binding agent (e.g, an antibody) can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *The Chemotherapy Source Book, 4th Edition,* 2008, M. C. Perry, Editor, Lippincott, Williams & Wilkins, Philadelphia, Pa.

Chemotherapeutic agents useful in the instant invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin. In certain embodiments, the additional therapeutic agent is paclitaxel (taxol). In some embodiments, a method comprises administering anti-RSPO1 antibody 89M5 or h89M5-H2L2 in combination with cisplatin. In some embodiments, a method comprises administering anti-RSPO2 antibody 130M23, h130M23-H1L2, or h130M23-H1L6 in combination with cisplatin.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan. Thus, in some embodiments, a method comprises administering a RSPO1-binding agent in combination with a topoisomerase inhibitor. In some embodiments, a method comprises administering anti-RSPO1 antibody 89M5 or h89M5-H2L2 in combination with irinotecan. In some embodiments, a method comprises administering a RSPO2-binding agent in combination with a topoisomerase inhibitor. In some embodiments, a method comprises administering anti-RSPO2 antibody 130M23 or h130M23-H1L2 in combination with irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine. Thus, in some embodiments, a method comprises administering a RSPO1-binding agent in combination with an anti-metabolite. In some embodiments, a method comprises administering anti-RSPO1 antibody 89M5 or h89M5-H2L2 in combination with gemcitabine. In some embodiments, a method comprises administering a RSPO2-binding agent in combination with an anti-metabolite. In some embodiments, a method comprises administering anti-RSPO2 antibody 130M23, h130M23-H1L2, or h130M23-H1L6 in combination with gemcitabine.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinca alkaloid, such as vincristine, binblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, where the chemotherapeutic agent administered in combination with a RSPO-binding agent is an anti-mitotic agent, the cancer or tumor being treated is breast cancer or a breast tumor.

In some embodiments, an additional therapeutic agent comprises an agent such as a small molecule. For example, treatment can involve the combined administration of a RSPO-binding agent (e.g. an antibody) of the present invention with a small molecule that acts as an inhibitor against additional tumor-associated antigens including, but not limited to, EGFR, ErbB2, HER2, and/or VEGF. In certain embodiments, the additional therapeutic agent is a small molecule that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is a molecule that inhibits β-catenin signaling.

In some embodiments, an additional therapeutic agent comprises a biological molecule, such as an antibody. For example, treatment can involve the combined administration of a RSPO-binding agent (e.g. an antibody) of the present invention with other antibodies against additional tumor-associated antigens including, but not limited to, antibodies that bind EGFR, ErbB2, HER2, and/or VEGF. In some embodiments, the additional therapeutic agent is a second anti-RSPO antibody. In some embodiments, the additional therapeutic agent is an anti-RSPO2 antibody, an anti-RSPO3 antibody, and/or an anti-RSPO4 antibody used in combination with an anti-RSPO1 antibody. In some embodiments, the additional therapeutic agent is an anti-RSPO1 antibody, an anti-RSPO3 antibody, and/or an anti-RSPO4 antibody used in combination with an anti-RSPO2 antibody. In some embodiments, an anti-RSPO1 antibody is used in combination with an anti-RSPO2 antibody. In certain embodiments, the additional therapeutic agent is an antibody specific for an anti-cancer stem cell marker. In some embodiments, the additional therapeutic agent is an antibody that binds a component of the Notch pathway. In some embodiments, the additional therapeutic agent is an antibody that binds a component of the Wnt pathway. In certain embodiments, the additional therapeutic agent is an antibody that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an antibody that inhibits β-catenin signaling. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), trastuzumab (HERCEPTIN), panitumumab (VECTIBIX), or cetuximab (ERBITUX).

In some embodiments, the methods described herein comprise administering a therapeutically effective amount of a RSPO-binding agent in combination with Wnt pathway inhibitors. In some embodiments, the Wnt pathway inhibitors are frizzled (FZD) protein binding agents, "FZD-binding agents". Non-limiting examples of FZD-binding agents can be found in U.S. Pat. No. 7,982,013, which is incorporated by reference herein in its entirety. FZD-binding agents may include, but are not limited to, anti-FZD antibodies. In some embodiments, a method comprises administering a RSPO-binding agent in combination with an anti-FZD antibody. In some embodiments, a method comprises administering a RSPO-binding agent in combination with the anti-FZD antibody 18RS. In some embodiments, the Wnt pathway inhibitors are Wnt protein binding agents, "Wnt-binding agents". Nonlimiting examples of Wnt-binding agents can be found in U.S. Pat. Nos. 7,723,477 and 7,947,277; and International Publications WO 2011/088127 and WO 2011/088123, which are incorporated by reference herein in their entirety. Wnt-binding agents may include, but are not limited to, anti-Wnt antibodies and FZD-Fc soluble receptors. In some embodiments, a method comprises administering a RSPO-binding agent in combination with a FZD-Fc soluble receptor. In some embodiments, a method comprises administering a RSPO-binding agent in combination with a FZD8-Fc soluble receptor. In some embodiments, a method comprises administering a RSPO1-binding agent in combination with an anti-FZD antibody. In some embodiments, a method comprises administering anti-RSPO1 antibody 89M5 or h89M5-H2L2 in combination with an anti-FZD antibody. In some embodiments, a method comprises administering anti-RSPO1 antibody 89M5 or h89M5H2L2 in combination with anti-FZD antibody 18R5. In some embodiments, a method comprises administering anti-RSPO1 antibody 89M5 or h89M5-H2L2 in combination with a FZD-Fc soluble receptor. In some embodiments, a method comprises administering anti-RSPO1 antibody 89M5 or h89M5-H2L2 in combination with a FZD8-Fc soluble receptor. In some embodiments, a method comprises administering a RSPO2-binding agent in combination with an anti-FZD antibody. In some embodiments, a method comprises administering anti-RSPO2 antibody 130M23 or h130M23-H1L2 in combination with an anti-FZD antibody. In some embodiments, a method comprises administering anti-RSPO2 antibody 130M23, h130M23-H1L2, or h130M23-H1L6 in combination with anti-FZD antibody 18R5. In some embodiments, a method comprises administering anti-RSPO2 antibody 130M23, h130M23-H1L2, or h130M23-H1L6 in combination with a FZD-Fc soluble receptor. In some embodiments, a method comprises administering anti-RSPO2 antibody 130M23, h130M23-H1L2, or h130M23-H1L6 in combination with a FZD8-Fc soluble receptor.

In some embodiments, the methods described herein comprise administering a therapeutically effective amount of a RSPO-binding agent in combination with more than one additional therapeutic agent. Thus, in some embodiments, a method comprises administering a RSPO-binding agent in combination with a chemotherapeutic agent and a Wnt pathway inhibitor. In some embodiments, a method comprises administering a RSPO2-binding agent in combination with a chemotherapeutic agent and a Wnt pathway inhibitor. In some embodiments, a method comprises administering a RSPO2-binding agent in combination with a chemotherapeutic agent and anti-FZD antibody 18R5. In some embodiments, a method comprises administering a RSPO2-binding agent in combination with a chemotherapeutic agent and a FZD8-Fc soluble receptor. In some embodiments, a method comprises administering a RSPO2-binding agent in combination with gemcitabine and a Wnt pathway inhibitor. In some embodiments, a method comprises administering anti-RSPO2 antibody 130M23, h130M23-H1L2, or h130M23-H1L6 in combination with gemcitabine and anti-FZD antibody 18R5. In some embodiments, a method comprises administering anti-RSPO2 antibody 130M23, h130M23-H1L2, or h130M23-H1L6 in combination with gemcitabine and FZD8-Fc soluble receptor.

Furthermore, treatment with a RSPO-binding agent described herein can include combination treatment with other biologic molecules, such as one or more cytokines (e.g., lymphokines, interleukins, tumor necrosis factors, and/or growth factors) or can be accompanied by surgical removal of tumors, cancer cells or any other therapy deemed necessary by a treating physician.

In certain embodiments, the treatment involves the administration of a RSPO-binding agent (e.g. an antibody) of the present invention in combination with radiation therapy. Treatment with a RSPO-binding agent can occur prior to, concurrently with, or subsequent to administration of radiation therapy. Dosing schedules for such radiation therapy can be determined by the skilled medical practitioner.

Combined administration can include co-administration, either in a single pharmaceutical formulation or using separate formulations, or consecutive administration in either order but generally within a time period such that all active agents can exert their biological activities simultaneously.

It will be appreciated that the combination of a RSPO-binding agent and at least one additional therapeutic agent may be administered in any order or concurrently. In some embodiments, the RSPO-binding agent will be administered to patients that have previously undergone treatment with a second therapeutic agent. In certain other embodiments, the RSPO-binding agent and a second therapeutic agent will be administered substantially simultaneously or concurrently. For example, a subject may be given a RSPO-binding agent (e.g., an antibody) while undergoing a course of treatment with a second therapeutic agent (e.g., chemotherapy). In certain embodiments, a RSPO-binding agent will be administered within 1 year of the treatment with a second therapeutic agent. In certain alternative embodiments, a RSPO-binding agent will be administered within 10, 8, 6, 4, or 2 months of any treatment with a second therapeutic agent. In certain other embodiments, a RSPO-binding agent will be administered within 4, 3, 2, or 1 weeks of any treatment with a second therapeutic agent. In some embodiments, a RSPO-binding agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of an RSPO-binding agent (e.g., an antibody) of the present invention depends on the type of disease to be treated, the severity and course of the disease, the responsiveness of the disease, whether the RSPO-binding agent or antibody is administered for therapeutic or preventative purposes, previous therapy, the patient's clinical history, and so on, all at the discretion of the treating physician. The RSPO-binding agent or antibody can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody or agent. The administering physician can easily determine optimum dosages, dosing methodologies, and repetition rates. In certain embodiments, dosage is from 0.01 μg to 100 mg/kg of body weight, from 0.1 μg to 100 mg/kg of body weight, from 1 μg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In certain embodiments, the dosage of the antibody or other RSPO-binding agent is from about 0.1 mg to about 20 mg/kg of body weight. In certain embodiments, dosage can be given once or more daily, weekly, monthly, or yearly. In certain embodiments, the antibody or other RSPO-binding agent is given once every week, once every two weeks or once every three weeks.

In some embodiments, a RSPO-binding agent (e.g., an antibody) may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

Thus, the present invention provides methods of treating cancer in a subject comprising using an intermittent dosing strategy for administering one or more agents, which may reduce side effects and/or toxicities associated with administration of a RSPO-binding agent, chemotherapeutic agent, etc. In some embodiments, a method for treating cancer in a human subject comprises administering to the subject a therapeutically effective dose of a RSPO-binding agent in combination with a therapeutically effective dose of a chemotherapeutic agent, wherein one or both of the agents are administered according to an intermittent dosing strategy. In some embodiments, the intermittent dosing strategy comprises administering an initial dose of a RSPO-binding agent to the subject, and administering subsequent doses of the RSPO-binding agent about once every 2 weeks. In some embodiments, the intermittent dosing strategy comprises administering an initial dose of a RSPO-binding agent to the subject, and administering subsequent doses of the RSPO-binding agent about once every 3 weeks. In some embodiments, the intermittent dosing strategy comprises administering an initial dose of a RSPO-binding agent to the subject, and administering subsequent doses of the RSPO-binding agent about once every 4 weeks. In some embodiments, the RSPO-binding agent is administered using an intermittent dosing strategy and the chemotherapeutic agent is administered weekly.

V. Kits Comprising RSPO-binding Agents

The present invention provides kits that comprise the RSPO-binding agents (e.g., antibodies) described herein and that can be used to perform the methods described herein. In certain embodiments, a kit comprises at least one purified antibody against at least one human RSPO protein in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed RSPO-binding agents of the present invention can be readily incorporated into one of the established kit formats which are well known in the art.

Further provided are kits comprising a RSPO-binding agent (e.g., an anti-RSPO antibody), as well as at least one additional therapeutic agent. In certain embodiments, the second (or more) therapeutic agent is a chemotherapeutic agent. In certain embodiments, the second (or more) therapeutic agent is a Wnt pathway inhibitor. In certain embodiments, the second (or more) therapeutic agent is an angiogenesis inhibitor.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXAMPLES

Example 1

Expression of RSPO and LGR in Human Tumors mRNA from normal tissue, benign tumor and malignant tumor samples of a large number of human patients was analyzed by microarray analysis (Genelogic BioExpress Datasuite). This data revealed elevated expression levels of RSPO1 in malignant tissue relative to normal tissue in several tumor types including kidney, endometrial, and ovarian. RSPO1 was noted to be frequently over-expressed in ovarian cancer (FIG. 1A). In addition, this data suggested elevated expression levels of RSPO3 in malignant tissue relative to normal tissue in several tumor types including ovarian, pancreas, and lung (FIG. 1C). In addition, it was found that LGR5 and LGR6 were over-expressed in malignant breast tumors, colon tumors, lung tumors, and ovarian tumors relative to normal tissue, while LGR4 was over-expressed in lung tumors. LGR5 and LGR6 over-expression appeared to be restricted to triple-negative ($ER^{neg}PR^{neg}HER2^{neg}$) breast tumors relative to other breast tumor subtypes.

RNA was isolated from a series of human tumors grown in murine xenografts. The RNA samples were prepared and processed using established Affymetrix protocols for the generation of labeled cRNA. The processed RNA was hybridized to Affymetrix HG-U133 plus 2.0 microarrays (Affymetrix, Santa Clara, Calif.) as outlined in the manufacturer's technical manuals. After hybridization, the microarrays were washed, scanned, and analyzed. Scanned array background adjustment and signal intensity normalization were performed using the GCRMA algorithm (Bioconductor, www-.bioconductor.org).

Particular human RSPOs and human LGRs were evaluated—RSPO1 (241450_at), RSPO2 (1554012_at), RSPO3 (228186_s_at), RSPO4 (237423_at), LGR4 (218326_sat), LGR5 (210393_at) and LGR6 (227819_at). Microarray analysis showed that, while LGR4 and LGR6 were broadly expressed in almost all tumors, many tumors were found to greatly over-express only particular RSPO family members and LGR5 (Table 2), although these expression levels were not compared to expression levels in normal tissue. Generally there is only a single RSPO family member that is highly expressed in a given tumor, suggesting that there may be functional redundancy within the RSPO family.

TABLE 2

| Tumor | RSPO1 | RSPO2 | RSPO3 | RSPO4 | LGR4 | LGR5 | LGR6 |
|---|---|---|---|---|---|---|---|
| Breast tumor | | | | | | | |
| B34 | 4.79 | 4.93 | 303.31 | 4.41 | | | |
| B39 | 20.59 | 588.88 | 22.60 | 4.40 | | | |
| B60 | 4.60 | 4.92 | 10.89 | 64.79 | | | |
| B02 | 4.60 | 4.92 | 692.34 | 4.41 | 2678.95 | 4.28 | 50.88 |
| B03 | 5.56 | 4.89 | 1870.42 | 4.41 | 686.47 | 30.78 | 73.49 |
| B06 | 4.60 | 4.91 | 4.51 | 120.72 | 274.54 | 4.26 | 20.77 |
| B59 | 4.60 | 4.91 | 4.53 | 1158.11 | 200.48 | 4.26 | 6467.15 |

TABLE 2-continued

| Tumor | RSPO1 | RSPO2 | RSPO3 | RSPO4 | LGR4 | LGR5 | LGR6 |
|---|---|---|---|---|---|---|---|
| | | | Colon tumors | | | | |
| C11 | 4.63 | 4.98 | 4.56 | 4.43 | 3852.26 | 6.22 | 11.31 |
| C17 | 4.64 | 5.00 | 4.57 | 4.44 | 2822.46 | 62.34 | 43.94 |
| C18 | 4.63 | 4.95 | 13.83 | 4.42 | 2454.15 | 4.29 | 723.15 |
| C27 | 6.66 | 980.49 | 4.75 | 4.40 | 5083.84 | 4.30 | 20.82 |
| | | | Lung tumors | | | | |
| LU02 | 4.62 | 15190.40 | 4.55 | 4.43 | 13.95 | 4.29 | 14.56 |
| LU11 | 4.60 | 4.92 | 4.53 | 4.41 | 999.55 | 4.27 | 146.67 |
| LU25 | 4.64 | 5.56 | 11123.06 | 4.44 | 1208.92 | 4.29 | 41089 |
| LU33 | 4.64 | 5.01 | 12.02 | 62.98 | 329.62 | 4.30 | 20.96 |
| LU45 | 4.64 | 4.99 | 4.62 | 4.44 | 3877.47 | 4.29 | 4.86 |
| | | | Melanoma tumors | | | | |
| M06 | 4.73 | 21.80 | 4.65 | 4.50 | 1077.93 | 4.34 | 3.90 |
| | | | Ovarian tumors | | | | |
| OV12 | 4.72 | 5.12 | 4.64 | 460.40 | 5383.63 | 1152.73 | 115.04 |
| OV19 | 960.19 | 4.74 | 69.77 | 20.90 | 494.67 | 5.72 | 4302.78 |
| OV22 | 4.66 | 5.10 | 132.85 | 37.43 | 3743.91 | 482.33 | 812.05 |
| OV27 | 4.55 | 4.86 | 125.78 | 4.92 | | | |
| OV38 | 9.19 | 4.83 | 3439.88 | 16.35 | 1528.12 | 4.24 | 19.49 |
| | | | Pancreatic tumors | | | | |
| PN07 | 4.58 | 689.52 | 4.51 | 4.40 | 6777.41 | 4.28 | 746.38 |
| PN18 | 4.72 | 2508.47 | 4.65 | 4.50 | 6750.73 | 51.15 | 564.94 |

Example 2

Binding of RSPO Proteins to LGR5

A cell surface LGR5 protein was generated by ligating amino acids 22-564 of human LGR5 to an N-terminal FLAG tag and to the transmembrane domain of CD4 and a C-terminal GFP protein tag using standard recombinant DNA techniques (FLAG-LGR5-CD4TM-GFP). RSPO-Fc constructs were generated using standard recombinant DNA techniques. Specifically, full-length human RSPO1, RSPO2, RSPO3 and RSPO4 were ligated in-frame to a human Fc region and the recombinant RSPO-Fc proteins were expressed in insect cells using baculovirus. The fusion proteins were purified from the insect medium using protein A chromatography.

HEK-293 cells were transiently transfected with the FLAG-LGR5-CD4TM-GFP construct. After 48 hours, transfected cells were suspended in ice cold PBS containing 2% FBS and heparin and incubated on ice in the presence of 10 μg/ml RSPO1-Fc, RSPO2-Fc, RSPO3-Fc, RSPO4-Fc, or FZD8-Fc fusion proteins for 15 minutes. A second incubation with 100 μl PE-conjugated anti-human Fe secondary antibody was performed to detect cells bound by the Fc fusion proteins. Cells were incubated with an anti-FLAG antibody (Sigma-Aldrich, St. Louis, Mo.) as a positive control and with an anti-PE antibody as a negative control. The cells were analyzed on a FACSCalibur instrument (BD Biosciences, San Jose, Calif.) and the data was processed using FlowJo software.

Figure 2:
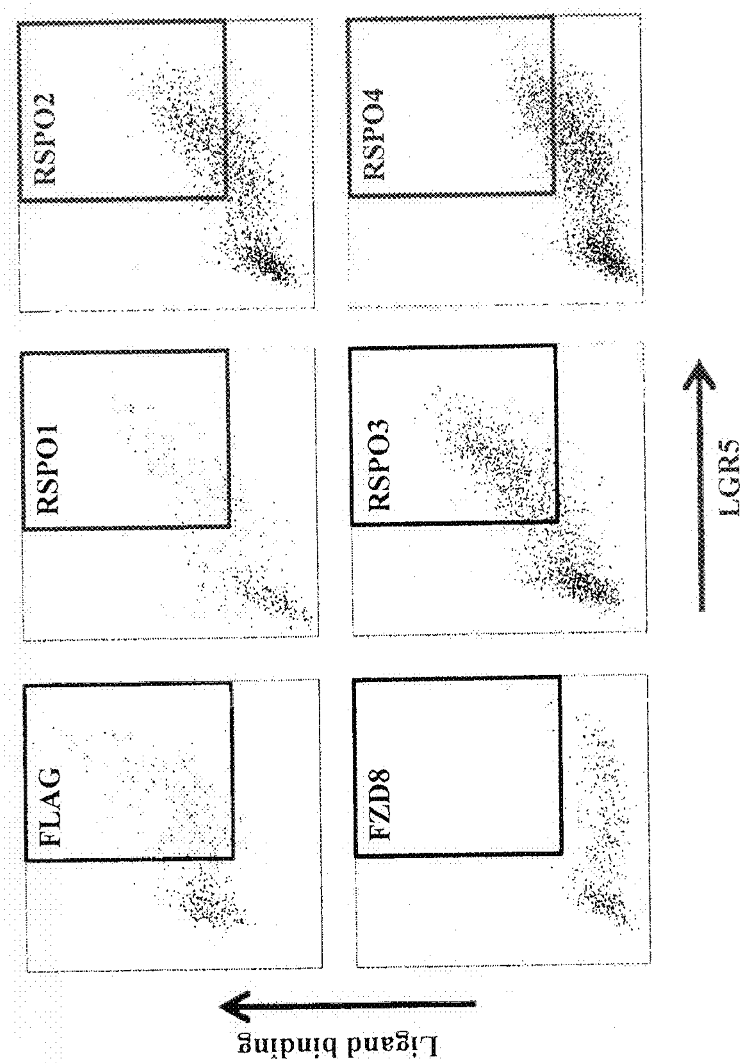
FIG. 2. Binding studies of RSPO proteins and LGR5. FACS analysis of HEK-293 cells expressing LGR5. HEK-293 cells were transiently transfected with a cDNA expression vector encoding FLAG-LGR5-CD4TM-GFP and then subsequently mixed with soluble RSPO1-Fc, RSPO2-Fc, RSPO3-Fc, or RSPO4-Fc fusion proteins. An anti-FLAG antibody was used as a positive control, and soluble FZD8-Fc was used as a negative control. Specific binding is indicated by the presence of signal within the dark lined box overlay on each FACS plot.

As shown in FIG. 2, RSPO1, RSPO2, RSPO3 and RSPO4 all bound to LGR5 expressed on the surface of the HEK-293 cells, while FZD8, the negative control, did not bind LGR5.

Binding affinities between RSPO proteins and LGR5 were analyzed by surface plasmon resonance. A soluble LGR5-Fc construct was generated using standard recombinant DNA techniques. Specifically, amino acids 1-564 of human LGR5 were ligated in frame to human Fc and the recombinant LGR5-Fc fusion protein was expressed in insect cells using baculovirus. The LGR5-Fc fusion protein was purified from the insect medium using protein A chromatography. Cleavage of the LGR5 signal sequence results in a mature LGR5-Fc fusion protein containing amino acids 22-564 of LGR5. Recombinant RSPO1-Fc, RSPO2-Fc, RSPO3-Fc and RSPO4-Fc fusion proteins were immobilized on CM5 chips using standard amine-based chemistry (NHS/EDC). Two-fold dilutions of soluble LGR5-Fc were injected over the chip surface (100 nM to 0.78 nM). Kinetic data were collected over time using a Biacore 2000 system from Biacore Life Sciences (GE Healthcare) and the data were fit using the simultaneous global fit equation to yield affinity constants ($K_D$ values) for each RSPO protein (Table 3).

TABLE 3

| | LGR5 (nM) |
|---|---|
| RSPO1 | 110 |
| RSPO2 | 14 |
| RSPO3 | <1.0 |
| RSPO4 | 73 |

Human RSPO1, RSPO2, RSPO3 and RSPO4 all bound to LGR5, demonstrating that RSPO proteins may be ligands for LGR proteins.

Example 3

In vitro Testing for Inhibition of β-catenin Signaling

To prepare cell suspensions, fresh human lung adenocarcinoma xenograft tumors (lung tumor #1 in Table 2) propagated in NOD/SCID mice were minced and digested in medium 199 (Invitrogen, Carlsbad, Calif.) containing 300 U/ml collagenase type 3 (Worthington, Lakewood, N.J.) and 200 U/ml DNase 1 (Worthington, Lakewood, N.J.) for 1 to 2 hours at 37° C. The lung tumor cells were filtered through a 40 μm nylon strainer (BD Falcon, Franklin Lakes, N.J.), and spun down at 82×g for 5 minutes. Red blood cells were lysed in ACK buffer (0.8% ammonium chloride, 0.1 mM EDTA, 10 mM sodium bicarbonate, 0.1N HCl), washed, and centrifuged at 150×g for 5 minutes in medium consisting of HBSS (Mediatech, Manassas, Va.), 25 mM HEPES buffer (Mediatech, Manassas, Va.) and 2% heat-inactivated fetal bovine serum (HI-FBS; Invitrogen, Carlsbad, Calif.). Dead cells and debris were removed by centrifugation on a cushion of HI-FBS at 82×g for 8 minutes. Mouse stroma cells were depleted using 50 μl MagnaBind streptavidin beads (Thermo Scientific, Waltham, Mass.) per $10^6$ cells/ml after staining with 5 μg/ml biotin-conjugated anti-H-2Kd and 2.5 μg/ml anti-mouse CD45 monoclonal antibodies (BioLegend, San Diego, Calif.) in SM.

To produce conditioned medium, the lung tumor cells were cultured in DMEM:F12 (3:1) medium (Invitrogen, Carlsbad, Calif.) supplemented with B27 supplement (Invitrogen, Carlsbad, Calif.), insulin-transferrin-selenium (Invitrogen, Carlsbad, Calif.), penicillin-streptomycin (Invitrogen, Carlsbad, Calif.), 0.5 μg/ml hydrocortisone (Stemcell Technologies, Vancouver, Canada), 20 ng/ml EGF (MBL International, Woburn, Mass.), 20 ng/ml basic FGF (MBL International, Woburn, Mass.) and 5 U/ml heparin (Sigma-Aldrich, St. Louis, Mo.). After 24 hours the conditioned medium was harvested (referred to herein as "LT").

STF-293 cells are stably transfected with a 6xTCF-luciferase reporter vector. One volume of lung tumor cell-conditioned medium (LT) or control medium was added to STF-293 cells in the presence of purified soluble LGR5-Fc, FZD8-Fc, Jag-Fc fusion proteins (10 μg/ml), an anti-FZD monoclonal antibody (40 μg/ml), or antibody LZ1 (40 μg/ml). In addition, Wnt3a L-cell-conditioned medium was used as a positive control and was tested in combination with the lung tumor cell-conditioned medium (LT) at a final dilution of 1:4. The cells were incubated for 16 hours and luciferase activity was measured using Steady-Glo® Luciferase Assay System according to the manufacturer's instructions (Promega, Madison, Wis.).

Figure 3:
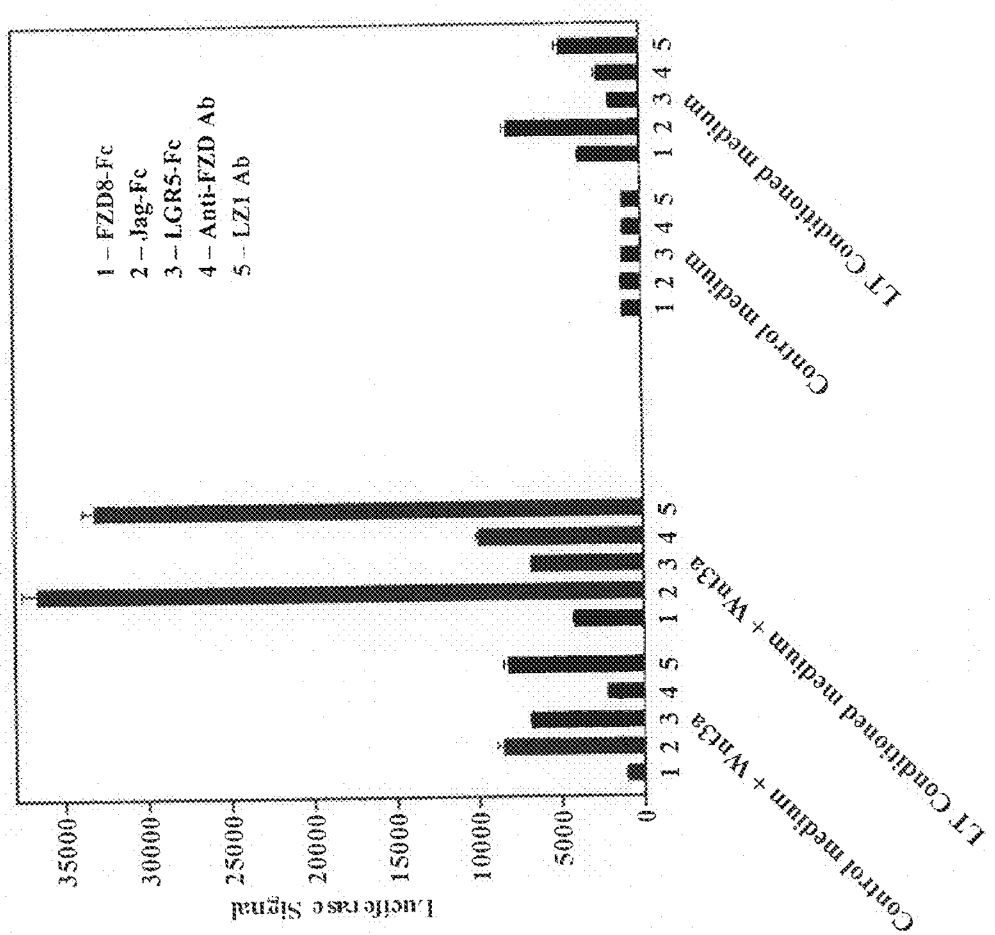
FIG. 3. Identification of inhibitory activity in lung tumor cell-conditioned medium. A 6xTCF-luciferase reporter assay was used to measure β-catenin signaling in HEK-293 cells. HEK-293 cells were exposed to control medium (DMEM media) containing Wnt3a L cell-conditioned medium or medium containing lung tumor cell-conditioned medium and Wnt3a L cell-conditioned medium in the presence of soluble LGR5-Fc. Soluble Jag-Fc and antibody LZ1 were used as negative controls. Soluble FZD8-Fc and an anti-FZD antibody which blocks Wnt3a were used as positive controls. Soluble LGR5-Fc, Jag-Fc and FZD8-Fc fusion proteins were used at 10 μg/ml. Anti-FZD antibody and LZ1 antibody were used at 40 μg/ml.

The effect of purified soluble LGR5-Fc and FZD8-Fc fusion proteins was compared to the control Jag1-Fc protein, and the effect of the anti-FZD monoclonal antibody was compared to the control anti-bacterial lysozyme antibody LZ1. As shown in FIG. 3 (left side), the lung tumor cell-conditioned medium (LT) contains an activity that potentiated the Wnt3a-induced β-catenin activity. The protein potentiating the β-catenin activity in the LT medium was inhibited by soluble LGR5-Fc which binds to RSPO proteins. This activity was also inhibited by FZD8-Fc and the anti-FZD antibody, agents that block Wnt signaling. Soluble Jag-Fc and LZ1 did not inhibit the activity. Even in the absence of Wnt3a (FIG. 3, right side), the LT medium induced β-catenin signaling. Soluble Jag-Fc and LZ1did not inhibit this activity. In contrast, soluble LGR5-Fc inhibited the LT medium-induced β-catenin signaling, reducing the response to almost control levels. This data suggested that the lung tumor cells produced a protein (or proteins) with RSPO-like activity, this activity was inhibited by LGR5, and this activity was separate from Wnt3a activity.

Similar experiments were undertaken using co-culture assays using lung tumor cell-conditioned medium and ovarian tumor cell-conditioned medium. As described above, freshly processed tumor cells depleted of stroma cells were cultured overnight. Culture medium and cells were transferred to STF-293 cells with or without Wnt3a L-cell-conditioned medium. LGR5-Fc fusion protein, a FZD8-Fc fusion protein, or a control Fc fusion protein was added (10 μg/ml). The cells were incubated for 20 hours and luciferase activity was measured as described above.

Figure 13:
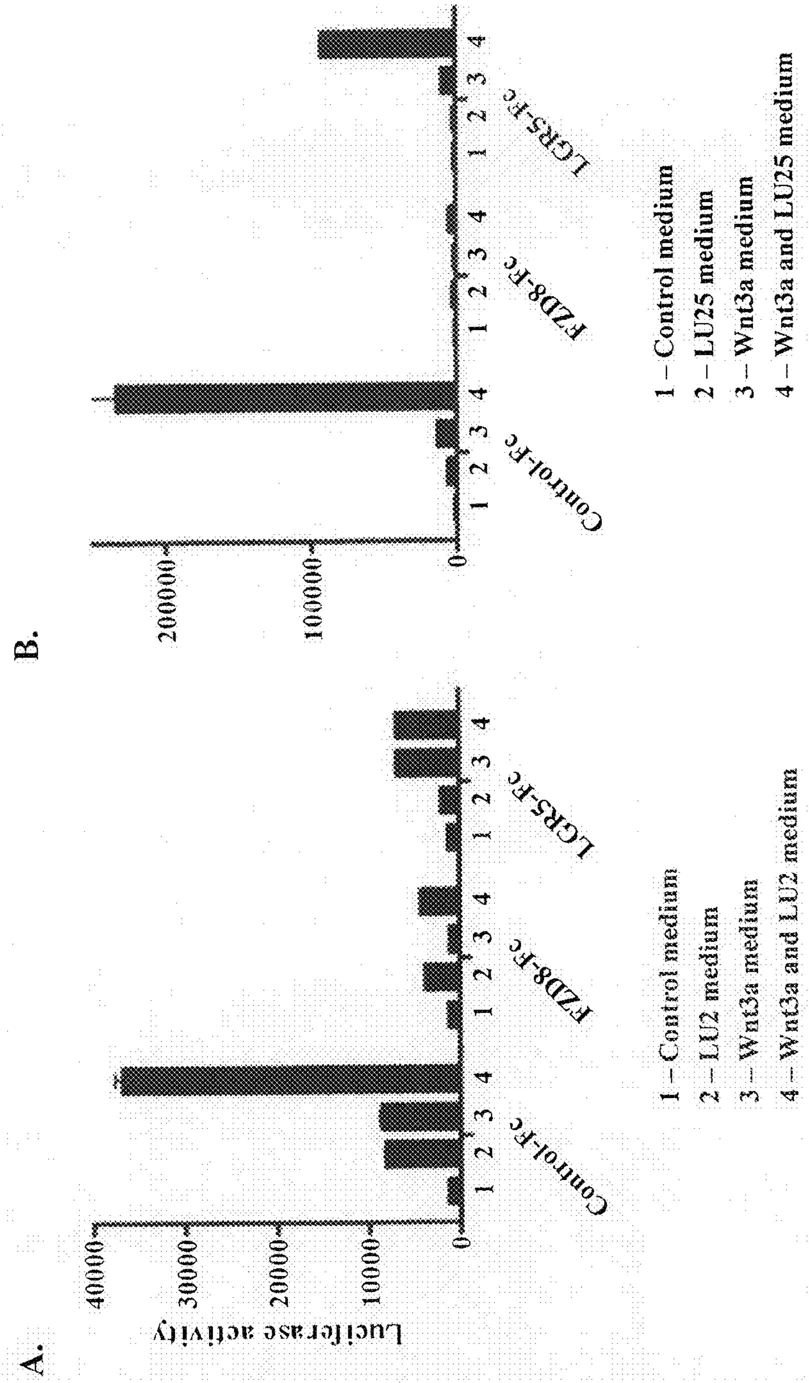
FIG. 13. Identification of inhibitory activity in tumor cell-conditioned medium. STF-293 cells were exposed to control medium (DMEM media), medium containing Wnt3a L cell-conditioned medium, medium containing tumor cell-conditioned medium, or medium containing tumor cell-conditioned medium and Wnt3a L cell-conditioned medium in the presence of soluble LGR5-Fc, FZD8-Fc, or a control fusion Fc protein. Soluble LGR5-Fc, FZD8-Fc, and control-Fc fusion proteins were used at 10 μg/ml. Tumor cell-conditioned medium was prepared from lung tumor LU2 (FIG. 13A), lung tumor LU25 (FIG. 13B), and ovarian tumor OV38 (FIG. 13C).
Figure 13:
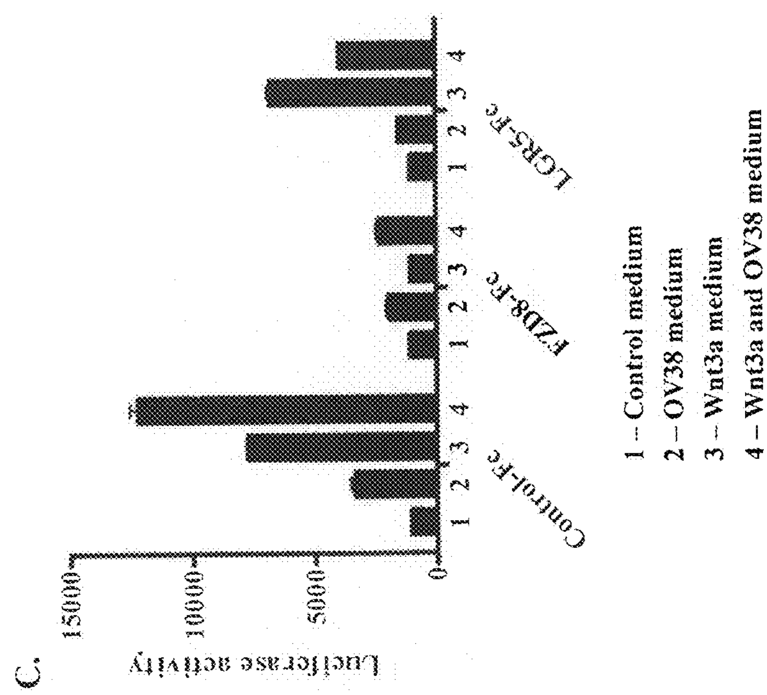

As shown in FIG. 13, β-catenin signaling activity was induced by the tumor cells and supernatants and further enhanced in combination with Wnt3a L-cell-conditioned medium (FIG. 13A, lung tumor LU2; FIG. 13B, lung tumor LU25; FIG. 13C, ovarian tumor OV38). FZD8-Fc, a Wnt pathway inhibitor, reduced the Wnt3a-induced β-catenin activity almost to background levels, while LGR5-Fc strongly reduced the tumor-derived β-catenin activity. As above, this data suggested that the lung and ovarian tumor cells produced a protein (or proteins) with RSPO-like activity, that this activity was inhibited by LGR5, and that this activity was separate from Wnt3a activity.

Example 4

In vitro Testing for Inhibition of RSPO Activity by Soluble LGR5

Conditioned medium from human lung tumor #1 cells was prepared as described in Example 3 and soluble LGR5-Fc and RSPO2-Fc were produced as described in Example 2. HEK-293 cells were transfected with a 6xTCF-luciferase reporter vector (TOPflash, Millipore, Billerica, Mass.). After 24-48 hrs, the transfected cells were incubated with medium containing 25% lung tumor cell-conditioned medium plus 25% Wnt3a-L cell-conditioned medium or medium containing RSPO2 (10 ng/ml) plus 25% Wnt3a-L cell-conditioned medium. Soluble LGR5 was added to the cells in 4-fold serially dilutions at 20 μg/ml to 0.02 μg/ml. Soluble Jag-Fc protein was used as a negative control at 20 μg/ml and FZD8-Fc protein was used as a positive control at 20 μg/ml. The cells were incubated for 16 hours and luciferase activity was measured using Steady-Glo® Luciferase Assay System according to the manufacturer's instructions (Promega, Madison, Wis.).

Figure 4:
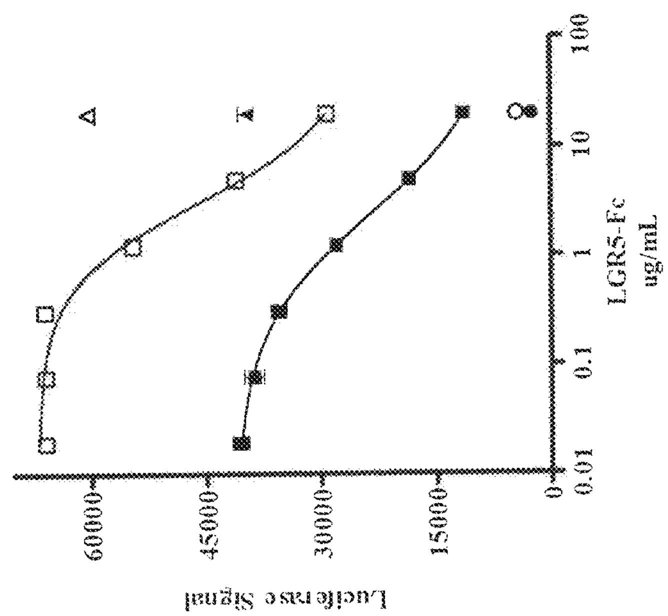
FIG. 4. Inhibition of induction of β-catenin signaling. A 6xTCF-luciferase reporter assay was used to measure β-catenin signaling in HEK-293 cells. HEK-293 cells were exposed to medium containing 10 ng/ml RSPO2 and 25% Wnt3a L cell-conditioned medium ("RSPO2") or medium containing 25% lung tumor cell-conditioned medium and 25% Wnt3a L cell-conditioned medium ("LT") in the presence of soluble LGR5-Fc at 4-fold dilutions from 20 μg/ml to 0.02 μg/ml; RSPO2 with LGR5-Fc (-□-) and LT with LGR5-Fc (-■-). Soluble Jag-Fc was used as a negative control at 20 μg/ml with RSPO2 (-Δ-) or with LT (-▲-). Soluble FZD8-Fc which blocks Wnt3a was used as a positive control at 20 μg/ml with RSPO2 (-○-) or with LT (-●-).

As shown in FIG. 4, increasing concentrations of soluble LGR5-Fc reduced the induction of luciferase activity by the combination of RSPO2-Fc plus Wnt3a-conditioned medium (-□-) as well as the induction of luciferase activity by the combination of lung tumor cell-conditioned medium and Wnt3a-conditioned medium (-■-). Negative control Jag-Fc protein did not block the luciferase activity, while FZD8-Fc, which blocks Wnt3a, blocked the luciferase activity. Importantly, LGR5 displayed the same EC50 for inhibition with both the RSPO2 protein and the lung tumor cell-conditioned medium. This data demonstrated that the protein(s) with RSPO-like activity produced by the lung tumor cells was inhibited by LGR5, behaved very similarly to a purified RSPO protein, and suggested that the activity in the lung tumor cell-conditioned media was due to a RSPO protein.

Example 5

Generation of Anti-RSPO1 Monoclonal Antibodies

Antibodies were generated against recombinant human RSPO1 protein amino acids 31-263 (R&D Systems, Minneapolis, Minn.). Mice (n=3) were immunized with RSPO1 protein using standard techniques. Sera from individual mice were screened against RSPO1 approximately 70 days after initial immunization using FACS analysis. The animal with the highest antibody titer was selected for final antigen boost after which spleen cells were isolated for hybridoma production. SP2/0 cells were used as fusion partners for the mouse spleen cells. Hybridoma cells were plated at 1 cell per well in 96 well plates, and the supernatants were screened against human RSPO1 by FACS analysis.

For FACS screening of anti-RSPO1 antibodies a chimeric fusion protein enabling cell surface expression of the N-terminal furin-like domains of human RSPO1 was constructed. As shown in FIG. 5A, the fusion protein contains a N-terminal FLAG tag, followed by the two furin-like domains of RSPO1 (aa 34-135) and fused to the transmembrane and intracellular domain of human CD4 and a C-terminal green fluorescent protein tag (FLAG-RSPO1 furin-CD4TM-GFP).

HEK-293 cells were transfected with FLAG-RSPO1furin-CD4TM-GFP. After 48 hours, transfected cells were suspended in ice cold PBS containing 2% FBS and heparin and incubated on ice in the presence of 50 μl of hybridoma supernatants for 30 minutes. A second incubation with 100 μl PE-conjugated anti-human Fc secondary antibody was performed to detect cells bound by antibody. Cells were incubated with an anti-FLAG antibody (Sigma-Aldrich, St. Louis, Mo.) as a positive control and an anti-PE antibody as a negative control. The cells were analyzed on a FACSCalibur instrument (BD Biosciences, San Jose, Calif.) and the data was processed using FlowJo software.

Several hybridomas were identified that bound RSPO1, including 89M2, 89M4, 89M5, 89M7, 89M19 and 89M25 (FIG. 5B). The heavy chain and light chain variable regions were sequenced from several of these antibodies. After analysis, it was found that antibodies 89M2, 89M4, 89M5, and 89M25 comprised the same heavy and light chain variable regions. The hybridoma cell line expressing antibody 89M5 was deposited with the ATCC, 10801 University Boulevard, Manassas, Va., USA, under the conditions of the Budapest Treaty on Jun. 30, 2011 and assigned ATCC deposit designation number PTA-11970. The amino acid sequences of the heavy chain and light chain variable regions of 89M5 are SEQ ID NO: 10 and SEQ ID NO: 11. The nucleotide sequences of the heavy chain and light chain variable regions of 89M5 are SEQ ID NO: 19 and SEQ ID NO:20. The heavy and light chain CDRs of 89M5 are listed in Table 1 herein. The amino acid sequences of the heavy chain and light chain of 89M5 are SEQ ID NO:21 and SEQ ID NO:22; the nucleotide sequences of the heavy chain and light chain of 89M5 are SEQ ID NO:23 and SEQ ID NO:24.

Example 6

Identification of Anti-RSPO1 Monoclonal Antibodies that Inhibit Induction of β-catenin Signaling by RSPO1

HEK-293 cells were transfected with a 6xTCF-luciferase reporter vector (TOPflash, Millipore, Billerica, Mass.). After 24-48 hrs, the transfected HEK-293 cells were incubated with a combination of Wnt3a (5 ng/ml) and human RSPO1 (10 ng/ml, R&D BioSystems) in the presence of anti-RSPO1 antibodies 89M2, 89M4, 89M5, 89M7, 89M19, and 89M25, or 2 irrelevant control antibodies 254M14 and 254M26 (2-fold dilutions at 10 μg/ml to 0.625 μg/ml). The cells were incubated for 16 hours and luciferase activity was measured using Steady-Glo® Luciferase Assay System according to the manufacturer's instructions (Promega, Madison, Wis.).

Figure 6:
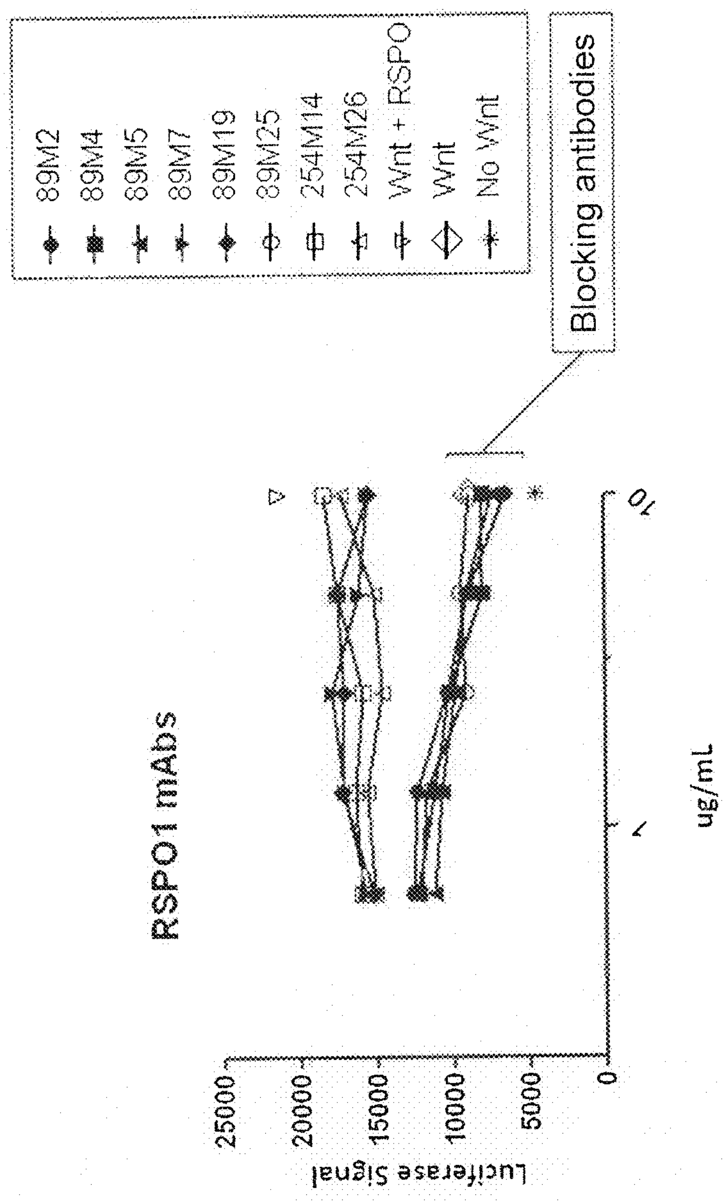
FIG. 6. Identification of anti-RSPO1 antibodies that inhibit β-catenin signaling induced by RSPO1. A TOPflash luciferase reporter assay was used to measure β-catenin signaling in HEK-293 cells after exposure to a combination of Wnt3a (5 ng/ml) and RSPO1 (10 ng/ml) and in the presence of increasing concentrations of anti-RSPO1 antibodies (89M2, 89M4, 89M5, 89M7, 89M19 or 89M25) or irrelevant control antibodies (254M14 or 254M26). Antibodies were used as 2-fold dilutions from 10 μg/ml to 0.625 μg/ml. Controls included exposure to control medium (no Wnt3a and no RSPO), Wnt3a alone, or a combination of Wnt3a and RSPO in the absence of antibody.

As shown in FIG. 6, anti-RSPO1 antibodies 89M2, 89M4, 89M5 and 89M25 each blocked signaling, whereas anti-RSPO1 antibodies 89M7 and 89M19 did not block signaling. As determined by sequencing of the heavy chain and light chain variable regions, antibodies 89M2, 89M4, 89M5 and 89M25 all comprise the same heavy chain and light chain variable regions and therefore, presumably, the same antigen binding site. These results demonstrated that an anti-RSPO1 antibody was able to block RSPO1-induced β-catenin signaling.

Example 7

Anti-RSPO1 Antibodies Block Binding of Soluble RSPO1 to LGR5

HEK-293 cells were transiently transfected with the FLAG-LGR5-CD4TM-GFP construct (previously described in Example 2). After 48 hours, transfected cells were suspended in ice cold PBS containing 2% FBS and heparin and incubated on ice in the presence of RSPO1-Fc protein (10 μg/ml) and antibodies 89M2, 89M4, 89M5, 89M7, 89M19 or 89M25 (10 μg/ml). A second incubation with 100 μl PE-conjugated anti-human Fc secondary antibody was performed to detect cells bound by the RSPO1-Fc fusion protein. The cells were analyzed on a FACSCalibur instrument (BD Biosciences, San Jose, Calif.) and the data was processed using FlowJo software.

Figure 7:
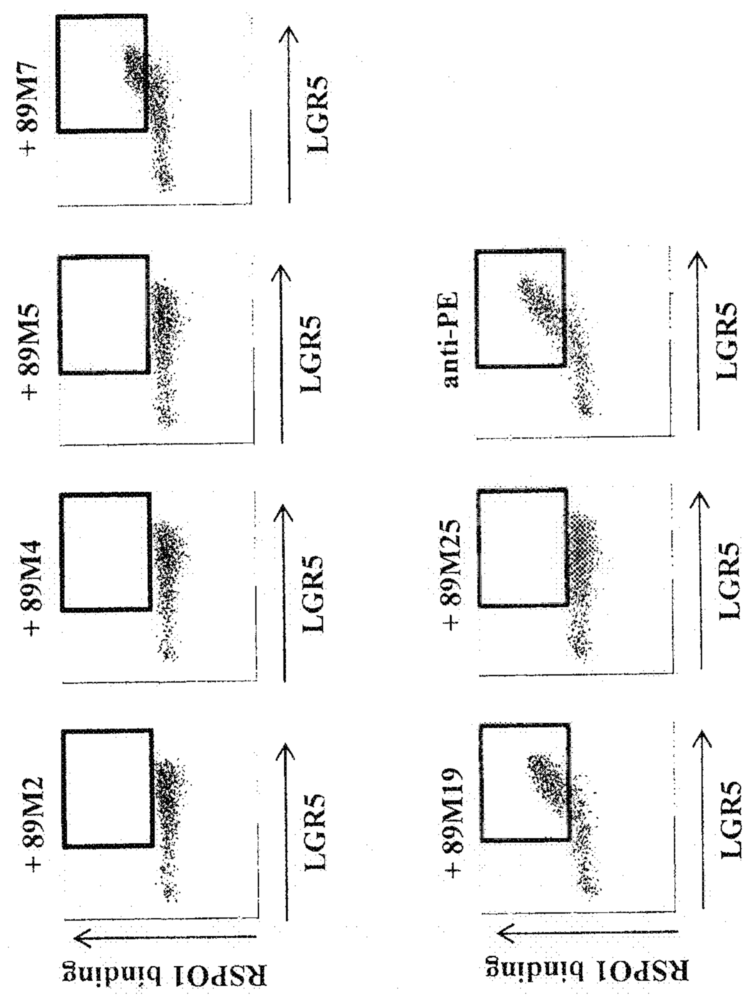
FIG. 7. Identification of anti-RSPO1 antibodies that block RSPO1/LGR5 binding. FACS analysis of HEK-293 cells expressing LGR5. HEK-293 cells were transiently transfected with a cDNA expression vector encoding FLAG-LGR5-CD4TM-GFP and then subsequently mixed with soluble RSPO1-Fc fusion protein in combination with individual anti-RSPO1 antibodies. Binding was detected with a PE-conjugated anti-human Fc secondary antibody. Relative RSPO1-Fc binding is shown on the y-axis and expression of the FLAG-LGR5-CD4TM-GFP fusion protein is indicated on the x-axis. Positive binding is indicated by the presence of signal within the dark lined box overlay on each FACS plot. An anti-PE antibody was used as a negative control.

As shown in FIG. 7, anti-RSPO1 antibodies 89M2, 89M4, 89M5 and 89M25 each blocked binding of RSPO1 to LGR5, whereas anti-RSPO1 antibodies 89M7 and 89M19 did not block binding of RSPO1 to LGR5. These results correlate with the results shown in Example 6 which demonstrated the ability of antibodies 89M2, 89M4, 89M5 and 89M25 to block RSPO1 signaling in an assay measuring induction of β-catenin activity in a 6xTCF luciferase reporter assay, whereas antibodies 89M7 and 89M19 were not able to block RSPO1 signaling. As discussed above, antibodies 89M2, 89M4, 89M5 and 89M25 all comprise the same heavy chain and light chain variable regions and presumably the same antigen binding site, therefore it would be expected that these antibodies all function in a similar, if not identical, manner.

Example 8

Binding Affinities of Anti-RSPO1 Antibodies

The $K_D$s of antibodies 89M4, 89M5, 89M7 and 89M25 were determined using a Biacore 2000 system from Biacore LifeSciences (GE Healthcare). Recombinant human RSPO1-Fc or mouse RSPO1-Fc proteins were immobilized on CM5 chips using standard amine-based chemistry (NHS/EDC). The antibodies were serially diluted 2-fold from 100 nM to 0.78 nM in HBS-P (0.01 M HEPES pH7.4, 0.1 SM NaCl, 0.005% v/v Surfactant P20) and were injected over the chip surface. Kinetic data were collected over time and were fit using the simultaneous global fit equation to yield affinity constants ($K_D$ values) for each antibody.

TABLE 4

| | Human RSPO1 (nM) | Mouse RSPO1 (nM) |
|---|---|---|
| 89M4 | <0.1 | <0.1 |
| 89M5 | <0.1 | <0.1 |
| 89M7 | <0.1 | <0.1 |
| 89M25 | <0.1 | <0.1 |

As shown in Table 4, antibodies 89M4, 89M5, 89M7 and 89M25 all had an affinity constants ($K_D$) for human RSPO1 of less than 0.1 nM. These antibodies also had $K_D$ of less than 0.1 nM for mouse RSPO1.

Example 9

Inhibition of Ovarian Tumor Growth in vivo by Anti-RSPO1 Antibodies

Dissociated OV19 ovarian tumor cells ($1\times10^5$cells) were injected in the mammary fat pads of 6-8 week old NOD/SCID mice. Tumors were allowed to grow for 45 days until they reached an average volume of 134 $mm^3$. The mice were randomized (n=10 per group) and treated with anti-RSPO1 antibody 89M5, 89M25, taxol, a combination of 89M5 and taxol, a combination of 89M25 and taxol, or control antibody 1B7.11. Antibodies were dosed at 15 mg/kg once a week, and taxol was dosed at 7.5 mg/ml once a week. Administration of the antibodies and taxol was performed via injection into the intraperitoneal cavity. Tumor growth was monitored and tumor volumes were measured with electronic calipers at the indicated time points. Data are expressed as mean±S.E.M.

Figure 8:
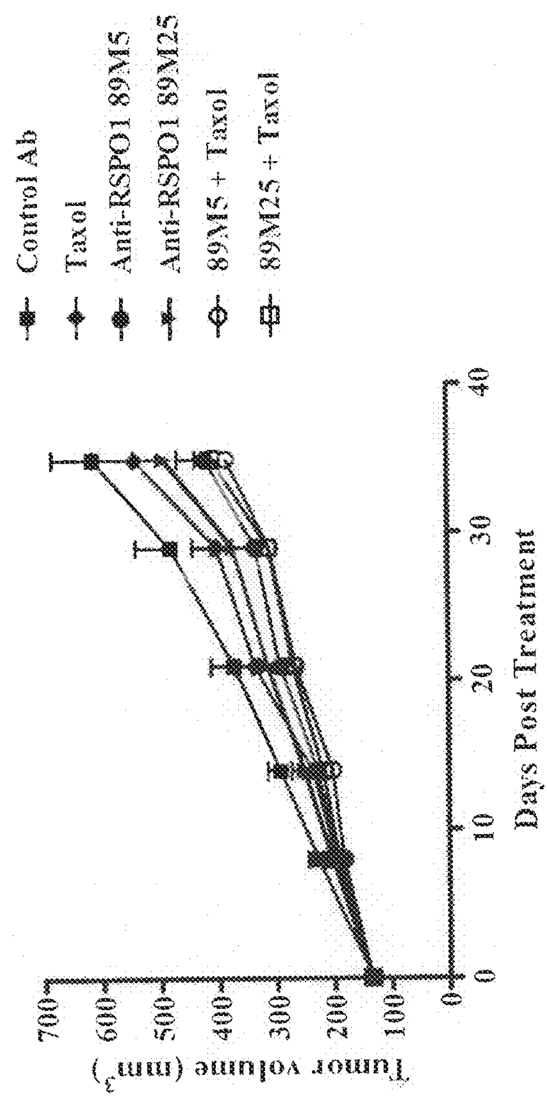
FIG. 8. Inhibition of tumor growth with anti-RSPO1 antibodies. OV19 ovarian tumor cells were injected subcutaneously into NOD/SCID mice. Mice were treated with 89M5 (-●-), 89M25 (-▼-), taxol (-●-), a combination of antibody 89M5 and taxol (-○-), a combination of antibody 89M25 and taxol (-□-), or control antibody 1B7.11 (-■-). Data is shown as tumor volume ($mm^3$) over days post-treatment.

At day 35, treatment with antibody 89M5 resulted in a 40% reduction in tumor growth and 89M25 resulted in a 25% reduction in tumor growth as compared to treatment with the control antibody (FIG. 8, p=0.37 and p=0.19, respectively). Treatment with 89M5 or 89M25 in combination with taxol resulted in a reduction of tumor growth greater than treatment with either agent alone. Treatment with 89M5 and taxol resulted in a 48% reduction in growth (p=0.12 vs. the control group), and treatment with 89M25 and taxol resulted in a 43% reduction in growth (p=0.16 vs. the control group). Thus, antibodies 89M5 and 89M25 demonstrated anti-tumor growth activity in the OV19 ovarian tumor model as a single agent, and also displayed anti-tumor growth activity in combination with taxol.

Subsequent analysis of the tumors from the mice used in this experiment (both control and treated mice) revealed that the tumors were a mixture of human ovarian tumor cells (OV19) and murine T-cell lymphoma cells.

Example 10

Epitope Mapping of Anti-RSPO1 Monoclonal Antibody 89M5

To further characterize the specific region(s) of RSPO1 that antibody 89M5 binds, an epitope mapping experiment was performed. A series of constructs comprising different regions of human RSPO1 were generated using standard recombinant DNA technology (see FIG. 9A). The constructs were fusion proteins each containing a N-terminal FLAG tag, followed by a portion of RSPO1 protein and fused to the transmembrane and intracellular domain of human CD4. In some versions the fusion proteins also comprise a C-terminal green fluorescent protein tag.

HEK-293 cells were transfected with the individual constructs. After 48 hours, transfected cells were suspended in ice cold PBS containing 2% FBS and heparin and incubated on ice in the presence of anti-RSPO1 antibody 89M5 for 30 minutes. A second incubation with 100 μl PE-conjugated anti-human Fc secondary antibody was performed to detect cells bound by antibody. Cells were incubated with an anti-FLAG antibody (Sigma-Aldrich, St. Louis, Mo.) as a positive control and an anti-PE antibody as a negative control. The cells were analyzed on a FACSCalibur instrument (BD Biosciences, San Jose, Calif.) and the data was processed using FlowJo software.

Figure 9:
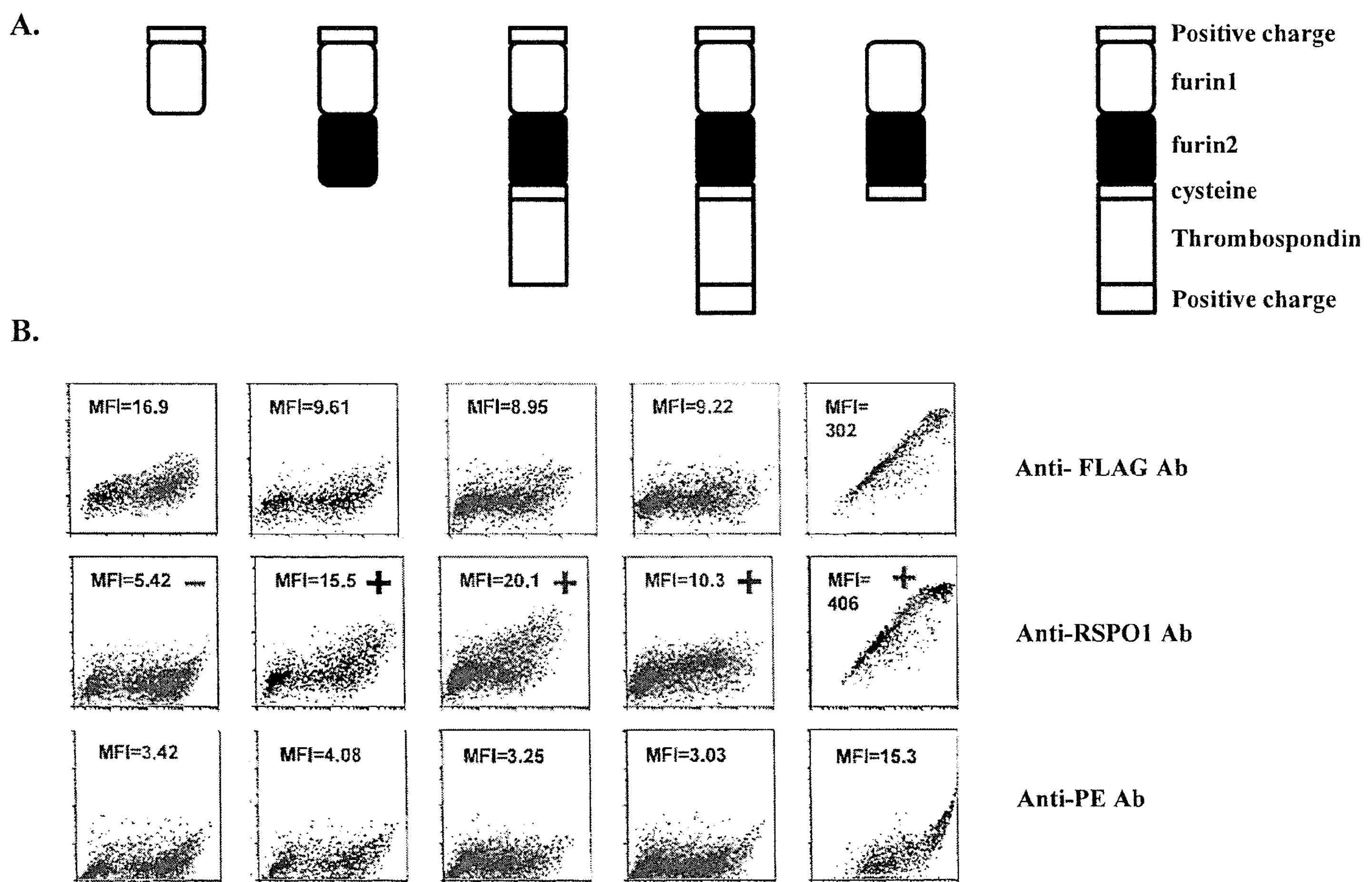
FIG. 9. Epitope mapping of anti-RSPO1 antibody. A) A diagram of fusion proteins constructed that contain a deletion series of RSPO1 domains. These constructs all comprise a CD4TM domain which allows for cell surface expression of the proteins. B) FACS analyses of anti-RSPO1 antibody binding to cells transfected with the fusion proteins. Relative antibody binding is shown on the y-axis and expression of the fusion protein is indicated on the x-axis. An anti-FLAG antibody was used as a positive control. An anti-PE antibody was used as a negative control.

As shown in FIG. 9B, the FACS analysis suggests that amino acids within the furin2 domain of RSPO1 are involved in the binding site for anti-RSPO1 antibody 89M5 (Example 10, FIG. 9). These preliminary results do not preclude that fact that amino acids in other RSPO1 domains may be involved in the binding site.

Example 11

Generation of Anti-RSPO2 Monoclonal Antibodies

Antibodies were generated against recombinant human RSPO2 protein amino acids 22-205 (R&D Systems, Minneapolis, Minn.). Mice (n=3) were immunized with RSPO2 protein using standard techniques. Sera from individual mice were screened against RSPO2 approximately 70 days after initial immunization using FACS analysis. The animal with the highest antibody titer was selected for final antigen boost after which spleen cells were isolated for hybridoma production. SP2/0 cells were used as fusion partners for the mouse spleen cells. Hybridoma cells were plated at 1 cell per well in 96 well plates, and the supernatants were screened against human RSPO2 by FACS analysis.

As described in Example 5, for FACS screening of anti-RSPO2 antibodies a chimeric fusion protein enabling cell surface expression of the N-terminal furin-like domains of human RSPO2 was constructed. Similar to what is depicted in FIG. 5A for RSPO1, the RSPO2 fusion protein contains a N-terminal FLAG tag, followed by the furin-like domains of RSPO2 (aa 31-146) and fused to the transmembrane and intracellular domain of human CD4 and a C-terminal green fluorescent protein tag (FLAG-RSPO2furin-CD4TM-GFP).

HEK-293 cells were transfected with FLAG-RSPO2furin-CD4TM-GFP. After 48 hours, transfected cells were suspended in ice cold PBS containing 2% FBS and heparin and incubated on ice in the presence of 50 μl of hybridoma supernatants for 30 minutes. A second incubation with 100 μl PE-conjugated anti-human Fc secondary antibody was performed to detect cells bound by antibody. Cells were incubated with an anti-FLAG antibody (Sigma-Aldrich, St. Louis, Mo.) as a positive control and an anti-PE antibody as a negative control. The cells were analyzed on a FACSCalibur instrument (BD Biosciences, San Jose, Calif.) and the data was processed using FlowJo software.

Several hybridomas were identified that bound RSPO2, including 130M23, 130M24, 130M25, 130M26, 130M27, and 130M28 (FIG. 10). The heavy chain and light chain variable regions were sequenced from several of these antibodies. The hybridoma cell line expressing antibody 130M23 was deposited with the ATCC, 10801 University Boulevard, Manassas, Va., USA, under the conditions of the Budapest Treaty on Aug. 10, 2011 and assigned ATCC deposit designation number PTA-12021. The amino acid sequences of the heavy chain variable region and light chain variable region of 130M23 are SEQ ID NO:27 and SEQ ID NO:28. The nucleotide sequences of the heavy chain and light chain variable regions of 130M23 are SEQ ID NO:35 and SEQ ID NO:36. The heavy chain and light chain CDRs of 130M23 are listed in Table 1 herein. The amino acid sequences of the heavy chain and light chain of 130M23 are SEQ ID NO:37 and SEQ ID NO:38; the nucleotide sequences of the heavy chain and light chain of 130M23 are SEQ ID NO:39 and SEQ ID NO:40.

Example 12

Identification of Anti-RSPO2 Monoclonal Antibodies that Inhibit Induction of β-catenin Signaling by RSPO2

HEK-293 cells were transfected with a 6xTCF-luciferase reporter vector (TOPflash, Millipore, Billerica, Mass.). After 24-48 hrs, the transfected HEK-293 cells were incubated with a combination of Wnt3a (5 ng/ml) and human RSPO2 (10 ng/ml, R&D BioSystems) or human RSPO3 (10 ng/ml, R&D BioSystems) in the presence of anti-RSPO2 antibodies 130M23, 130M24, 130M25, 130M26, 130M27, and 130M28. Cells were incubated with a combination of Wnt3a and RSPO, Wnt3a only or with no addition as controls. The cells were incubated for 16 hours and luciferase activity was measured using Steady-Glo® Luciferase Assay System according to the manufacturer's instructions (Promega, Madison, Wis.).

Figure 11:
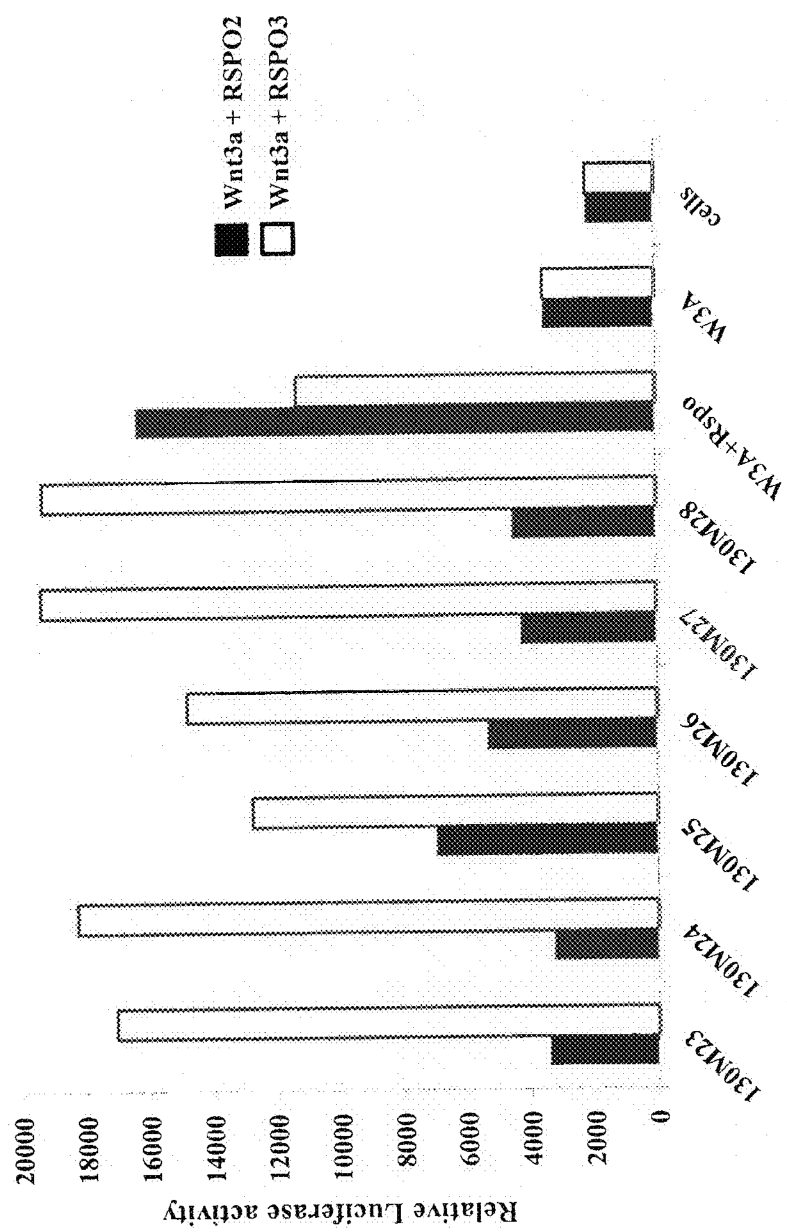
FIG. 11. Identification of anti-RSPO2 antibodies that inhibit induction of β-catenin signaling by RSPO2. A TOP-flash luciferase reporter assay was used to measure β-catenin signaling in HEK-293 cells after exposure to a combination of Wnt3a (5 ng/ml) and human RSPO2 (10 ng/ml) or Wnt3a (5 ng/ml) and human RSPO3 (10 ng/ml) and in the presence of antibodies to RSPO2 (mAbs 130M23, 130M24, 130M25, 130M26, 130M27, and 130M28). Controls included exposure to control medium (no added Wnt3a and no RSPO—labeled "cells"), Wnt3a alone (labeled "W3A"), or a combination of Wnt3a and RSPO in the absence of antibody.

As shown in FIG. 11, anti-RSPO2 antibodies 130M23, 130M24, 130M25, 130M26, 130M27, and 130M28 each reduced RSPO2-induced β-catenin signaling, and anti-RSPO2 antibodies 130M23, 130M24 completely blocked RSPO2-induced β-catenin signaling. In contrast these antibodies did not block β-catenin signaling induced by RSPO3. These results demonstrated that antibodies 130M23, 130M24, 130M25, 130M26, 130M27, and 130M28 are specific inhibitors of RSPO2 and are capable of reducing and/or completely blocking RSPO2-induced iβ-catenin signaling.

Example 13

Anti-RSPO2 Antibodies Block Binding of Soluble RSPO2 to LGR5

HEK-293 cells were transiently transfected with the FLAG-LGR5-CD4TM-GFP construct (previously described in Example 2). After 48 hours, transfected cells were suspended in ice cold PBS containing 2% FBS and heparin and incubated on ice in the presence of RSPO2-Fc protein (10 μg/ml) and antibodies 130M23, 130M24, 130M25, 130M26, 130M27, and 130M28. A second incubation with 100 μl PE-conjugated anti-human Fc secondary antibody was performed to detect cells bound by the RSPO2-Fc fusion protein. The cells were analyzed on a FACSCalibur instrument (BD Biosciences, San Jose, Calif.) and the data was processed using FlowJo software.

Figure 12:
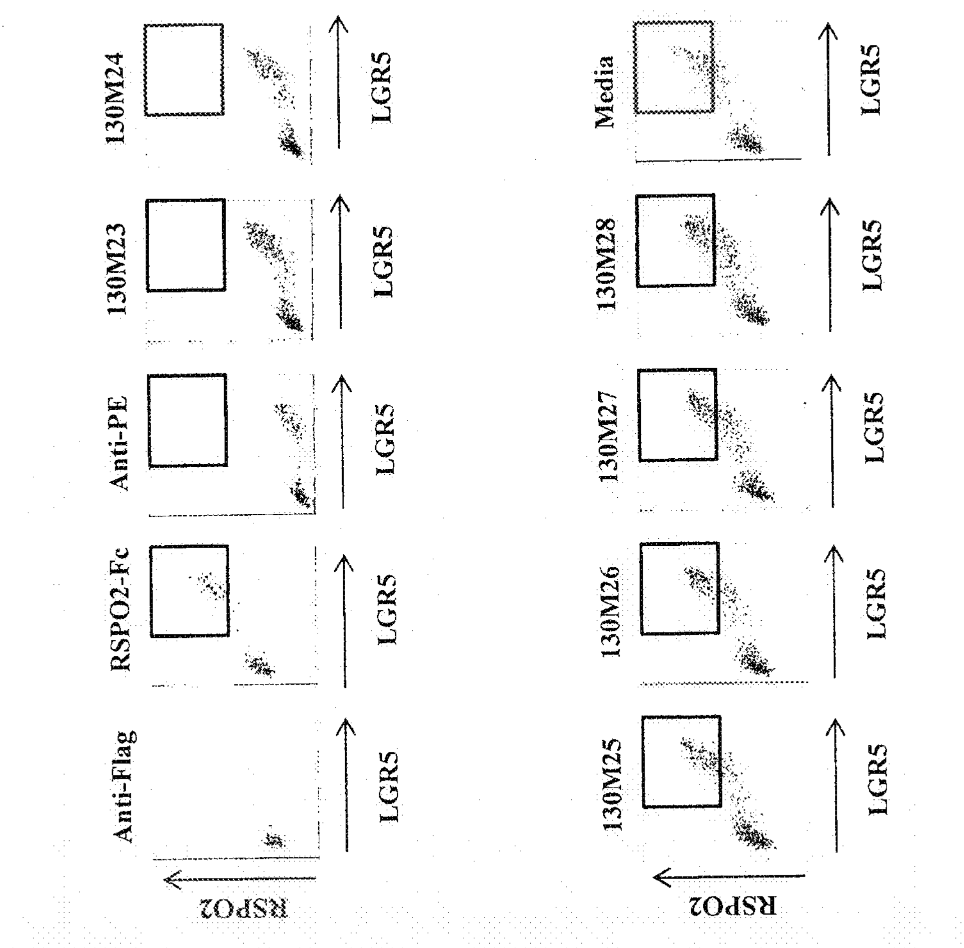
FIG. 12. Identification of anti-RSPO2 antibodies that block RSPO2/LGR5 binding. FACS analysis of HEK-293 cells expressing LGR5. HEK-293 cells were transiently transfected with a cDNA expression vector encoding FLAG-LGR5-CD4TM-GFP and then subsequently mixed with soluble RSPO2-fc fusion protein in combination with individual anti-RSPO2 antibodies. Binding was detected with a PE-conjugated anti-human Fc secondary antibody. Relative RSPO2-Fc binding is shown on the y-axis and expression of the FLAG-LGR5-CD4TM-GFP fusion protein is indicated on the x-axis. Positive binding is indicated by the presence of signal within the dark-lined box overlay on each FACS plot. An anti-FLAG antibody was used as a positive control and an anti-PE antibody was used as a negative control.

As shown in FIG. 12, anti-RSPO2 antibodies 130M23 and 130M24 each blocked binding of RSPO2 to LGR5, whereas anti-RSPO2 antibodies 130M25, 130M26, 130M27, and 130M28 only weakly blocked or did not block binding of RSPO2 to LGR5. These results correlate with the results shown in Example 11 which demonstrated the ability of antibodies 130M23 and 130M24 to completely block RSPO2-induced β-catenin signaling, whereas antibodies 130M25, 130M26, 130M27, and 130M28 were less potent inhibitors of RSPO2-induced β-catenin signaling.

Example 14

Generation of Anti-RSPO3 Monoclonal Antibodies

Antibodies are generated against recombinant human RSPO3 protein amino acids 22-272 (R&D Systems, Minneapolis, Minn.). Mice (n=3) are immunized with RSPO3 protein using standard techniques. Sera from individual mice are screened against RSPO3 approximately 70 days after initial immunization using FACS analysis. The animal with the highest antibody titer is selected for final antigen boost after which spleen cells are isolated for hybridoma production. SP2/0 cells are used as fusion partners for the mouse spleen cells. Hybridoma cells are plated at 1 cell per well in 96 well plates, and the supernatants are screened against human RSPO3 by FACS analysis.

As described in Example 5, for FACS screening of anti-RSPO3 antibodies a chimeric fusion protein enabling cell surface expression of the N-terminal furin-like domains of human RSPO was constructed. Similar to what is depicted in FIG. 5A for RSPO1, the RSPO3 fusion protein contains a N-terminal FLAG tag, followed by the furin-like domains of RSPO3 (aa 32-141) and fused to the transmembrane and intracellular domain of human CD4 and a C-terminal green fluorescent protein tag (FLAG-RSPO3 furin-CD4TM-GFP).

HEK-293 cells are transfected with FLAG-RSPO3furin-CD4TM-GFP. After 48 hours, transfected cells are suspended in ice cold PBS containing 2% FBS and heparin and incubated on ice in the presence of 50 μl of hybridoma supernatants for 30 minutes. A second incubation with 100 μl PE-conjugated anti-human Fc secondary antibody is performed to detect cells bound by antibody. Cells are incubated with an anti-FLAG antibody (Sigma-Aldrich, St. Louis, Mo.) as a positive control and an anti-PE antibody as a negative control. The cells are analyzed on a FACSCalibur instrument (BD Biosciences, San Jose, Calif.) and the data is processed using FlowJo software.

Example 15

Binding Affinity of Anti-RSPO2 Antibody 130M23

The $K_D$ of 130M23 was determined using a Biacore 2000 system from Biacore LifeSciences (GE Healthcare). Recombinant human RSPO2-Fc or mouse RSPO2-Fc proteins were immobilized on CM5 chips using standard amine-based chemistry (NHS/EDC). The antibodies were serially diluted 2-fold from 100 nM to 0.78 nM in HBS-P (0.01M HEPES pH7.4, 0.15M NaCl, 0.005% v/v Surfactant P20) and were injected over the chip surface. Kinetic data were collected over time and were fit using the simultaneous global fit equation to yield affinity constants ($K_D$ values) for each antibody.

Antibody 130M23 had an affinity constant ($K_D$) for human RSPO2 of 0.14 nM and a $K_D$ of 0.35 nM for mouse RSPO2.

Example 16

In vitro Testing for Inhibition of RSPO Activity by Anti-RSPO2 Antibody

Conditioned medium from human lung tumor LU2 cells was prepared as described in Example 3 and soluble LGR5-Fc was produced as described in Example 2.

STF-293 cells were incubated with LU2 cells plus 25% lung tumor cell-conditioned medium plus 25% Wnt3a-L cell-conditioned medium. Antibody 130M23 and soluble LGR5-Fc were added to the cells in 5-fold serially dilutions from 50 μg/ml to 0.0006 μg/ml. An irrelevant monoclonal antibody, similarly diluted, and a control Fc fusion protein (50 ug/ml) were used as negative controls. The cells were incubated for 20 hours and luciferase activity was measured using Steady-Glo® Luciferase Assay System according to the manufacturer's instructions (Promega, Madison, Wis.).

Figure 14:
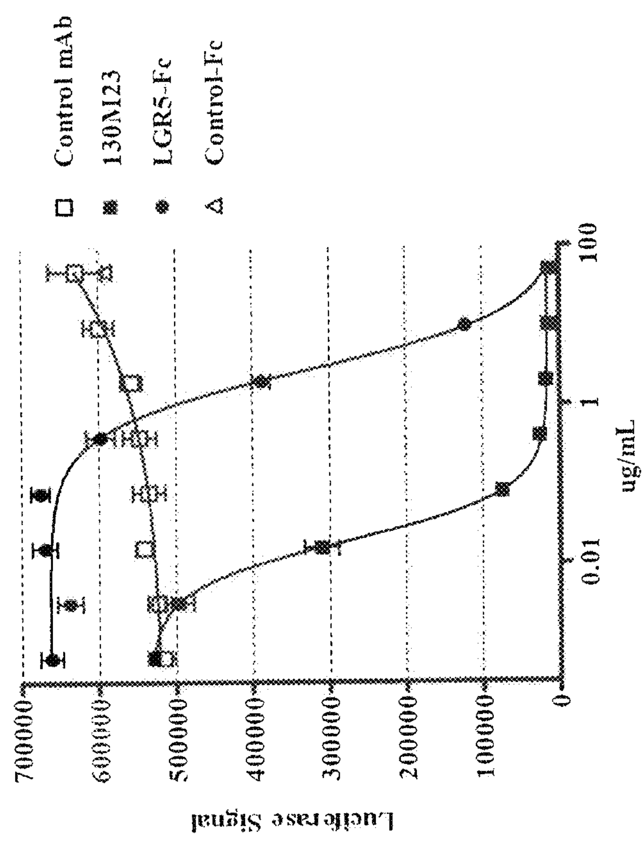
FIG. 14. Inhibition of induction of β-catenin signaling. STF-293 cells were incubated with LU2 cells plus 25% lung tumor cell-conditioned medium plus 25% Wnt3a-L cell-conditioned medium. Antibody 130M23 (-■-) and soluble LGR5-Fc (-●-) were added to the cells in 5-fold serially dilutions from 50 μg/ml to 0.0006 μg/ml. An irrelevant monoclonal antibody (-□-), similarly diluted, and a control Fc fusion protein (-Δ-, 50 ug/ml) were used as negative controls.

As shown in FIG. 14, increasing concentrations of soluble LGR5-Fc (-●-) reduced the induction of luciferase activity by the combination of lung tumor cell-conditioned medium and Wnt3a-conditioned medium. Increasing concentrations of anti-RSPO2 antibody 130M23 (-■-) also reduced the induction of luciferase activity by the combination of lung tumor cell-conditioned medium and Wnt3a-conditioned medium. 130M23 blocked conditioned medium induced activity with an $IC_{50}$ of 129 nM and was greater than 100-fold more potent than LGR5-Fc. A control Fc fusion protein (-Δ-), as well as an irrelevant antibody (-□-) did not block the luciferase activity.

Example 17

Inhibition of Pancreatic Tumor Growth in vivo by Anti-RSPO Antibodies

Dissociated PN31 pancreatic tumor cells ($1\times10^5$ cells) were injected subcutaneously into the flanks of 6-8 week old NOD/SCID mice. Tumors were allowed to grow for 61 days until they reached an average volume of 120 $mm^3$. The mice were randomized (n=10 per group) and treated with anti-RSPO1 antibody 89M5, anti-RSPO2 antibody 130M23, gemcitabine, a combination of 89M5 and gemcitabine, a combination of 130M23 and gemcitabine, or control antibody 1B7.11. Antibodies were dosed at 15 mg/kg once a week, and gemcitabine was dosed at 30 mg/ml once a week. Administration of the antibodies and gemcitabine was performed via injection into the intraperitoneal cavity. Tumor growth was monitored and tumor volumes were measured with electronic calipers at specific time points. Data are expressed as mean±S.E.M.

Figure 15:
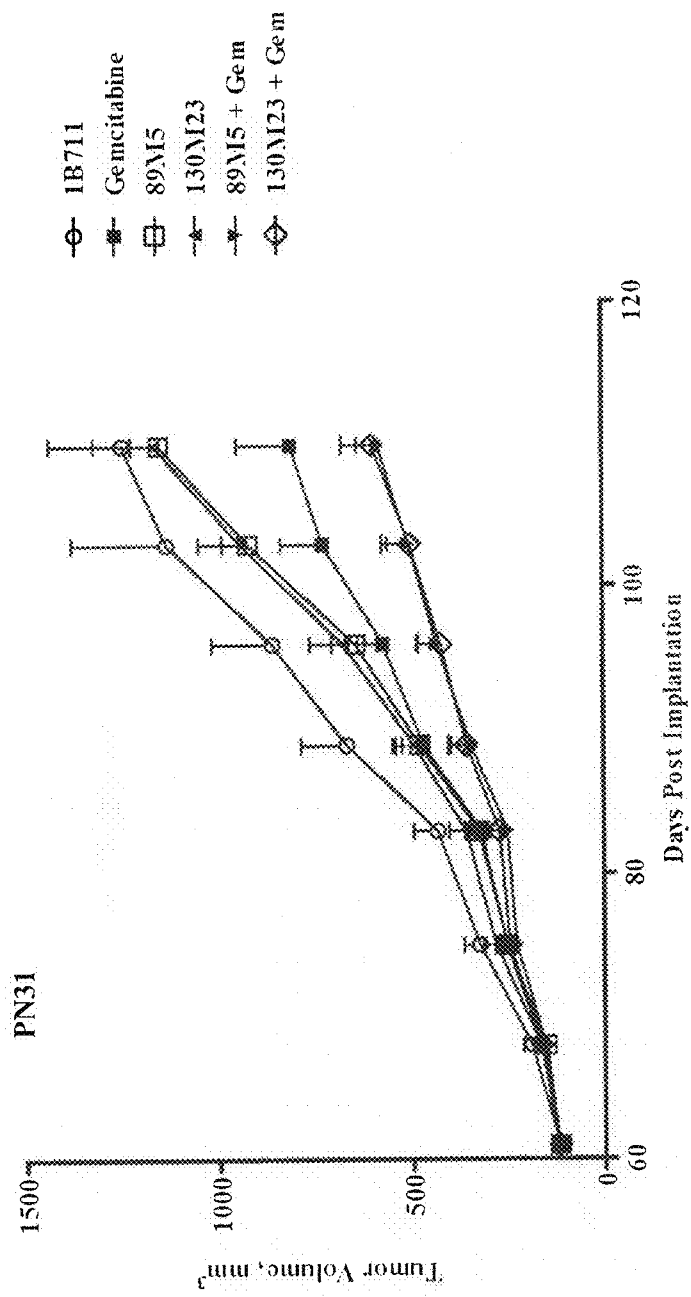
FIG. 15. Inhibition of tumor growth with anti-RSPO antibodies. PN31 pancreatic tumor cells were injected subcutaneously into NOD/SCID mice. Mice were treated with anti-RSPO1 antibody 89M5 (-□-), anti-RSPO2 antibody 130M23 (-▲-), gemcitabine (-■-), a combination of antibody 89M5 and gemcitabine (-▼-), a combination of antibody 130M23 and gemcitabine (-◇-), or control antibody 1B7.11 (-○-). Data is shown as tumor volume (mm$^3$) over days post-implantation.
Figure 16:
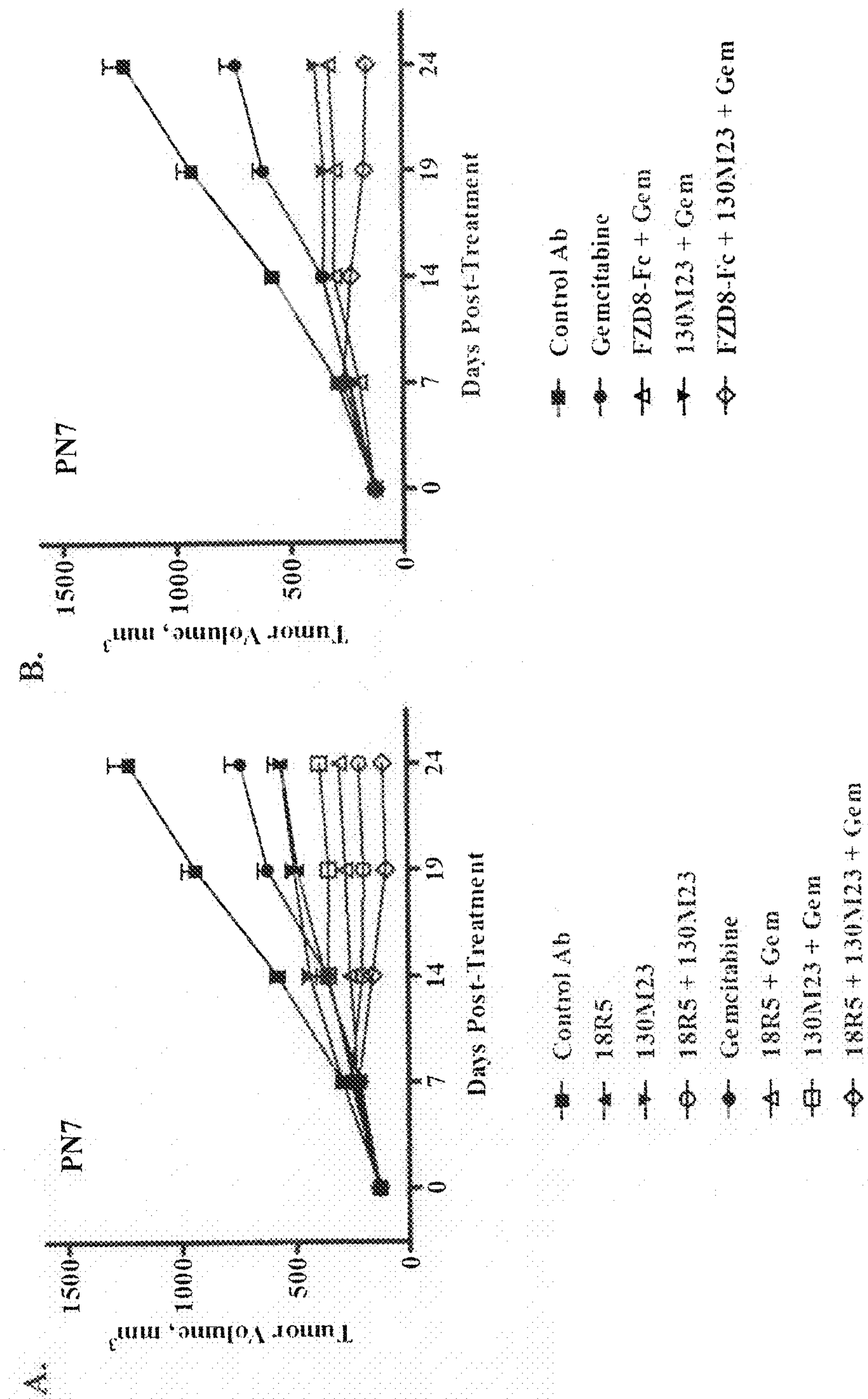
FIG. 16. Inhibition of tumor growth with anti-RSPO antibodies. PN7 pancreatic tumor cells were injected subcutaneously into NOD/SCID mice. Mice were treated with anti-RSPO2 antibody 130M23 (-▼-), anti-FZD antibody 18R5 (-▲-), gemcitabine (-●-), a combination of 130M23 and 18R5 (-○-), a combination of 130M23 and gemcitabine (-□-), a combination of 18R5 and gemcitabine (-Δ-), a combination of 130M23, 18R5, and gemcitabine (-◇-), or control antibody 1B7.11 (-■-). Data is shown as tumor volume (mm$^3$) over days post-treatment (FIG. 16A). Mice were treated with a combination of a Wnt pathway inhibitor FZD8-Fc and gemcitabine (-Δ-), a combination with 30M23 and gemcitabine (-▼-), combination of 130M23, FZD8-Fc, and gemcitabine (-◇-), gemcitabine (-●-), or control antibody 1B7.11 (-■-). Data is shown as tumor volume (mm$^3$) over days post-treatment (FIG. 16B). The resulting tumors were processed to single cell suspensions, and serially transplanted into mice. 90 cells from tumors obtained from each treatment group were injected subcutaneously into NOD/SCID mice. Tumors were allowed to grow with no treatment. Data is shown as tumor volume (mm$^3$) on day 40 (FIG. 16C).
Figure 16:
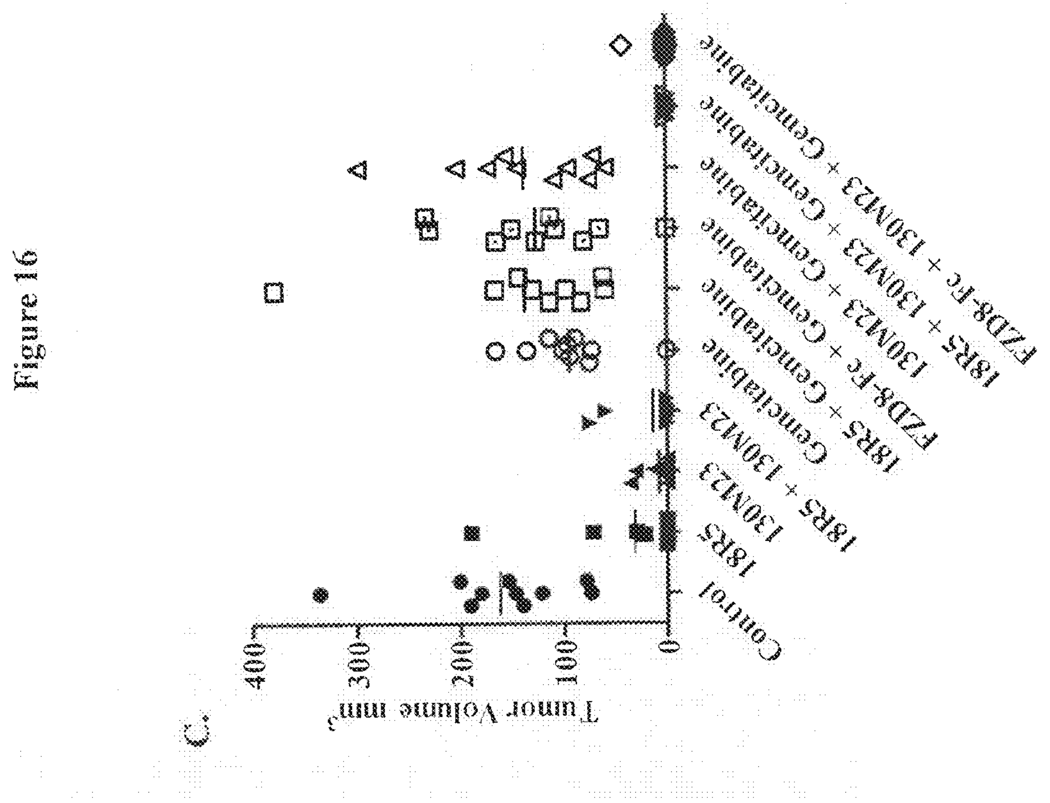

As shown in FIG. 15, treatment with anti-RSPO1 antibody 89M5 or anti-RSPO2 antibody 130M23 as single agents had only a minimal effect on tumor growth. Treatment with gemcitabine alone reduced tumor growth by 49% as compared to the controls (p=0.09). However, treatment with 89M5 or 130M23 in combination with gemcitabine resulted in a reduction of tumor growth greater than treatment with either agent alone. Treatment with 89M5 and gemcitabine resulted in a 59% reduction in growth (p=0.015 vs. the control group), and treatment with 130M23 and gemcitabine resulted in a 58% reduction in growth (p=0.016 vs. the control group). Thus, anti-RSPO1 antibody 89M5 and anti-RSPO2 antibody 130M23 demonstrated strong anti-tumor growth activity in combination with gemcitabine in a pancreatic xenograft model.

Example 18

Inhibition of Pancreatic Tumor Growth in vivo by Anti-RSPO Antibodies in Combination with Wnt Pathway Inhibitors Dissociated PN7 pancreatic tumor cells ($1\times10^5$cells) were injected subcutaneously into the flanks of 6-8 week old NOD/SCID mice. Tumors were allowed to grow for 25 days until they reached an average volume of 130 $mm^3$, The mice were randomized (n=10 per group) and treated with anti-RSPO2 antibody 130M23, anti-FZD antibody 18RS, gemcitabine, a combination of 130M23 and gemcitabine, a combination of 18R5 and gemcitabine, a combination of 130M23 and 18R5, a combination of 130M23, 18R5 and gemcitabine, or control antibody 1B7.11. Anti-RSPO2 antibody 130M23 was dosed at 10 mg/kg once a week, anti-FZD antibody 18R5 was dosed at 20 mg/kg once a week, and gemcitabine was dosed at 30 mg/ml once a week. Administration of the antibodies and gemcitabine was performed via injection into the intraperitoneal cavity. Tumor growth was monitored and tumor volumes were measured with electronic calipers at specific time points. Data are expressed as mean±S.E.M. A parallel set of experiments included mice treated with a FZD8-Fc soluble receptor (10 mg/kg) in combination with gemcitabine and FZD8-Fc in combination with 130M23 and gemcitabine.

Treatment with antibody 130M23 or antibody 18R5 as a single agent resulted in approximately 55% reduction in tumor growth as compared to treatment with the control antibody (FIG. 16A, p<0.001). Treatment with 130M23 or 18R5 in combination with gemcitabine resulted in a reduction of tumor growth greater than treatment with either agent alone. Treatment with 130M23 and gemcitabine resulted in a 68% reduction in growth (p<0.001 vs. the control group), and treatment with 18R5 and gemcitabine resulted in a 75% reduction in growth (p<0.001 vs. the control group). Furthermore, a combination of 130M23, gemcitabine and 18R5 resulted in almost complete inhibition of growth of the PN7 tumors (FIG. 16A). Similar results were seen with a combination of 130M23, gemcitabine and a FZD8-Fc soluble receptor (FIG. 16B). Thus, an anti-RSPO2 antibody such as 130M23 has single agent activity in inhibiting pancreatic tumor growth. Furthermore, combination of an anti-RSPO2 antibody with gemcitabine, or a combination of an anti-RSPO2 antibody with gemcitabine and a Wnt pathway inhibitor such as anti-FZD antibody 18R5 or a FZD8-Fc soluble receptor, was shown to be a very effective therapy for inhibiting tumor growth in a pancreatic tumor model.

IHC studies showed that the anti-RSPO2 antibody 130M23 induced morphological changes in the PN7 tumors of treated mice as compared to untreated mice. These cells also displayed a significant decrease in proliferation using an anti-Ki67 antibody. These results possibly reflect a loss in tumor cells and an increase in stroma.

The PN7 tumors described above were processed to yield single cell suspensions. Mouse cells were depleted from the cell mixtures using biotinylated anti-H2K$^d$ and anti-CD45 antibodies and streptavidin-conjugated magnetic beads. The remaining human tumor cells were serially transplanted into a new cohort of mice. 90 tumor cells from each treatment group were injected into the flanks of NOD-SCID mice (n=10 mice per group). Tumors were allowed to grow for 40 days with no treatment and tumor volumes were measured with electronic calipers.

FIG. 16C shows the tumor volume from individual mice in each group. Cells isolated from mice treated with anti-RSPO2 antibody 130M23 or anti-FZD antibody 18R5 as single agents or in a combination had greatly decreased tumorigenicity as compared to cells isolated from mice treated with control antibody. This reduced tumorigenicity was much greater than the decrease in tumorigenicity observed with gemcitabine alone. Cells from mice treated with combinations of gemcitabine and 130M23, gemcitabine and 18R5, or gemcitabine and FZD8-Fc showed tumorigenicity that was only slightly reduced as compared to cell isolated from mice treated with control antibody. Interestingly, cells isolated from mice treated with a combination of 130M23, 18R5 and gemcitabine or 130M23, FZD8-Fc and gemcitabine demonstrated a significant and striking lack of tumor growth, greater than any of the agents alone or in two agent combinations. These results showed that inhibiting multiple pathways in addition to standard chemotherapy has an additive, and possibly a synergistic effect in reducing tumorigenicity and cancer stem cells.

Example 19

Humanization of RSPO Antibodies

Humanized antibodies against human RSPO1 and RSPO2 were generated. The heavy chain variable region and the light chain variable region of the murine monoclonal antibodies 89M5 and 130M23 were isolated and sequenced from the hybridoma line using degenerate PCR essentially as described in Larrick, J. M., et al., 1989, *Biochem. Biophys. Res. Comm.* 160: 1250 and Jones, S. T. & Bendig, M. M., 1991, *Bio/Technology* 9: 88. Human heavy and light chain variable framework regions likely to be structurally similar to the parental 89M5 or 130M23 antibody amino acid sequences were then considered as reference human framework regions to help guide the design of novel synthetic frameworks. To identify the human framework regions bearing similarity to murine frameworks, the predicted protein sequences encoded by the murine heavy chain and light chain variable domains of 89M5 and 130M23 were compared with human antibody sequences encoded by expressed human cDNA using BLAST searches for human sequence deposited in Genbank. The amino acid differences between candidate humanized framework heavy chains and the parent murine monoclonal antibody heavy chain variable regions and light chain variable regions were evaluated for likely importance, and a judgment made as to whether each difference in position contributes to proper folding and function of the variable region. This analysis was guided by examination of solved crystal structures of other antibody fragments (e.g., the structure of Fab 2E8 as described in Trakhanov et al, *Acta Crystallogr D Biol Crystallogr,* 1999, 55:122-28, as well as other protein crystal structures (e.g., protein data bank structures IADQ and IGIG)). Structures were modeled using computer software including Jmol, quick PDB, and Pymol. Consideration was given to the potential impact of an amino acid at a given position on the packing of the n-sheet framework, the interaction between the heavy and light chain variable regions, the degree of solvent exposure of the amino acid side chain, and the likelihood that an amino acid would impact the positioning of the CDR loops. From this analysis, candidate heavy chain variable regions fused in-frame to the human IgG2 constant region and candidate light chain variable regions fused in frame with the human IgKC1 constant region were conceived and chemically synthesized. The candidate heavy chains and light chains comprise: i) a synthetic framework designed to resemble natural human frameworks and ii) the parental 89M5 or 130M23 murine antibody CDRs.

The functionality of each candidate variant humanized heavy chain and light chain was tested by cotransfection into mammalian cells. Each candidate humanized heavy chain described above was cotransfected into HEK-293 cells with the murine light chain cDNA, and conditioned media was assayed by FACS for RSPO binding activity. Humanized 89M5 heavy chain variant "89M5-H2" (SEQ ID NO:68) exhibited the most robust binding and was selected. The 89M5-H2 humanized heavy chain was cotransfected into HEK-293 cells with each of the candidate humanized light chains, and conditioned media was again assayed for antigen binding by FACS. Light chain variant "89M5-L2" (SEQ ID NO:69) exhibited the most robust binding and was selected. Similarly the humanized 130M23 heavy chain variant "130M23-H1" (SEQ ID NO:70) exhibited the most robust binding and was selected. The 130M23-H1 humanized heavy chain was cotransfected into HEK-293 cells with each of the candidate humanized light chains, and conditioned media was again assayed for antigen binding by FACS. Light chain variant "130M23-L2" (SEQ ID NO:71) exhibited the most robust binding and was selected.

To increase antibody production, a variant of 130M23-H1L2 was generated. The variant comprises the same heavy chain as 130M23-H1L2, but has a modified light chain and is referred to as h130M23-H1L6.

Example 20

Binding Affinity of Humanized 89M5 and Humanized 130M23

The $K_D$ of h89M5-H2L2 was determined using a Biacore 2000 system from Biacore LifeSciences (GE Healthcare). Recombinant human RSPO1-Fc or mouse RSPO1-Fc proteins were immobilized on CM5 chips using standard amine-based chemistry (NHS/EDC). The antibodies were serially diluted 2-fold from 100 nM to 0.78 nM in HBS-P (0.01M HEPES pH7.4, 0.15M NaCl, 0.005% v/v Surfactant P20) and were injected over the chip surface. Kinetic data were collected over time and were fit using the simultaneous global fit equation to yield affinity constants ($K_D$ values) for each antibody.

h89M5-H2L2 had an affinity constant ($K_D$) for human RSPO1 and mouse RSPO1 of less than 0.1 nM.

The $K_D$ of h130M23-H1L2 and h130M23-H1L6 were determined using a Biacore 2000 system from Biacore LifeSciences (GE Healthcare). Recombinant human RSPO2-Fc protein was immobilized on CM5 chips using standard amine-based chemistry (NHS/EDC). The antibodies were serially diluted 2-fold from 100 nM to 0.78 nM in HBS-P (0.01M HEPES pH7.4, 0.15M NaCl, 0.005% v/v Surfactant P20) and were injected over the chip surface. Kinetic data were collected over time and were fit using the simultaneous global fit equation to yield affinity constants ($K_D$ values) for each antibody.

h130M23-H1L2 had an affinity constant ($K_D$) for human RSPO2 of 0.13 nM and h130M23-H1L6 had an affinity constant ($K_D$) for human RSPO2 of 0.15 nM.

Example 21

FACS Binding of Anti-RSPO Antibodies

HEK293 cells were transiently transfected with an expression vector encoding FLAG-RSPO1furin-CD4TM-GFP. As described in Example 5, FLAG-RSPO furin-CD4TM-GFP is a chimeric fusion protein enabling cell surface expression of the N-terminal furin-like domains of human RSPO1. FLAG-RSPO1 furin-CD4TM-GFP transfected cells were incubated in the presence of anti-RSPO1 antibody 89M5 or humanized anti-RSPO1 antibody h89M5-H2L2. Five-fold serial dilutions of each antibody were examined for their ability to bind to the RSPO1 expressing cells. The cells were stained with Phycoerythrin conjugated anti-IgG to reveal bound antibody. The cells were analyzed on a FACSCalibur instrument (BD Biosciences, San Jose, Calif.) and the data was processed using FlowJo software.

Figure 17:
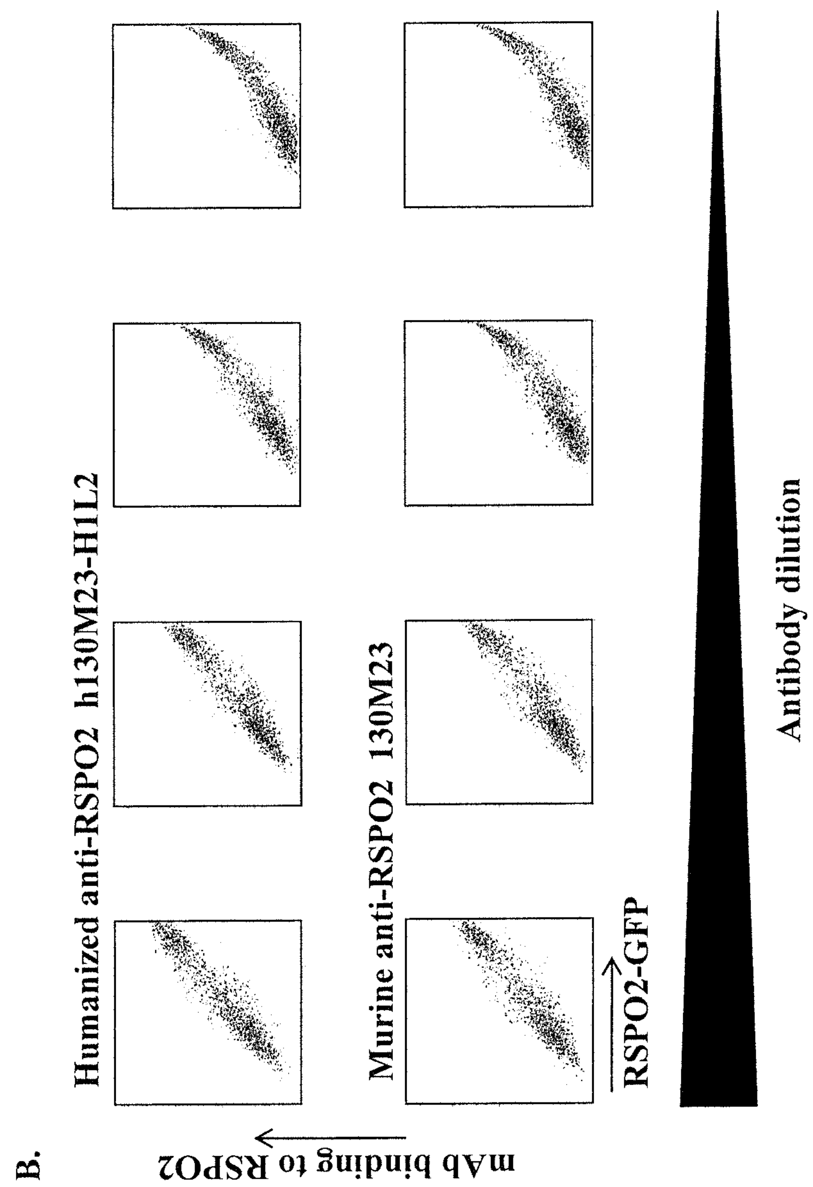
FIG. 17. FACS analysis of humanized RSPO antibodies. A) FACS analyses of humanized 89M5 antibody (h89M5-H2L2) and parental 89M5 antibody. Five-fold serial dilutions of each antibody were tested. Relative antibody binding is shown on the y-axis and expression of the FLAG-RSPO1 furin-CD4TM-GFP fusion protein is indicated on the x-axis. B) FACS analyses of humanized 130M23 antibody (h130M23-H1L2) and parental 130M23 antibody. Five-fold serial dilutions of each antibody were tested. Relative antibody binding is shown on the y-axis and expression of the FLAG-RSPO2furin-CD4TM-GFP fusion protein is indicated on the x-axis.

As shown in FIG. 17A, these studies indicate that both anti-RSPO1 antibody 89M5 and humanized anti-RSPO1 antibody h89M5-H2L2 bind to human RSPO1.

HEK293 cells were transiently transfected with an expression vector encoding FLAG-RSPO2furin-CD4TM-GFP. As described in Example 1, FLAG-RSPO2furin-CD4TM-GFP is a chimeric fusion protein enabling cell surface expression of the N-terminal furin-like domains of human RSPO2. FLAG-RSPO2furin-CD4TM-GFP transfected cells were incubated in the presence of anti-RSPO2 antibody 130M23 or humanized anti-RSPO2 antibody h130M5-H1L2. Five-fold serial dilutions of each antibody were examined for their ability to bind to the RSPO2 expressing cells. The cells were stained with Phycoerythrin conjugated anti-IgG to reveal bound antibody. The cells were analyzed on a FACSCalibur instrument (BD Biosciences, San Jose, Calif.) and the data was processed using FlowJo software.

As shown in FIG. 17B, these studies indicate that both anti-RSPO2 antibody 130M23 and humanized anti-RSPO2 antibody h130M23-H1L2 bind to human RSPO2.

Example 22

Inhibition of Breast Tumor Growth In Vivo by Anti-RSPO Antibodies in Combination with a Chemotherapeutic Agent Dissociated OMP-B39 breast tumor cells ($4\times10^5$ cells) were injected subcutaneously into the flanks of 6-8 week old NOD/SCID mice. OMP-039 is a triple negative breast cancer tumor with a high level of RSPO2 expression. In addition, the level of RSPO1 is higher than other breast tumors characterized in Example 1 (see Table 2). Tumors were allowed to grow for 39 days until they reached an average volume of 120 mm3. The mice were randomized (n=10 per group) and treated with a combination of anti-RSPO1 antibody 89M5 and anti-RSPO2 antibody 130M23, cisplatin, a combination of anti-RSPO1 and RSPO2 antibodies and cisplatin, or a control antibody. Antibodies were dosed at 15 mg/kg once a week and cisplatin was dosed at 1.5 mg/kg twice a week. Administration of the antibodies and cisplatin was performed via injection into the intraperitoneal cavity. Tumor growth was monitored and tumor volumes were measured with electronic calipers on the indicated days. Data are expressed as mean±S.E.M.

Figure 18:
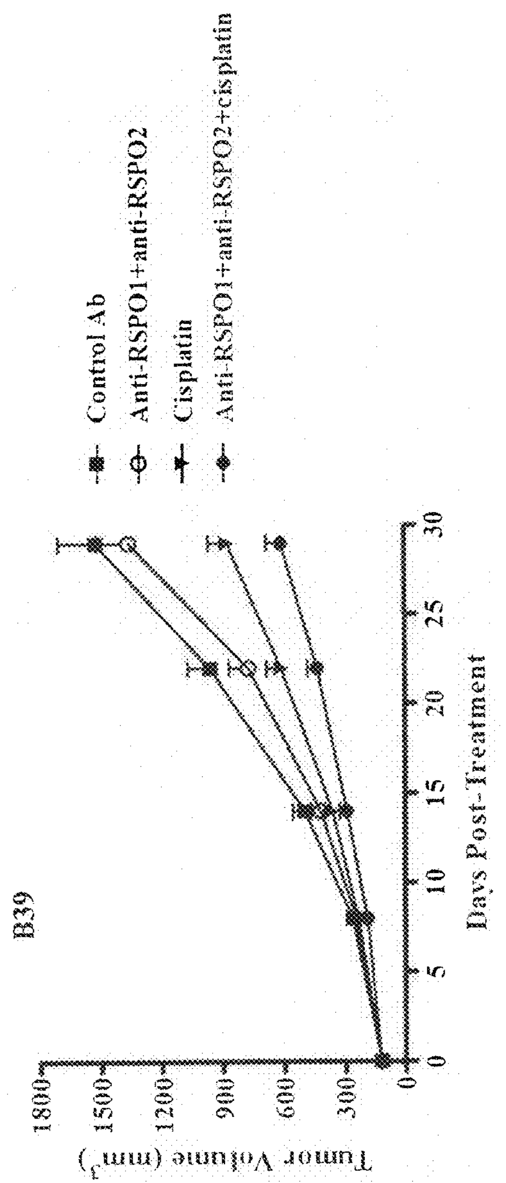
FIG. 18. Inhibition of tumor growth with anti-RSPO1 and anti-RSPO2 antibodies. B39 triple negative breast cancer tumor cells were injected subcutaneously into NOD/SCID mice. Mice were treated with a combination of anti-RSPO1 antibody 89M5 and anti-RSPO2 antibody 130M23 (-○-), cisplatin (-▼-), a combination of 89M5, 130M23 and cisplatin (-●-), or control antibody 1B7.11 (-■-). Data is shown as tumor volume (mm$^3$) over days post-treatment.

As shown in FIG. 18, a combination of anti-RSPO1 antibody 89M5 and anti-RSPO2 antibody 130M23 with cisplatin inhibited tumor growth better than cisplatin alone (p=0.04, combination group vs cisplatin alone). The triple combination had a significant effect, despite the fact that the combination of antibodies 89M5 and 130M25 without cisplatin had only a minimal effect on this tumor.

It is understood that the examples and embodiments described herein are for illustrative purposes only and that various modifications or changes in light thereof will be suggested to person skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

Human RSPO1 protein sequence with signal sequence (SEQ ID NO: 1)

MRLGLCVVALVLSWTHLTISSRGIKGKRQRRISAEGSQACAKGCELCSEV
NGCLKCSPKLFILLERNDIRQVGVCLPSCPPGYFDARNPDMNKCIKCKIE
HCEACFSHNFCTKCKEGLYLHKGRCYPACPEGSSAANGTMECSSPAQCEM
SEWSPWGPCSKKQQLCGFRRGSEERTRRVLHAPVGDHAACSDTKETRRCT
VRRVPCPEGQKRRKGGQGRRENANRNLARKESKEAGAGSRRRKGQQQQQQ
QGTVGPLTSAGPA

Human RSPO2 protein sequence with signal sequence (SEQ ID NO: 2)

MQFRLFSFALIIILNCMDYSHCQGNRWRRSKRASYVSNPICKGCLSCSKDN
GCSRCQQKLFFFLRREGMRQYGECLHSCPSGYYGHRAPDMNRCARCRIEN
CDSCFSKDFCTKCKVGFYLHRGRCFDECPDGFAPLEETMECVEGCEVGHW
SEWGTCSRNNRTCGFKWGLETRTRQIVKKPVKDTIPCPTIAESRRCKMTM
RHCPGGKRTPKAKEKRNKKKKRKLIERAQEQHSVFLATDRANQ

Human RSPO3 protein sequence with signal sequence (SEQ ID NO: 3)

MHLRLISWLFIILNFMEYIGSQNASRGRRQRRMHPNVSQGCQGGCATCSD
YNGCLSCKPRLFFALERIGMKQIGVCLSSCPSGYYGTRYPDINKCTKCKA
DCDTCFNKNFCTKCKSGFYLHLGKCLDNCPEGLEANNHTMECVSIVHCEV
SEWNPWSPCTKKGKTCGFKRGTETRVREIIQHPSAKGNLCPPTNETRKCT
VQRKKCQKGERGKKGRERKRKKPNKGESKEAIPDSKSLESSKEIPEQREN
KQQQKKRKVQDKQKSVSVSTVH

Human RSPO4 protein sequence with signal sequence (SEQ ID NO: 4)

MRAPLCLLLLVAHAVDMLALNRRKKQVGTGLGGNCTGCIICSEENGCSTC
QQRLFLFIRREGIRQYGKCLHDCPPGYFGIRGQEVNRCKKCGATCESCFS
QDFCIRCKRQFYLYKGKCLPTCPPGTLAHQNTRECQGECELGPWGGWSPC
THNGKTCGSAWGLESRVREAGRAGHEEAATCQVLSESRKCPIQRPCPGER
SPGQKKGRKDRRPRKDRKLDRRLDVRPRQPGLQP

Human RSPO1 protein sequence without predicted signal sequence (SEQ ID NO: 5)

SRGIKGKRQRRISAEGSQACAKGCELCSEVNGCLKCSPKLFILLERNDIR
QVGVCLPSCPPGYFDARNPDMNKCIKCKIEHCEACFSHNFCTKCKEGLYL

-continued

HKGRCYPACPEGSSAANGTMECSSPAQCEMSEWSPWGPCSKKQQLCGFRR
GSEERTRRVLHAPVGDHAACSDTKETRRCTVRRVPCPEGQKRRKGGQGRR
ENANRNLARKESKEAGAGSRRRKGQQQQQQQGTVGPLTSAGPA

Human RSPO1 furin-like domain 1 (SEQ ID NO: 6)

AEGSQACAKGCELCSEVNGCLKCSPKLFILLERNDIRQVGVCLPSCPPGY
FD

Human RSPO1 furin-like domain 2 (SEQ ID NO: 7)

MNKCIKCKIEHCEACFSHNECTKCKEGLYLHKGRCYPACPEGSSA

Human RSPO1 thrombospondin domain (SEQ ID NO: 8)

QCEMSEWSPWGPCSKKQQLCGFRRGSEERTRRVLHAPVGDHAACSDTKET
RRCTVRRVPCP

Human RSPO1 amino acids 31-263 (SEQ ID NO: 9)

RISAEGSQACAKGCELCSEVNGCLKCSPKLFILLERNDIRQVGVCLPSCP
PGYFDARNPDMNKCIKCKIEHCEACFSHNFCTKCKEGLYLHKGRCYPACP
EGSSAANGTMECSSPAQCEMSEWSPWGPCSKKQQLCGFRRGSEERTRRVL
HAPVGDHAACSDTKETRRCTVRRVPCPEGQKRRKGGQGRRENANRNLARK
ESKEAGAGSRRRKGQQQQQQQGTVGPLTSAGPA

89M5 Heavy chain variable region (SEQ ID NO: 10)

EVQLQQSGPELVKPGASVKISCKTSGYTFTGYTMHWVRQSHGKTLEWIGG
INPNNGGTTYNQNFKGKATLTVEKSSTTAYLELRSLTSEDSALYYCARKE
FSDGYYFFAYWGQGTLVTVSA

89M5 Light chain variable region (SEQ ID NO: 11)

DIVMTQSHKFMSTSVGDRVNITCKASQDVIFAVAWYQQKPGQSPKLLIYW
ASTRHTGVPDRFTGSVSGTDYTLTISSVQAEDLALYYCQQHYSTPWTFGG
GTKLEIK

89M5 Heavy chain CDR1 (SEQ ID NO: 12)

TGYTMH

89M5 Heavy chain CDR2 (SEQ ID NO: 13)

GINPNNGGTTYNQNFKG

89M5 Heavy chain CDR3 (SEQ ID NO: 14)

KEFSDGYYFFAY

89M5 Light chain CDR1 (SEQ ID NO: 15)

KASQDVIFAVA

89M5 Light chain CDR2 (SEQ ID NO: 16)

WASTRHT

89M5 Light chain CDR3 (SEQ ID NO: 17)

QQHYSTPW

FLAG Tag (SEQ ID NO: 18)

DYKDDDDK

-continued

89M5 Heavy chain variable region nucleotide sequence (SEQ ID NO: 19)

```
GAGGTCCAGCTGCAACAGTCTGGACCTGAGCTGGTGAAGCCTGGGGCTTC
AGTGAAGATATCCTGCAAGACTTCTGGATACACATTCACTGGATACACCA
TGCACTGGGTGAGGCAGAGCCATGGAAAGACCCTTGAGTGGATTGGAGGT
ATTAATCCTAACAATGGTGGTACTACTTACAACCAGAACTTCAAGGGCAA
GGCCACATTGACTGTAGAGAAGTCCTCCACCACAGCCTACTTGGAGCTCC
GCAGCCTGACATCTGAGGATTCTGCACTCTATTACTGTGCAAGAAAGGAG
TTCTCTGATGGTTACTACTTTTTTGCTTACTGGGGCCAAGGGACTCTGGT
CACTGTCTCTGCA
```

89M5 Light chain variable region nucleotide sequence (SEQ ID NO: 20)

```
GACATTGTGATGACCCAGTCTCACAAATTCATGTCCACATCAGTGGGAGA
CAGGGTCAACATCACCTGCAAGGCCAGTCAGGATGTGATTTTTGCTGTAG
CCTGGTATCAACAGAAACCAGGACAATCTCCTAAACTACTGATTTACTGG
GCATCCACCCGGCACACTGGAGTCCCTGATCGCTTCACAGGCAGTGTATC
TGGGACAGATTATACTCTCACCATCAGCAGTGTGCAGGCTGAAGACCTGG
CACTTTATTACTGTCAGCAACATTATAGCACTCCGTGGACGTTCGGTGGA
GGCACCAAGCTGGAAATCAAA
```

89M5 Heavy chain amino acid sequence with predicted signal sequence underlined (SEQ ID NO: 21)

<u>MGWSWIFLFLLSGTAGVLS</u>EVQLQQSGPELVKPGASVKISCKTSGYTFTG
YTMHWVRQSHGKTLEWIGGINPNNGGTTYNQNFKGKATLTVEKSSTAYL
ELRSLTSEDSALYYCARKEFSDGYYFFAYWGQGTLVTVSSAKTTPPSVYP
LAPGSAAQTNSMVTLGCLVKGYFPEPVTVTWNSGSLSSGVHTFPAVLQSD
LYTLSSSVTVPSSTWPSETVTCNVAHPASSTKVDKKIVPRDCGCKPCICT
VPEVSSVFIFPPKPKDVLTITLTPKVTCVVVDISKDDPEVQFSWFVDDVE
VHTAQTQPREEQFNSTFRSVSELPIMHQDWLNGKEFKCRVNSAAFPAPIE
KTISKTKGRPKAPQVYTIPPPKEQMAKDKVSLTCMITDFFPEDITVEWQW
NGQPAENYKNTQPIMDTDGSYFVYSKLNVQKSNWEAGNTFTCSVLHEGLH
NHHTEKSLSHSPGK

89M5 Light chain amino acid sequence with predicted signal sequence underlined (SEQ ID NO: 22)

<u>MGFKMESQIQAFVFVFLWLSGVDG</u>DIVMTQSHKFMSTSVGDRVNITCKAS
QDVIFAVAWYQQKPGQSPKLLIYWASTRHTGVPDRFTGSVSGTDYTLTIS
SVQAEDLALYYCQQHYSTPWTFGGGTKLEIKRADAAPTVSIFPPSSEQLT
SGGASVVCFLNNFYPKDINVKWKIDGSERQNGVLNSWTDQDSKDSTYSMS
STLTLTKDEYERHNSYTCEATHKTSTSPIVKSFNRNEC

89M5 Heavy chain nucleotide sequence (SEQ ID NO: 23)

```
ATGGGATGGAGCTGGATCTTTCTCTTTCTCCTGTCAGGAACTGCAGGTGT
CCTCTCTGAGGTCCAGCTGCAACAGTCTGGACCTGAGCTGGTGAAGCCTG
GGGCTTCAGTGAAGATATCCTGCAAGACTTCTGGATACACATTCACTGGA
```

-continued

```
TACACCATGCACTGGGTGAGGCAGAGCCATGGAAAGACCCTTGAGTGGAT
TGGAGGTATTAATCCTAACAATGGTGGTACTACTTACAACCAGAACTTCA
AGGGCAAGGCCACATTGACTGTAGAGAAGTCCTCCACCACAGCCTACTTG
GAGCTCCGCAGCCTGACATCTGAGGATTCTGCACTCTATTACTGTGCAAG
AAAGGAGTTCTCTGATGGTTACTACTTTTTTGCTTACTGGGGCCAAGGGA
CTCTGGTCACTGTCTCTTCAGCCAAAACGACACCCCCATCTGTCTATCCA
CTGGCCCCTGGATCTGCTGCCCAAACTAACTCCATGGTGACCCTGGGATG
CCTGGTCAAGGGCTATTTCCCTGAGCCAGTGACAGTGACCTGGAACTCTG
GATCCCTGTCCAGCGGTGTGCACACCTTCCCAGCTGTCCTGCAGTCTGAC
CTCTACACTCTGAGCAGCTCAGTGACTGTCCCCTCCAGCACCTGGCCCAG
CGAGACCGTCACCTGCAACGTTGCCCACCCGGCCAGCAGCACCAAGGTGG
ACAAGAAAATTGTGCCCAGGGATTGTGGTTGTAAGCCTTGCATATGTACA
GTCCCAGAAGTATCATCTGTCTTCATCTTCCCCCCAAAGCCCAAGGATGT
GCTCACCATTACTCTGACTCCTAAGGTCACGTGTGTTGTGGTAGACATCA
GCAAGGATGATCCCGAGGTCCAGTTCAGCTGGTTTGTAGATGATGTGGAG
GTGCACACAGCTCAGACGCAACCCCGGGAGGAGCAGTTCAACAGCACTTT
CCGCTCAGTCAGTGAACTTCCCATCATGCACCAGGACTGGCTCAATGGCA
AGGAGTTCAAATGCAGGGTCAACAGTGCAGCTTTCCCTGCCCCCATCGAG
AAAACCATCTCCAAAACCAAAGGCAGACCGAAGGCTCCACAGGTGTACAC
CATTCCACCTCCCAAGGAGCAGATGGCCAAGGATAAAGTCAGTCTGACCT
GCATGATAACAGACTTCTTCCCTGAAGACATTACTGTGGAGTGGCAGTGG
AATGGGCAGCCAGCGGAGAACTACAAGAACACTCAGCCCATCATGGACAC
AGATGGCTCTTACTTCGTCTACAGCAAGCTCAATGTGCAGAAGAGCAACT
GGGAGGCAGGAAATACTTTCACCTGCTCTGTGTTACATGAGGGCCTGCAC
AACCACCATACTGAGAAGAGCCTCTCCCACTCTCCTGGTAAATGATAA
```

89M5 Light chain nucleotide sequence (SEQ ID NO: 24)

```
ATGGGCTTCAAGATGGAGTCACAGATTCAGGCATTTGTATTCGTGTTTCT
CTGGTTGTCTGGTGTTGACGGAGACATTGTGATGACCCAGTCTCACAAAT
TCATGTCCACATCAGTGGGAGACAGGGTCAACATCACCTGCAAGGCCAGT
CAGGATGTGATTTTTGCTGTAGCCTGGTATCAACAGAAACCAGGACAATC
TCCTAAACTACTGATTTACTGGGCATCCACCCGGCACACTGGAGTCCCTG
ATCGCTTCACAGGCAGTGTATCTGGGACAGATTATACTCTCACCATCAGC
AGTGTGCAGGCTGAAGACCTGGCACTTTATTACTGTCAGCAACATTATAG
CACTCCGTGGACGTTCGGTGGAGGCACCAAGCTGGAAATCAAACGGGCTG
ATGCTGCACCAACTGTATCCATCTTCCCACCATCCAGTGAGCAGTTAACA
TCTGGAGGTGCCTCAGTCGTGTGCTTCTTGAACAACTTCTACCCCAAAGA
CATCAATGTCAAGTGGAAGATTGATGGCAGTGAACGACAAAATGGCGTCC
TGAACAGTTGGACTGATCAGGACAGCAAAGACAGCACCTACAGCATGAGC
AGCACCCTCACGTTGACCAAGGACGAGTATGAACGACATAACAGCTATAC
CTGTGAGGCCACTCACAAGACATCAACTTCACCCATTGTCAAGAGCTTCA
ACAGGAATGAGTGTTAGTGA
```

-continued

89M5 Heavy chain amino acid sequence without predicted signal sequence (SEQ ID NO: 25)

EVQLQQSGPELVKPGASVKISCKTSGYTFTGYTMHWVRQSHGKTLEWIGG

INPNNGGTTYNQNFKGKATLTVEKSSTTAYLELRSLTSEDSALYYCARKE

FSDGYYFFAYWGQGTLVTVSSAKTTPPSVYPLAPGSAAQTNSMVTLGCLV

KGYFPEPVTVTWNSGSLSSGVHTFPAVLQSDLYTLSSSVTVPSSTWPSET

VTCNVAHPASSTKVDKKIVPRDCGCKPCICTVPEVSSVFIFPPKPKDVLT

ITLTPKVTCVVVDISKDDPEVQFSWFVDDVEVHTAQTQPREEQFNSTFRS

VSELPIMHQDWLNGKEFKCRVNSAAFPAPIEKTISKTKGRPKAPQVYTIP

PPKEQMAKDKVSLTCMITDFFPEDITVEWQWNGQPAENYKNTQPIMDTDG

SYFVYSKLNVQKSNWEAGNTFTCSVLHEGLHNHHTEKSLSHSPGK

89M5 Light chain amino acid sequence without predicted signal sequence (SEQ ID NO: 26)

DIVMTQSHKFMSTSVGDRVNITCKASQDVIFAVAWYQQKPGQSPKLLIYW

ASTRHTGVPDRFTGSVSGTDYTLTISSVQAEDLALYYCQQHYSTPWTFGG

GTKLEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC

130M23 Heavy chain variable region (SEQ ID NO: 27)

EVKLVESGGGLVKPGGSLKFSCAASGFSFSSYAMSWVRQTPEKRLEWVAS

ISSGGSTYYPDSVKGRFTISRDNVRNILYLQMSSLRSEDTAMYTCARGGD

PGVYNGDYEDAMDYWGQGTSVTVSS

130M23 Light chain variable region (SEQ ID NO: 28)

DIVMTQSHKFMSTSVGDRVSITCKASQDVSSAVAWYQQKPGQSPKLLIYW

ASTRHTGVPDRFTNSGSGTDYTLTISSVQAEDLALYYCQQHYSTPWTFGG

GTKLEIK

130M23 Heavy chain CDR1

(SEQ ID NO: 29)

SSYAMS

130M23 Heavy chain CDR2

(SEQ ID NO: 30)

SISSGGSTYYPDSVKG

130M23 Heavy chain CDR3

(SEQ ID NO: 31)

RGGDPGVYNGDYEDAMDY

130M23 Light chain CDR1

(SEQ ID NO: 32)

KASQDVSSAVA

130M23 Light chain CDR2

(SEQ ID NO: 33)

WASTRHT

130M23 Light chain CDR3

(SEQ ID NO: 34)

QQHYSTP

130M23 Heavy chain variable region nucleotide sequence (SEQ ID NO: 35)

GAAGTGAAGCTGGTGGAGTCTGGGGGAGGCTTAGTGAAGCCTGGAGGGTC

CCTGAAATTTTCCTGTGCAGCCTCTGGATTCAGTTTCAGTAGTTATGCCA

-continued

TGTCTTGGGTTCGCCAGACTCCAGAGAAGAGGCTGGAGTGGGTCGCATCC

ATTAGTAGTGGTGGTAGTACCTACTATCCAGACAGTGTGAAGGGCCGATT

CACCATCTCCAGAGATAATGTCAGGAACATCCTGTACCTGCAAATGAGCA

GTCTGAGGTCTGAGGACACGGCCATGTATTTCTGTGCACGAGGCGGGGAT

CCGGGGGTCTACAATGGTGACTACGAAGATGCTATGGACTACTGGGGTCA

AGGAACCTCAGTCACCGTCTCCTCA

130M23 Light chain variable region nucleotide sequence (SEQ ID NO: 36)

GACATTGTGATGACCCAGTCTCACAAATTCATGTCCACATCAGTCGGAGA

CAGGGTCAGCATCACCTGCAAGGCCAGTCAGGATGTGAGTTCTGCTGTAG

CCTGGTATCAACAAAAACCAGGGCAATCTCCTAAACTACTGATTTACTGG

GCATCCACCCGGCACACTGGAGTCCCTGATCGCTTCACAAACAGTGGATC

TGGGACAGATTATACTCTCACCATCAGTAGTGTGCAGGCTGAAGACCTGG

CACTTTATTACTGTCAGCAACATTATAGCACTCCGTGGACGTTCGGTGGA

GGCACCAAGCTGGAAATCAAA

130M23 Heavy chain amino acid sequence with predicted signal sequence underlined (SEQ ID NO: 37)

<u>MNFGLRLVFLVLVLKGVQC</u>EVKLVESGGGLVKPGGSLKFSCAASGFSFSS

YAMSWVRQTPEKRLEWVASISSGGSTYYPDSVKGRFTISRDNVRNILYLQ

MSSLRSEDTAMYFCARGGDPGVYNGDYEDAMDYWGQGTSVTVSSAKTTPP

SVYPLAPGSAAQTNSMVTLGCLVKGYFPEPVTVTWNSGSLSSGVHTFPAV

LQSDLYTLSSSVTVPSSTWPSETVTCNVAHPASSTKVDKKIVPRDCGCKP

CICTVPEVSSVFIFPPKPKDVLTITLTPKVTCVVVDISKDDPEVQFSWFV

DDVEVHTAQTQPREEQFNSTFRSVSELPIMHQDWLNGKEFKCRVNSAAFP

APIEKTISKTKGRPKAPQVYTIPPPKEQMAKDKVSLTCMITDFFPEDITV

EWQWNGQPAENYKNTQPIMDTDGSYFVYSKLNVQKSNWEAGNTFTCSVLH

WGLHNHHTEKSLSHSPGK

130M23 Light chain amino acid sequence with predicted signal sequence underlined (SEQ ID NO: 38)

<u>MGIKMESQIQAFVFVFLWLSGVDG</u>DIVMTQSHKFMSTSVGDRVSITCKAS

QDVSSAVAWYQQKPGQSPKLLIYWASTRHTGVPDRFTNSGSGTDYTLTIS

SVQAEDLALYYCQQHYSTPWTFGGGTKLEILRADAAPTVSIFPPSSEQLT

SGGASVVCFLNNFYPKDINVKWKIDGSERQNGVLNSWTDQDSKDSTYSMS

STLTLTKDEYERHNSYTCEATHKTSTSPIVKSFNRNEC

130M23 Heavy chain nucleotide sequence (SEQ ID NO: 39)

ATGAACTTCGGGCTGAGATTGGTTTTCCTTGTCCTTGTTTTAAAAGGTGT

CCAGTGTGAAGTGAAGCTGGTGGAGTCTGGGGGAGGCTTAGTGAAGCCTG

GAGGGTCCCTGAAATTTTCCTGTGCAGCCTCTGGATTCAGTTTCAGTAGT

TATGCCATGTCTTGGGTTCGCCAGACTCCAGAGAAGAGGCTGGAGTGGGT

CGCATCCATTAGTAGTGGTGGTAGTACCTACTATCCAGACAGTGTGAAGG

GCCGATTCACCATCTCCAGAGATAATGTCAGGAACATCCTGTACCTGCAA

ATGAGCAGTCTGAGGTCTGAGGACACGGCCATGTATTTCTGTGCACGAGG

-continued

CGGGGATCCGGGGGTCTACAATGGTGACTACGAAGATGCTATGGACTACT

GGGGTCAAGGAACCTCAGTCACCGTCTCCTCAGCCAAAACGACACCCCCA

TCTGTCTATCCACTGGCCCCTGGATCTGCTGCCCAAACTATCTCCATGGT

GACCCTGGGATGCCTGGTCAAGGGCTATTTCCCTGAGCCAGTGACAGTGA

CCTGGAACTCTGGATCCCTGTCCAGCGGTGTGCACACCTTCCCAGCTGTC

CTGCAGTCTGACCTCTACACTCTGAGCAGCTCAGTGACTGTCCCCTCCAG

CACCTGGCCCAGCGAGACCGTCACCTGCAACGTTGCCCACCCGGCCAGCA

GCACCAAGGTGGACAAGAAAATTGTGCCCAGGGATTGTGGTTGTAAGCCT

TGCATATGTACAGTCCCAGAAGTATCATCTGTCTTCATCTTCCCCCCAAA

GCCCAAGGATGTGCTCACCATTACTCTGACTCCTAAGGTCACGTGTGTTG

TGGTAGACATCAGCAAGGATGATCCCGAGGTCCAGTTCAGCTGGTTTGTA

GATGATGTGGAGGTGCACACAGCTCAGACGCAACCCCGGGAGGAGCAGTT

CAACAGCACTTTCCGCTCAGTCAGTGAACTTCCCATCATGCACCAGGACT

GGCTCAATGGCAAGGAGTTCAAATGCAGGGTCAACAGTGCAGCTTTCCCT

GCCCCCATCGAGAAAACCATCTCCAAAACCAAAGGCAGACCGAAGGCTCC

ACAGGTGTACACCATTCCACCTCCCAAGGAGCAGATGGCCAAGGATAAAG

TCAGTCTGACCTGCATGATAACAGACTTCTTCCCTGAAGACATTACTGTG

GAGTGGCAGTGGAATGGGCAGCCAGCGGAGAACTACAAGAACACTCAGCC

CATCATGGACACAGATGGCTCTTACTTCGTCTACAGCAAGCTCAATGTGC

AGAAGAGCAACTGGGAGGCAGGAAATACTTTCACCTGCTCTGTGTTACAT

GAGGGCCTGCACAACCACCATACTGAGAAGAGCCTCTCCCACTCTCCTGG

TAAATGA

130M23 Light chain nucleotide sequence (SEQ ID NO: 40)

ATGGGCATCAAGATGGAGTCACAGATTCAGGCATTTGTATTCGTGTTTCT

CTGGTTGTCTGGTGTTGACGGAGACATTGTGATGACCCAGTCTCACAAAT

TCATGTCCACATCAGTCGGAGACAGGGTCAGCATCACCTGCAAGGCCAGT

CAGGATGTGAGTTCTGCTGTAGCCTGGTATCAACAAAAACCAGGGCAATC

TCCTAAACTACTGATTTACTGGGCATCCACCCGGCACACTGGAGTCCCTG

ATCGCTTCACAAACAGTGGATCTGGGACAGATTATACTCTCACCATCAGT

AGTGTGCAGGCTGAAGACCTGGCACTTTATTACTGTCAGCAACATTATAG

CACTCCGTGGACGTTCGGTGGAGGCACCAAGCTGGAAATCAAACGGGCTG

ATGCTGCACCAACTGTATCCATCTTCCCACCATCCAGTGAGCAGTTAACA

TCTGGAGGTGCCTCAGTCGTGTGCTTCTTGAACAACTTCTACCCCAAAGA

CATCAATGTCAAGTGGAAGATTGATGGCAGTGAACGACAAAATGGCGTCC

TGAACAGTTGGACTGATCAGGACAGCAAAGACAGCACCTACAGCATGAGC

AGCACCCTCACGTTGACCAAGGACGAGTATGAACGACATAACAGCTATAC

CTGTGAGGCCACTCACAAGACATCAACTTCACCCATTGTCAAGAGCTTCA

ACAGGAATGAGTGTTAG

-continued

130M23 Heavy chain amino acid sequence without predicted signal sequence (SEQ ID NO: 41)

EVKLVESGGGLVKPGGSLKFSCAASGFSFSSYAMSWVRQTPEKRLEWVAS

ISSGGSTYYPDSVKGRFTISRDNVRNILYLQMSSLRSEDTAMYFCARGGD

PGVYNGDYEDAMDYWGQGTSVTVSSAKTTPPSVYPLAPGSAAQTNSMVTL

GCLVKGYFPEPVTVTWNSGSLSSGVHTFPAVLQSDLYTLSSSVTVPSSTW

PSETVTCNVAHPASSTKVDKKIVPRDCGCKPCICTVPEVSSVFIFPPKPK

DVLTITLTPKVTCVVVDISKDDPEVQFSWFVDDVEVHTAQTQPREEQFNS

TFRSVSELPIMHQDWLNGKEFKCRVNSAAFPAPIEKTISKTKGRPKAPQV

YTIPPPKEQMAKDKVSLTCMITDFFPEDITVEWQWNGQPAENYKNTQPIM

DTDGSYFVYSKLNVQKSNWEAGNTFTCSVLHEGLHNHHTEKSLSHSPGK

130M23 Light chain amino acid sequence without predicted signal sequence (SEQ ID NO: 42)

DIVMTQSHKFMSTSVGDRVSITCKASQDVSSAVAWYQQKPGQSPKLLIYW

ASTRHTGVPDRFTNSGSGTDYTLTISSVQAEDLALYYCQQHYSTPWTEGG

GTKLEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC

Human RSPO2 protein sequence without predicted signal sequence (SEQ ID NO: 43)

QGNRWRRSKRASYVSNPICKGCLSCSKDNGCSRCQQKLFFFLRREGMRQY

GECLHSCPSGYYGHRAPDMNRCARCRIENCDSCFSKDFCTKCKVGFYLHR

GRCFDECPDGFAPLEETMECVEGCEVGHWSEWGTCSRNNRTCGFKWGLET

RTRQIVKKPVKDTIPCPTIAESRRCKMTMRHCPGGKRTPKAKEKRNKKKK

RKLIERAQEQHSVFLATDRANQ

Human RSPO2 amino acids 22-205

(SEQ ID NO: 44)

QGNRWRRSKRASYVSNPICKGCLSCSKDNGCSRCQQKLFFFLRREGMRQY

GECLHSCPSGYYGHRAPDMNRCARCRIENCDSCFSKDFCTKCKVGFYLHR

GRCFDECPDGFAPLEETMECVEGCEVGHWSEWGTCSRNNRTCGFKWGLET

RTRQIVKKPVKDTIPCPTIAESRRCKMTMRHCPG

Human RSPO2 furin-like domain 1

(SEQ ID NO: 45)

YVSNPICKGCLSCSKDNGCSRCQQKLFFFLRREGMRQYGECLHSCPSGY

YG

Human RSPO2 furin-like domain 2

(SEQ ID NO: 46)

MNRCARCRIENCDSCFSKDFCTKCKVGFYLHRGRCFDECPDGFAP

Human RSPO2 thrombospondin domain (SEQ ID NO: 47)

GCEVGHWSEWGTCSRNNRTCGFKWGLETRTRQIVKKPVKDTIPCPTIAES

RRCKMTMRHCP

Human RSPO3 protein sequence without predicted signal sequence (SEQ ID NO: 48)

QNASRGRRQRRMHPNVSQGCQGGCATCSDYNGCLSCKPRLFFALERIGM

KQIGVCLSSCPSGYYGTRYPDINKCTKCKADCDTCFNKNECTKCKSGFY

-continued

LHLGKCLDNCPEGLEANNHTMECVSIVHCEVSEWNPWSPCTKKGKTCGF

KRGTETRVREIIQHPSAKGNLCPPTNETRKCTVQRKKCQKGERGKKGRE

RKRKKPNKGESKEAIPDSKSLESSKEIPEQRENKQQQKKRKVQDKQKSV

SVSTVH

Human RSPO3 furin-like domain 1

(SEQ ID NO: 49)

PNVSQGCQGGCATCSDYNGCLSCKPRLFFALERIGMKQIGVCLSSCPSGY

YG

Human RSPO3 furin-like domain 2

(SEQ ID NO: 50)

INKCTKCKADCDTCFNKNFCTKCKSGFYLHLGKCLDNCPEGLEA

Human RSPO3 thrombospondin domain (SEQ ID NO: 51)

HCEVSEWNPWSPCTKKGKTCGFKRGTETRVREIIQHPSAKGNLCPPTNET

RKCTVQRKKCQ h89M5-H2L2 Heavy chain nucleotide sequence (SEQ ID NO: 52)

ATGGACTGGACCTGGAGGATACTCTTTCTCGTGGCAGCAGCCACAGGAGC

CCACTCCCAGGTCCAGCTCGTGCAGTCTGGGGCTGAGGTGAAGAAGCCTG

GGGCCTCTGTGAAGGTTTCCTGCAAGACTTCTGGATACACCTTCACTGGA

TACACCATGCACTGGGTTAGACAGGCCCCCGGACAAAGGCTGGAGTGGAT

GGGAGGTATTAATCCTAACAATGGTGGTACTACTTACAACCAGAACTTCA

AGGGCAGAGTCACCATTACCAGGGACACATCCGCAAGCACAGCCTACATG

GAGCTGTCCAGCCTGAGATCTGAAGACACAGCTGTGTATTACTGTGCAAG

AAAGGAGTTCTCTGATGGATACTACTTTTTTGCTTACTGGGGCCAAGGGA

CCCTGGTCACCGTCAGCTCAGCCAGCACAAAGGGCCCTAGCGTCTTCCCT

CTGGCTCCCTGCAGCAGGAGCACCAGCGAGAGCACAGCCGCCCTGGGCTG

CCTGGTCAAGGACTACTTCCCCGAACCGGTGACGGTGTCGTGGAACTCAG

GCGCTCTGACCAGCGGCGTGCACACCTTCCCAGCTGTCCTACAGTCCTCA

GGACTCTACTCCCTCAGCAGCGTGGTGACCGTGCCCTCCAGCAACTTCGG

CACCCAGACCTACACCTGCAACGTAGATCACAAGCCCAGCAACACCAAGG

TGGACAAGACAGTTGAGCGCAAATGTTGTGTCGAGTGCCCACCGTGCCCA

GCACCACCTGTGGCAGGACCGTCAGTCTTCCTCTTCCCCCCAAAACCCAA

GGACACCCTCATGATCTCCCGGACCCCTGAGGTCACGTGCGTGGTGGTGG

ACGTGAGCCACGAAGACCCCGAGGTCCAGTTCAACTGGTACGTGGACGGC

GTGGAGGTGCATAATGCCAAGACAAAGCCACGGGAGGAGCAGTTCAACAG

CACGTTCCGTGTGGTCAGCGTCCTCACCGTTGTGCACCAGGACTGGCTGA

ACGGCAAGGAGTACAAGTGCAAGGTCTCCAACAAAGGCCTCCCAGCCCCC

ATCGAGAAAACCATCTCCAAAACCAAAGGGCAGCCCCGAGAACCACAGGT

GTACACCCTGCCCCCATCCCGGGAGGAGATGACCAAGAACCAGGTCAGCC

TGACCTGCCTGGTCAAAGGCTTCTACCCCAGCGACATCGCCGTGGAGTGG

GAGAGCAATGGGCAGCCGGAGAACAACTACAAGACCACACCTCCCATGCT

GGACTCCGACGGCTCCTTCTTCCTCTACAGCAAGCTCACCGTGGACAAGA

GCAGGTGGCAGCAGGGGAACGTCTTCTCATGCTCCGTGATGCATGAGGCT

CTGCACAACCACTACACGCAGAAGAGCCTCTCCCTGTCTCCGGGTAAAT

GA h89M5-H2L2 Heavy chain amino acid sequence with predicted signal sequence underlined (SEQ ID NO: 53)

<u>MDWTWRILFLVAAATGAHS</u>QVQLVQSGAEVKKPGASVKVSCKTSGYTFTG

YTMHWVRQAPGQRLEWMGGINPNNGGTTYNQNFKGRVTITRDTSASTAYM

ELSSLRSEDTAVYYCARKEFSDGYYFFAYWGQGTLVTVSSASTKGPSVFP

LAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCP

APPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKGLPAP

IEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEA

LHNHYTQKSLSLSPGK h89M5-H2L2 Heavy chain variable region nucleotide sequence (SEQ ID NO: 54)

CAGGTCCAGCTCGTGCAGTCTGGGGCTGAGGTGAAGAAGCCTGGGGCCTC

TGTGAAGGTTTCCTGCAAGACTTCTGGATACACCTTCACTGGATACACCA

TGCACTGGGTTAGACAGGCCCCCGGACAAAGGCTGGAGTGGATGGGAGGT

ATTAATCCTAACAATGGTGGTACTACTTACAACCAGAACTTCAAGGGCAG

AGTCACCATTACCAGGGACACATCCGCAAGCACAGCCTACATGGAGCTGT

CCAGCCTGAGATCTGAAGACACAGCTGTGTATTACTGTGCAAGAAAGGAG

TTCTCTGATGGATACTACTTTTTTGCTTACTGGGGCCAAGGGACCCTGGT

CACCGTCAGCTCA h89M5-H2L2 Heavy chain variable region amino acid sequence (SEQ ID NO: 55)

QVQLVQSGAEVKKPGASVKVSCKTSGYTFTGYTMHWVRQAPGQRLEWMGG

INPNNGGTTYNQNFKGRVTITRDTSASTAYMELSSLRSEDTAVYYCARKE

FSDGYYFFAYWGQGTLVTVSS h89M5-H2L2 Light chain nucleotide sequence (SEQ ID NO: 56)

ATGGACATGAGGGTCCCCGCACAGCTCCTGGGGCTCCTGCTCCTCTGGCT

CCGGGGTGCCAGATGTGACATCCAGATGACCCAGTCTCCATCCTCCCTGT

CTGCATCTGTCGGAGACAGAGTCACCATCACTTGCAAGGCCTCCCAGGAT

GTGATTTTTGCTGTTGCCTGGTATCAGCAGAAACCAGGGAAAGCCCCTAA

GCTCCTGATCTATTGGGCATCCACCCGGCACACTGGGGTCCCATCAAGGT

TCAGTGGCAGTGGATCTGGGACAGATTACACTCTCACCATCAGCAGTCTG

CAACCTGAAGATTTTGCAACTTACTACTGTCAGCAACATTATAGCACTCC

TTGGACTTTCGGCGGAGGGACCAAGGTGGAGATCAAACGGACTGTGGCTG

CACCATCTGTCTTCATCTTCCCTCCATCTGATGAGCAGTTGAAATCTGGA

ACTGCCTCTGTTGTGTGCCTGCTGAATAACTTCTATCCCAGAGAGGCCAA

AGTCCAGTGGAAGGTGGATAACGCCCTCCAATCCGGTAACTCCCAGGAGA

GTGTCACAGAGCAGGACAGCAAGGACAGCACCTACAGCCTCAGCAACACC

CTGACACTGAGCAAAGCAGACTACGAGAAACACAAAGTCTACGCCTGCGA AGTCACCCATCAGGGCCTGAGCTCCCCCGTCACAAAGAGCTTCAACAGGG GAGAGTGCTAA h89M5-H2L2 Light chain amino acid sequence with predicted signal sequence underlined (SEQ ID NO: 57)

MDMRVPAQLLGLLLLWLRGARCDIQMTQSPSSLSASVGDRVTITCKASQD VIFAVAWYQQKPGKAPKLLIYWASTRHTGVPSRFSGSGSGTDYTLTISSL QPEDFATYYCQQHYSTPWTFGGGTKVEIKRTVAAPSVFIFPPSDEQLKSG TASVVCLLNNFYPREAKVQWKVDNALQSGNSQESVTEQDSKDSTYSLSNT LTLSKADYEKHKVYACEVTHQGLSSPVTKSFNRGEC h89M5-H2L2 Light chain variable region nucleotide sequence (SEQ ID NO: 58)

GACATCCAGATGACCCAGTCTCCATCCTCCCTGTCTGCATCTGTCGGAGA CAGAGTCACCATCACTTGCAAGGCCTCCCAGGATGTGATTTTTGCTGTTG CCTGGTATCAGCAGAAACCAGGGAAAGCCCCTAAGCTCCTGATCTATTGG GCATCCACCCGGCACACTGGGGTCCCATCAAGGTTCAGTGGCAGTGGATC TGGGACAGATTACACTCTCACCATCAGCAGTCTGCAACCTGAAGATTTTG CAACTTACTACTGTCAGCAACATTATAGCACTCCTTGGACTTTCGGCGGA GGGACCAAGGTGGAGATCAAA h89M5-H2L2 Light chain variable region amino acid sequence (SEQ ID NO: 59)

DIQMTQSPSSLSASVGDRVTITCKASQDVIFAVAWYQQKPGKAPKLLIYW ASTRHTGVPSRFSGSGSGTDYTLTISSLQPEDFATYYCQQHYSTPWTFGG GTKVEIK h130M23-H1L2 Heavy chain nucleotide sequence (SEQ ID NO: 60)

ATGGAACTGGGACTCAGATGGGTTTTCCTCGTTGCTATTCTGGAAGGAGT CCAGTGTGAGGTGCAGCTGGTGGAGTCTGGGGGAGGCCTGGTCAAGCCTG GAGGATCTCTGCGGCTCTCCTGTGCAGCCTCTGGATTCACCTTCTCCTCT TATGCCATGTCTTGGGTCCGGCAGGCTCCAGGGAAGGGGCTGGAATGGGT CTCATCCATTTCTAGTGGAGGTAGCACATATTATCCTGACAGCGTGAAGG GCCGGTTCACCATCTCCAGAGACAACGCCAAGAACAGCCTGTATCTGCAA ATGAACAGCCTGAGAGCCGAGGACACAGCTGTGTATTACTGTGCTAGAGG TGGAGATCCTGGGGTCTACAATGGAGATTACGAAGATGCTATGGACTACT GGGGGCAAGGAACAACAGTCACAGTCAGCTCAGCCAGCACAAAGGGCCCT AGCGTCTTCCCTCTGGCTCCCTGCAGCAGGAGCACCAGCGAGAGCACAGC CGCCCTGGGCTGCCTGGTCAAGGACTACTTCCCCGAACCGGTGACGGTGT CGTGGAACTCAGGCGCTCTGACCAGCGGCGTGCACACCTTCCCAGCTGTC CTACAGTCCTCAGGACTCTACTCCCTCAGCAGCGTGGTGACCGTGCCCTC CAGCAACTTCGGCACCCAGACCTACACCTGCAACGTAGATCACAAGCCCA GCAACACCAAGGTGGACAAGACAGTTGAGCGCAAATGTTGTGTCGAGTGC CCACCGTGCCCAGCACCACCTGTGGCAGGACCGTCAGTCTTCCTCTTCCC CCCAAAACCCAAGGACACCCTCATGATCTCCCGGACCCCTGAGGTCACGT

GCGTGGTGGTGGACGTGAGCCACGAAGACCCCGAGGTCCAGTTCAACTGG TACGTGGACGGCGTGGAGGTGCATAATGCCAAGACAAAGCCACGGGAGGA GCAGTTCAACAGCACGTTCCGTGTGGTCAGCGTCCTCACCGTTGTGCACC AGGACTGGCTGAACGGCAAGGAGTACAAGTGCAAGGTCTCCAACAAAGGC CTCCCAGCCCCCATCGAGAAAACCATCTCCAAAACCAAAGGGCAGCCCCG AGAACCACAGGTGTACACCCTGCCCCCATCCCGGGAGGAGATGACCAAGA ACCAGGTCAGCCTGACCTGCCTGGTCAAAGGCTTCTACCCCAGCGACATC GCCGTGGAGTGGGAGAGCAATGGGCAGCCGGAGAACAACTACAAGACCAC ACCTCCCATGCTGGACTCCGACGGCTCCTTCTTCCTCTACAGCAAGCTCA CCGTGGACAAGAGCAGGTGGCAGCAGGGGAACGTCTTCTCATGCTCCGTG ATGCATGAGGCTCTGCACAACCACTACACGCAGAAGAGCCTCTCCCTGTC TCCGGGTAAATGA h130M23-H1L2 Heavy chain amino acid Sequence with predicted signal sequence underlined (SEQ ID NO: 61)

MELGLRWVFLVAILEGVQCEVQLVESGGGLVKPGGSLRLSCAASGFTFSS YAMSWVRQAPGKGLEWVSSISSGGSTYYPDSVKGRFTISRDNAKNSLYLQ MNSLRAEDTAVYYCARGGDPGVYNGDYEDAMDYWGQGTTVTVSSASTKGP SVFPLAPCSRSTSESTAALGCLVKDYFPEPVTVSWNSGALTSGVHTFPAV LQSSGLYSLSSVVTVPSSNFGTQTYTCNVDHKPSNTKVDKTVERKCCVEC PPCPAPPVAGPSVFLFPPKPKDTLMISRTPEVTCVVVDVSHEDPEVQFNW YVDGVEVHNAKTKPREEQFNSTFRVVSVLTVVHQDWLNGKEYKCKVSNKG LPAPIEKTISKTKGQPREPQVYTLPPSREEMTKNQVSLTCLVKGFYPSDI AVEWESNGQPENNYKTTPPMLDSDGSFFLYSKLTVDKSRWQQGNVFSCSV MHEALHNHYTQKSLSLSPGK h130M23-H1L2 Heavy chain variable region nucleotide sequence (SEQ ID NO: 62)

GAGGTGCAGCTGGTGGAGTCTGGGGGAGGCCTGGTCAAGCCTGGAGGATC TCTGCGGCTCTCCTGTGCAGCCTCTGGATTCACCTTCTCCTCTTATGCCA TGTCTTGGGTCCGGCAGGCTCCAGGGAAGGGGCTGGAATGGGTCTCATCC ATTTCTAGTGGAGGTAGCACATATTATCCTGACAGCGTGAAGGGCCGGTT CACCATCTCCAGAGACAACGCCAAGAACAGCCTGTATCTGCAAATGAACA GCCTGAGAGCCGAGGACACAGCTGTGTATTACTGTGCTAGAGGTGGAGAT CCTGGGGTCTACAATGGAGATTACGAAGATGCTATGGACTACTGGGGGCA AGGAACAACAGTCACAGTCAGCTCA h130M23-H1L2 Heavy chain variable region amino acid sequence (SEQ ID NO: 63)

EVQLVESGGGLVKPGGSLRLSCAASGFTFSSYAMSWVRQAPGKGLEWVSS ISSGGSTYYPDSVKGRFTISRDNAKNSLYLQMNSLRAEDTAVYYCARGGD PGVYNGDYEDAMDYWGQGTTVTVSS h130M23-H1L2 Light chain nucleotide sequence (SEQ ID NO: 64)

ATGAAATACCTCCTCCCTACAGCTGCCGCTGGACTCCTCCTCCTCGCTGC CCAGCCTGCCATGGCCGACATCCAGATGACCCAGTCCCCTTCCTCCCTGT

-continued

CTGCTTCCGTCGGAGACAGAGTCACCATCACTTGCAAGGCCTCCCAGGAT

GTGTCCTCTGCTGTCGCTTGGTATCAGCAGAAACCAGGAAAAGCTCCTAA

GCTCCTGATCTATTGGGCATCCACCAGGCACACAGGAGTCCCTTCCAGGT

TCTCCGGCTCTGGATCTGGGACAGATTTCACTCTCACCATCAGCTCCGTG

CAAGCTGAAGATTTTGCAACTTACTACTGTCAGCAACATTATAGCACTCC

TTGGACATTCGGACAAGGGACCAAGGTGGAAATCAAAAGAACTGTGGCTG

CACCTTCTGTCTTCATCTTCCCTCCATCTGATGAGCAGCTCAAATCTGGA

ACTGCCTCCGTTGTGTGCCTGCTGAATAACTTCTATCCTAGAGAGGCCAA

AGTCCAGTGGAAGGTGGATAACGCCCTCCAATCCGGTAACTCCCAGGAGT

CTGTCACAGAGCAGGACTCCAAGGACAGCACCTACTCCCTCAGCAACACC

CTGACACTGTCTAAAGCTGACTACGAGAAACACAAAGTCTACGCCTGCGA

AGTCACCCATCAGGGACTGAGCTCCCCGTCACAAAATCCTTCAACAGGGG

AGAGTGCTAA h130M23-H1L2 Light chain amino acid sequence with predicted signal sequence underlined (SEQ ID NO: 65)

MKYLLPTAAAGLLLLAAQPAMADIQMTQSPSSLSASVGDRVTITCKASQD

VSSAVAWYQQKPGKAPKLLIYWASTRHTGVPSRFSGSGSGTDFTLTISSV

QAEDFATYYCQQHYSTPWTFGQGTKVEIKRTVAAPSVFIFPPSDEQLKSG

TASVVCLLNNFYPREAKVQWKVDNALQSGNSQESVTEQDSKDSTYSLSNT

LTLSKADYEKHKVYACEVTHQGLSSPVTKSFNRGEC h130M23-H1L2 Light chain variable region nucleotide sequence (SEQ ID NO: 66)

GACATCCAGATGACCCAGTCCCCTTCCTCCCTGTCTGCTTCCGTCGGAGA

CAGAGTCACCATCACTTGCAAGGCCTCCCAGGATGTGTCCTCTGCTGTCG

CTTGGTATCAGCAGAAACCAGGAAAAGCTCCTAAGCTCCTGATCTATTGG

GCATCCACCAGGCACACAGGAGTCCCTTCCAGGTTCTCCGGCTCTGGATC

TGGGACAGATTTCACTCTCACCATCAGCTCCGTGCAAGCTGAAGATTTTG

CAACTTACTACTGTCAGCAACATTATAGCACTCCTTGGACATTCGGACAA

GGGACCAAGGTGGAAATCAAA h130M23-H1L2 Light chain variable region amino acid sequence (SEQ ID NO: 67)

DIQMTQSPSSLSASVGDRVTITCKASQDVSSAVAWYQQKPGKAPKLLIYW

ASTRHTGVPSRFSGSGSGTDFTLTISSVQAEDFATYYCQQHYSTPWTFGQ

GTKVEIK h89M5-H2L2 Heavy chain amino acid sequence without predicted signal sequence (SEQ ID NO: 68)

QVQLVQSGAEVKKPGASVKVSCKTSGYTFTGYTMHWVRQAPGQRLEWMGG

INPNNGGTTYNQNFKGRVTITRDTSASTAYMELSSLRSEDTAVYYCARKE

FSDGYYFFAYWGQGTLVTVSSASTKGPSVFPLAPCSRSTSESTAALGCLV

KDYFPEPVTVSWNSGALTSGVHTFPAVLQSSGLYSLSSVVTVPSSNFGTQ

TYTCNVDHKPSNTKVDKTVERKCCVECPPCPAPPVAGPSVFLFPPKPKDT

LMISRTPEVTCVVVDVSHEDPEVQFNWYVDGVEVHNAKTKPREEQFNSTF

RVVSVLTVVHQDWLNGKEYKCKVSNKGLPAPIEKTISKTKGQPREPQVYT

-continued

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK h89M5-H2L2 Light chain amino acid sequence without predicted signal sequence underlined (SEQ ID NO: 69)

DIQMTQSPSSLSASVGDRVTITCKASQDVIFAVAWYQQKPGKAPKLLIYW

ASTRHTGVPSRFSGSGSGTDYTLTISSLQPEDFATYYCQQHYSTPWTFGG

GTKVEIKRTVAAPSVFIFPPSDEQLKSGTASVVCLLNNFYPREAKVQWKV

DNALQSGNSQESVTEQDSKDSTYSLSNTLTLSKADYEKHKVYACEVTHQG

LSSPVTKSFNRGEC h130M23-H1L2 Heavy chain amino acid sequence without predicted signal sequence underlined (SEQ ID NO: 70)

EVQLVESGGGLVKPGGSLRLSCAASGFTFSSYAMSWVRQAPGKGLEWVSS

ISSGGSTYYPDSVKGRFTISRDNAKNSLYLQMNSLRAEDTAVYYCARGGD

PGVYNGDYEDAMDYWGQGTTVTVSSASTKGPSVFPLAPCSRSTSESTAAL

GCLVKDYFPEPVTVSWNSGALTSGVHTFPAVLQSSGLYSLSSVVTVPSSN

FGTQTYTCNVDHKPSNTKVDKTVERKCCVECPPCPAPPVAGPSVFLFPPK

PKDTLMISRTPEVTCVVVDVSHEDPEVQFNWYVDGVEVHNAKTKPREEQF

NSTFRVVSVLTVVEQDWLNGKEYKCKVSNKGLPAPIEKTISKTKGQPREP

QVYTLPPSREEMTKNQVSLTCLVKGFYPSDIAVEWESNGQPENNYKTTPP

MLDSDGSFFLYSKLTVDKSRWQQGNVFSCSVMHEALHNHYTQKSLSLSP

GK h130M23-H1L2 Light chain amino acid sequence without predicted signal sequence underlined (SEQ ID NO: 71)

DIQMTQSPSSLSASVGDRVTITCKASQDVSSAVAWYQQKPGKAPKLLIYW

ASTRHTGVPSRFSGSGSGTDFTLTISSVQAEDFATYYCQQHYSTPWTFGQ

GTKVEIKRTVAAPSVFIFPPSDEQLKSGTASVVCLLNNFYPREAKVQWKV

DNALQSGNSQESVTEQDSKDSTYSLSNTLTLSKADYEKHKVYACEVTHQG

LSSPVTKSFNRGEC h130M23-H1L6 Light chain nucleotide sequence (SEQ ID NO: 72)

ATGGGCATCAAGATGGAGTCACAGATTCAGGCATTTGTATTCGTGTTTCT

CTGGTTGTCTGGTGTTGACGGAGACATCCAGATGACCCAGTCCCCTTCCT

CCCTGTCTGCTTCCGTCGGAGACAGAGTCACCATCACTTGCAAGGCCTCC

CAGGATGTGTCCTCTGCTGTCGCTTGGTATCAGCAGAAACCAGGAAAAGC

TCCTAAGCTCCTGATCTATTGGGCATCCACCAGGCACACAGGAGTCCCTT

CCAGGTTCTCCGGCTCTGGATCTGGGACAGATTTCACTCTCACCATCAGC

TCCCTGCAACCTGAAGATTTTGCAACTTACTACTGTCAGCAACATTATAG

CACTCCTTGGACATTCGGACAAGGGACCAAGGTGGAAATCAAAAGAACTG

TGGCTGCACCTTCTGTCTTCATCTTCCCTCCATCTGATGAGCAGCTCAAA

TCTGGAACTGCCTCCGTTGTGTGCCTGCTGAATAACTTCTATCCTAGAGA

GGCCAAAGTCCAGTGGAAGGTGGATAACGCCCTCCAATCCGGTAACTCCC

AGGAGTCTGTCACAGAGCAGGACTCCAAGGACAGCACCTACTCCCTCAGC

-continued

AACACCCTGACACTGTCTAAAGCTGACTACGAGAAACACAAAGTCTACGC

CTGCGAAGTCACCCATCAGGGACTGAGCTCCCCCGTCACAAAATCCTTCA

ACAGGGGAGAGTGCTAA h130M23-H1L6 Light chain amino acid sequence with predicted signal sequence underlined (SEQ ID NO: 73)

MGIKMESQIQAFVFVFLWLSGVDGDIQMTQSPSSLSASVGDRVTITCKAS

QDVSSAVAWYQQKPGKAPKLLIYWASTRHTGVPSRFSGSGSGTDFTLTIS

SLQPEDFATYYCQQHYSTPWTFGQGTKVEIKRTVAAPSVFIFPPSDEQLK

SGTASVVCLLNNFYPREAKVQWKVDNALQSGNSQESVTEQDSKDSTYSLS

NTLTLSKADYEKHKVYACEVTHQGLSSPVTKSFNRGEC h130M23-H1L6 Light chain amino acid sequence without predicted signal sequence underlined (SEQ ID NO: 74)

DIQMTQSPSSLSASVGDRVTITCKASQDVSSAVAWYQQKPGKAPKLLIYW

ASTRHTGVPSRFSGSGSGTDFTLTISSLQPEDFATYYCQQHYSTPWTFGQ

GTKVEIKRTVAAPSVFIFPPSDEQLKSGTASVVCLLNNFYPREAKVQWKV

-continued

DNALQSGNSQESVTEQDSKDSTYSLSNTLTLSKADYEKHKVYACEVTHQG

LSSPVTKSFNRGEC h130M23-H1L6 Light chain variable region nucleotide sequence (SEQ ID NO: 75)

GACATCCAGATGACCCAGTCCCCTTCCTCCCTGTCTGCTTCCGTCGGAGA

CAGAGTCACCATCACTTGCAAGGCCTCCCAGGATGTGTCCTCTGCTGTCG

CTTGGTATCAGCAGAAACCAGGAAAAGCTCCTAAGCTCCTGATCTATTGG

GCATCCACCAGGCACACAGGAGTCCCTTCCAGGTTCTCCGGCTCTGGATC

TGGGACAGATTTCACTCTCACCATCAGCTCCCTGCAACCTGAAGATTTTG

CAACTTACTACTGTCAGCAACATTATAGCACTCCTTGGACATTCGGACAA

GGGACCAAGGTGGAAATCAAA h130M23-H1L6 Light chain variable region amino acid sequence (SEQ ID NO: 76)

DIQMTQSPSSLSASVGDRVTITCKASQDVSSAVAWYQQKPGKAPKLLIYW

ASTRHTGVPSRFSGSGSGTDFTLTISSLQPEDFATYYCQQHYSTPWTFGQ

GTKVEIK

What is claimed is:

1. An isolated antibody that specifically binds human R-spondin 2 (RSPO2), which comprises:

(a) a heavy chain CDR1 comprising SSYAMS (SEQ ID NO:29), a heavy chain CDR2 comprising SISSGGSTYYPDSVKG (SEQ ID NO:30), and a heavy chain CDR3 comprising RGGDPGVYNGDYEDAMDY (SEQ ID NO:31); and (b) a light chain CDR1 comprising KASQDVSSAVA (SEQ ID NO:32), a light chain CDR2 comprising WASTRHT (SEQ ID NO:33), and a light chain CDR3 comprising QQHYSTP (SEQ ID NO:34).

2. The antibody of claim 1, which comprises a heavy chain variable region having at least 90% sequence identity to SEQ ID NO:27 and a light chain variable region having at least 90% sequence identity to SEQ ID NO:28.

3. The antibody of claim 1, which comprises a heavy chain variable region having at least 90% sequence identity to SEQ ID NO:63 and a light chain variable region having at least 90% sequence identity to SEQ ID NO:67.

4. The antibody of claim 1, which comprises a heavy chain variable region having at least 90% sequence identity to SEQ ID NO:63 and a light chain variable region having at least 90% sequence identity to SEQ ID NO:76.

5. The antibody of claim 1, which comprises a heavy chain variable region of SEQ ID NO:27 and a light chain variable region of SEQ ID NO:28.

6. The antibody of claim 1, which comprises a heavy chain variable region of SEQ ID NO:63 and a light chain variable region of SEQ ID NO:67.

7. The antibody of claim 1, which comprises a heavy chain variable region of SEQ ID NO:63 and a light chain variable region of SEQ ID NO:76.

8. The antibody of claim 1, which is a recombinant antibody, a monoclonal antibody, a chimeric antibody, a bispecific antibody, a humanized antibody, a human antibody, an IgG1 antibody, an IgG2 antibody, or an antibody fragment comprising an antigen-binding site.

9. The antibody of claim 8, which is a monoclonal antibody.

10. The antibody of claim 8, which is a humanized antibody.

11. The antibody of claim 8, which is a human antibody.

12. The antibody of claim 1, which inhibits binding of RSPO2 to at least one leucine-rich repeat containing G protein coupled receptor (LGR).

13. The antibody of claim 12, wherein the LGR is selected from the group consisting of LGR4, LGR5, and LGR6.

14. A pharmaceutical composition comprising the antibody of claim 1 and a pharmaceutically acceptable carrier.

15. An isolated monoclonal antibody that competes with the antibody of claim 1 for specific binding to RSPO2.

16. The antibody of claim 15, which:

(a) inhibits RSPO2 signaling;

(b) inhibits activation of β-catenin;

(c) inhibits β-catenin signaling; and/or (d) inhibits tumor growth.

17. A hybridoma cell line having ATCC deposit number PTA-12021.

18. An antibody produced by the cell line of claim 17.

19. A humanized form of the antibody of claim 18.

* * * * *

SEQUENCE LISTING

```
<160> NUMBER OF SEQ ID NOS: 76

<210> SEQ ID NO 1
<211> LENGTH: 263
<212> TYPE: PRT
<213> ORGANISM: Homo sapiens

<400> SEQUENCE: 1

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190
```

```
Thr Lys Glu Thr Arg Arg Cys Thr Val Arg Arg Val Pro Cys Pro Glu
        195                 200                 205

Gly Gln Lys Arg Arg Lys Gly Gly Gln Gly Arg Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gln Gly Thr Val Gly Pro
                245                 250                 255

Leu Thr Ser Ala Gly Pro Ala
            260


<210> SEQ ID NO 2
<211> LENGTH: 243
<212> TYPE: PRT
<213> ORGANISM: Homo sapiens

<400> SEQUENCE: 2

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Pro Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Lys Arg Lys Leu
    210                 215                 220

Ile Glu Arg Ala Gln Glu Gln His Ser Val Phe Leu Ala Thr Asp Arg
225                 230                 235                 240

Ala Asn Gln


<210> SEQ ID NO 3
<211> LENGTH: 272
<212> TYPE: PRT
<213> ORGANISM: Homo sapiens

<400> SEQUENCE: 3

Met His Leu Arg Leu Ile Ser Trp Leu Phe Ile Ile Leu Asn Phe Met
```

```
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Lys Gly Arg Glu Arg Lys Arg Lys Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser Val Ser Val Ser Thr Val His
            260                 265                 270
```

<210> SEQ ID NO 4
<211> LENGTH: 234
<212> TYPE: PRT
<213> ORGANISM: Homo sapiens

<400> SEQUENCE: 4

```
Met Arg Ala Pro Leu Cys Leu Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
        35                  40                  45

Thr Cys Gln Gln Arg Leu Phe Leu Phe Ile Arg Arg Glu Gly Ile Arg
    50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110
```

```
Leu Tyr Lys Gly Lys Cys Leu Pro Thr Cys Pro Pro Gly Thr Leu Ala
        115                 120                 125

His Gln Asn Thr Arg Glu Cys Gln Gly Glu Cys Glu Leu Gly Pro Trp
    130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro Cys Pro Gly Glu Arg Ser Pro Gly Gln Lys Lys Gly Arg
        195                 200                 205

Lys Asp Arg Arg Pro Arg Lys Asp Arg Lys Leu Asp Arg Arg Leu Asp
    210                 215                 220

Val Arg Pro Arg Gln Pro Gly Leu Gln Pro
225                 230


<210> SEQ ID NO 5
<211> LENGTH: 243
<212> TYPE: PRT
<213> ORGANISM: Homo sapiens

<400> SEQUENCE: 5

Ser Arg Gly Ile Lys Gly Lys Arg Gln Arg Arg Ile Ser Ala Glu Gly
1               5                   10                  15

Ser Gln Ala Cys Ala Lys Gly Cys Glu Leu Cys Ser Glu Val Asn Gly
            20                  25                  30

Cys Leu Lys Cys Ser Pro Lys Leu Phe Ile Leu Leu Glu Arg Asn Asp
        35                  40                  45

Ile Arg Gln Val Gly Val Cys Leu Pro Ser Cys Pro Pro Gly Tyr Phe
    50                  55                  60

Asp Ala Arg Asn Pro Asp Met Asn Lys Cys Ile Lys Cys Lys Ile Glu
65                  70                  75                  80

His Cys Glu Ala Cys Phe Ser His Asn Phe Cys Thr Lys Cys Lys Glu
                85                  90                  95

Gly Leu Tyr Leu His Lys Gly Arg Cys Tyr Pro Ala Cys Pro Glu Gly
            100                 105                 110

Ser Ser Ala Ala Asn Gly Thr Met Glu Cys Ser Ser Pro Ala Gln Cys
        115                 120                 125

Glu Met Ser Glu Trp Ser Pro Trp Gly Pro Cys Ser Lys Lys Gln Gln
    130                 135                 140

Leu Cys Gly Phe Arg Arg Gly Ser Glu Glu Arg Thr Arg Arg Val Leu
145                 150                 155                 160

His Ala Pro Val Gly Asp His Ala Ala Cys Ser Asp Thr Lys Glu Thr
                165                 170                 175

Arg Arg Cys Thr Val Arg Arg Val Pro Cys Pro Glu Gly Gln Lys Arg
            180                 185                 190

Arg Lys Gly Gly Gln Gly Arg Arg Glu Asn Ala Asn Arg Asn Leu Ala
        195                 200                 205

Arg Lys Glu Ser Lys Glu Ala Gly Ala Gly Ser Arg Arg Arg Lys Gly
    210                 215                 220

Gln Gln Gln Gln Gln Gln Gln Gly Thr Val Gly Pro Leu Thr Ser Ala
225                 230                 235                 240

Gly Pro Ala
```

<210> SEQ ID NO 6
<211> LENGTH: 52
<212> TYPE: PRT
<213> ORGANISM: Homo sapiens

<400> SEQUENCE: 6

```
Ala Glu Gly Ser Gln Ala Cys Ala Lys Gly Cys Glu Leu Cys Ser Glu
1               5                   10                  15

Val Asn Gly Cys Leu Lys Cys Ser Pro Lys Leu Phe Ile Leu Leu Glu
            20                  25                  30

Arg Asn Asp Ile Arg Gln Val Gly Val Cys Leu Pro Ser Cys Pro Pro
        35                  40                  45

Gly Tyr Phe Asp
    50
```

<210> SEQ ID NO 7
<211> LENGTH: 45
<212> TYPE: PRT
<213> ORGANISM: Homo sapiens

<400> SEQUENCE: 7

```
Met Asn Lys Cys Ile Lys Cys Lys Ile Glu His Cys Glu Ala Cys Phe
1               5                   10                  15

Ser His Asn Phe Cys Thr Lys Cys Lys Glu Gly Leu Tyr Leu His Lys
            20                  25                  30

Gly Arg Cys Tyr Pro Ala Cys Pro Glu Gly Ser Ser Ala
        35                  40                  45
```

<210> SEQ ID NO 8
<211> LENGTH: 61
<212> TYPE: PRT
<213> ORGANISM: Homo sapiens

<400> SEQUENCE: 8

```
Gln Cys Glu Met Ser Glu Trp Ser Pro Trp Gly Pro Cys Ser Lys Lys
1               5                   10                  15

Gln Gln Leu Cys Gly Phe Arg Arg Gly Ser Glu Glu Arg Thr Arg Arg
            20                  25                  30

Val Leu His Ala Pro Val Gly Asp His Ala Ala Cys Ser Asp Thr Lys
        35                  40                  45

Glu Thr Arg Arg Cys Thr Val Arg Arg Val Pro Cys Pro
    50                  55                  60
```

<210> SEQ ID NO 9
<211> LENGTH: 233
<212> TYPE: PRT
<213> ORGANISM: Homo sapiens

<400> SEQUENCE: 9

```
Arg Ile Ser Ala Glu Gly Ser Gln Ala Cys Ala Lys Gly Cys Glu Leu
1               5                   10                  15

Cys Ser Glu Val Asn Gly Cys Leu Lys Cys Ser Pro Lys Leu Phe Ile
            20                  25                  30

Leu Leu Glu Arg Asn Asp Ile Arg Gln Val Gly Val Cys Leu Pro Ser
        35                  40                  45

Cys Pro Pro Gly Tyr Phe Asp Ala Arg Asn Pro Asp Met Asn Lys Cys
    50                  55                  60

Ile Lys Cys Lys Ile Glu His Cys Glu Ala Cys Phe Ser His Asn Phe
65                  70                  75                  80
```

```
Cys Thr Lys Cys Lys Glu Gly Leu Tyr Leu His Lys Gly Arg Cys Tyr
                85                  90                  95

Pro Ala Cys Pro Glu Gly Ser Ser Ala Ala Asn Gly Thr Met Glu Cys
            100                 105                 110

Ser Ser Pro Ala Gln Cys Glu Met Ser Glu Trp Ser Pro Trp Gly Pro
        115                 120                 125

Cys Ser Lys Lys Gln Gln Leu Cys Gly Phe Arg Arg Gly Ser Glu Glu
    130                 135                 140

Arg Thr Arg Arg Val Leu His Ala Pro Val Gly Asp His Ala Ala Cys
145                 150                 155                 160

Ser Asp Thr Lys Glu Thr Arg Arg Cys Thr Val Arg Arg Val Pro Cys
                165                 170                 175

Pro Glu Gly Gln Lys Arg Arg Lys Gly Gly Gln Gly Arg Arg Glu Asn
            180                 185                 190

Ala Asn Arg Asn Leu Ala Arg Lys Glu Ser Lys Glu Ala Gly Ala Gly
        195                 200                 205

Ser Arg Arg Arg Lys Gly Gln Gln Gln Gln Gln Gln Gln Gly Thr Val
    210                 215                 220

Gly Pro Leu Thr Ser Ala Gly Pro Ala
225                 230


<210> SEQ ID NO 10
<211> LENGTH: 121
<212> TYPE: PRT
<213> ORGANISM: Artificial sequence
<220> FEATURE:
<223> OTHER INFORMATION: 89M5 Heavy chain variable region

<400> SEQUENCE: 10

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Gly Tyr
            20                  25                  30

Thr Met His Trp Val Arg Gln Ser His Gly Lys Thr Leu Glu Trp Ile
        35                  40                  45

Gly Gly Ile Asn Pro Asn Asn Gly Gly Thr Thr Tyr Asn Gln Asn Phe
    50                  55                  60

Lys Gly Lys Ala Thr Leu Thr Val Glu Lys Ser Ser Thr Thr Ala Tyr
65                  70                  75                  80

Leu Glu Leu Arg Ser Leu Thr Ser Glu Asp Ser Ala Leu Tyr Tyr Cys
                85                  90                  95

Ala Arg Lys Glu Phe Ser Asp Gly Tyr Tyr Phe Phe Ala Tyr Trp Gly
            100                 105                 110

Gln Gly Thr Leu Val Thr Val Ser Ala
        115                 120


<210> SEQ ID NO 11
<211> LENGTH: 107
<212> TYPE: PRT
<213> ORGANISM: Artificial sequence
<220> FEATURE:
<223> OTHER INFORMATION: 89M5 Light chain variable region

<400> SEQUENCE: 11

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Ile Phe Ala
```

```
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Val Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys
            100                 105


<210> SEQ ID NO 12
<211> LENGTH: 6
<212> TYPE: PRT
<213> ORGANISM: Artificial sequence
<220> FEATURE:
<223> OTHER INFORMATION: 89M5 Heavy chain CDR1

<400> SEQUENCE: 12

Thr Gly Tyr Thr Met His
1               5


<210> SEQ ID NO 13
<211> LENGTH: 17
<212> TYPE: PRT
<213> ORGANISM: Artificial sequence
<220> FEATURE:
<223> OTHER INFORMATION: 89M5 Heavy chain CDR2

<400> SEQUENCE: 13

Gly Ile Asn Pro Asn Asn Gly Gly Thr Thr Tyr Asn Gln Asn Phe Lys
1               5                   10                  15

Gly


<210> SEQ ID NO 14
<211> LENGTH: 12
<212> TYPE: PRT
<213> ORGANISM: Artificial sequence
<220> FEATURE:
<223> OTHER INFORMATION: 89M5 Heavy chain CDR3

<400> SEQUENCE: 14

Lys Glu Phe Ser Asp Gly Tyr Tyr Phe Phe Ala Tyr
1               5                   10


<210> SEQ ID NO 15
<211> LENGTH: 11
<212> TYPE: PRT
<213> ORGANISM: Artificial sequence
<220> FEATURE:
<223> OTHER INFORMATION: 89M5 Light chain CDR1

<400> SEQUENCE: 15

Lys Ala Ser Gln Asp Val Ile Phe Ala Val Ala
1               5                   10


<210> SEQ ID NO 16
<211> LENGTH: 7
<212> TYPE: PRT
<213> ORGANISM: Artificial sequence
<220> FEATURE:
<223> OTHER INFORMATION: 89M5 Light chain CDR2
```

<400> SEQUENCE: 16

Trp Ala Ser Thr Arg His Thr
1 5

<210> SEQ ID NO 17
<211> LENGTH: 8
<212> TYPE: PRT
<213> ORGANISM: Artificial sequence
<220> FEATURE:
<223> OTHER INFORMATION: 89M5 Light chain CDR3

<400> SEQUENCE: 17

Gln Gln His Tyr Ser Thr Pro Trp
1 5

<210> SEQ ID NO 18
<211> LENGTH: 8
<212> TYPE: PRT
<213> ORGANISM: Artificial sequence
<220> FEATURE:
<223> OTHER INFORMATION: FLAG Tag

<400> SEQUENCE: 18

Asp Tyr Lys Asp Asp Asp Asp Lys
1 5

<210> SEQ ID NO 19
<211> LENGTH: 363
<212> TYPE: DNA
<213> ORGANISM: Artificial sequence
<220> FEATURE:
<223> OTHER INFORMATION: 89M5 Heavy chain variable region nucleotide sequence

<400> SEQUENCE: 19
gaggtccagc tgcaacagtc tggacctgag ctggtgaagc ctggggcttc agtgaagata 60
tcctgcaaga cttctggata cacattcact ggatacacca tgcactgggt gaggcagagc 120
catggaaaga cccttgagtg gattggaggt attaatccta acaatggtgg tactacttac 180
aaccagaact tcaagggcaa ggccacattg actgtagaga agtcctccac cacagcctac 240
ttggagctcc gcagcctgac atctgaggat tctgcactct attactgtgc aagaaaggag 300
ttctctgatg gttactactt ttttgcttac tggggccaag ggactctggt cactgtctct 360
gca 363

<210> SEQ ID NO 20
<211> LENGTH: 321
<212> TYPE: DNA
<213> ORGANISM: Artificial sequence
<220> FEATURE:
<223> OTHER INFORMATION: 89M5 Light chain variable region nucleotide

<400> SEQUENCE: 20
gacattgtga tgacccagtc tcacaaattc atgtccacat cagtgggaga cagggtcaac 60
atcacctgca aggccagtca ggatgtgatt tttgctgtag cctggtatca acagaaacca 120
ggacaatctc ctaaactact gatttactgg gcatccaccc ggcacactgg agtccctgat 180
cgcttcacag gcagtgtatc tgggacagat tatactctca ccatcagcag tgtgcaggct 240
gaagacctgg cactttatta ctgtcagcaa cattatagca ctccgtggac gttcggtgga 300
ggcaccaagc tggaaatcaa a 321

```
<210> SEQ ID NO 21
<211> LENGTH: 464
<212> TYPE: PRT
<213> ORGANISM: Artificial sequence
<220> FEATURE:
<223> OTHER INFORMATION: 89M5 Heavy chain amino acid sequence

<400> SEQUENCE: 21

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Thr Ser Gly Tyr Thr Phe
        35                  40                  45

Thr Gly Tyr Thr Met His Trp Val Arg Gln Ser His Gly Lys Thr Leu
    50                  55                  60

Glu Trp Ile Gly Gly Ile Asn Pro Asn Asn Gly Gly Thr Thr Tyr Asn
65                  70                  75                  80

Gln Asn Phe Lys Gly Lys Ala Thr Leu Thr Val Glu Lys Ser Ser Thr
                85                  90                  95

Thr Ala Tyr Leu Glu Leu Arg Ser Leu Thr Ser Glu Asp Ser Ala Leu
            100                 105                 110

Tyr Tyr Cys Ala Arg Lys Glu Phe Ser Asp Gly Tyr Tyr Phe Phe Ala
        115                 120                 125

Tyr Trp Gly Gln Gly Thr Leu Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
```

```
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460


<210> SEQ ID NO 22
<211> LENGTH: 238
<212> TYPE: PRT
<213> ORGANISM: Artificial sequence
<220> FEATURE:
<223> OTHER INFORMATION: 89M5 Light chain amino acid sequence

<400> SEQUENCE: 22

Met Gly Phe Lys Met Glu Ser Gln Ile Gln Ala Phe Val Phe Val Phe
1               5                   10                  15

Leu Trp Leu Ser Gly Val Asp Gly Asp Ile Val Met Thr Gln Ser His
            20                  25                  30

Lys Phe Met Ser Thr Ser Val Gly Asp Arg Val Asn Ile Thr Cys Lys
        35                  40                  45

Ala Ser Gln Asp Val Ile Phe Ala Val Ala Trp Tyr Gln Gln Lys Pro
    50                  55                  60

Gly Gln Ser Pro Lys Leu Leu Ile Tyr Trp Ala Ser Thr Arg His Thr
65                  70                  75                  80

Gly Val Pro Asp Arg Phe Thr Gly Ser Val Ser Gly Thr Asp Tyr Thr
                85                  90                  95

Leu Thr Ile Ser Ser Val Gln Ala Glu Asp Leu Ala Leu Tyr Tyr Cys
            100                 105                 110

Gln Gln His Tyr Ser Thr Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235


<210> SEQ ID NO 23
<211> LENGTH: 1398
<212> TYPE: DNA
<213> ORGANISM: Artificial sequence
<220> FEATURE:
<223> OTHER INFORMATION: 89M5 Heavy chain nucleotide sequence
```

<400> SEQUENCE: 23

```
atgggatgga gctggatctt tctctttctc ctgtcaggaa ctgcaggtgt cctctctgag     60
gtccagctgc aacagtctgg acctgagctg gtgaagcctg gggcttcagt gaagatatcc    120
tgcaagactt ctggatacac attcactgga tacaccatgc actgggtgag gcagagccat    180
ggaaagaccc ttgagtggat tggaggtatt aatcctaaca atggtggtac tacttacaac    240
cagaacttca agggcaaggc cacattgact gtagagaagt cctccaccac agcctacttg    300
gagctccgca gcctgacatc tgaggattct gcactctatt actgtgcaag aaaggagttc    360
tctgatggtt actacttttt tgcttactgg ggccaaggga ctctggtcac tgtctcttca    420
gccaaaacga cacccccatc tgtctatcca ctggcccctg gatctgctgc ccaaactaac    480
tccatggtga ccctgggatg cctggtcaag ggctatttcc ctgagccagt gacagtgacc    540
tggaactctg gatccctgtc cagcggtgtg cacaccttcc cagctgtcct gcagtctgac    600
ctctacactc tgagcagctc agtgactgtc ccctccagca cctggcccag cgagaccgtc    660
acctgcaacg ttgcccaccc ggccagcagc accaaggtgg acaagaaaat tgtgcccagg    720
gattgtggtt gtaagccttg catatgtaca gtcccagaag tatcatctgt cttcatcttc    780
cccccaaagc ccaaggatgt gctcaccatt actctgactc ctaaggtcac gtgtgttgtg    840
gtagacatca gcaaggatga tcccgaggtc cagttcagct ggtttgtaga tgatgtggag    900
gtgcacacag ctcagacgca accccgggag gagcagttca acagcacttt ccgctcagtc    960
agtgaacttc ccatcatgca ccaggactgg ctcaatggca aggagttcaa atgcagggtc   1020
aacagtgcag ctttccctgc ccccatcgag aaaaccatct ccaaaaccaa aggcagaccg   1080
aaggctccac aggtgtacac cattccacct cccaaggagc agatggccaa ggataaagtc   1140
agtctgacct gcatgataac agacttcttc cctgaagaca ttactgtgga gtggcagtgg   1200
aatgggcagc cagcggagaa ctacaagaac actcagccca tcatggacac agatggctct   1260
tacttcgtct acagcaagct caatgtgcag aagagcaact gggaggcagg aaatactttc   1320
acctgctctg tgttacatga gggcctgcac aaccaccata ctgagaagag cctctcccac   1380
tctcctggta aatgataa                                                  1398
```

<210> SEQ ID NO 24
<211> LENGTH: 720
<212> TYPE: DNA
<213> ORGANISM: Artificial sequence
<220> FEATURE:
<223> OTHER INFORMATION: 89M5 Light chain nucleotide sequence

<400> SEQUENCE: 24

```
atgggcttca agatggagtc acagattcag gcatttgtat tcgtgtttct ctggttgtct     60
ggtgttgacg gagacattgt gatgacccag tctcacaaat tcatgtccac atcagtggga    120
gacagggtca acatcacctg caaggccagt caggatgtga tttttgctgt agcctggtat    180
caacagaaac caggacaatc tcctaaacta ctgatttact gggcatccac ccggcacact    240
ggagtccctg atcgcttcac aggcagtgta tctgggacag attatactct caccatcagc    300
agtgtgcagg ctgaagacct ggcactttat tactgtcagc aacattatag cactccgtgg    360
acgttcggtg gaggcaccaa gctggaaatc aaacgggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
```

```
aatggcgtcc tgaacagttg gactgatcag gacagcaaag acagcaccta cagcatgagc    600

agcaccctca cgttgaccaa ggacgagtat gaacgacata acagctatac ctgtgaggcc    660

actcacaaga catcaacttc acccattgtc aagagcttca acaggaatga gtgttagtga    720


<210> SEQ ID NO 25
<211> LENGTH: 445
<212> TYPE: PRT
<213> ORGANISM: Artificial sequence
<220> FEATURE:
<223> OTHER INFORMATION: 89M5 Heavy chain amino acid sequence

<400> SEQUENCE: 25

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Gly Tyr
            20                  25                  30

Thr Met His Trp Val Arg Gln Ser His Gly Lys Thr Leu Glu Trp Ile
        35                  40                  45

Gly Gly Ile Asn Pro Asn Asn Gly Gly Thr Thr Tyr Asn Gln Asn Phe
    50                  55                  60

Lys Gly Lys Ala Thr Leu Thr Val Glu Lys Ser Ser Thr Thr Ala Tyr
65                  70                  75                  80

Leu Glu Leu Arg Ser Leu Thr Ser Glu Asp Ser Ala Leu Tyr Tyr Cys
                85                  90                  95

Ala Arg Lys Glu Phe Ser Asp Gly Tyr Tyr Phe Phe Ala Tyr Trp Gly
            100                 105                 110

Gln Gly Thr Leu Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335
```

```
Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445


<210> SEQ ID NO 26
<211> LENGTH: 214
<212> TYPE: PRT
<213> ORGANISM: Artificial sequence
<220> FEATURE:
<223> OTHER INFORMATION: 89M5 Light chain amino acid sequence without
      predicted signal sequence

<400> SEQUENCE: 26

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Ile Phe Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Val Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 27
<211> LENGTH: 125
<212> TYPE: PRT
<213> ORGANISM: Artificial sequence
```

<220> FEATURE:
<223> OTHER INFORMATION: 130M23 Heavy chain variable region

<400> SEQUENCE: 27

Glu Val Lys Leu Val Glu Ser Gly Gly Gly Leu Val Lys Pro Gly Gly
1 5 10 15

Ser Leu Lys Phe Ser Cys Ala Ala Ser Gly Phe Ser Phe Ser Ser Tyr
20 25 30

Ala Met Ser Trp Val Arg Gln Thr Pro Glu Lys Arg Leu Glu Trp Val
35 40 45

Ala Ser Ile Ser Ser Gly Gly Ser Thr Tyr Tyr Pro Asp Ser Val Lys
50 55 60

Gly Arg Phe Thr Ile Ser Arg Asp Asn Val Arg Asn Ile Leu Tyr Leu
65 70 75 80

Gln Met Ser Ser Leu Arg Ser Glu Asp Thr Ala Met Tyr Phe Cys Ala
85 90 95

Arg Gly Gly Asp Pro Gly Val Tyr Asn Gly Asp Tyr Glu Asp Ala Met
100 105 110

Asp Tyr Trp Gly Gln Gly Thr Ser Val Thr Val Ser Ser
115 120 125

<210> SEQ ID NO 28
<211> LENGTH: 107
<212> TYPE: PRT
<213> ORGANISM: Artificial sequence
<220> FEATURE:
<223> OTHER INFORMATION: 130M23 Light chain variable region

<400> SEQUENCE: 28

Asp Ile Val Met Thr Gln Ser His Lys Phe Met Ser Thr Ser Val Gly
1 5 10 15

Asp Arg Val Ser Ile Thr Cys Lys Ala Ser Gln Asp Val Ser Ser Ala
20 25 30

Val Ala Trp Tyr Gln Gln Lys Pro Gly Gln Ser Pro Lys Leu Leu Ile
35 40 45

Tyr Trp Ala Ser Thr Arg His Thr Gly Val Pro Asp Arg Phe Thr Asn
50 55 60

Ser Gly Ser Gly Thr Asp Tyr Thr Leu Thr Ile Ser Ser Val Gln Ala
65 70 75 80

Glu Asp Leu Ala Leu Tyr Tyr Cys Gln Gln His Tyr Ser Thr Pro Trp
85 90 95

Thr Phe Gly Gly Gly Thr Lys Leu Glu Ile Lys
100 105

<210> SEQ ID NO 29
<211> LENGTH: 6
<212> TYPE: PRT
<213> ORGANISM: Artificial sequence
<220> FEATURE:
<223> OTHER INFORMATION: 130M23 Heavy chain CDR1

<400> SEQUENCE: 29

Ser Ser Tyr Ala Met Ser
1 5

<210> SEQ ID NO 30
<211> LENGTH: 16
<212> TYPE: PRT
<213> ORGANISM: Artificial sequence
<220> FEATURE:

<223> OTHER INFORMATION: 130M23 Heavy chain CDR2

<400> SEQUENCE: 30

Ser Ile Ser Ser Gly Gly Ser Thr Tyr Tyr Pro Asp Ser Val Lys Gly
1               5                   10                  15

<210> SEQ ID NO 31
<211> LENGTH: 18
<212> TYPE: PRT
<213> ORGANISM: Artificial sequence
<220> FEATURE:
<223> OTHER INFORMATION: 130M23 Heavy chain CDR3

<400> SEQUENCE: 31

Arg Gly Gly Asp Pro Gly Val Tyr Asn Gly Asp Tyr Glu Asp Ala Met
1               5                   10                  15

Asp Tyr

<210> SEQ ID NO 32
<211> LENGTH: 11
<212> TYPE: PRT
<213> ORGANISM: Artificial sequence
<220> FEATURE:
<223> OTHER INFORMATION: 130M23 Light chain CDR1

<400> SEQUENCE: 32

Lys Ala Ser Gln Asp Val Ser Ser Ala Val Ala
1               5                   10

<210> SEQ ID NO 33
<211> LENGTH: 7
<212> TYPE: PRT
<213> ORGANISM: Artificial sequence
<220> FEATURE:
<223> OTHER INFORMATION: 130M23 Light chain CDR2

<400> SEQUENCE: 33

Trp Ala Ser Thr Arg His Thr
1               5

<210> SEQ ID NO 34
<211> LENGTH: 7
<212> TYPE: PRT
<213> ORGANISM: Artificial sequence
<220> FEATURE:
<223> OTHER INFORMATION: 130M23 Light chain CDR3

<400> SEQUENCE: 34

Gln Gln His Tyr Ser Thr Pro
1               5

<210> SEQ ID NO 35
<211> LENGTH: 375
<212> TYPE: DNA
<213> ORGANISM: Artificial sequence
<220> FEATURE:
<223> OTHER INFORMATION: 130M23 Heavy chain variable region nucleotide sequence

<400> SEQUENCE: 35
gaagtgaagc tggtggagtc tgggggaggc ttagtgaagc ctggagggtc cctgaaattt     60
tcctgtgcag cctctggatt cagtttcagt agttatgcca tgtcttgggt tcgccagact    120
ccagagaaga ggctggagtg ggtcgcatcc attagtagtg gtggtagtac ctactatcca    180
gacagtgtga agggccgatt caccatctcc agagataatg tcaggaacat cctgtacctg    240

```
caaatgagca gtctgaggtc tgaggacacg gccatgtatt tctgtgcacg aggcggggat    300

ccgggggtct acaatggtga ctacgaagat gctatggact actggggtca aggaacctca    360

gtcaccgtct cctca                                                     375


<210> SEQ ID NO 36
<211> LENGTH: 321
<212> TYPE: DNA
<213> ORGANISM: Artificial sequence
<220> FEATURE:
<223> OTHER INFORMATION: 130M23 Light chain variable region nucleotide
      sequence

<400> SEQUENCE: 36

gacattgtga tgacccagtc tcacaaattc atgtccacat cagtcggaga cagggtcagc     60

atcacctgca aggccagtca ggatgtgagt tctgctgtag cctggtatca acaaaaacca    120

gggcaatctc ctaaactact gatttactgg gcatccaccc ggcacactgg agtccctgat    180

cgcttcacaa acagtggatc tgggacagat tatactctca ccatcagtag tgtgcaggct    240

gaagacctgg cactttatta ctgtcagcaa cattatagca ctccgtggac gttcggtgga    300

ggcaccaagc tggaaatcaa a                                              321


<210> SEQ ID NO 37
<211> LENGTH: 468
<212> TYPE: PRT
<213> ORGANISM: Artificial sequence
<220> FEATURE:
<223> OTHER INFORMATION: 130M23 Heavy chain amino acid sequence

<400> SEQUENCE: 37

Met Asn Phe Gly Leu Arg Leu Val Phe Leu Val Leu Val Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Phe Ser Cys Ala Ala Ser Gly Phe Ser Phe
        35                  40                  45

Ser Ser Tyr Ala Met Ser Trp Val Arg Gln Thr Pro Glu Lys Arg Leu
    50                  55                  60

Glu Trp Val Ala Ser Ile Ser Ser Gly Gly Ser Thr Tyr Tyr Pro Asp
65                  70                  75                  80

Ser Val Lys Gly Arg Phe Thr Ile Ser Arg Asp Asn Val Arg Asn Ile
                85                  90                  95

Leu Tyr Leu Gln Met Ser Ser Leu Arg Ser Glu Asp Thr Ala Met Tyr
            100                 105                 110

Phe Cys Ala Arg Gly Gly Asp Pro Gly Val Tyr Asn Gly Asp Tyr Glu
        115                 120                 125

Asp Ala Met Asp Tyr Trp Gly Gln Gly Thr Ser Val Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205
```

```
Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365

Val Tyr Thr Ile Pro Pro Pro Lys Glu Gln Met Ala Lys Asp Lys Val
    370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Val Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465
```

<210> SEQ ID NO 38
<211> LENGTH: 238
<212> TYPE: PRT
<213> ORGANISM: Artificial sequence
<220> FEATURE:
<223> OTHER INFORMATION: 130M23 Light chain amino acid sequence

<400> SEQUENCE: 38

```
Met Gly Ile Lys Met Glu Ser Gln Ile Gln Ala Phe Val Phe Val Phe
1               5                   10                  15

Leu Trp Leu Ser Gly Val Asp Gly Asp Ile Val Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Ser Ser Ala Val Ala Trp Tyr Gln Gln Lys Pro
    50                  55                  60

Gly Gln Ser Pro Lys Leu Leu Ile Tyr Trp Ala Ser Thr Arg His Thr
65                  70                  75                  80

Gly Val Pro Asp Arg Phe Thr Asn Ser Gly Ser Gly Thr Asp Tyr Thr
                85                  90                  95
```

```
Leu Thr Ile Ser Ser Val Gln Ala Glu Asp Leu Ala Leu Tyr Tyr Cys
            100                 105                 110

Gln Gln His Tyr Ser Thr Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235


<210> SEQ ID NO 39
<211> LENGTH: 1407
<212> TYPE: DNA
<213> ORGANISM: Artificial sequence
<220> FEATURE:
<223> OTHER INFORMATION: 130M23 Heavy chain nucleotide sequence

<400> SEQUENCE: 39

atgaacttcg ggctgagatt ggttttcctt gtccttgttt taaaaggtgt ccagtgtgaa      60

gtgaagctgg tggagtctgg gggaggctta gtgaagcctg gagggtccct gaaattttcc     120

tgtgcagcct ctggattcag tttcagtagt tatgccatgt cttgggttcg ccagactcca     180

gagaagaggc tggagtgggt cgcatccatt agtagtggtg gtagtaccta ctatccagac     240

agtgtgaagg gccgattcac catctccaga gataatgtca ggaacatcct gtacctgcaa     300

atgagcagtc tgaggtctga ggacacggcc atgtatttct gtgcacgagg cggggatccg     360

ggggtctaca atggtgacta cgaagatgct atggactact ggggtcaagg aacctcagtc     420

accgtctcct cagccaaaac gacaccccca tctgtctatc cactggcccc tggatctgct     480

gcccaaacta actccatggt gaccctggga tgcctggtca agggctattt ccctgagcca     540

gtgacagtga cctggaactc tggatccctg tccagcggtg tgcacacctt cccagctgtc     600

ctgcagtctg acctctacac tctgagcagc tcagtgactg tcccctccag cacctggccc     660

agcgagaccg tcacctgcaa cgttgcccac ccggccagca gcaccaaggt ggacaagaaa     720

attgtgccca gggattgtgg ttgtaagcct tgcatatgta cagtcccaga agtatcatct     780

gtcttcatct tccccccaaa gcccaaggat gtgctcacca ttactctgac tcctaaggtc     840

acgtgtgttg tggtagacat cagcaaggat gatcccgagg tccagttcag ctggtttgta     900

gatgatgtgg aggtgcacac agctcagacg caaccccggg aggagcagtt caacagcact     960

ttccgctcag tcagtgaact tcccatcatg caccaggact ggctcaatgg caaggagttc    1020

aaatgcaggg tcaacagtgc agctttccct gcccccatcg agaaaaccat ctccaaaacc    1080

aaaggcagac cgaaggctcc acaggtgtac accattccac ctcccaagga gcagatggcc    1140

aaggataaag tcagtctgac ctgcatgata acagacttct tccctgaaga cattactgtg    1200

gagtggcagt ggaatgggca gccagcggag aactacaaga acactcagcc catcatggac    1260
```

```
acagatggct cttacttcgt ctacagcaag ctcaatgtgc agaagagcaa ctgggaggca   1320

ggaaatactt tcacctgctc tgtgttacat gagggcctgc acaaccacca tactgagaag   1380

agcctctccc actctcctgg taaatga                                        1407


<210> SEQ ID NO 40
<211> LENGTH: 717
<212> TYPE: DNA
<213> ORGANISM: Artificial sequence
<220> FEATURE:
<223> OTHER INFORMATION: 130M23 Light chain nucleotide sequence

<400> SEQUENCE: 40

atgggcatca agatggagtc acagattcag gcatttgtat tcgtgtttct ctggttgtct     60

ggtgttgacg gagacattgt gatgacccag tctcacaaat tcatgtccac atcagtcgga    120

gacagggtca gcatcacctg caaggccagt caggatgtga gttctgctgt agcctggtat    180

caacaaaaac cagggcaatc tcctaaacta ctgatttact gggcatccac ccggcacact    240

ggagtccctg atcgcttcac aaacagtgga tctgggacag attatactct caccatcagt    300

agtgtgcagg ctgaagacct ggcactttat tactgtcagc aacattatag cactccgtgg    360

acgttcggtg gaggcaccaa gctggaaatc aaacgggctg atgctgcacc aactgtatcc    420

atcttcccac catccagtga gcagttaaca tctggaggtg cctcagtcgt gtgcttcttg    480

aacaacttct accccaaaga catcaatgtc aagtggaaga ttgatggcag tgaacgacaa    540

aatggcgtcc tgaacagttg gactgatcag gacagcaaag acagcaccta cagcatgagc    600

agcaccctca cgttgaccaa ggacgagtat gaacgacata acagctatac ctgtgaggcc    660

actcacaaga catcaacttc acccattgtc aagagcttca acaggaatga gtgttag       717


<210> SEQ ID NO 41
<211> LENGTH: 449
<212> TYPE: PRT
<213> ORGANISM: Artificial sequence
<220> FEATURE:
<223> OTHER INFORMATION: 130M23 Heavy chain amino acid sequence

<400> SEQUENCE: 41

Glu Val Lys Leu Val Glu Ser Gly Gly Gly Leu Val Lys Pro Gly Gly
1               5                   10                  15

Ser Leu Lys Phe Ser Cys Ala Ala Ser Gly Phe Ser Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Phe Cys Ala
                85                  90                  95

Arg Gly Gly Asp Pro Gly Val Tyr Asn Gly Asp Tyr Glu Asp Ala Met
            100                 105                 110

Asp Tyr Trp Gly Gln Gly Thr Ser Val Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160
```

```
Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys


<210> SEQ ID NO 42
<211> LENGTH: 214
<212> TYPE: PRT
<213> ORGANISM: Artificial sequence
<220> FEATURE:
<223> OTHER INFORMATION: 130M23 Light chain amino acid sequence

<400> SEQUENCE: 42

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Asn
    50                  55                  60
```

```
Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 43
<211> LENGTH: 222
<212> TYPE: PRT
<213> ORGANISM: Homo sapiens

<400> SEQUENCE: 43

Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
            20                  25                  30

Arg Cys Gln Gln Lys Leu Phe Phe Phe Leu Arg Arg Glu Gly Met Arg
        35                  40                  45

Gln Tyr Gly Glu Cys Leu His Ser Cys Pro Ser Gly Tyr Tyr Gly His
    50                  55                  60

Arg Ala Pro Asp Met Asn Arg Cys Ala Arg Cys Arg Ile Glu Asn Cys
65                  70                  75                  80

Asp Ser Cys Phe Ser Lys Asp Phe Cys Thr Lys Cys Lys Val Gly Phe
                85                  90                  95

Tyr Leu His Arg Gly Arg Cys Phe Asp Glu Cys Pro Asp Gly Phe Ala
            100                 105                 110

Pro Leu Glu Glu Thr Met Glu Cys Val Glu Gly Cys Glu Val Gly His
        115                 120                 125

Trp Ser Glu Trp Gly Thr Cys Ser Arg Asn Asn Arg Thr Cys Gly Phe
    130                 135                 140

Lys Trp Gly Leu Glu Thr Arg Thr Arg Gln Ile Val Lys Lys Pro Val
145                 150                 155                 160

Lys Asp Thr Ile Pro Cys Pro Thr Ile Ala Glu Ser Arg Arg Cys Lys
                165                 170                 175

Met Thr Met Arg His Cys Pro Gly Gly Lys Arg Thr Pro Lys Ala Lys
            180                 185                 190

Glu Lys Arg Asn Lys Lys Lys Lys Arg Lys Leu Ile Glu Arg Ala Gln
        195                 200                 205

Glu Gln His Ser Val Phe Leu Ala Thr Asp Arg Ala Asn Gln
    210                 215                 220
```

```
<210> SEQ ID NO 44
<211> LENGTH: 184
<212> TYPE: PRT
<213> ORGANISM: Homo sapiens

<400> SEQUENCE: 44

Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
            20                  25                  30

Arg Cys Gln Gln Lys Leu Phe Phe Phe Leu Arg Arg Glu Gly Met Arg
        35                  40                  45

Gln Tyr Gly Glu Cys Leu His Ser Cys Pro Ser Gly Tyr Tyr Gly His
    50                  55                  60

Arg Ala Pro Asp Met Asn Arg Cys Ala Arg Cys Arg Ile Glu Asn Cys
65                  70                  75                  80

Asp Ser Cys Phe Ser Lys Asp Phe Cys Thr Lys Cys Lys Val Gly Phe
                85                  90                  95

Tyr Leu His Arg Gly Arg Cys Phe Asp Glu Cys Pro Asp Gly Phe Ala
            100                 105                 110

Pro Leu Glu Glu Thr Met Glu Cys Val Glu Gly Cys Glu Val Gly His
        115                 120                 125

Trp Ser Glu Trp Gly Thr Cys Ser Arg Asn Asn Arg Thr Cys Gly Phe
    130                 135                 140

Lys Trp Gly Leu Glu Thr Arg Thr Arg Gln Ile Val Lys Lys Pro Val
145                 150                 155                 160

Lys Asp Thr Ile Pro Cys Pro Thr Ile Ala Glu Ser Arg Arg Cys Lys
                165                 170                 175

Met Thr Met Arg His Cys Pro Gly
            180


<210> SEQ ID NO 45
<211> LENGTH: 51
<212> TYPE: PRT
<213> ORGANISM: Homo sapiens

<400> SEQUENCE: 45

Tyr Val Ser Asn Pro Ile Cys Lys Gly Cys Leu Ser Cys Ser Lys Asp
1               5                   10                  15

Asn Gly Cys Ser Arg Cys Gln Gln Lys Leu Phe Phe Phe Leu Arg Arg
            20                  25                  30

Glu Gly Met Arg Gln Tyr Gly Glu Cys Leu His Ser Cys Pro Ser Gly
        35                  40                  45

Tyr Tyr Gly
    50


<210> SEQ ID NO 46
<211> LENGTH: 45
<212> TYPE: PRT
<213> ORGANISM: Homo sapiens

<400> SEQUENCE: 46

Met Asn Arg Cys Ala Arg Cys Arg Ile Glu Asn Cys Asp Ser Cys Phe
1               5                   10                  15

Ser Lys Asp Phe Cys Thr Lys Cys Lys Val Gly Phe Tyr Leu His Arg
            20                  25                  30
```

```
Gly Arg Cys Phe Asp Glu Cys Pro Asp Gly Phe Ala Pro
        35                  40                  45


<210> SEQ ID NO 47
<211> LENGTH: 61
<212> TYPE: PRT
<213> ORGANISM: Homo sapiens

<400> SEQUENCE: 47

Gly Cys Glu Val Gly His Trp Ser Glu Trp Gly Thr Cys Ser Arg Asn
1               5                   10                  15

Asn Arg Thr Cys Gly Phe Lys Trp Gly Leu Glu Thr Arg Thr Arg Gln
            20                  25                  30

Ile Val Lys Lys Pro Val Lys Asp Thr Ile Pro Cys Pro Thr Ile Ala
        35                  40                  45

Glu Ser Arg Arg Cys Lys Met Thr Met Arg His Cys Pro
    50                  55                  60


<210> SEQ ID NO 48
<211> LENGTH: 251
<212> TYPE: PRT
<213> ORGANISM: Homo sapiens

<400> SEQUENCE: 48

Gln Asn Ala Ser Arg Gly Arg Arg Gln Arg Arg Met His Pro Asn Val
1               5                   10                  15

Ser Gln Gly Cys Gln Gly Gly Cys Ala Thr Cys Ser Asp Tyr Asn Gly
            20                  25                  30

Cys Leu Ser Cys Lys Pro Arg Leu Phe Phe Ala Leu Glu Arg Ile Gly
        35                  40                  45

Met Lys Gln Ile Gly Val Cys Leu Ser Ser Cys Pro Ser Gly Tyr Tyr
    50                  55                  60

Gly Thr Arg Tyr Pro Asp Ile Asn Lys Cys Thr Lys Cys Lys Ala Asp
65                  70                  75                  80

Cys Asp Thr Cys Phe Asn Lys Asn Phe Cys Thr Lys Cys Lys Ser Gly
                85                  90                  95

Phe Tyr Leu His Leu Gly Lys Cys Leu Asp Asn Cys Pro Glu Gly Leu
            100                 105                 110

Glu Ala Asn Asn His Thr Met Glu Cys Val Ser Ile Val His Cys Glu
        115                 120                 125

Val Ser Glu Trp Asn Pro Trp Ser Pro Cys Thr Lys Lys Gly Lys Thr
    130                 135                 140

Cys Gly Phe Lys Arg Gly Thr Glu Thr Arg Val Arg Glu Ile Ile Gln
145                 150                 155                 160

His Pro Ser Ala Lys Gly Asn Leu Cys Pro Pro Thr Asn Glu Thr Arg
                165                 170                 175

Lys Cys Thr Val Gln Arg Lys Lys Cys Gln Lys Gly Glu Arg Gly Lys
            180                 185                 190

Lys Gly Arg Glu Arg Lys Arg Lys Lys Pro Asn Lys Gly Glu Ser Lys
        195                 200                 205

Glu Ala Ile Pro Asp Ser Lys Ser Leu Glu Ser Ser Lys Glu Ile Pro
    210                 215                 220

Glu Gln Arg Glu Asn Lys Gln Gln Gln Lys Lys Arg Lys Val Gln Asp
225                 230                 235                 240

Lys Gln Lys Ser Val Ser Val Ser Thr Val His
                245                 250
```

<210> SEQ ID NO 49
<211> LENGTH: 52
<212> TYPE: PRT
<213> ORGANISM: Homo sapiens

<400> SEQUENCE: 49

Pro Asn Val Ser Gln Gly Cys Gln Gly Gly Cys Ala Thr Cys Ser Asp
1 5 10 15

Tyr Asn Gly Cys Leu Ser Cys Lys Pro Arg Leu Phe Phe Ala Leu Glu
20 25 30

Arg Ile Gly Met Lys Gln Ile Gly Val Cys Leu Ser Ser Cys Pro Ser
35 40 45

Gly Tyr Tyr Gly
50

<210> SEQ ID NO 50
<211> LENGTH: 44
<212> TYPE: PRT
<213> ORGANISM: Homo sapiens

<400> SEQUENCE: 50

Ile Asn Lys Cys Thr Lys Cys Lys Ala Asp Cys Asp Thr Cys Phe Asn
1 5 10 15

Lys Asn Phe Cys Thr Lys Cys Lys Ser Gly Phe Tyr Leu His Leu Gly
20 25 30

Lys Cys Leu Asp Asn Cys Pro Glu Gly Leu Glu Ala
35 40

<210> SEQ ID NO 51
<211> LENGTH: 61
<212> TYPE: PRT
<213> ORGANISM: Homo sapiens

<400> SEQUENCE: 51

His Cys Glu Val Ser Glu Trp Asn Pro Trp Ser Pro Cys Thr Lys Lys
1 5 10 15

Gly Lys Thr Cys Gly Phe Lys Arg Gly Thr Glu Thr Arg Val Arg Glu
20 25 30

Ile Ile Gln His Pro Ser Ala Lys Gly Asn Leu Cys Pro Pro Thr Asn
35 40 45

Glu Thr Arg Lys Cys Thr Val Gln Arg Lys Lys Cys Gln
50 55 60

<210> SEQ ID NO 52
<211> LENGTH: 1401
<212> TYPE: DNA
<213> ORGANISM: Artificial sequence
<220> FEATURE:
<223> OTHER INFORMATION: h89M5-H2L2 Heavy chain nucleotide sequence

<400> SEQUENCE: 52
atggactgga cctggaggat actctttctc gtggcagcag ccacaggagc ccactcccag 60
gtccagctcg tgcagtctgg ggctgaggtg aagaagcctg gggcctctgt gaaggtttcc 120
tgcaagactt ctggatacac cttcactgga tacaccatgc actgggttag acaggccccc 180
ggacaaaggc tggagtggat gggaggtatt aatcctaaca atggtggtac tacttacaac 240
cagaacttca agggcagagt caccattacc agggacacat ccgcaagcac agcctacatg 300
gagctgtcca gcctgagatc tgaagacaca gctgtgtatt actgtgcaag aaaggagttc 360

```
tctgatggat actacttttt tgcttactgg ggccaaggga ccctggtcac cgtcagctca    420

gccagcacaa agggccctag cgtcttccct ctggctccct gcagcaggag caccagcgag    480

agcacagccg ccctgggctg cctggtcaag gactacttcc ccgaaccggt gacggtgtcg    540

tggaactcag gcgctctgac cagcggcgtg cacaccttcc cagctgtcct acagtcctca    600

ggactctact ccctcagcag cgtggtgacc gtgccctcca gcaacttcgg cacccagacc    660

tacacctgca acgtagatca caagcccagc aacaccaagg tggacaagac agttgagcgc    720

aaatgttgtg tcgagtgccc accgtgccca gcaccacctg tggcaggacc gtcagtcttc    780

ctcttccccc caaaacccaa ggacaccctc atgatctccc ggacccctga ggtcacgtgc    840

gtggtggtgg acgtgagcca cgaagacccc gaggtccagt tcaactggta cgtggacggc    900

gtggaggtgc ataatgccaa gacaaagcca cgggaggagc agttcaacag cacgttccgt    960

gtggtcagcg tcctcaccgt tgtgcaccag gactggctga acggcaagga gtacaagtgc   1020

aaggtctcca acaaaggcct cccagccccc atcgagaaaa ccatctccaa aaccaaaggg   1080

cagccccgag aaccacaggt gtacaccctg cccccatccc gggaggagat gaccaagaac   1140

caggtcagcc tgacctgcct ggtcaaaggc ttctacccca gcgacatcgc cgtggagtgg   1200

gagagcaatg ggcagccgga gaacaactac aagaccacac ctcccatgct ggactccgac   1260

ggctccttct tcctctacag caagctcacc gtggacaaga gcaggtggca gcaggggaac   1320

gtcttctcat gctccgtgat gcatgaggct ctgcacaacc actacacgca gaagagcctc   1380

tccctgtctc cgggtaaatg a                                             1401
```

```
<210> SEQ ID NO 53
<211> LENGTH: 466
<212> TYPE: PRT
<213> ORGANISM: Artificial sequence
<220> FEATURE:
<223> OTHER INFORMATION: h89M5-H2L2  Heavy chain amino acid sequence

<400> SEQUENCE: 53

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Thr Ser Gly Tyr Thr Phe
        35                  40                  45

Thr Gly Tyr Thr Met His Trp Val Arg Gln Ala Pro Gly Gln Arg Leu
    50                  55                  60

Glu Trp Met Gly Gly Ile Asn Pro Asn Asn Gly Gly Thr Thr Tyr Asn
65                  70                  75                  80

Gln Asn Phe Lys Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Lys Glu Phe Ser Asp Gly Tyr Tyr Phe Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175
```

```
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 54
<211> LENGTH: 363
<212> TYPE: DNA
<213> ORGANISM: Artificial sequence
<220> FEATURE:
<223> OTHER INFORMATION: h89M5-H2L2 Heavy chain variable region nucleotide sequence

<400> SEQUENCE: 54

```
caggtccagc tcgtgcagtc tggggctgag gtgaagaagc ctggggcctc tgtgaaggtt     60

tcctgcaaga cttctggata caccttcact ggatacacca tgcactgggt tagacaggcc    120

cccggacaaa ggctggagtg gatgggaggt attaatccta acaatggtgg tactacttac    180

aaccagaact tcaagggcag agtcaccatt accagggaca catccgcaag cacagcctac    240

atggagctgt ccagcctgag atctgaagac acagctgtgt attactgtgc aagaaaggag    300

ttctctgatg gatactactt ttttgcttac tggggccaag ggaccctggt caccgtcagc    360
```

tca 363

<210> SEQ ID NO 55
<211> LENGTH: 121
<212> TYPE: PRT
<213> ORGANISM: Artificial sequence
<220> FEATURE:
<223> OTHER INFORMATION: h89M5-H2L2 Heavy chain variable region amino acid sequence

<400> SEQUENCE: 55

Gln Val Gln Leu Val Gln Ser Gly Ala Glu Val Lys Lys Pro Gly Ala
1 5 10 15

Ser Val Lys Val Ser Cys Lys Thr Ser Gly Tyr Thr Phe Thr Gly Tyr
20 25 30

Thr Met His Trp Val Arg Gln Ala Pro Gly Gln Arg Leu Glu Trp Met
35 40 45

Gly Gly Ile Asn Pro Asn Asn Gly Gly Thr Thr Tyr Asn Gln Asn Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Lys Glu Phe Ser Asp Gly Tyr Tyr Phe Phe Ala Tyr Trp Gly
100 105 110

Gln Gly Thr Leu Val Thr Val Ser Ser
115 120

<210> SEQ ID NO 56
<211> LENGTH: 711
<212> TYPE: DNA
<213> ORGANISM: Artificial sequence
<220> FEATURE:
<223> OTHER INFORMATION: h89M5-H2L2 Light chain nucleotide sequence

<400> SEQUENCE: 56
atggacatga gggtccccgc acagctcctg gggctcctgc tcctctggct ccggggtgcc 60
agatgtgaca tccagatgac ccagtctcca tcctccctgt ctgcatctgt cggagacaga 120
gtcaccatca cttgcaaggc ctcccaggat gtgatttttg ctgttgcctg gtatcagcag 180
aaaccaggga aagcccctaa gctcctgatc tattgggcat ccacccggca cactggggtc 240
ccatcaaggt tcagtggcag tggatctggg acagattaca ctctcaccat cagcagtctg 300
caacctgaag attttgcaac ttactactgt cagcaacatt atagcactcc ttggactttc 360
ggcggaggga ccaaggtgga gatcaaacgg actgtggctg caccatctgt cttcatcttc 420
cctccatctg atgagcagtt gaaatctgga actgcctctg ttgtgtgcct gctgaataac 480
ttctatccca gagaggccaa agtccagtgg aaggtggata acgccctcca atccggtaac 540
tcccaggaga gtgtcacaga gcaggacagc aaggacagca cctacagcct cagcaacacc 600
ctgacactga gcaaagcaga ctacgagaaa cacaaagtct acgcctgcga agtcacccat 660
cagggcctga gctcccccgt cacaaagagc ttcaacaggg gagagtgcta a 711

<210> SEQ ID NO 57
<211> LENGTH: 236
<212> TYPE: PRT
<213> ORGANISM: Artificial sequence
<220> FEATURE:
<223> OTHER INFORMATION: h89M5-H2L2 Light chain amino acid

<400> SEQUENCE: 57

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Ile Phe Ala Val Ala Trp Tyr Gln Gln Lys Pro Gly Lys
    50                  55                  60

Ala Pro Lys Leu Leu Ile Tyr Trp Ala Ser Thr Arg His Thr Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
            100                 105                 110

His Tyr Ser Thr Pro Trp Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Asn Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 58
<211> LENGTH: 321
<212> TYPE: DNA
<213> ORGANISM: Artificial sequence
<220> FEATURE:
<223> OTHER INFORMATION: h89M5-H2L2 Light chain variable region nucleotide sequence

<400> SEQUENCE: 58

```
gacatccaga tgacccagtc tccatcctcc ctgtctgcat ctgtcggaga cagagtcacc     60

atcacttgca aggcctccca ggatgtgatt tttgctgttg cctggtatca gcagaaacca    120

gggaaagccc ctaagctcct gatctattgg gcatccaccc ggcacactgg ggtcccatca    180

aggttcagtg gcagtggatc tgggacagat tacactctca ccatcagcag tctgcaacct    240

gaagattttg caacttacta ctgtcagcaa cattatagca ctccttggac tttcggcgga    300

gggaccaagg tggagatcaa a                                              321
```

<210> SEQ ID NO 59
<211> LENGTH: 107
<212> TYPE: PRT
<213> ORGANISM: Artificial sequence
<220> FEATURE:
<223> OTHER INFORMATION: h89M5-H2L2 Light chain variable region amino acid sequence

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ile Phe Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
            100                 105
```

<210> SEQ ID NO 60
<211> LENGTH: 1413
<212> TYPE: DNA
<213> ORGANISM: Artificial sequence
<220> FEATURE:
<223> OTHER INFORMATION: h130M23-H1L2 Heavy chain nucleotide

<400> SEQUENCE: 60

```
atggaactgg gactcagatg ggttttcctc gttgctattc tggaaggagt ccagtgtgag     60

gtgcagctgg tggagtctgg gggaggcctg gtcaagcctg gaggatctct gcggctctcc    120

tgtgcagcct ctggattcac cttctcctct tatgccatgt cttgggtccg gcaggctcca    180

gggaaggggc tggaatgggt ctcatccatt tctagtggag gtagcacata ttatcctgac    240

agcgtgaagg gccggttcac catctccaga gacaacgcca agaacagcct gtatctgcaa    300

atgaacagcc tgagagccga ggacacagct gtgtattact gtgctagagg tggagatcct    360

ggggtctaca atggagatta cgaagatgct atggactact gggggcaagg aacaacagtc    420

acagtcagct cagccagcac aaagggccct agcgtcttcc ctctggctcc ctgcagcagg    480

agcaccagcg agagcacagc cgccctgggc tgcctggtca aggactactt ccccgaaccg    540

gtgacggtgt cgtggaactc aggcgctctg accagcggcg tgcacacctt cccagctgtc    600

ctacagtcct caggactcta ctccctcagc agcgtggtga ccgtgccctc cagcaacttc    660

ggcacccaga cctacacctg caacgtagat cacaagccca gcaacaccaa ggtggacaag    720

acagttgagc gcaaatgttg tgtcgagtgc ccaccgtgcc cagcaccacc tgtggcagga    780

ccgtcagtct tcctcttccc cccaaaaccc aaggacaccc tcatgatctc ccggacccct    840

gaggtcacgt gcgtggtggt ggacgtgagc cacgaagacc ccgaggtcca gttcaactgg    900

tacgtggacg gcgtggaggt gcataatgcc aagacaaagc cacgggagga gcagttcaac    960

agcacgttcc gtgtggtcag cgtcctcacc gttgtgcacc aggactggct gaacggcaag   1020

gagtacaagt gcaaggtctc caacaaaggc ctcccagccc ccatcgagaa aaccatctcc   1080

aaaaccaaag ggcagccccg agaaccacag gtgtacaccc tgcccccatc ccgggaggag   1140

atgaccaaga accaggtcag cctgacctgc ctggtcaaag gcttctaccc cagcgacatc   1200

gccgtggagt gggagagcaa tgggcagccg gagaacaact acaagaccac acctcccatg   1260

ctggactccg acggctcctt cttcctctac agcaagctca ccgtggacaa gagcaggtgg   1320

cagcagggga acgtcttctc atgctccgtg atgcatgagg ctctgcacaa ccactacacg   1380
```

```
cagaagagcc tctccctgtc tccgggtaaa tga                               1413


<210> SEQ ID NO 61
<211> LENGTH: 470
<212> TYPE: PRT
<213> ORGANISM: Artificial sequence
<220> FEATURE:
<223> OTHER INFORMATION: h130M23-H1L2  Heavy chain amino acid sequence

<400> SEQUENCE: 61

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ser Ile Ser Ser Gly Gly Ser Thr Tyr Tyr Pro Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Gly Gly Asp Pro Gly Val Tyr Asn Gly Asp Tyr Glu
        115                 120                 125

Asp Ala Met Asp Tyr Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350
```

```
Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470


<210> SEQ ID NO 62
<211> LENGTH: 375
<212> TYPE: DNA
<213> ORGANISM: Artificial sequence
<220> FEATURE:
<223> OTHER INFORMATION: h130M23-H1L2  Heavy chain variable region
      nucleotide sequence

<400> SEQUENCE: 62

gaggtgcagc tggtggagtc tgggggaggc ctggtcaagc ctggaggatc tctgcggctc     60

tcctgtgcag cctctggatt caccttctcc tcttatgcca tgtcttgggt ccggcaggct    120

ccagggaagg ggctggaatg ggtctcatcc atttctagtg gaggtagcac atattatcct    180

gacagcgtga agggccggtt caccatctcc agagacaacg ccaagaacag cctgtatctg    240

caaatgaaca gcctgagagc cgaggacaca gctgtgtatt actgtgctag aggtggagat    300

cctggggtct acaatggaga ttacgaagat gctatggact actgggggca aggaacaaca    360

gtcacagtca gctca                                                     375


<210> SEQ ID NO 63
<211> LENGTH: 125
<212> TYPE: PRT
<213> ORGANISM: Artificial sequence
<220> FEATURE:
<223> OTHER INFORMATION: h130M23-H1L2  Heavy chain variable region amino
      acid sequence

<400> SEQUENCE: 63

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Asp Pro Gly Val Tyr Asn Gly Asp Tyr Glu Asp Ala Met
```

```
            100                 105                 110

Asp Tyr Trp Gly Gln Gly Thr Thr Val Thr Val Ser Ser
        115                 120                 125


<210> SEQ ID NO 64
<211> LENGTH: 711
<212> TYPE: DNA
<213> ORGANISM: Artificial sequence
<220> FEATURE:
<223> OTHER INFORMATION: h130M23-H1L2  Light chain nucleotide sequence

<400> SEQUENCE: 64

atgaaatacc tcctccctac agctgccgct ggactcctcc tcctcgctgc ccagcctgcc      60

atggccgaca tccagatgac ccagtcccct tcctccctgt ctgcttccgt cggagacaga     120

gtcaccatca cttgcaaggc ctcccaggat gtgtcctctg ctgtcgcttg gtatcagcag     180

aaaccaggaa aagctcctaa gctcctgatc tattgggcat ccaccaggca cacaggagtc     240

ccttccaggt tctccggctc tggatctggg acagatttca ctctcaccat cagctccgtg     300

caagctgaag attttgcaac ttactactgt cagcaacatt atagcactcc ttggacattc     360

ggacaaggga ccaaggtgga aatcaaaaga actgtggctg caccttctgt cttcatcttc     420

cctccatctg atgagcagct caaatctgga actgcctccg ttgtgtgcct gctgaataac     480

ttctatccta gagaggccaa agtccagtgg aaggtggata acgccctcca atccggtaac     540

tcccaggagt ctgtcacaga gcaggactcc aaggacagca cctactccct cagcaacacc     600

ctgacactgt ctaaagctga ctacgagaaa cacaaagtct acgcctgcga agtcacccat     660

cagggactga gctcccccgt cacaaaatcc ttcaacaggg gagagtgcta a              711


<210> SEQ ID NO 65
<211> LENGTH: 236
<212> TYPE: PRT
<213> ORGANISM: Artificial sequence
<220> FEATURE:
<223> OTHER INFORMATION: h130M23-H1L2  Light chain amino acid

<400> SEQUENCE: 65

Met Lys Tyr Leu Leu Pro Thr Ala Ala Ala Gly Leu Leu Leu Leu Ala
1               5                   10                  15

Ala Gln Pro Ala Met Ala Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Ser Ser Ala Val Ala Trp Tyr Gln Gln Lys Pro Gly Lys
    50                  55                  60

Ala Pro Lys Leu Leu Ile Tyr Trp Ala Ser Thr Arg His Thr Gly Val
65                  70                  75                  80

Pro Ser Arg Phe Ser Gly Ser Gly Ser Gly Thr Asp Phe Thr Leu Thr
                85                  90                  95

Ile Ser Ser Val Gln Ala Glu Asp Phe Ala Thr Tyr Tyr Cys Gln Gln
            100                 105                 110

His Tyr Ser Thr Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160
```

```
Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Asn Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 66
<211> LENGTH: 321
<212> TYPE: DNA
<213> ORGANISM: Artificial sequence
<220> FEATURE:
<223> OTHER INFORMATION: h130M23-H1L2  Light chain variable region
      nucleotide sequence

<400> SEQUENCE: 66

gacatccaga tgacccagtc cccttcctcc ctgtctgctt ccgtcggaga cagagtcacc      60

atcacttgca aggcctccca ggatgtgtcc tctgctgtcg cttggtatca gcagaaacca     120

ggaaaagctc ctaagctcct gatctattgg gcatccacca ggcacacagg agtcccttcc     180

aggttctccg gctctggatc tgggacagat ttcactctca ccatcagctc cgtgcaagct     240

gaagattttg caacttacta ctgtcagcaa cattatagca ctccttggac attcggacaa     300

gggaccaagg tggaaatcaa a                                               321


<210> SEQ ID NO 67
<211> LENGTH: 107
<212> TYPE: PRT
<213> ORGANISM: Artificial sequence
<220> FEATURE:
<223> OTHER INFORMATION: h130M23-H1L2  Light chain variable region amino
      acid sequence

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Val Gln Ala
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys
            100                 105


<210> SEQ ID NO 68
<211> LENGTH: 447
<212> TYPE: PRT
<213> ORGANISM: Artificial sequence
<220> FEATURE:
<223> OTHER INFORMATION: h89M5-H2L2  Heavy chain amino acid sequence

<400> SEQUENCE: 68
```

```
Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
            20                  25                  30

Thr Met His Trp Val Arg Gln Ala Pro Gly Gln Arg Leu Glu Trp Met
        35                  40                  45

Gly Gly Ile Asn Pro Asn Asn Gly Gly Thr Thr Tyr Asn Gln Asn Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Glu Phe Ser Asp Gly Tyr Tyr Phe Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 69
<211> LENGTH: 214
<212> TYPE: PRT
<213> ORGANISM: Artificial sequence
<220> FEATURE:
<223> OTHER INFORMATION: h89M5-H2L2  Light chain amino acid sequence

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ile Phe Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 70
<211> LENGTH: 451
<212> TYPE: PRT
<213> ORGANISM: Artificial sequence
<220> FEATURE:
<223> OTHER INFORMATION: h130M23-H1L2  Heavy chain amino acid sequence

<400> SEQUENCE: 70

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Ser Thr Tyr Tyr Pro Asp Ser Val Lys
    50                  55                  60
```

```
Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Asp Pro Gly Val Tyr Asn Gly Asp Tyr Glu Asp Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 71
<211> LENGTH: 214
```

<212> TYPE: PRT
<213> ORGANISM: Artificial sequence
<220> FEATURE:
<223> OTHER INFORMATION: h130M23-H1L2 Light chain amino acid sequence

<400> SEQUENCE: 71

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Val Gln Ala
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 72
<211> LENGTH: 717
<212> TYPE: DNA
<213> ORGANISM: Artificial sequence
<220> FEATURE:
<223> OTHER INFORMATION: h130M23-H1L6 Light chain nucleotide sequence

<400> SEQUENCE: 72

```
atgggcatca agatggagtc acagattcag gcatttgtat tcgtgtttct ctggttgtct     60

ggtgttgacg gagacatcca gatgacccag tccccttcct ccctgtctgc ttccgtcgga    120

gacagagtca ccatcacttg caaggcctcc caggatgtgt cctctgctgt cgcttggtat    180

cagcagaaac caggaaaagc tcctaagctc ctgatctatt gggcatccac caggcacaca    240

ggagtccctt ccaggttctc cggctctgga tctgggacag atttcactct caccatcagc    300

tccctgcaac ctgaagattt tgcaacttac tactgtcagc aacattatag cactccttgg    360

acattcggac aagggaccaa ggtggaaatc aaaagaactg tggctgcacc ttctgtcttc    420

atcttccctc catctgatga gcagctcaaa tctggaactg cctccgttgt gtgcctgctg    480

aataacttct atcctagaga ggccaaagtc cagtggaagg tggataacgc cctccaatcc    540

ggtaactccc aggagtctgt cacagagcag gactccaagg acagcaccta ctccctcagc    600
```

```
aacaccctga cactgtctaa agctgactac gagaaacaca aagtctacgc ctgcgaagtc    660

acccatcagg gactgagctc ccccgtcaca aaatccttca acaggggaga gtgctaa       717


<210> SEQ ID NO 73
<211> LENGTH: 238
<212> TYPE: PRT
<213> ORGANISM: Artificial sequence
<220> FEATURE:
<223> OTHER INFORMATION: h130M23-H1L6  Light chain amino acid sequence

<400> SEQUENCE: 73

Met Gly Ile Lys Met Glu Ser Gln Ile Gln Ala Phe Val Phe Val Phe
1               5                   10                  15

Leu Trp Leu Ser Gly Val Asp Gly Asp Ile Gln Met Thr Gln Ser Pro
            20                  25                  30

Ser Ser Leu Ser Ala Ser Val Gly Asp Arg Val Thr Ile Thr Cys Lys
        35                  40                  45

Ala Ser Gln Asp Val Ser Ser Ala Val Ala Trp Tyr Gln Gln Lys Pro
    50                  55                  60

Gly Lys Ala Pro Lys Leu Leu Ile Tyr Trp Ala Ser Thr Arg His Thr
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln His Tyr Ser Thr Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Asn Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 74
<211> LENGTH: 214
<212> TYPE: PRT
<213> ORGANISM: Artificial sequence
<220> FEATURE:
<223> OTHER INFORMATION: h130M23-H1L6  Light chain amino acid sequence

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 75
<211> LENGTH: 321
<212> TYPE: DNA
<213> ORGANISM: Artificial sequence
<220> FEATURE:
<223> OTHER INFORMATION: h130M23-H1L6  Light chain variable region
      nucleotide sequence

<400> SEQUENCE: 75

gacatccaga tgacccagtc cccttcctcc ctgtctgctt ccgtcggaga cagagtcacc     60

atcacttgca aggcctccca ggatgtgtcc tctgctgtcg cttggtatca gcagaaacca    120

ggaaaagctc ctaagctcct gatctattgg gcatccacca ggcacacagg agtcccttcc    180

aggttctccg gctctggatc tgggacagat ttcactctca ccatcagctc cctgcaacct    240

gaagattttg caacttacta ctgtcagcaa cattatagca ctccttggac attcggacaa    300

gggaccaagg tggaaatcaa a                                              321


<210> SEQ ID NO 76
<211> LENGTH: 107
<212> TYPE: PRT
<213> ORGANISM: Artificial sequence
<220> FEATURE:
<223> OTHER INFORMATION: h130M23-H1L6  Light chain variable region amino
      acid sequence

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys
            100                 105
```